US010945992B1

(12) United States Patent
Sippy et al.

(10) Patent No.: US 10,945,992 B1
(45) Date of Patent: Mar. 16, 2021

(54) DOSAGE FORMS OF ROFECOXIB AND RELATED METHODS

(71) Applicant: Tremeau Pharmaceuticals, Inc., Concord, MA (US)

(72) Inventors: Bradford C. Sippy, Acton, MA (US); Raymond D. Skwierczynski, Andover, MA (US); Travis E. Helm, Acton, MA (US)

(73) Assignee: Tremeau Pharmaceuticals, Inc., Concord, MA (US)

( * ) Notice: Subject to any disclaimer, the term of this patent is extended or adjusted under 35 U.S.C. 154(b) by 0 days.

(21) Appl. No.: 16/867,514

(22) Filed: May 5, 2020

Related U.S. Application Data

(60) Provisional application No. 63/018,136, filed on Apr. 30, 2020, provisional application No. 62/934,898, filed on Nov. 13, 2019.

(51) Int. Cl.
 *A61K 31/365* (2006.01)
 *A61K 9/20* (2006.01)
 *A61K 9/16* (2006.01)

(52) U.S. Cl.
 CPC .............. *A61K 31/365* (2013.01); *A61K 9/16* (2013.01); *A61K 9/20* (2013.01)

(58) Field of Classification Search
 CPC .................................................. A61K 31/365
 See application file for complete search history.

(56) References Cited

U.S. PATENT DOCUMENTS

| | | |
|---|---|---|
| 3,854,480 A | 12/1974 | Zaffaroni |
| 4,452,775 A | 6/1984 | Kent |
| 4,675,189 A | 6/1987 | Kent et al. |
| 5,075,109 A | 12/1991 | Tice et al. |
| 5,133,974 A | 7/1992 | Paradissis et al. |
| 5,407,686 A | 4/1995 | Patel et al. |
| 5,474,995 A | 12/1995 | Ducharme et al. |
| 5,736,152 A | 4/1998 | Dunn |
| 5,840,924 A | 11/1998 | Desmond et al. |
| 5,849,943 A | 12/1998 | Atkinson et al. |
| 6,063,811 A | 5/2000 | Hancock et al. |
| 6,407,686 B1 | 6/2002 | Otani et al. |
| 2002/0049233 A1 | 4/2002 | Kararli et al. |

FOREIGN PATENT DOCUMENTS

| | | |
|---|---|---|
| EP | 0754687 A1 | 1/1997 |
| EP | 0822190 A1 | 2/1998 |
| EP | 0705254 B1 | 5/1998 |
| EP | 0980866 A2 | 2/2000 |
| JP | 2000-38375 A | 2/2000 |
| WO | WO-9500501 A2 | 1/1995 |
| WO | WO-9518799 A1 | 7/1995 |
| WO | WO-9608482 A1 | 3/1996 |
| WO | WO-9613483 A1 | 5/1996 |
| WO | WO-9744028 A1 | 11/1997 |
| WO | WO-98/00416 A1 | 1/1998 |
| WO | WO-04/72057 A1 | 8/2004 |
| WO | WO-2005016906 | 2/2005 |
| WO | WO 2005/025564 A1 | 3/2005 |
| WO | WO 2019/193417 A1 | 10/2019 |
| WO | WO-2020/106522 | 5/2020 |

OTHER PUBLICATIONS

Ahuja et al., Rofecoxib: an update on physicochemical, pharmaceutical, pharmacodynamics and pharmacokinetic aspects, J. Pharmacy and Pharmacology, 1003, 55:859-894.*
U.S. Prescribing Information, US. Food and Drug Administration, Reference ID 3928121, available at https://www.accessdata.fda.gov/drugsatfda_docs/label/2016/021042s033,021052s024lbl.pdf.*
Ahuja et al., Rofecoxib: an update on physicochemical, pharmaceutical, pharmacodynamics and pharmacokinetic aspects, J. Pharmacy and Pharmacology, 2003, 55:859-894.*
"Guideline on the Limits of Genotoxic Impurities", EMEA/CHMP/QWP/251344/2006, Jun. 28, 2006 (8 pages).
"M7 Assessment and Control of DNA Reactive (Mutagenic) Impurities in Pharmaceuticals to Limit Potential Carcinogenic Risk: Guidance for Industry", U.S. Department of Health and Human Services, Food and Drug Administration, Center for Drug Evaluation and Research (CDER), Center for Biologics Evaluation and Research (CBER), May 2015 (35 pages).
"M7(R1) Assessment and Control of DNA Reactive (Mutagenic) Impurities in Pharmaceuticals to Limit Potential Carcinogenic Risk: Guidance for Industry", U.S. Department of Health and Human Services, Food and Drug Administration, Center for Drug Evaluation and Research (CDER), Center for Biologics Evaluation and Research (CBER), Mar. 2018 (131 pages).
Abou-Taleb, A.E. et al., "Formulation and Evaluation of Rofecoxib Tablets in Comparison With Marketed Product", Saudi Pharmaceutical Journal, vol. 14, Nos. 3-4, Jul.-Oct. 2006, pp. 187-195 (9 pages).
Ahuja, N. et al., "Rofecoxib: an update on physicochemical, pharmaceutical, pharmacodynamic and pharmacokinetic aspects", Journal of Pharmacy and Pharmacology, 55:859-894, 2003 (36 pages).
Andrews, A.W. et al., "A Comparison of the Mutagenic Properties of Vinyl Chloride and Methyl Chloride", Mutation Research, 40:273-275, 1976 (3 pages).
Azuma, S et al., "Mutagenicity of 12 HPLC Labeling Reagents for Analysing Carboxyl Compounds", Journal of Environmental Chemistry, 7(2):249-255, 1997 (7 pages)—English Abstract.
Sathesh Babu, P.R., et al., "Solubility Enhancement of Cox-II Inhibitors by Cosolvency Approach", Dhaka Univ. J. Pharm. Sci. 7(2): 119-126, 2008 (Dec.) (8 pages).
Berge, S.M. et al., "Pharmaceutical Salts", Journal of Pharmaceutical Sciences, 66(1):1-19, Jan. 1977 (19 Pages).
Bresalier, R.S. et al., "Cardiovascular Events Associated with Rofecoxib in a Colorectal Adenoma Chemoprevention Trial", N Engl J Med:352:1092-1102, 2005 (11 pages).

(Continued)

*Primary Examiner* — Svetlana M Ivanova
(74) *Attorney, Agent, or Firm* — Wolf, Greenfield & Sacks, P.C.

(57) ABSTRACT

The subject matter disclosed herein relates to novel doses and dosage forms of rofecoxib having a therapeutic benefit.

28 Claims, 108 Drawing Sheets

(56) References Cited

OTHER PUBLICATIONS

Caturla, F., et al., "Racemic and chiral sulfoxides as potential prodrugs of the COX-2 inhibitors Vioxx® and Arcoxia®", Bioorganic & Medicinal Chemistry Letters, 16:3209-3212, available online Apr. 17, 2006 (4 pages).

CSD Entry: CAXMUJ, https://www.ccdc.cam.ac.uk/structures/Search?Compound=Rofecoxib&DatabaseToSearch=Published, Accessed May 27, 2020 (3 pages).

Chan, C.-C., et al., "Rofecoxib [Vioxx, MK-0966; 4-(4'-Methylsulfonylphenyl)-3-phenyl-2-(5H)-furanone]: A Potent and Orally Active Cyclooxygenase-2 Inhibitor. Pharmacological and Biochemical Profiles", The Journal of Pharmacology and Experimental Therapeutics, vol. 290, No. 2, 1999, pp. 551-560 (10 pages).

Davies, N.M., et al., "Pharmacokinetics of Rofecoxib: A Specific Cyclo-Oxygenase-2 Inhibitor", Clin Pharmacokinet 2003; 42 (6): 545-556 (2003) (12 pages).

Dean, P.M., "Structural Examination of 6-Methylsulphonylphenanthro-[9,10-C]furan-1(3H)-one—A Rofecoxib Degradation Product", Pharmaceuticals, 3(2):369-378, Feb. 1, 2010 (10 pages).

Depré, M., et al., "Pharmacokinetics, COX-2 specificity, and tolerability of supratherapeutic doses of rofecoxib in humans", Eur J Clin Pharmacol, 56: 167-174 (2000) (9 pages).

Dobo, K.L., et al., "In silico methods combined with expert knowledge rule out mutagenic potential of pharmaceutical impurities: An industry survey", Regulatory Toxicology and Pharmacology, 62(3):449-455, available online Jan. 31, 2012 (7 pages).

Dong, J.J., et al., "Manganese-Catalyzed Selective Oxidation of Aliphatic C-H groups and Secondary Alcohols to Ketones with Hydrogen Peroxide", ChemSusChem, 6(9):1774-1778, 2013 (6 Pages).

El-Say, K.M., et al., "Formulation and Evaluation of Rofecoxib Liquisolid Tablets", International Journal of Pharmaceutical Sciences Review and Research, vol. 3, Issue 1, Jul.-Aug. 2010; Article 028, pp. 135-142 (8 pages).

El-Say, K.M., et al., "Optimization of Rofecoxib Liquisolid Tablets using Box-Behnken Design and Desirability Function", Journal of Pharmacy Research, 3(10):2388-2392, Oct. 10, 2010 (5 pages).

Groom, C.R., et al., "The Cambridge Structural Database", Acta Cryst, B72:171-179, 2016 (9 pages).

Porras, A., et al., Abstract PII-89, "Single and Multiple Dose Pharmacokinetics (PK) of Rofecoxib (R) in Healthy Subjects", American Society for Clinical Pharmacology and Therapeutics, Abstracts of Papers, 2000 Annual Meeting, Clinical Pharmacology & Therapeutics, vol. 67, No. 2, p. 137, Feb. 2000 (2 pages).

Hansen, K., et al., "Benchmark Data Set for in Silico Prediction of Ames Mutagenicity", Journal of Chemical Information and Modeling, 49(9):2077-2081, 2009 (5 Pages).

Jenkins, J.K., et al., "Analysis and recommendations for Agency action regarding non-steroidal anti-inflammatory drugs and cardiovascular risk", Memorandum to NDA files 20-998, 21-156, 21-341, 21-042 Apr. 6, 2005 (19 pages).

Koytchev, R., et al., "Bioequivalence Study of Rofecoxib Tablets", Arzneim.-Forsch./Drug Res. 54, No. 9a, pp. 624-628 (2004) (6 pages).

Langer, R., "New Methods of Drug Delivery", Science, 249:1527-1533, 23, Sep. 28, 1990 (8 Pages).

Leber, A. P., et al., "p-Chlorophenyl Methyl Sulfide, p-Chlorophenyl Methyl Sulfoxide, and p-Chlorophenyl Methyl Sulfone. I. Acute Toxicity and Bacterial Mutagenicity Studies", J. Am. Coll. Toxicol., 12(4):369-376, 1993 (8 pages).

Martin, T., "User's Guide for T.E.S.T. (version 4.2) (Toxicity Estimation Software Tool): A Program to Estimate Toxicity from Molecular Structure", EPA/600/R-16/058, Version 4.2.1, 2016 (63 pages).

Matthews, C.Z., et al., "Improved procedure for the determination of rofecoxib in human plasma involving 96-well solid-phase extraction and fluorescence detection", Journal of Chromatography A, 949 (2002) 83-89 (7 pages).

Matthews, E. J., et al., "Combined Use of MC4PC, MDL-QSAR, BioEpisteme, Leadscope PDM, and Derek for Windows Software to Achieve High-Performance, High-Confidence, Mode of Action-Based Predictions of Chemical Carcinogenesis in Rodents", Toxicology Mechanisms and Methods, 18:189-206, published online Oct. 9, 2008 (19 pages).

Muller, L., et al., "A rationale for determining, testing, and controlling specific impurities in pharmaceuticals that possess potential for genotoxicity", Regul Toxicol Pharmacol, 44:198-211, 2006 (14 pages).

Nicoll-Griffith, D.A., et al., "Synthesis, Characterization, and Activity of Metabolites Derived from the Cyclooxygenase-2 Inhibitor Rofecoxib (MK-0966, Vioxx™)", Bioorganic & Medicinal Chemistry Letters 10 (2000) 2683-2686 (4 pages).

Rabbaa, L., et al., "Bioequivalence Study and Pharmacokinetic Evaluation of Two Brands of Rofecoxib 25 mg Tablets in a Lebanese Population", The Journal of Applied Research, vol. 4, No. 4, 2004, pp. 630-634 (5 pages).

Rajendrakumar, K., et al., "Comparative Study on Co-Ground Products of Rofecoxib with β-Cyclodextrin and Its Sulfobutyl Ether-7 Derivative in Solution and in the Solid State", Journal of Inclusion Phenomena and Macrocyclic Chemistry 49: 259-266, 2004 (8 pages).

Rattray, B.N., et al., "The Use of Rofecoxib (Vioxx) in the Treatment of Hemophilia.", Blood 2004 104:3097 pp. 1-6 (6 pages).

Reddy, K., et al., "Isolation and characterisation of process-related impurities in rofecoxib", Journal of Pharmaceutical and Biomedical Analysis 29:355-360, 2002 (6 pages).

Reddy, L.R., et al., "Facile air oxidation of the conjugate base of rofecoxib (Vioxx™), a possible contributor to chronic human toxicity", Tetrahedron Letters, 46:927-929, 2005, available online Dec. 25, 2004 (3 pages).

Sammour, et al., "Formulation and Optimization of Mouth Dissolve Tablets Containing Rofecoxib Solid Dispersion", AAPS PharmSciTech, Article 55, 7(2):E1-E9, 2006 (9 pages).

Schwartz, J.I., et al., "Pharmacokinetic Evaluation of Rofecoxib: Comparison of Tablet and Suspension Formulations", Clin Drug Invest 2003; 23(8):503-509 (7 pages).

Schwartz, J.I., et al., Abstract 369, "Rofecoxib steady-state pharmacokinetics [PK] in moderate hepatic insufficiency patients (HI)", American Journal of Gastroenterology, p. 2519 (Sep. 2000) (2 pages).

Seedher, N., et al., "Solubility Enhancement of Cox-2 Inhibitors Using Various Solvent Systems", AAPS PharmSciTech; 4 (3) Article 33 (http://www.pharmscitech.org)., pp. 1-9, 2003 (9 pages).

Sobera, L.A., et al., "Rofecoxib", Drugs of the Future, 23(12):1287-1296, 1998 (10 pages).

Steinbeck, C., et al., "The Chemistry Development Kit (CDK): An Open-Source Java Library for Chemo- and Bioinformatics", Journal of Chemical Information and Computer Sciences, 43:493-500, 2003 (8 pages).

Sutter, A., et al., "Use of in silico systems and expert knowledge for structure-based assessment of potentially mutagenic impurities", http://dx.doi.org/10.1016/j.yrtph.2013.05.001, Regulatory Toxicology and Pharmacology, Article in Press, 67:39-52, 2013 (14 pages).

Therien, M., et al., "Synthesis of Rofecoxib, (MK 0966, Vioxx® 4-(4'-Methylsulfonylphenyl)-3-Phenyl-2(5H)-Furanone), a Selective and Orally Active Inhibitor of Cyclooxygenase-2", Synthesis (Stuttgart), 12:1778, 2001 (1 page).

Tsoukas, C., et al., "Evaluation of the efficacy and safety of etoricoxib in the treatment of hemophilic arthropathy", Blood, 107(5):1785-1790, Mar. 2006, published online Nov. 15, 2005 (7 pages).

U.S. Food and Drug Administration, "Analysis and Recommendations for Agency Action Regarding Nonsteroidal Anti-Inflammatory Drugs and Cardiovascular Risk", J. Pain Palliat Care Pharmacother, 19(4):83-97, 2005 (16 pages).

Vioxx (Rofecoxib), Food and Drug Administration Office of Clinical Pharmacology and Biopharmaceutics Review, NDAs 21-042/(SE5-026) & 21-052/(SE5-019), Merck & Co., Inc. Sponsor, accessed https://www.fda.gov/media/91448/download, 2004 (28 pages) (Redacted).

(56) References Cited

OTHER PUBLICATIONS

Vioxx (Rofecoxib), U.S. Prescribing Information, U.S. Food and Drug Administration, Reference ID 3928121, accessed at https://www.accessdata.fda.gov/drugsatfda_docs/label/2016/021042s033,021052s024lbl.pdf, 2002 (31 pages).
Werner, U., et al., "Selective and rapid liquid chromatography—mass spectrometry method for the quantification of rofecoxib in pharmacokinetic studies with humans", Journal of Chromatography B, 760 (2001) pp. 83-90 (8 pages).
Zeiger, E., et al., "*Salmonella* Mutagenicity Tests: V. Results from the Testing of 311 Chemicals", Environmental and Molecular Mutagenesis, 19(Supplement 21):2-141, 1992 (140 Pages).
FDA, "Vioxx (rofecoxib) Questions and Answers", https://www.fda.gov/drugs/postmarket-drug-safety-information-patients-and-providers/vioxx-rofecoxib-questions-and-answers, Sep. 30, 2004 (4 pages).
International Search Report and Written Opinion issued by U.S. Patent and Trademark Office as International Searching Authority, in International Application No. PCT/US19/61178, dated Apr. 14, 2020 (13 pages).
Krauskopf, L. "Merck agrees to pay $4.85 billion in Vioxx settlement", Reuters, Business News, Nov. 9, 2007 (6 pages).
Lenzer, J. "FDA is incapable of protecting US against another Vioxx", BMJ, 329:1253, Nov. 27, 2004 (1 page).
Morrison, B.W. et al., "The Optimal Analgesic Dose of Rofecoxib: Overview of Six Randomized Controlled Trials", Clinical Pharmacology, JADA, 131:1729-1737, Dec. 2000 (9 pages).
Sibbald, B. "Rofecoxib (Vioxx) voluntarily withdrawn from market", Synopsis, CMAJ, 171:1027-1028, Oct. 26, 2004 (2 pages).
[No Author Listed], An Overview of USP Monographs. Retrieved from usp.org/publicstandards. 2 pages.
[No Author Listed], Etoricoxib—Final Authorized Version 2.0. USPC Medicins Compendium. 6 pages. Retrieved from mc.usp.org/monographs/etoricoxiv-2-0 on Jul. 4, 2020. 6 pages.
[No Author Listed], First Supplement to USP 35-NF 30. Official Monographs / Celecoxib. The United States Pharmacopeial Convention. Aug. 1, 2012:5447-5448.
[No Author Listed], Guidance for Industry—ANDAs: Impurities in Drug Subtances. US Department of Health and Human Servies. Food and Drug Administration, Center for Drug Evaluation and Research (CDER). Nov. 19, 1999 19 pages.
[No Author Listed], Safety Data Sheet for 3-Chloroperoxybenzoic acid. Cat Nos. AC255790000; AC255790010' AC255790250; AC255791000; AC255795000. ThermoFisher Scientific. Jan. 23, 2009. 8 pages.
Erk et al., Comparison of derivative spectrophotometric and liquid chromatographic methods for the determination of rofecoxib. Pharmazie. Jun. 2004;59(6):453-6.
European Medicines Agency, Note for Guidance on Impurities Testing: Impurities in New Drug Substances. EMEA. Retrieved from www.emea.europa.eu. Oct. 15, 2006 15 pages.
Forgione et al., Magnesium mediated carbometallation of propargyl alcohols: direct routes to furans and furanones. Tetra Lett. 2000;41:17-20.
Garde, 'I just white-knuckler it': Hemophilia patients pin their hopes on the revival of Vioxx to fill a void in pain relief. STAT. Dec. 9, 2020. 6 pages.
Kubota et al., An Unexpected Incident with m-CPBA. Organic Process Research & Development. 2004;8:1076-7078.
[No Author Listed] Vioxx Final. N-21,042. Merck & Co. No date. 15 pages.
[No Author Listed], Rofecoxib (Vioxx) voluntarily withdrawn from market. CMAJ. Oct. 26, 2004;171(9). 2 pages.
Mao et al., Mao B, Abrahim A, Ge Z, Ellison DK, Hartman R, Prabhu SV, Reamer RA, Wyvratt J. Examination of rofecoxib solution decomposition under alkaline and photolytic stress conditions. J Pharm Biomed Anal. Jun. 15, 2002;28(6):1101-13. doi: 10.1016/s0731-7085(01)00716-6.
Radhakrishna et al., LC determination of rofecoxib in bulk and pharmaceutical formulations. J Pharm Biomed Anal. Nov. 2001;26(4):617-28. doi: 10.1016/s0731-7085(01)00493-9.
Reddy et al., Novel approaches for colon cancer prevention by cyclooxygenase-2 inhibitors. J Environ Pathol Toxicol Oncol. 2002;21(2):155-64.

\* cited by examiner

Composition of Prototype 25-mg Rofecoxib Tablets

| Components | Prototype Batches 1-4 % (w/w) per tablet | Prototype Batches 5-6 % (w/w) per tablet | Prototype Batches 7-8 % (w/w) per tablet | Function |
|---|---|---|---|---|
| Intragranular | | | | |
| Rofecoxib | 12.50 | 12.50 | 12.50 | Active ingredient |
| Lactose monohydrate | 39.85 | 39.70 | 37.70 | Diluent |
| Microcrystalline cellulose | 39.85 | 39.70 | 37.70 | Diluent |
| Hydroxypropylcellulose | 3.00 | 3.00 | 3.00 | Binder |
| Croscarmellose sodium | 0.00 | 2.00 | 4.00 | Disintegrant |
| Water | NA[a] | NA[a] | NA[a] | Granulation Medium |
| Extragranular | | | | |
| Pigment blend yellow | 0.30 | 0.60 | 0.60 | Coloring agent |
| Croscarmellose sodium | 4.00 | 2.00 | 4.00 | Disintegrant |
| Magnesium stearate | 0.50 | 0.50 | 0.50 | Lubricant |
| Totals | 100.00 | 100.00 | 100.00 | |

[a] Water for granulation is removed upon drying of the wet mass.

FIG. 1A

Composition of 25-mg Rofecoxib Tablets

| Components | % (w/w) per tablet | mg per tablet | Function | Reference to Standards[a] |
|---|---|---|---|---|
| Intragranular | | | | |
| Rofecoxib [b] | 12.50 | 25.0 | Active ingredient | In-House |
| Lactose monohydrate | 39.85 | 79.7 | Diluent | USP-NF, Ph.Eur., JP |
| Microcrystalline cellulose | 39.85 | 79.7 | Diluent | USP-NF, Ph.Eur., JP |
| Hydroxypropylcellulose | 3.00 | 6.0 | Binder | USP-NF, Ph.Eur., JP |
| Croscarmellose sodium | 2.00 | 4.0 | Disintegrant | USP-NF, Ph.Eur., JP |
| Water | NA[c] | NA[c] | Granulation Medium | USP-NF, Ph.Eur. |
| Extragranular | | | | |
| Pigment blend yellow | 0.30 | 0.6 | Coloring Agent | See Table 2 |
| Croscarmellose sodium | 2.00 | 4.0 | Disintegrant | USP-NF, Ph.Eur., JP |
| Magnesium stearate | 0.50 | 1.0 | Lubricant | USP-NF, Ph.Eur., JP |
| Totals | 100.00 | 200.00 | | |

USP = United States Pharmacopeia; NF = National Formulary; Ph. Eur. = European Pharmacopeia; JP = Japanese Pharmacopeia.

[a] When referred to a Pharmacopeia, the current edition of the Pharmacopeia is applied.

[b] Note that the amount of rofecoxib may be adjusted for purity and moisture content. An adjustment will be made to the amounts of lactose monohydrate and microcrystalline cellulose used to maintain tablet weight.

[c] Water for granulation is removed upon drying of the wet mass.

FIG. 1B

Process conditions for Prototype Batches 1-4

| Prototype Batch 1 (lot number B18079) | Prototype Batch 2 (lot number B18080) |
|---|---|
| • Composition: See Figure 1A.<br>• Scale: 2.3 kg<br>• Process: A$_1$<br>　○ Amount of water added = 26%<br>　○ Spray rate = 100 g/min<br>• Manufacturing observation:<br>　○ The pigment did not disperse well and yellow spots were observed on the tablet surface. | • Composition: See Figure 1A.<br>• Scale: 2.3 kg<br>• Process: A$_2$<br>　○ Amount of water added = 41%<br>　○ Spray rate = 100 g/min<br>　○ Changes made from Process A$_1$<br>　　▪ The pigment was blended with croscarmellose sodium in Step 1T prior to sieving. See Figure 11A-B.<br>• Manufacturing observation:<br>　○ The rofecoxib adhered to the sieve in Step 1G and required washing with other excipients.<br>　○ The tablets were soft and had slower disintegration times than that for the lot B18079. |
| Prototype Batch 3 (lot number B18084) | Prototype Batch 4 (lot number B18085) |
| • Composition: See Figure 1A.<br>• Scale: 2.3 kg<br>• Process: A$_3$<br>　○ Amount of water added = 26%<br>　○ Spray rate = 175 g/min<br>　○ Changes made from Process A$_2$<br>　　▪ The rofecoxib was blended with lactose monohydrate in Step 1G prior to sieving. See Figure 12A-B | • Composition: See Figure 1A.<br>• Scale: 2.3 kg<br>• Process: A$_3$<br>　○ Amount of water added = 30%<br>　○ Spray rate = 100 g/min |

FIG. 2

Process conditions for Prototype Batches 5-8

| Prototype Batch 5 (lot number B18090) | Prototype Batch 6 (lot number B18091) |
|---|---|
| • Composition: See Figure 1A.<br>   ◦ Intragranular disintegrant = 2%<br>   ◦ Extragranular disintegrant = 2%<br>   ◦ Total disintegrant = 4%<br>• Scale: 1.2 kg<br>• Process: $B_1$<br>   ◦ Amount of water added = 26%<br>   ◦ Spray rate = 100 g/min | • Composition: See Figure 1A.<br>   ◦ Intragranular disintegrant = 2%<br>   ◦ Extragranular disintegrant = 2%<br>   ◦ Total disintegrant = 4%<br>• Scale: 1.2 kg<br>• Process: $B_1$<br>   ◦ Amount of water added = 32%<br>   ◦ Spray rate = 100 g/min |
| Prototype Batch 7 (lot number B18092) | Prototype Batch 8 (lot number B18093) |
| • Composition: See Figure 1A.<br>   ◦ Intragranular disintegrant = 4%<br>   ◦ Extragranular disintegrant = 4%<br>   ◦ Total disintegrant = 8%<br>• Scale: 1.2 kg<br>• Process: $B_1$<br>   ◦ Amount of water added = 26%<br>   ◦ Spray rate = 100 g/min | • Composition: See Figure 1A.<br>   ◦ Intragranular disintegrant = 4%<br>   ◦ Extragranular disintegrant = 4%<br>   ◦ Total disintegrant = 8%<br>• Scale: 1.2 kg<br>• Process: $B_1$<br>   ◦ Amount of water added = 32%<br>   ◦ Spray rate = 100 g/min |

FIG. 5

Composition of 25-mg Rofecoxib Tablets

| Components | Prototype Batches 5-6 % (w/w) per tablet | Clinical Batch % (w/w) per tablet | Function |
|---|---|---|---|
| Intragranular | | | |
| Rofecoxib | 12.50 | 12.50 | Active ingredient |
| Lactose monohydrate | 39.70 | 39.85 | Diluent |
| Microcrystalline cellulose | 39.70 | 39.85 | Diluent |
| Hydroxypropylcellulose | 3.00 | 3.00 | Binder |
| Croscarmellose sodium | 2.00 | 2.00 | Disintegrant |
| Water | NA[a] | NA[a] | Granulation Medium |
| Extragranular | | | |
| Pigment blend yellow | 0.60 | 0.30 | Coloring agent |
| Croscarmellose sodium | 2.00 | 2.00 | Disintegrant |
| Magnesium stearate | 0.50 | 0.50 | Lubricant |
| Totals | 100.00 | 100.00 | |

[a] Water for granulation is removed upon drying of the wet mass.

FIG. 8

| Process A1 | Process A2 | Process A3 | Process B1 |
|---|---|---|---|
| Preparation of Rofecoxib Granules<br>Step 1G: Pass the lactose, rofecoxib, microcrystalline cellulose, hydroxypropylcellulose, and croscarmellose sodium through an appropriate-sized sieve screen as the granulator is charged.<br>Step 2G: Mix the dry powder in the high-shear granulator.<br>Step 3G: Spray the water of granulation onto the contents of the high-shear granulator while mixing. The target amount of water of granulation added is given relative to the mass of the dry powder in the granulator.<br>Step 4G: Discharge the wet granules from the granulator into a high-speed mill equipped with an appropriate-sized screen. Mill the wet granules.<br>Step 5G: Dry the wet-milled | Preparation of Rofecoxib Granules<br>Same as Process A1. | Preparation of Rofecoxib Granules<br>Step 1G: *Blend lactose monohydrate and rofecoxib.*<br>Step 2G: Pass the lactose-rofecoxib blend, microcrystalline cellulose, and hydroxypropylcellulose, through an appropriate-sized sieve screen as the granulator is charged.<br>Step 3G: Mix the dry powder in the high-shear granulator.<br>Step 4G: Spray the water of granulation onto the contents of the high-shear granulator while mixing. The target amount of water of granulation added is given relative to the mass of the dry powder in the granulator.<br>Step 5G: Discharge the wet granules from the granulator into a high-speed mill equipped with an appropriate-sized screen. Mill the wet granules. | Preparation of Rofecoxib Granules<br>Step 1G: Blend lactose monohydrate and rofecoxib.<br>Step 2G: *Pass the lactose-rofecoxib blend, microcrystalline cellulose, hydroxypropylcellulose, and croscarmellose sodium through an appropriate-sized sieve screen as the granulator is charged.*<br>Step 3G: Mix the dry powder in the high-shear granulator.<br>Step 4G: Spray the water of granulation onto the contents of the high-shear granulator while mixing. The target amount of water of granulation added is given relative to the mass of the dry powder in the granulator.<br>Step 5G: Discharge the wet granules from the granulator into a high-speed |

FIG. 9

| | | |
|---|---|---|
| granules into a fluid-bed drier.<br>Step 6G: Mill the dried granules using a high-speed mill equipped with an appropriate-sized screen. | Step 6G: Dry the wet-milled granules into a fluid-bed drier.<br>Step 7G: Mill the dried granules using a high-speed mill equipped with an appropriate-sized screen. | mill equipped with an appropriate-sized screen. Mill the wet granules.<br>Step 6G: Dry the wet-milled granules into a fluid-bed drier.<br>Step 7G: Mill the dried granules using a high-speed mill equipped with an appropriate-sized screen. |
| Preparation of Rofecoxib Tablets<br>Step 1T: Pass the rofecoxib granules, croscarmellose sodium, pigment, and magnesium stearate through an appropriate-sized sieve screen as the blender is charged.<br>Step 2T: Blend the powders.<br>Step 3T: Compress the blended powder into tablets.<br>Step 4T: Dedust and metal check the tablets. | Preparation of Rofecoxib Tablets<br>*Step 1T: Blend croscarmellose sodium and pigment.*<br>Step 2T: Pass the rofecoxib granules, croscarmellose sodium-pigment blend, and magnesium stearate through an appropriate-sized sieve screen as the blender is charged.<br>Step 3T: Blend the powders.<br>Step 4T: Compress the blended powder into tablets.<br>Step 5T: Dedust and metal check the tablets. | Preparation of Rofecoxib Tablets<br>Same as Process A2. |

Changes relative to the previous process are shown in italicized bold font.

FIG. 9 CONT.

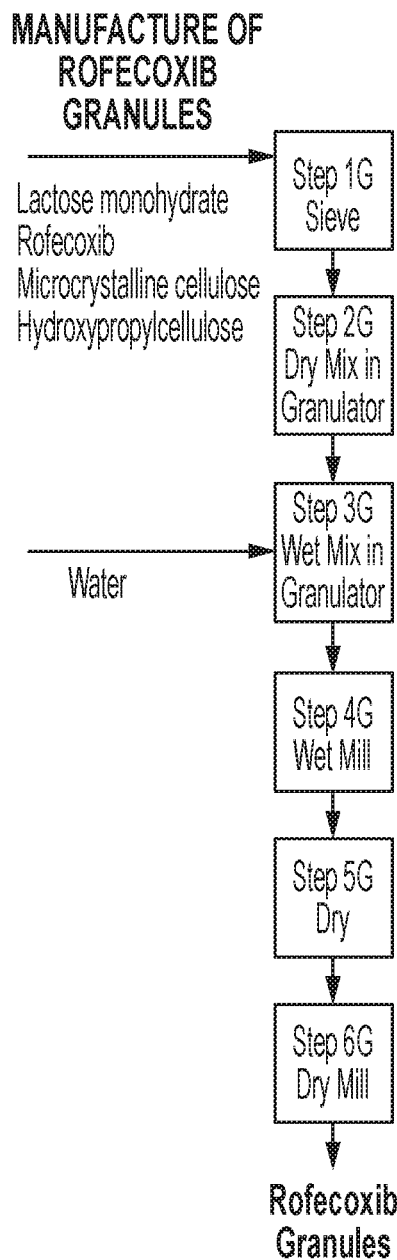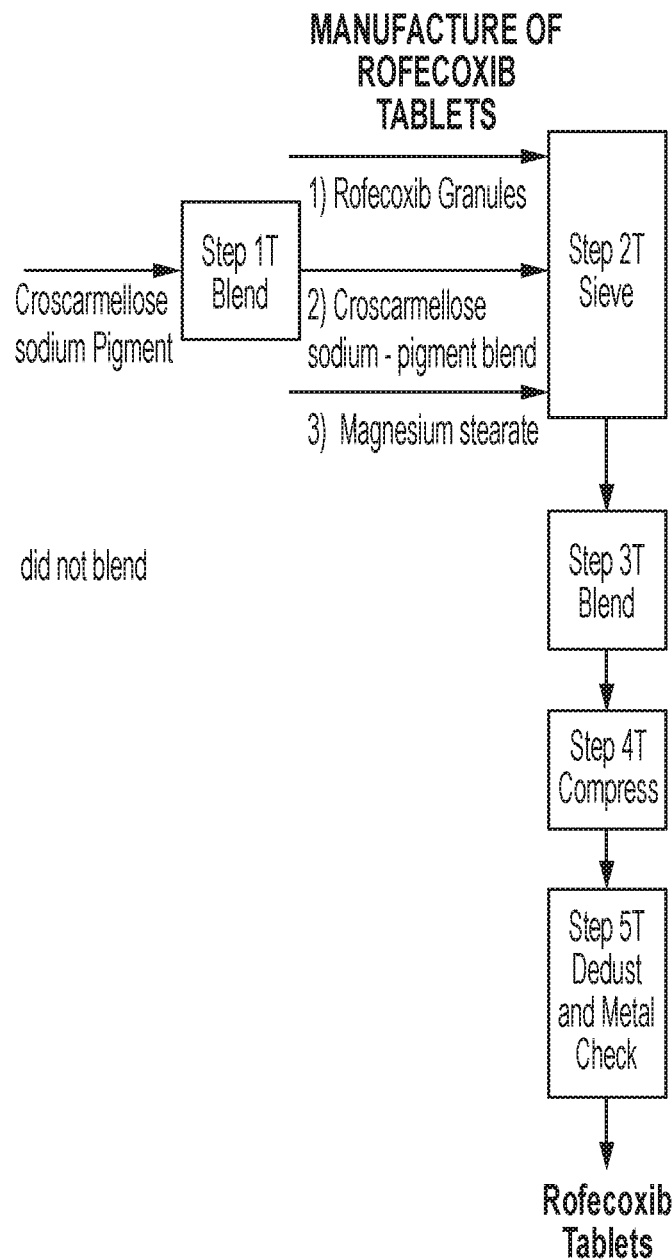
FIG. 11A
FIG. 11B

Summary of Fasted $AUC_{0-\infty}$ and $C_{max}$ in Pharmacokinetic Study

| Parameter | TRM-201 (N=52) |
|---|---|
| $AUC_{0-\infty}$ (ng.hr/mL) | |
| n | 52 |
| Arithmetic Mean (SD) | 4890 (1650) |
| CV | 33.8 |
| Geometric Mean (Natural – log SD) | 4640 (0.327) |
| Geometric CV | 33.6 |
| Median | 4680 |
| Min, Max | 2400, 10000 |
| 90% CI | 4300, 5010 |
| | |
| $C_{max}$ (ng/mL) | |
| n | 52 |
| Arithmetic Mean (SD) | 331 (96.5) |
| CV | 29.2 |
| Geometric Mean (Natural – log SD) | 318 (0.277) |
| Geometric CV | 28.2 |
| Median | 302 |
| Min, Max | 188, 589 |
| 90% CI | 298, 339 |

FIG. 25

Analysis AUC$_{0-\infty}$ and C$_{max}$ Compared to Historical Data

| Parameter | TRM-201 | | Historical | TRM-201/Historical | |
|---|---|---|---|---|---|
| | N | GM | GM | GMR | 90% CI |
| AUC$_{0-\infty}$ (ng·hr/mL) | 52 | 4640 | 3799 | 1.22 | 1.13, 1.32 |
| C$_{max}$ (ng/mL) | 52 | 318 | 217 | 1.47 | 1.38, 1.56 |

GM = geometric mean; GMR = geometric mean ratio
GMR is calculated on the natural-log-scale and back-transformed to the ratio scale.

FIG. 28

|  | 25 mg | 25 mg | Extrapolated PK Values | | | |
|---|---|---|---|---|---|---|
|  | AUCINF_obs (h*ng/mL) | $C_{max}$ (ng/mL) | AUC 17.5 mg | $C_{max}$ 17.5 mg | AUC 20 mg | $C_{max}$ 20 mg |
| TRM-201 Study | 4640 | 318 | 3248 | 222.6 | 3712 | 254.4 |

FIG. 31

|  | Overall |
|---|---|
| Age (years) | |
| n | 24 |
| Mean (SD) | 45.1 (12.45) |
| Median | 49.0 |
| Min, Max | 20, 60 |
| Gender | |
| Male | 11 (45.8) |
| Female | 13 (54.2) |
| Race | |
| American Indian or Alaskan Native | 0 |
| Asian | 0 |
| Black or African American | 5 (20.8) |
| Native Hawaiian or Other Pacific Islander | 0 |
| White | 19 (79.2) |
| Other | 0 |
| Ethnicity | |
| Hispanic or Latino | 12 (50.0) |
| Not Hispanic or Latino | 12 (50.0) |
| Height (cm) | |
| n | 24 |
| Mean (SD) | 166.89 (9.602) |
| Median | 165.50 |
| Min, Max | 150.0, 188.5 |
| Weight (kg) | |
| n | 24 |
| Mean (SD) | 74.45 (8.535) |
| Median | 74.35 |
| Min, Max | 58.2, 89.0 |

FIG. 33

| BMI (kg/m2) | Overall |
|---|---|
| n | 24 |
| Mean (SD) | 26.639 (2.8648) |
| Median | 26.950 |
| Min, Max | 20.96, 31.91 |

FIG. 34

|  | Overall |
|---|---|
| Age (years) | |
| n | 24 |
| Mean (SD) | 45.1 (12.45) |
| Median | 49.0 |
| Min, Max | 20, 60 |
| Gender | |
| Male | 11 (45.8) |
| Female | 13 (54.2) |
| Race | |
| American Indian or Alaskan Native | 0 |
| Asian | 0 |
| Black or African American | 5 (20.8) |
| Native Hawaiian or Other Pacific Islander | 0 |
| White | 19 (79.2) |
| Other | 0 |
| Ethnicity | |
| Hispanic or Latino | 12 (50.0) |
| Not Hispanic or Latino | 12 (50.0) |
| Height (cm) | |
| n | 24 |
| Mean (SD) | 166.89 (9.602) |
| Median | 165.50 |
| Min, Max | 150.0, 188.5 |
| Weight (kg) | |
| n | 24 |
| Mean (SD) | 74.45 (8.535) |
| Median | 74.35 |
| Min, Max | 58.2, 89.0 |

FIG. 35

| BMI (kg/m²) | Overall |
|---|---|
| n | 24 |
| Mean (SD) | 26.639 (2.8648) |
| Median | 26.950 |
| Min, Max | 20.96, 31.91 |

FIG. 36

| Time point (hour) | TRM-201 12.5 mg (N=24) | TRM-201 17.5 mg (N=24) | TRM-201 20 mg (N=24) | TRM-201 25 mg (N=24) |
|---|---|---|---|---|
| 0.00 | | | | |
| n | 24 | 24 | 24 | 24 |
| Arithmetic Mean (SD) | BLQ (NA) | BLQ (NA) | BLQ (NA) | BLQ (NA) |
| CV | NA | NA | NA | NA |
| Geometric Mean (SD, natural log scale) | BLQ (NA) | BLQ (NA) | BLQ (NA) | BLQ (NA) |
| Geometric CV | NA | NA | NA | NA |
| Median | BLQ | BLQ | BLQ | BLQ |
| Min, Max | BLQ, BLQ | BLQ, BLQ | BLQ, BLQ | BLQ, BLQ |
| 0.25 | | | | |
| n | 24 | 24 | 24 | 24 |
| Arithmetic Mean (SD) | 1.03 (1.60) | 2.42 (6.27) | 5.75 (14.1) | 5.63 (10.0) |
| CV | 155.9 | 258.7 | 245.5 | 178.3 |
| Geometric Mean (SD, natural log scale) | 0.529 (1.05) | 0.669 (1.35) | 1.16 (1.64) | 1.37 (1.71) |
| Geometric CV | 141.4 | 227.7 | 370.9 | 418.9 |
| Median | BLQ | BLQ | 0.924 | 1.40 |
| Min, Max | BLQ, 7.44 | BLQ, 29.7 | BLQ, 63.6 | BLQ, 34.1 |
| 0.5 | | | | |
| n | 24 | 24 | 24 | 24 |
| Arithmetic Mean (SD) | 22.3 (31.9) | 43.2 (64.7) | 64.6 (91.9) | 74.8 (81.2) |
| CV | 143.0 | 150.0 | 142.2 | 108.5 |
| Geometric Mean (SD, natural log scale) | 9.82 (1.29) | 15.0 (1.52) | 28.1 (1.33) | 32.0 (1.55) |
| Geometric CV | 208.3 | 301.1 | 222.3 | 319.6 |
| Median | 8.40 | 10.8 | 25.7 | 34.7 |
| Min, Max | 1.60, 136 | 1.14, 228 | 2.96, 338 | 1.23, 259 |

Plasma concentrations that are below the limit of quantification (BLQ) are imputed to ½ LQ, unless the pharmacokineticist indicated them as outliers, in which case they may be assigned missing values. Summary statistic values less than LQ are reported as "BLQ".

FIG. 37

| Time point (hour) | TRM-201 12.5 mg (N=24) | TRM-201 17.5 mg (N=24) | TRM-201 20 mg (N=24) | TRM-201 25 mg (N=24) |
|---|---|---|---|---|
| 0.75 | | | | |
| n | 24 | 24 | 24 | 24 |
| Arithmetic Mean (SD) | 56.8 (58.8) | 93.0 (104) | 121 (120) | 159 (115) |
| CV | 103.6 | 111.8 | 99.3 | 72.2 |
| Geometric Mean (SD, natural log scale) | 33.9 (1.07) | 51.6 (1.14) | 72.6 (1.13) | 97.6 (1.29) |
| Geometric CV | 146.8 | 163.5 | 159.8 | 206.3 |
| Median | 27.0 | 49.4 | 96.2 | 142 |
| Min, Max | 6.00, 223 | 7.85, 393 | 5.77, 437 | 2.91, 390 |
| 1 | | | | |
| n | 24 | 24 | 24 | 24 |
| Arithmetic Mean (SD) | 83.1 (62.9) | 127 (111) | 173 (134) | 216 (125) |
| CV | 75.6 | 87.6 | 77.1 | 58.0 |
| Geometric Mean (SD, natural log scale) | 58.7 (0.930) | 87.6 (0.926) | 124 (0.905) | 151 (1.14) |
| Geometric CV | 117.3 | 116.4 | 112.6 | 162.2 |
| Median | 67.7 | 114 | 140 | 223 |
| Min, Max | 9.27, 230 | 18.2, 473 | 20.2, 484 | 4.29, 439 |
| 1.5 | | | | |
| n | 24 | 24 | 24 | 24 |
| Arithmetic Mean (SD) | 117 (64.9) | 168 (106) | 231 (138) | 270 (145) |
| CV | 55.5 | 63.1 | 60.0 | 53.5 |
| Geometric Mean (SD, natural log scale) | 93.1 (0.810) | 133 (0.777) | 187 (0.718) | 201 (1.03) |
| Geometric CV | 96.3 | 91.1 | 82.1 | 137.5 |
| Median | 122 | 166 | 214 | 294 |
| Min, Max | 10.7, 245 | 22.1, 466 | 33.5, 552 | 7.38, 600 |

Plasma concentrations that are below the limit of quantification (BLQ) are imputed to ½ LQ, unless the pharmacokineticist indicated them as outliers, in which case they may be assigned missing values. Summary statistic values less than LQ are reported as "BLQ".

FIG. 38

| Time point (hour) | TRM-201 12.5 mg (N=24) | TRM-201 17.5 mg (N=24) | TRM-201 20 mg (N=24) | TRM-201 25 mg (N=24) |
|---|---|---|---|---|
| 2 | | | | |
| n | 24 | 24 | 24 | 24 |
| Arithmetic Mean (SD) | 128 (57.7) | 182 (87.6) | 228 (115) | 280 (118) |
| CV | 44.9 | 48.1 | 50.7 | 42.2 |
| Geometric Mean (SD, natural log scale) | 112 (0.605) | 156 (0.637) | 196 (0.594) | 225 (0.917) |
| Geometric CV | 66.5 | 70.8 | 65.1 | 114.9 |
| Median | 129 | 187 | 205 | 323 |
| Min, Max | 14.5, 253 | 27.6, 361 | 51.5, 470 | 7.21, 444 |
| 3 | | | | |
| n | 24 | 24 | 24 | 24 |
| Arithmetic Mean (SD) | 114 (37.8) | 188 (63.1) | 194 (78.2) | 261 (84.0) |
| CV | 33.3 | 33.5 | 40.3 | 32.2 |
| Geometric Mean (SD, natural log scale) | 104 (0.492) | 178 (0.354) | 177 (0.470) | 230 (0.713) |
| Geometric CV | 52.3 | 36.6 | 49.7 | 81.3 |
| Median | 116 | 186 | 198 | 272 |
| Min, Max | 19.4, 171 | 92.8, 311 | 70.3, 337 | 10.9, 426 |
| 4 | | | | |
| n | 24 | 24 | 24 | 24 |
| Arithmetic Mean (SD) | 102 (33.3) | 168 (56.6) | 186 (75.1) | 238 (63.0) |
| CV | 32.6 | 33.7 | 40.3 | 26.4 |
| Geometric Mean (SD, natural log scale) | 94.2 (0.481) | 160 (0.322) | 173 (0.388) | 215 (0.671) |
| Geometric CV | 51.0 | 33.1 | 40.3 | 75.4 |
| Median | 113 | 158 | 178 | 234 |
| Min, Max | 19.0, 155 | 89.9, 308 | 75.2, 438 | 10.1, 332 |

Plasma concentrations that are below the limit of quantification (BLQ) are imputed to ½ LQ, unless the pharmacokineticist indicated them as outliers, in which case they may be assigned missing values. Summary statistic values less than LQ are reported as "BLQ".

FIG. 39

| Time point (hour) | TRM-201 12.5 mg (N=24) | TRM-201 17.5 mg (N=24) | TRM-201 20 mg (N=24) | TRM-201 25 mg (N=24) |
|---|---|---|---|---|
| 5 | | | | |
| n | 24 | 24 | 24 | 24 |
| Arithmetic Mean (SD) | 99.5 (23.6) | 165 (40.5) | 186 (42.4) | 232 (51.3) |
| CV | 23.8 | 24.5 | 22.8 | 22.2 |
| Geometric Mean (SD, natural log scale) | 96.4 (0.267) | 161 (0.254) | 180 (0.268) | 227 (0.208) |
| Geometric CV | 27.1 | 25.8 | 27.3 | 21.0 |
| Median | 102 | 162 | 186 | 225 |
| Min, Max | 46.3, 150 | 83.6, 247 | 74.4, 257 | 167, 374 |
| 6 | | | | |
| n | 24 | 24 | 24 | 24 |
| Arithmetic Mean (SD) | 84.1 (21.5) | 131 (25.2) | 155 (34.4) | 186 (37.0) |
| CV | 25.6 | 19.3 | 22.2 | 19.9 |
| Geometric Mean (SD, natural log scale) | 81.2 (0.285) | 128 (0.201) | 151 (0.248) | 183 (0.191) |
| Geometric CV | 29.1 | 20.3 | 25.1 | 19.3 |
| Median | 87.0 | 132 | 149 | 186 |
| Min, Max | 40.5, 123 | 80.7, 172 | 67.7, 211 | 128, 293 |
| 7.5 | | | | |
| n | 24 | 24 | 24 | 24 |
| Arithmetic Mean (SD) | 75.2 (20.6) | 123 (28.3) | 138 (34.6) | 168 (33.4) |
| CV | 27.3 | 23.0 | 25.1 | 19.9 |
| Geometric Mean (SD, natural log scale) | 72.2 (0.305) | 120 (0.253) | 133 (0.277) | 165 (0.192) |
| Geometric CV | 31.2 | 25.7 | 28.3 | 19.4 |
| Median | 74.9 | 120 | 130 | 164 |
| Min, Max | 33.9, 124 | 57.8, 174 | 55.8, 206 | 116, 254 |

Plasma concentrations that are below the limit of quantification (BLQ) are imputed to ½ LQ, unless the pharmacokineticist indicated them as outliers, in which case they may be assigned missing values. Summary statistic values less than LQ are reported as "BLQ".

FIG. 40

| Time point (hour) | TRM-201 12.5 mg (N=24) | TRM-201 17.5 mg (N=24) | TRM-201 20 mg (N=24) | TRM-201 25 mg (N=24) |
| --- | --- | --- | --- | --- |
| 9 | | | | |
| n | 24 | 24 | 24 | 24 |
| Arithmetic Mean (SD) | 79.9 (28.5) | 125 (44.3) | 144 (49.4) | 174 (53.3) |
| CV | 35.7 | 35.5 | 34.4 | 30.6 |
| Geometric Mean (SD, natural log scale) | 74.4 (0.410) | 118 (0.339) | 135 (0.380) | 167 (0.289) |
| Geometric CV | 42.8 | 34.9 | 39.4 | 29.5 |
| Median | 80.8 | 114 | 140 | 174 |
| Min, Max | 26.7, 150 | 44.7, 250 | 44.6, 275 | 104, 337 |
| 12 | | | | |
| n | 24 | 24 | 24 | 24 |
| Arithmetic Mean (SD) | 54.3 (17.9) | 85.9 (21.1) | 101 (24.3) | 123 (29.2) |
| CV | 32.9 | 24.5 | 24.0 | 23.7 |
| Geometric Mean (SD, natural log scale) | 50.8 (0.400) | 83.1 (0.271) | 97.9 (0.278) | 120 (0.253) |
| Geometric CV | 41.7 | 27.6 | 28.4 | 25.7 |
| Median | 56.0 | 87.6 | 102 | 122 |
| Min, Max | 18.9, 94.0 | 38.1, 128 | 39.4, 146 | 63.1, 193 |
| 15 | | | | |
| n | 24 | 24 | 24 | 24 |
| Arithmetic Mean (SD) | 44.4 (16.6) | 76.4 (32.4) | 80.6 (25.0) | 99.3 (28.3) |
| CV | 37.4 | 42.5 | 31.1 | 28.5 |
| Geometric Mean (SD, natural log scale) | 40.7 (0.466) | 70.9 (0.391) | 76.4 (0.352) | 95.8 (0.278) |
| Geometric CV | 49.2 | 40.7 | 36.3 | 28.3 |
| Median | 43.6 | 73.1 | 83.9 | 98.2 |
| Min, Max | 13.5, 76.2 | 25.7, 193 | 25.2, 151 | 48.9, 194 |

Plasma concentrations that are below the limit of quantification (BLQ) are imputed to ½ LQ, unless the pharmacokineticist indicated them as outliers, in which case they may be assigned missing values. Summary statistic values less than LQ are reported as "BLQ".

FIG. 41

| Time point (hour) | TRM-201 12.5 mg (N=24) | TRM-201 17.5 mg (N=24) | TRM-201 20 mg (N=24) | TRM-201 25 mg (N=24) |
|---|---|---|---|---|
| 18 | | | | |
| n | 24 | 24 | 24 | 24 |
| Arithmetic Mean (SD) | 38.3 (14.9) | 64.7 (24.9) | 73.4 (27.2) | 87.1 (26.3) |
| CV | 39.0 | 38.5 | 37.1 | 30.2 |
| Geometric Mean (SD, natural log scale) | 34.6 (0.512) | 59.8 (0.425) | 68.0 (0.424) | 83.1 (0.328) |
| Geometric CV | 54.7 | 44.5 | 44.3 | 33.7 |
| Median | 39.4 | 61.4 | 75.4 | 88.3 |
| Min, Max | 9.27, 72.3 | 17.6, 126 | 19.5, 154 | 38.1, 163 |
| 21 | | | | |
| n | 24 | 24 | 24 | 24 |
| Arithmetic Mean (SD) | 32.8 (13.6) | 54.5 (19.7) | 60.7 (21.2) | 75.7 (24.3) |
| CV | 41.6 | 36.2 | 34.9 | 32.1 |
| Geometric Mean (SD, natural log scale) | 28.9 (0.589) | 50.7 (0.416) | 55.8 (0.468) | 71.5 (0.365) |
| Geometric CV | 64.4 | 43.5 | 49.5 | 37.8 |
| Median | 33.8 | 55.0 | 64.1 | 73.6 |
| Min, Max | 6.52, 54.1 | 14.6, 101 | 14.0, 90.6 | 29.7, 117 |
| 24 | | | | |
| n | 24 | 24 | 24 | 24 |
| Arithmetic Mean (SD) | 32.1 (15.5) | 54.8 (25.2) | 63.5 (28.2) | 78.7 (28.4) |
| CV | 48.2 | 46.0 | 44.4 | 36.1 |
| Geometric Mean (SD, natural log scale) | 27.4 (0.651) | 48.9 (0.512) | 56.0 (0.572) | 73.4 (0.401) |
| Geometric CV | 72.6 | 54.7 | 62.2 | 41.7 |
| Median | 32.2 | 51.8 | 63.5 | 74.0 |
| Min, Max | 5.24, 73.0 | 12.6, 113 | 10.0, 138 | 27.5, 150 |

Plasma concentrations that are below the limit of quantification (BLQ) are imputed to ½ LQ, unless the pharmacokineticist indicated them as outliers, in which case they may be assigned missing values. Summary statistic values less than LQ are reported as "BLQ".

FIG. 42

| Time point (hour) | TRM-201 12.5 mg (N=24) | TRM-201 17.5 mg (N=24) | TRM-201 20 mg (N=24) | TRM-201 25 mg (N=24) |
|---|---|---|---|---|
| 27 | | | | |
| n | 24 | 24 | 24 | 24 |
| Arithmetic Mean (SD) | 23.0 (11.3) | 39.4 (15.9) | 42.8 (18.8) | 53.0 (20.4) |
| CV | 49.2 | | 43.9 | 38.5 |
| Geometric Mean (SD, natural log scale) | 19.4 (0.681) | 36.0 (0.471) | 38.2 (0.539) | 48.8 (0.438) |
| Geometric CV | 76.8 | 49.9 | 58.0 | 46.0 |
| Median | 22.1 | 38.4 | 41.3 | 51.1 |
| Min, Max | 3.14, 47.4 | 8.79, 80.5 | 7.08, 98.1 | 16.3, 94.5 |
| 30 | | | | |
| n | 24 | 24 | 24 | 24 |
| Arithmetic Mean (SD) | 20.9 (11.9) | 33.7 (13.7) | 36.5 (14.9) | 45.7 (18.7) |
| CV | 56.8 | 40.8 | 40.8 | 41.0 |
| Geometric Mean (SD, natural log scale) | 16.7 (0.808) | 30.5 (0.503) | 32.6 (0.560) | 41.5 (0.480) |
| Geometric CV | 95.9 | 53.6 | 60.7 | 50.9 |
| Median | 20.0 | 32.9 | 35.2 | 42.8 |
| Min, Max | 1.85, 55.8 | 7.20, 61.1 | 5.47, 68.8 | 11.7, 86.9 |
| 33 | | | | |
| n | 24 | 24 | 24 | 24 |
| Arithmetic Mean (SD) | 17.5 (9.89) | 31.0 (19.7) | 32.7 (19.4) | 40.7 (20.2) |
| CV | 56.4 | 63.4 | 59.4 | 49.6 |
| Geometric Mean (SD, natural log scale) | 13.6 (0.881) | 25.9 (0.642) | 27.6 (0.645) | 35.2 (0.598) |
| Geometric CV | 108.4 | 71.4 | 71.8 | 65.6 |
| Median | 15.8 | 28.1 | 31.8 | 36.6 |
| Min, Max | 1.26, 39.7 | 5.47, 101 | 4.11, 106 | 8.38, 79.2 |

Plasma concentrations that are below the limit of quantification (BLQ) are imputed to ½ LQ, unless the pharmacokineticist indicated them as outliers, in which case they may be assigned missing values. Summary statistic values less than LQ are reported as "BLQ".

FIG. 43

| Time point (hour) | TRM-201 12.5 mg (N=24) | TRM-201 17.5 mg (N=24) | TRM-201 20 mg (N=24) | TRM-201 25 mg (N=24) |
|---|---|---|---|---|
| 36 | | | | |
| n | 24 | 24 | 24 | 24 |
| Arithmetic Mean (SD) | 13.1 (7.35) | 21.8 (9.45) | 24.7 (12.0) | 31.1 (15.1) |
| CV | 56.2 | 43.3 | 48.8 | 48.4 |
| Geometric Mean (SD, natural log scale) | 9.99 (0.932) | 19.2 (0.572) | 21.0 (0.670) | 27.2 (0.572) |
| Geometric CV | 117.5 | 62.3 | 75.3 | 62.2 |
| Median | 12.8 | 21.2 | 23.9 | 29.1 |
| Min, Max | 0.675, 28.0 | 3.59, 39.1 | 3.01, 53.2 | 7.62, 67.7 |
| 39 | | | | |
| n | 24 | 24 | 24 | 24 |
| Arithmetic Mean (SD) | 11.8 (8.09) | 19.8 (11.9) | 21.6 (12.9) | 25.9 (13.2) |
| CV | 68.3 | 60.2 | 59.6 | 51.0 |
| Geometric Mean (SD, natural log scale) | 8.31 (1.10) | 16.2 (0.703) | 17.6 (0.739) | 22.1 (0.642) |
| Geometric CV | 152.4 | 80.0 | 85.2 | 71.4 |
| Median | 10.1 | 17.2 | 18.6 | 23.9 |
| Min, Max | BLQ, 36.2 | 2.80, 53.0 | 2.04, 61.4 | 4.15, 52.9 |
| 42 | | | | |
| n | 24 | 24 | 24 | 24 |
| Arithmetic Mean (SD) | 11.3 (7.48) | 18.3 (9.88) | 21.2 (13.6) | 26.3 (14.8) |
| CV | 66.0 | 54.1 | 64.3 | 56.4 |
| Geometric Mean (SD, natural log scale) | 7.93 (1.11) | 15.3 (0.680) | 16.5 (0.841) | 21.2 (0.759) |
| Geometric CV | 155.6 | 76.7 | 101.4 | 88.2 |
| Median | 10.2 | 16.4 | 19.1 | 22.8 |
| Min, Max | BLQ, 30.4 | 2.45, 43.1 | 1.49, 63.1 | 3.80, 61.6 |

Plasma concentrations that are below the limit of quantification (BLQ) are imputed to ½ LQ, unless the pharmacokineticist indicated them as outliers, in which case they may be assigned missing values. Summary statistic values less than LQ are reported as "BLQ".

FIG. 44

| Time point (hour) | TRM-201 12.5 mg (N=24) | TRM-201 17.5 mg (N=24) | TRM-201 20 mg (N=24) | TRM-201 25 mg (N=24) |
|---|---|---|---|---|
| 48 | | | | |
| n | 24 | 24 | 24 | 24 |
| Arithmetic Mean (SD) | 10.2 (7.63) | 17.6 (11.2) | 19.3 (12.8) | 24.1 (15.5) |
| CV | 74.5 | 63.7 | 66.4 | 64.2 |
| Geometric Mean (SD, natural log scale) | 6.24 (1.36) | 13.6 (0.848) | 14.4 (0.935) | 18.5 (0.853) |
| Geometric CV | 231.9 | 102.6 | 118.2 | 103.4 |
| Median | 8.77 | 14.8 | 16.7 | 19.7 |
| Min, Max | BLQ, 30.0 | 1.15, 40.7 | 0.951, 51.4 | 1.98, 58.6 |
| 52 | | | | |
| n | 24 | 24 | 24 | 24 |
| Arithmetic Mean (SD) | 6.85 (5.63) | 11.0 (7.10) | 13.6 (11.3) | 15.4 (10.4) |
| CV | 82.2 | 64.8 | 83.3 | 67.9 |
| Geometric Mean (SD, natural log scale) | 4.22 (1.25) | 8.45 (0.835) | 9.47 (1.01) | 11.3 (0.939) |
| Geometric CV | 195.7 | 100.4 | 134.0 | 119.0 |
| Median | 5.67 | 10.2 | 11.4 | 13.7 |
| Min, Max | BLQ, 20.2 | 0.944, 27.9 | 0.570, 55.4 | 1.03, 38.5 |
| 60 | | | | |
| n | 24 | 24 | 24 | 24 |
| Arithmetic Mean (SD) | 3.51 (2.80) | 6.13 (5.13) | 6.67 (5.10) | 8.25 (5.82) |
| CV | 79.8 | 83.6 | 76.4 | 70.6 |
| Geometric Mean (SD, natural log scale) | 2.32 (1.07) | 4.10 (1.10) | 4.56 (1.09) | 5.43 (1.20) |
| Geometric CV | 147.4 | 152.3 | 150.1 | 178.6 |
| Median | 2.69 | 5.86 | 5.06 | 7.24 |
| Min, Max | BLQ, 10.2 | BLQ, 24.3 | BLQ, 20.1 | BLQ, 20.0 |

Plasma concentrations that are below the limit of quantification (BLQ) are imputed to ½ LQ, unless the pharmacokineticist indicated them as outliers, in which case they may be assigned missing values. Summary statistic values less than LQ are reported as "BLQ".

FIG. 45

| Time point (hour) | TRM-201 12.5 mg (N=24) | TRM-201 17.5 mg (N=24) | TRM-201 20 mg (N=24) | TRM-201 25 mg (N=24) |
|---|---|---|---|---|
| 72 | | | | |
| n | 24 | 24 | 24 | 24 |
| Arithmetic Mean (SD) | 2.67 (2.48) | 4.69 (4.33) | 5.34 (5.15) | 6.96 (6.44) |
| CV | 92.6 | 92.5 | 96.5 | 92.6 |
| Geometric Mean (SD, natural log scale) | 1.68 (1.06) | 2.79 (1.20) | 3.22 (1.15) | 4.03 (1.29) |
| Geometric CV | 144.6 | 178.3 | 167.0 | 207.4 |
| Median | 1.70 | 3.36 | 3.81 | 4.98 |
| Min, Max | BLQ, 9.47 | BLQ, 14.9 | BLQ, 18.7 | BLQ, 26.4 |
| 96 | | | | |
| n | 24 | 24 | 24 | 24 |
| Arithmetic Mean (SD) | 0.695 (0.728) | 1.12 (1.24) | 1.41 (1.87) | 1.73 (2.04) |
| CV | 104.7 | 111.0 | 133.4 | 118.0 |
| Geometric Mean (SD, natural log scale) | BLQ (0.864) | 0.658 (1.03) | 0.763 (1.09) | 0.991 (1.08) |
| Geometric CV | 105.4 | 138.2 | 150.3 | 148.7 |
| Median | BLQ | 0.601 | 0.704 | 0.964 |
| Min, Max | BLQ, 2.71 | BLQ, 4.66 | BLQ, 8.26 | BLQ, 8.91 |
| 120 | | | | |
| n | 24 | 24 | 24 | 24 |
| Arithmetic Mean (SD) | BLQ (0.171) | BLQ (0.399) | BLQ (0.549) | 0.588 (0.650) |
| CV | 55.1 | 98.0 | 115.8 | 110.5 |
| Geometric Mean (SD, natural log scale) | BLQ (0.363) | BLQ (0.571) | BLQ (0.682) | BLQ (0.795) |
| Geometric CV | 37.5 | 62.0 | 77.0 | 93.9 |
| Median | BLQ | BLQ | BLQ | BLQ |
| Min, Max | BLQ, 0.918 | BLQ, 2.01 | BLQ, 2.47 | BLQ, 2.56 |

Plasma concentrations that are below the limit of quantification (BLQ) are imputed to ½ LQ, unless the pharmacokineticist indicated them as outliers, in which case they may be assigned missing values. Summary statistic values less than LQ are reported as "BLQ".

FIG. 46

| Parameter | TRM-201 12.5 mg (N=24) | TRM-201 17.5 mg (N=24) | TRM-201 20 mg (N=24) | TRM-201 25 mg (N=76) |
|---|---|---|---|---|
| $AUC_{0-\infty}$ (ng.hr/mL) | | | | |
| n | 24 | 24 | 24 | 76 |
| Arithmetic Mean (SD) | 2010 (691) | 3290 (1100) | 3750 (1170) | 4810 (1500) |
| CV | 34.3 | 33.4 | 31.3 | 31.3 |
| Geometric Mean (SD, natural log scale) | 1880 (0.415) | 3110 (0.347) | 3550 (0.362) | 4590 (0.305) |
| Geometric CV | 43.3 | 35.8 | 37.4 | 31.2 |
| Median | 2010 | 3170 | 3700 | 4680 |
| Min, Max | 661, 3550 | 1210, 5930 | 1170, 6460 | 2400, 10000 |
| 90% CI | 1620, 2170 | 2760, 3510 | 3120, 4030 | 4330, 4870 |
| | | | | |
| Model based: | | | | |
| Geometric Mean | 1910 | 3170 | 3610 | 4600 |
| TRM-201/Historical GMR | 0.504 | 0.835 | 0.951 | 1.21 |
| 90% CI of TRM-201/Historical GMR | 0.467, 0.543 | 0.773, 0.901 | 0.882, 1.03 | 1.14, 1.29 |
| | | | | |
| $C_{max}$ (ng/mL) | | | | |
| n | 24 | 24 | 24 | 76 |
| Arithmetic Mean (SD) | 151 (50.0) | 236 (80.6) | 277 (107) | 336 (91.3) |
| CV | 33.0 | 34.1 | 38.8 | 27.1 |
| Geometric Mean (SD, natural log scale) | 144 (0.333) | 224 (0.329) | 259 (0.369) | 325 (0.260) |
| Geometric CV | 34.2 | 33.8 | 38.2 | 26.4 |
| Median | 142 | 230 | 255 | 332 |
| Min, Max | 75.3, 253 | 129, 473 | 132, 552 | 188, 600 |
| 90% CI | 128, 161 | 200, 251 | 228, 295 | 309, 342 |
| | | | | |
| Model based: | | | | |
| Geometric Mean | 141 | 220 | 254 | 326 |
| TRM-201/Historical GMR | 0.650 | 1.01 | 1.17 | 1.50 |
| 90% CI of TRM-201/Historical GMR | 0.597, 0.708 | 0.930, 1.10 | 1.08, 1.28 | 1.43, 1.59 |

101 = TRM-201-PK-101; 102 = TRM-201-PK-102
GMR = geometric mean ratio
Model based statistics are calculated via an MMRM model with covariates of weight, gender, and race/ethnicity.
Historical geometric means of $AUC_{0-\infty}$ and $C_{max}$ are 3799 ng.hr/mL and 217 ng/mL respectively.

FIG. 47

| Parameter | TRM-201 12.5 mg (N=24) | TRM-201 17.5 mg (N=24) | TRM-201 20 mg (N=24) | TRM-201 25 mg (N=24) |
|---|---|---|---|---|
| $AUC_{0-\infty}$ (ng.hr/mL) | | | | |
| n | 24 | 24 | 24 | 24 |
| Arithmetic Mean (SD) | 2010 (691) | 3290 (1100) | 3750 (1170) | 4630 (1130) |
| CV | 34.3 | 33.4 | 31.3 | 24.4 |
| Geometric Mean (SD, natural log scale) | 1880 (0.415) | 3110 (0.347) | 3550 (0.362) | 4490 (0.257) |
| Geometric CV | 43.3 | 35.8 | 37.4 | 26.1 |
| Median | 2010 | 3170 | 3700 | 4680 |
| Min, Max | 661, 3550 | 1210, 5930 | 1170, 6460 | 2740, 7110 |
| 90% CI | 1620, 2170 | 2760, 3510 | 3120, 4030 | 4110, 4910 |
| Model 1 based : | | | | |
| Geometric Mean | 1800 | 2990 | 3410 | 4310 |
| TRM-201/Historical GMR | 0.475 | 0.787 | 0.897 | 1.14 |
| 90% CI of TRM-201/Historical GMR | 0.421, 0.535 | 0.698, 0.887 | 0.795, 1.01 | 1.01, 1.28 |
| Model 2 based : | | | | |
| Geometric Mean | 1880 | 3110 | 3550 | 4490 |
| TRM-201/Historical GMR | 0.494 | 0.819 | 0.934 | 1.18 |
| 90% CI of TRM-201/Historical GMR | 0.438, 0.558 | 0.725, 0.925 | 0.827, 1.05 | 1.05, 1.34 |

GMR = geometric mean ratio
Model 1: MMRM model with covariates of weight, gender, and race/ethnicity.
Model 2: MMRM model with covariate of period.
Historical geometric means of $AUC_{0-\infty}$ and $C_{max}$ are 3799 ng.hr/mL and 217 ng/mL respectively.

FIG. 48

| Parameter | TRM-201 12.5 mg (N=24) | TRM-201 17.5 mg (N=24) | TRM-201 20 mg (N=24) | TRM-201 25 mg (N=24) |
|---|---|---|---|---|
| $C_{max}$ (ng/mL) | | | | |
| n | 24 | 24 | 24 | 24 |
| Arithmetic Mean (SD) | 151 (50.0) | 236 (80.6) | 277 (107) | 349 (79.5) |
| CV | 33.0 | 34.1 | 38.8 | 22.8 |
| Geometric Mean (SD, natural log scale) | 144 (0.333) | 224 (0.329) | 259 (0.369) | 341 (0.216) |
| Geometric CV | 34.2 | 33.8 | 38.2 | 21.9 |
| Median | 142 | 230 | 255 | 342 |
| Min, Max | 75.3, 253 | 129, 473 | 132, 552 | 224, 600 |
| 90% CI | 128, 161 | 200, 251 | 228, 295 | 316, 368 |
| Model 1 based: | | | | |
| Geometric Mean | 143 | 223 | 258 | 339 |
| TRM-201/Historical GMR | 0.658 | 1.03 | 1.19 | 1.56 |
| 90% CI of TRM-201/Historical GMR | 0.591, 0.732 | 0.922, 1.14 | 1.07, 1.32 | 1.40, 1.74 |
| Model 2 based: | | | | |
| Geometric Mean | 144 | 224 | 259 | 341 |
| TRM-201/Historical GMR | 0.662 | 1.03 | 1.19 | 1.57 |
| 90% CI of TRM-201/Historical GMR | 0.594, 0.738 | 0.926, 1.15 | 1.07, 1.33 | 1.41, 1.75 |

GMR = geometric mean ratio
Model 1: MMRM model with covariates of weight, gender, and race/ethnicity.
Model 2: MMRM model with covariate of period.
Historical geometric means of $AUC_{0-\infty}$ and $C_{max}$ are 3799 ng.hr/mL and 217 ng/mL respectively.

FIG. 49

| Treatment Dose | Parameter | Male (N=11) | Female (N=13) |
|---|---|---|---|
| 12.5 mg | $AUC_{0-\infty}$ (ng.hr/mL) | | |
| | n | 11 | 13 |
| | Arithmetic Mean (SD) | 1750 (716) | 2240 (604) |
| | CV | 41.0 | 27.0 |
| | Geometric Mean (SD, natural log scale) | 1580 (0.502) | 2170 (0.264) |
| | Geometric CV | 53.5 | 26.9 |
| | Median | 1940 | 2180 |
| | Min, Max | 661, 2850 | 1360, 3550 |
| | 90% CI | 1200, 2080 | 1910, 2470 |
| | $C_{max}$ (ng/mL) | | |
| | n | 11 | 13 |
| | Arithmetic Mean (SD) | 132 (39.3) | 168 (53.5) |
| | CV | 29.7 | 31.9 |
| | Geometric Mean (SD, natural log scale) | 127 (0.306) | 160 (0.327) |
| | Geometric CV | 31.3 | 33.6 |
| | Median | 122 | 150 |
| | Min, Max | 75.3, 207 | 82.3, 253 |
| | 90% CI | 107, 150 | 136, 188 |

FIG. 50

| Treatment Dose | Parameter | Male (N=11) | Female (N=13) |
|---|---|---|---|
| 17.5 mg | $AUC_{0-\infty}$ (ng.hr/mL) | | |
| | n | 11 | 13 |
| | Arithmetic Mean (SD) | 2860 (890) | 3650 (1160) |
| | CV | 31.1 | 31.7 |
| | Geometric Mean (SD, natural log scale) | 2710 (0.357) | 3490 (0.306) |
| | Geometric CV | 36.8 | 31.3 |
| | Median | 2960 | 3180 |
| | Min, Max | 1210, 4170 | 2080, 5930 |
| | 90% CI | 2230, 3300 | 3000, 4060 |
| | $C_{max}$ (ng/mL) | | |
| | n | 11 | 13 |
| | Arithmetic Mean (SD) | 201 (48.9) | 266 (91.6) |
| | CV | 24.3 | 34.5 |
| | Geometric Mean (SD, natural log scale) | 196 (0.255) | 251 (0.349) |
| | Geometric CV | 26.0 | 36.0 |
| | Median | 208 | 279 |
| | Min, Max | 129, 279 | 137, 473 |
| | 90% CI | 170, 225 | 212, 299 |

FIG. 51

| Treatment Dose | Parameter | Male (N=11) | Female (N=13) |
|---|---|---|---|
| 20 mg | $AUC_{0-\infty}$ (ng.hr/mL) | | |
| | n | 11 | 13 |
| | Arithmetic Mean (SD) | 3130 (1060) | 4270 (1030) |
| | CV | 33.9 | 24.1 |
| | Geometric Mean (SD, natural log scale) | 2940 (0.404) | 4160 (0.235) |
| | Geometric CV | 42.1 | 23.9 |
| | Median | 3220 | 3870 |
| | Min, Max | 1170, 4580 | 2810, 6460 |
| | 90% CI | 2360, 3660 | 3700, 4670 |
| | $C_{max}$ (ng/mL) | | |
| | n | 11 | 13 |
| | Arithmetic Mean (SD) | 234 (68.6) | 314 (123) |
| | CV | 29.4 | 39.1 |
| | Geometric Mean (SD, natural log scale) | 224 (0.310) | 293 (0.381) |
| | Geometric CV | 31.7 | 39.5 |
| | Median | 222 | 275 |
| | Min, Max | 132, 332 | 180, 552 |
| | 90% CI | 189, 265 | 243, 354 |

FIG. 52

| Treatment Dose | Parameter | Male (N=11) | Female (N=13) |
|---|---|---|---|
| 25 mg | $AUC_{0-\infty}$ (ng.hr/mL) | | |
| | n | 11 | 13 |
| | Arithmetic Mean (SD) | 4080 (1140) | 5090 (928) |
| | CV | 27.9 | 18.2 |
| | Geometric Mean (SD, natural log scale) | 3940 (0.280) | 5020 (0.179) |
| | Geometric CV | 28.6 | 18.0 |
| | Median | 4090 | 5130 |
| | Min, Max | 2740, 5860 | 3750, 7110 |
| | 90% CI | 3380, 4590 | 4600, 5480 |
| | $C_{max}$ (ng/mL) | | |
| | n | 11 | 13 |
| | Arithmetic Mean (SD) | 302 (47.6) | 388 (80.6) |
| | CV | 15.8 | 20.8 |
| | Geometric Mean (SD, natural log scale) | 298 (0.164) | 382 (0.193) |
| | Geometric CV | 16.5 | 19.5 |
| | Median | 301 | 375 |
| | Min, Max | 224, 362 | 280, 600 |
| | 90% CI | 273, 326 | 347, 420 |

FIG. 53

| Treatment Dose | Parameter | 18-40 Years (N=8) | 41-52 Years (N=8) | 53-60 Years (N=8) |
|---|---|---|---|---|
| 12.5 mg | $AUC_{0-\infty}$ (ng.hr/mL) | | | |
| | n | 8 | 8 | 8 |
| | Arithmetic Mean (SD) | 1680 (568) | 2090 (930) | 2270 (411) |
| | CV | 33.8 | 44.4 | 18.1 |
| | Geometric Mean (SD, natural log scale) | 1570 (0.423) | 1880 (0.531) | 2240 (0.178) |
| | Geometric CV | 44.2 | 57.0 | 18.0 |
| | Median | 1870 | 2090 | 2140 |
| | Min, Max | 703, 2230 | 661, 3550 | 1800, 2850 |
| | 90% CI | 1180, 2080 | 1320, 2680 | 1990, 2530 |
| | $C_{max}$ (ng/mL) | | | |
| | n | 8 | 8 | 8 |
| | Arithmetic Mean (SD) | 164 (51.8) | 140 (51.3) | 150 (50.4) |
| | CV | 31.6 | 36.7 | 33.6 |
| | Geometric Mean (SD, natural log scale) | 156 (0.347) | 133 (0.338) | 143 (0.338) |
| | Geometric CV | 35.8 | 34.8 | 34.8 |
| | Median | 165 | 128 | 142 |
| | Min, Max | 80.1, 245 | 75.3, 253 | 82.3, 235 |
| | 90% CI | 124, 197 | 106, 167 | 114, 179 |

FIG. 54

| Treatment Dose | Parameter | 18-40 Years (N=8) | 41-52 Years (N=8) | 53-60 Years (N=8) |
|---|---|---|---|---|
| 17.5 mg | $AUC_{0-\infty}$ (ng.hr/mL) | | | |
| | n | 8 | 8 | 8 |
| | Arithmetic Mean (SD) | 2820 (705) | 3520 (1650) | 3510 (615) |
| | CV | 25.0 | 46.8 | 17.5 |
| | Geometric Mean (SD, natural log scale) | 2750 (0.253) | 3160 (0.519) | 3470 (0.178) |
| | Geometric CV | 25.7 | 55.6 | 18.0 |
| | Median | 2960 | 3200 | 3480 |
| | Min, Max | 1940, 4030 | 1210, 5930 | 2630, 4290 |
| | 90% CI | 2320, 3250 | 2230, 4480 | 3080, 3910 |
| | $C_{max}$ (ng/mL) | | | |
| | n | 8 | 8 | 8 |
| | Arithmetic Mean (SD) | 237 (64.7) | 232 (112) | 239 (67.7) |
| | CV | 27.3 | 48.3 | 28.3 |
| | Geometric Mean (SD, natural log scale) | 229 (0.293) | 213 (0.416) | 230 (0.305) |
| | Geometric CV | 30.0 | 43.5 | 31.2 |
| | Median | 230 | 176 | 244 |
| | Min, Max | 137, 311 | 134, 473 | 129, 357 |
| | 90% CI | 188, 278 | 162, 282 | 188, 282 |

FIG. 55

| Treatment Dose | Parameter | 18-40 Years (N=8) | 41-52 Years (N=8) | 53-60 Years (N=8) |
|---|---|---|---|---|
| 20 mg | $AUC_{0-\infty}$ (ng.hr/mL) | | | |
| | n | 8 | 8 | 8 |
| | Arithmetic Mean (SD) | 3580 (1100) | 3730 (1640) | 3940 (734) |
| | CV | 30.7 | 44.1 | 18.6 |
| | Geometric Mean (SD, natural log scale) | 3420 (0.329) | 3360 (0.522) | 3880 (0.188) |
| | Geometric CV | 33.8 | 56.0 | 19.0 |
| | Median | 3770 | 3500 | 3800 |
| | Min, Max | 1990, 5450 | 1170, 6460 | 2930, 4930 |
| | 90% CI | 2750, 4270 | 2370, 4770 | 3420, 4400 |
| | $C_{max}$ (ng/mL) | | | |
| | n | 8 | 8 | 8 |
| | Arithmetic Mean (SD) | 308 (111) | 262 (127) | 260 (88.6) |
| | CV | 36.1 | 48.4 | 34.0 |
| | Geometric Mean (SD, natural log scale) | 289 (0.395) | 242 (0.412) | 249 (0.316) |
| | Geometric CV | 41.1 | 43.1 | 32.4 |
| | Median | 299 | 229 | 220 |
| | Min, Max | 147, 481 | 132, 552 | 178, 431 |
| | 90% CI | 222, 377 | 184, 319 | 201, 307 |

FIG. 56

| Treatment Dose | Parameter | 18-40 Years (N=8) | 41-52 Years (N=8) | 53-60 Years (N=8) |
|---|---|---|---|---|
| 25 mg | $AUC_{0-\infty}$ (ng·hr/mL) | | | |
| | n | 8 | 8 | 8 |
| | Arithmetic Mean (SD) | 4140 (873) | 4810 (1540) | 4940 (793) |
| | CV | 21.1 | 32.1 | 16.0 |
| | Geometric Mean (SD, natural log scale) | 4050 (0.228) | 4580 (0.338) | 4880 (0.174) |
| | Geometric CV | 23.1 | 34.8 | 17.5 |
| | Median | 4260 | 4800 | 5190 |
| | Min, Max | 2780, 5360 | 2740, 7110 | 3510, 5730 |
| | 90% CI | 3480, 4720 | 3650, 5750 | 4350, 5480 |
| | $C_{max}$ (ng/mL) | | | |
| | n | 8 | 8 | 8 |
| | Arithmetic Mean (SD) | 366 (105) | 326 (63.9) | 354 (69.3) |
| | CV | 28.5 | 19.6 | 19.6 |
| | Geometric Mean (SD, natural log scale) | 356 (0.248) | 321 (0.199) | 347 (0.215) |
| | Geometric CV | 25.2 | 20.1 | 21.7 |
| | Median | 340 | 336 | 358 |
| | Min, Max | 280, 600 | 242, 426 | 224, 444 |
| | 90% CI | 301, 420 | 281, 367 | 301, 401 |

FIG. 57

| Treatment Dose | Parameter | Black or African American (N=5) | White (N=19) |
|---|---|---|---|
| 12.5 mg | $AUC_{0-\infty}$ (ng·hr/mL) | | |
| | n | 5 | 19 |
| | Arithmetic Mean (SD) | 1660 (503) | 2110 (714) |
| | CV | 30.3 | 33.9 |
| | Geometric Mean (SD, natural log scale) | 1590 (0.335) | 1960 (0.430) |
| | Geometric CV | 34.5 | 45.1 |
| | Median | 1780 | 2110 |
| | Min, Max | 963, 2230 | 661, 3550 |
| | 90% CI | 1160, 2190 | 1650, 2330 |
| | $C_{max}$ (ng/mL) | | |
| | n | 5 | 19 |
| | Arithmetic Mean (SD) | 143 (24.3) | 153 (55.1) |
| | CV | 16.9 | 35.9 |
| | Geometric Mean (SD, natural log scale) | 142 (0.166) | 144 (0.368) |
| | Geometric CV | 16.7 | 38.1 |
| | Median | 133 | 146 |
| | Min, Max | 117, 179 | 75.3, 253 |
| | 90% CI | 121, 166 | 125, 167 |

FIG. 58

| Treatment Dose | Parameter | Black or African American (N=5) | White (N=19) |
|---|---|---|---|
| 17.5 mg | AUC$_{0-\infty}$ (ng.hr/mL) | | |
| | n | 5 | 19 |
| | Arithmetic Mean (SD) | 2840 (499) | 3400 (1190) |
| | CV | 17.6 | 34.9 |
| | Geometric Mean (SD, natural log scale) | 2800 (0.184) | 3200 (0.378) |
| | Geometric CV | 18.5 | 39.2 |
| | Median | 3160 | 3180 |
| | Min, Max | 2230, 3230 | 1210, 5930 |
| | 90% CI | 2350, 3340 | 2750, 3720 |
| | C$_{max}$ (ng/mL) | | |
| | n | 5 | 19 |
| | Arithmetic Mean (SD) | 217 (57.9) | 241 (86.2) |
| | CV | 26.7 | 35.7 |
| | Geometric Mean (SD, natural log scale) | 211 (0.254) | 228 (0.351) |
| | Geometric CV | 25.8 | 36.2 |
| | Median | 208 | 241 |
| | Min, Max | 167, 308 | 129, 473 |
| | 90% CI | 166, 269 | 198, 262 |

FIG. 59

| Treatment Dose | Parameter | Black or African American (N=5) | White (N=19) |
|---|---|---|---|
| 20 mg | $AUC_{0-\infty}$ (ng·hr/mL) | | |
| | n | 5 | 19 |
| | Arithmetic Mean (SD) | 3380 (811) | 3850 (1250) |
| | CV | 24.0 | 32.5 |
| | Geometric Mean (SD, natural log scale) | 3300 (0.256) | 3610 (0.389) |
| | Geometric CV | 26.0 | 40.4 |
| | Median | 3630 | 3730 |
| | Min, Max | 2300, 4260 | 1170, 6460 |
| | 90% CI | 2590, 4210 | 3100, 4220 |
| | $C_{max}$ (ng/mL) | | |
| | n | 5 | 19 |
| | Arithmetic Mean (SD) | 298 (45.8) | 271 (119) |
| | CV | 15.4 | 43.8 |
| | Geometric Mean (SD, natural log scale) | 295 (0.155) | 250 (0.403) |
| | Geometric CV | 15.6 | 42.0 |
| | Median | 292 | 220 |
| | Min, Max | 238, 361 | 132, 552 |
| | 90% CI | 254, 342 | 213, 294 |

FIG. 60

| Treatment Dose | Parameter | Black or African American (N=5) | White (N=19) |
|---|---|---|---|
| 25 mg | AUC$_{0-\infty}$ (ng.hr/mL) | | |
| | n | 5 | 19 |
| | Arithmetic Mean (SD) | 3990 (669) | 4800 (1180) |
| | CV | 16.7 | 24.6 |
| | Geometric Mean (SD, natural log scale) | 3940 (0.179) | 4650 (0.267) |
| | Geometric CV | 18.1 | 27.2 |
| | Median | 4140 | 4930 |
| | Min, Max | 2960, 4650 | 2740, 7110 |
| | 90% CI | 3320, 4680 | 4180, 5170 |
| | C$_{max}$ (ng/mL) | | |
| | n | 5 | 19 |
| | Arithmetic Mean (SD) | 340 (37.2) | 351 (88.0) |
| | CV | 10.9 | 25.1 |
| | Geometric Mean (SD, natural log scale) | 339 (0.112) | 341 (0.239) |
| | Geometric CV | 11.3 | 24.2 |
| | Median | 341 | 343 |
| | Min, Max | 284, 388 | 224, 600 |
| | 90% CI | 304, 377 | 310, 375 |

FIG. 61

| Treatment Dose | Parameter | 47-70 kg (N=8) | 70.1-77 kg (N=7) | 77.1-90 kg (N=9) |
|---|---|---|---|---|
| 12.5 mg | $AUC_{0-\infty}$ (ng.hr/mL) | | | |
| | n | 8 | 7 | 9 |
| | Arithmetic Mean (SD) | 1850 (738) | 2500 (660) | 1790 (531) |
| | CV | 39.9 | 26.5 | 29.7 |
| | Geometric Mean (SD, natural log scale) | 1690 (0.496) | 2420 (0.274) | 1690 (0.378) |
| | Geometric CV | 52.8 | 27.9 | 39.2 |
| | Median | 2000 | 2700 | 1940 |
| | Min, Max | 661, 3000 | 1560, 3550 | 703, 2470 |
| | 90% CI | 1210, 2350 | 1980, 2960 | 1340, 2140 |
| | $C_{max}$ (ng/mL) | | | |
| | n | 8 | 7 | 9 |
| | Arithmetic Mean (SD) | 175 (60.3) | 155 (52.2) | 127 (26.9) |
| | CV | 34.4 | 33.7 | 21.1 |
| | Geometric Mean (SD, natural log scale) | 165 (0.395) | 147 (0.351) | 125 (0.219) |
| | Geometric CV | 41.1 | 36.3 | 22.1 |
| | Median | 165 | 149 | 122 |
| | Min, Max | 75.3, 253 | 82.3, 235 | 80.1, 179 |
| | 90% CI | 126, 215 | 114, 191 | 109, 143 |

FIG. 62

| Treatment Dose | Parameter | 47-70 kg (N=8) | 70.1-77 kg (N=7) | 77.1-90 kg (N=9) |
|---|---|---|---|---|
| 17.5 mg | $AUC_{0-\infty}$ (ng·hr/mL) | | | |
| | n | 8 | 7 | 9 |
| | Arithmetic Mean (SD) | 3180 (1310) | 3890 (1180) | 2910 (642) |
| | CV | 41.3 | 30.4 | 22.1 |
| | Geometric Mean (SD, natural log scale) | 2930 (0.450) | 3730 (0.324) | 2850 (0.223) |
| | Geometric CV | 47.4 | 33.3 | 22.5 |
| | Median | 3100 | 4030 | 2960 |
| | Min, Max | 1210, 5720 | 2080, 5930 | 1940, 4110 |
| | 90% CI | 2170, 3970 | 2940, 4730 | 2480, 3270 |
| | $C_{max}$ (ng/mL) | | | |
| | n | 8 | 7 | 9 |
| | Arithmetic Mean (SD) | 261 (109) | 254 (67.6) | 200 (48.6) |
| | CV | 41.9 | 26.6 | 24.4 |
| | Geometric Mean (SD, natural log scale) | 242 (0.410) | 246 (0.299) | 194 (0.247) |
| | Geometric CV | 42.8 | 30.6 | 25.0 |
| | Median | 254 | 262 | 180 |
| | Min, Max | 134, 473 | 137, 357 | 129, 279 |
| | 90% CI | 184, 319 | 197, 306 | 167, 227 |

FIG. 63

| Treatment Dose | Parameter | 47-70 kg (N=8) | 70.1-77 kg (N=7) | 77.1-90 kg (N=9) |
|---|---|---|---|---|
| 20 mg | $AUC_{0-\infty}$ (ng.hr/mL) | | | |
| | n | 8 | 7 | 9 |
| | Arithmetic Mean (SD) | 3650 (1410) | 4500 (1060) | 3250 (765) |
| | CV | 38.6 | 23.6 | 23.5 |
| | Geometric Mean (SD, natural log scale) | 3340 (0.501) | 4400 (0.228) | 3170 (0.245) |
| | Geometric CV | 53.4 | 23.1 | 24.9 |
| | Median | 3770 | 4570 | 3220 |
| | Min, Max | 1170, 5450 | 3200, 6460 | 1990, 4580 |
| | 90% CI | 2390, 4660 | 3720, 5200 | 2720, 3690 |
| | $C_{max}$ (ng/mL) | | | |
| | n | 8 | 7 | 9 |
| | Arithmetic Mean (SD) | 336 (142) | 259 (88.5) | 238 (63.8) |
| | CV | 42.3 | 34.2 | 26.8 |
| | Geometric Mean (SD, natural log scale) | 307 (0.476) | 248 (0.310) | 231 (0.273) |
| | Geometric CV | 50.5 | 31.7 | 27.8 |
| | Median | 320 | 217 | 222 |
| | Min, Max | 132, 552 | 180, 431 | 147, 332 |
| | 90% CI | 223, 423 | 197, 311 | 195, 273 |

FIG. 64

| Treatment Dose | Parameter | 47-70 kg (N=8) | 70.1-77 kg (N=7) | 77.1-90 kg (N=9) |
|---|---|---|---|---|
| 25 mg | $AUC_{0-\infty}$ (ng.hr/mL) | | | |
| | n | 8 | 7 | 9 |
| | Arithmetic Mean (SD) | 4450 (1180) | 5470 (912) | 4130 (952) |
| | CV | 26.5 | 16.7 | 23.0 |
| | Geometric Mean (SD, natural log scale) | 4310 (0.285) | 5410 (0.166) | 4040 (0.231) |
| | Geometric CV | 29.1 | 16.7 | 23.5 |
| | Median | 4530 | 5480 | 4090 |
| | Min, Max | 2740, 6230 | 4160, 7110 | 2780, 5860 |
| | 90% CI | 3560, 5210 | 4790, 6110 | 3500, 4660 |
| | $C_{max}$ (ng/mL) | | | |
| | n | 8 | 7 | 9 |
| | Arithmetic Mean (SD) | 385 (99.4) | 371 (48.0) | 299 (56.7) |
| | CV | 25.8 | 12.9 | 19.0 |
| | Geometric Mean (SD, natural log scale) | 376 (0.233) | 368 (0.127) | 294 (0.189) |
| | Geometric CV | 23.6 | 12.8 | 19.1 |
| | Median | 340 | 354 | 287 |
| | Min, Max | 280, 600 | 310, 444 | 224, 388 |
| | 90% CI | 321, 439 | 336, 404 | 262, 331 |

FIG. 65

| Treatment Dose | Parameter | Hispanic or Latino (N=12) | Not Hispanic or Latino (N=12) |
|---|---|---|---|
| 12.5 mg | $AUC_{0-\infty}$ (ng.hr/mL) | | |
| | n | 12 | 12 |
| | Arithmetic Mean (SD) | 2210 (624) | 1820 (723) |
| | CV | 28.2 | 39.8 |
| | Geometric Mean (SD, natural log scale) | 2090 (0.398) | 1680 (0.419) |
| | Geometric CV | 41.5 | 43.8 |
| | Median | 2200 | 1860 |
| | Min, Max | 661, 3000 | 703, 3550 |
| | 90% CI | 1700, 2570 | 1360, 2090 |
| | $C_{max}$ (ng/mL) | | |
| | n | 12 | 12 |
| | Arithmetic Mean (SD) | 157 (59.1) | 146 (40.8) |
| | CV | 37.7 | 27.9 |
| | Geometric Mean (SD, natural log scale) | 146 (0.396) | 141 (0.272) |
| | Geometric CV | 41.2 | 27.7 |
| | Median | 148 | 135 |
| | Min, Max | 75.3, 253 | 80.1, 245 |
| | 90% CI | 119, 179 | 123, 163 |

FIG. 66

| Treatment Dose | Parameter | Hispanic or Latino (N=12) | Not Hispanic or Latino (N=12) |
|---|---|---|---|
| 17.5 mg | $AUC_{0-\infty}$ (ng.hr/mL) | | |
| | n | 12 | 12 |
| | Arithmetic Mean (SD) | 3520 (1100) | 3050 (1090) |
| | CV | 31.3 | 35.6 |
| | Geometric Mean (SD, natural log scale) | 3330 (0.382) | 2910 (0.311) |
| | Geometric CV | 39.6 | 31.8 |
| | Median | 3480 | 3000 |
| | Min, Max | 1210, 5720 | 1940, 5930 |
| | 90% CI | 2730, 4050 | 2480, 3420 |
| | $C_{max}$ (ng/mL) | | |
| | n | 12 | 12 |
| | Arithmetic Mean (SD) | 258 (94.5) | 214 (59.7) |
| | CV | 36.6 | 27.9 |
| | Geometric Mean (SD, natural log scale) | 243 (0.373) | 207 (0.271) |
| | Geometric CV | 38.6 | 27.6 |
| | Median | 254 | 194 |
| | Min, Max | 129, 473 | 137, 311 |
| | 90% CI | 200, 295 | 180, 238 |

FIG. 67

| Treatment Dose | Parameter | Hispanic or Latino (N=12) | Not Hispanic or Latino (N=12) |
|---|---|---|---|
| 20 mg | $AUC_{0-\infty}$ (ng.hr/mL) | | |
| | n | 12 | 12 |
| | Arithmetic Mean (SD) | 3840 (1100) | 3660 (1280) |
| | CV | 28.7 | 35.1 |
| | Geometric Mean (SD, natural log scale) | 3630 (0.399) | 3470 (0.338) |
| | Geometric CV | 41.5 | 34.8 |
| | Median | 3860 | 3580 |
| | Min, Max | 1170, 5140 | 1990, 6460 |
| | 90% CI | 2950, 4460 | 2910, 4130 |
| | $C_{max}$ (ng/mL) | | |
| | n | 12 | 12 |
| | Arithmetic Mean (SD) | 281 (128) | 272 (88.6) |
| | CV | 45.3 | 32.5 |
| | Geometric Mean (SD, natural log scale) | 258 (0.430) | 260 (0.315) |
| | Geometric CV | 45.1 | 32.3 |
| | Median | 218 | 274 |
| | Min, Max | 132, 552 | 147, 481 |
| | 90% CI | 206, 322 | 221, 307 |

FIG. 68

| Treatment Dose | Parameter | Hispanic or Latino (N=12) | Not Hispanic or Latino (N=12) |
|---|---|---|---|
| 25 mg | $AUC_{0-\infty}$ (ng.hr/mL) | | |
| | n | 12 | 12 |
| | Arithmetic Mean (SD) | 4980 (1020) | 4280 (1170) |
| | CV | 20.4 | 27.3 |
| | Geometric Mean (SD, natural log scale) | 4870 (0.238) | 4150 (0.260) |
| | Geometric CV | 24.1 | 26.4 |
| | Median | 5290 | 4150 |
| | Min, Max | 2740, 6230 | 2780, 7110 |
| | 90% CI | 4300, 5500 | 3620, 4740 |
| | $C_{max}$ (ng/mL) | | |
| | n | 12 | 12 |
| | Arithmetic Mean (SD) | 358 (70.0) | 340 (90.2) |
| | CV | 19.6 | 26.6 |
| | Geometric Mean (SD, natural log scale) | 351 (0.216) | 331 (0.222) |
| | Geometric CV | 21.9 | 22.5 |
| | Median | 358 | 324 |
| | Min, Max | 224, 444 | 253, 600 |
| | 90% CI | 313, 392 | 295, 372 |

FIG. 69

| Treatment Dose | Parameter | TRM-201 N | TRM-201 GM | Historical GM | TRM-201/Historical GMR | TRM-201/Historical 90% CI |
|---|---|---|---|---|---|---|
| 17.5 mg | $AUC_{0-\infty}$ (ng.hr/mL) | 24 | 3110 | 3799 | 0.819 | 0.725, 0.925 |
| | $C_{max}$ (ng/mL) | 24 | 224 | 217 | 1.03 | 0.920, 1.16 |
| | Age-adjusted $AUC_{0-\infty}$ (ng.hr/mL) | 24 | 3070 | 3799 | 0.807 | 0.788, 0.828 |
| | Age-adjusted $C_{max}$ (ng/mL) | 24 | 226 | 217 | 1.04 | 1.02, 1.07 |
| | Race/ethnicity-adjusted $AUC_{0-\infty}$ (ng.hr/mL) | 24 | 3090 | 3799 | 0.813 | 0.793, 0.833 |
| | Race/ethnicity-adjusted $C_{max}$ (ng/mL) | 24 | 222 | 217 | 1.02 | 0.999, 1.05 |
| | Weight-adjusted $AUC_{0-\infty}$ (ng.hr/mL) | 24 | 3120 | 3799 | 0.822 | 0.802, 0.842 |
| | Weight-adjusted $C_{max}$ (ng/mL) | 24 | 228 | 217 | 1.05 | 1.03, 1.07 |
| 20 mg | $AUC_{0-\infty}$ (ng.hr/mL) | 24 | 3550 | 3799 | 0.934 | 0.822, 1.06 |
| | $C_{max}$ (ng/mL) | 24 | 259 | 217 | 1.19 | 1.05, 1.36 |
| | Age-adjusted $AUC_{0-\infty}$ (ng.hr/mL) | 24 | 3540 | 3799 | 0.933 | 0.909, 0.958 |
| | Age-adjusted $C_{max}$ (ng/mL) | 24 | 266 | 217 | 1.23 | 1.20, 1.26 |
| | Race/ethnicity-adjusted $AUC_{0-\infty}$ (ng.hr/mL) | 24 | 3540 | 3799 | 0.931 | 0.907, 0.956 |
| | Race/ethnicity-adjusted $C_{max}$ (ng/mL) | 24 | 259 | 217 | 1.19 | 1.16, 1.23 |
| | Weight-adjusted $AUC_{0-\infty}$ (ng.hr/mL) | 24 | 3570 | 3799 | 0.940 | 0.917, 0.965 |
| | Weight-adjusted $C_{max}$ (ng/mL) | 24 | 265 | 217 | 1.22 | 1.19, 1.25 |

GM = geometric mean; GMR = geometric mean ratio
GMR is calculated on the natural-log-scale and back-transformed to the ratio scale.
Age-, Weight- and race/ethnicity- adjusted GMs match the mean age, weight and race distribution of the historical control data.
The mean age from historical data is 42 years, race/ethnicity proportions from historical data are 33% White, 44% Hispanic, and 23% Black, and the mean weight from historical data is 73.15 kg.

FIG. 70

| Parameter | TRM-201 12.5 mg (N=24) | TRM-201 17.5 mg (N=24) | TRM-201 20 mg (N=24) | TRM-201 25 mg (N=76) |
|---|---|---|---|---|
| $T_{max}$ (h) | | | | |
| n | 24 | 24 | 24 | 76 |
| Arithmetic Mean (SD) | 2.40 (1.20) | 2.71 (1.44) | 2.73 (1.88) | 3.02 (2.06) |
| CV | 50.0 | 53.3 | 68.9 | 68.1 |
| Median | 2.00 | 2.00 | 2.00 | 2.50 |
| Min, Max | 1.00, 5.00 | 1.00, 6.00 | 1.00, 9.00 | 0.750, 15.0 |
| 90% CI | 1.98, 2.81 | 2.20, 3.21 | 2.07, 3.39 | 2.63, 3.42 |
| $t_{1/2}$ (h) | | | | |
| n | 24 | 24 | 24 | 76 |
| Arithmetic Mean (SD) | 11.6 (2.94) | 11.8 (2.69) | 11.7 (2.61) | 11.6 (2.83) |
| CV | 25.3 | 22.8 | 22.3 | 24.3 |
| Harmonic Mean (Jack-knife SD) | 10.6 (4.55) | 11.1 (2.94) | 11.0 (3.10) | 11.3 (2.34) |
| Median | 12.0 | 11.7 | 12.2 | 11.6 |
| Min, Max | 4.15, 16.7 | 6.71, 17.1 | 6.32, 16.4 | 5.11, 24.7 |
| 90% CI | 9.23, 12.3 | 10.2, 12.3 | 10.1, 12.2 | 10.5, 11.6 |

90% CI for $T_{max}$ median via normal approximation.

90% CI for $t_{1/2}$ is computed on the inverse scale and back-transformed to the actual scale.

FIG. 71

| Parameter | TRM-201 12.5 mg (N=24) | TRM-201 17.5 mg (N=24) | TRM-201 20 mg (N=24) | TRM-201 25 mg (N=24) |
|---|---|---|---|---|
| CL/F (L/h) | | | | |
| n | 24 | 24 | 24 | 24 |
| Arithmetic Mean (SD) | 7.33 (3.90) | 5.98 2.37 | 6.06, (2.85) | 5.75 (1.56) |
| CV | 53.3 | 39.7 | 46.9 | 27.1 |
| Geometric Mean (SD, natural log scale) | 6.66 (0.415) | 5.62 (0.347) | 5.64 (0.362) | 5.57 (0.257) |
| Median | 6.23 | 5.52 | 5.40 | 5.35 |
| Min, Max | 3.52, 18.9 | 2.95, 14.4 | 3.10, 17.1 | 3.52, 9.13 |
| 90% CI | 5.76, 7.70 | 4.98, 6.35 | 4.97, 6.40 | 5.09, 6.09 |
| $V_d/F$ (L) | | | | |
| n | 24 | 24 | 24 | 24 |
| Arithmetic Mean (SD) | 110 (25.5) | 95.7 (23.3) | 96.1, (26.7) | 92.3 (16.9) |
| CV | 23.2 | 24.4 | 27.8 | 18.4 |
| Geometric Mean (SD, natural log scale) | 107 (0.217) | 93.1 (0.244) | 92.6 (0.276) | 90.8 (0.178) |
| Median | 106 | 94.6 | 90.5 | 88.1 |
| Min, Max | 72.3, 182 | 55.2, 157 | 51.0, 165 | 58.1, 140 |
| 90% CI | 99.4, 116 | 85.5, 101 | 84.1, 102 | 85.3, 96.7 |

90% CIs are computed on the natural-log-scale and back-transformed to the original measurement scale.

FIG. 72

| Parameter | Predicted Dose | Estimated Mean Parameter/Historical GMR (90% CI) |
|---|---|---|
| $AUC_{0-\infty}$ (ng.hr/mL) | 18.776 mg | 0.8190 (0.7997, 0.8388) |
| | 18.784 mg | 0.8195 (0.8002, 0.8392) |
| | 24.336 mg | 1.2029 (1.1581, 1.2494) |
| | 24.344 mg | 1.2036 (1.1587, 1.2502) |
| $C_{max}$ (ng/mL) | 15.256 mg | 0.8370 (0.7997, 0.8761) |
| | 15.264 mg | 0.8375 (0.8002, 0.8765) |
| | 20.526 mg | 1.2021 (1.1565, 1.2496) |
| | 20.534 mg | 1.2028 (1.1571, 1.2503) |

Predicted doses are calculated via a linear regression fit in the MMRM analysis of the log-transformed observations across the 12.5 to 25 mg range of doses in this study.

FIG. 73

|  | TRM 12.5 mg (N=24) | TRM 17.5 mg (N=24) | TRM 20 mg (N=24) | TRM 25 mg (N=24) |
|---|---|---|---|---|
| Subjects with at Least One | | | | |
| TEAE | 1 (4.2) | 0 | 0 | 2 (8.3) |
| Related TEAE | 0 | 0 | 0 | 0 |
| Serious TEAE | 0 | 0 | 0 | 0 |
| TEAE Leading to Study Discontinuation | 0 | 0 | 0 | 0 |
| Severe TEAE | 0 | 0 | 0 | 0 |

The investigator classifies a TEAE as a Related TEAE if there is a reasonable possibility of relationship to study drug. The AE follows a reasonable temporal sequence from study drug administration and cannot be reasonably explained by the subject's clinical state or other factors (e.g., disease under study, concurrent diseases, and concomitant medications).

FIG. 74

| System Organ Class<br>Preferred Term | TRM 12.5 mg<br>(N=24) | TRM 17.5 mg<br>(N=24) | TRM 20 mg<br>(N=24) | TRM 25 mg<br>(N=24) |
|---|---|---|---|---|
| Subjects with at Least One TEAE | 1 (4.2) | 0 | 0 | 2 (8.3) |
| Ear and labyrinth disorders | 0 | 0 | 0 | 1 (4.2) |
|   Ear discomfort | 0 | 0 | 0 | 1 (4.2) |
| Gastrointestinal disorders | 1 (4.2) | 0 | 0 | 0 |
|   Constipation | 1 (4.2) | 0 | 0 | 0 |
| Nervous system disorders | 0 | 0 | 0 | 1 (4.2) |
|   Headache | 0 | 0 | 0 | 1 (4.2) |

For each subject, multiple adverse events of the same system organ class and/or preferred term will be counted only once within each system organ class and preferred term. Adverse events are listed in descending order of frequency within system organ class and preferred term.

All adverse events are coded using MedDRA Version 22.0.

FIG. 75

| System Organ Class<br>Preferred Term | TRM 12.5 mg<br>(N=24) | TRM 17.5 mg<br>(N=24) | TRM 20 mg<br>(N=24) | TRM 25 mg<br>(N=24) |
|---|---|---|---|---|
| No Related Treatment -Emergent Adverse Events occurred. | | | | |

For each subject, multiple adverse events of the same system organ class and/or preferred term will be counted only once within each system organ class and preferred term. Adverse events are listed in descending order of frequency within system organ class and preferred term.

All adverse events are coded using MedDRA Version 22.0.

FIG. 76

| System Organ Class  Preferred Term | TRM 12.5 mg (N=24) | TRM 17.5 mg (N=24) | TRM 20 mg (N=24) | TRM 25 mg (N=24) |
|---|---|---|---|---|
| No Serious Treatment-Emergent Adverse Events occurred. | | | | |

For each subject, multiple adverse events of the same system organ class and/or preferred term will be counted only once within each system organ class and preferred term. Adverse events are listed in descending order of frequency within system organ class and preferred term.

All adverse events are coded using MedDRA Version 22.0.

FIG. 77

| System Organ Class  Preferred Term | TRM 12.5 mg (N=24) | TRM 17.5 mg (N=24) | TRM 20 mg (N=24) | TRM 25 mg (N=24) |
|---|---|---|---|---|
| No Treatment-Emergent Adverse Events Leading to Study Discontinuation occurred. | | | | |

For each subject, multiple adverse events of the same system organ class and/or preferred term will be counted only once within each system organ class and preferred term. Adverse events are listed in descending order of frequency within system organ class and preferred term.

All adverse events are coded using MedDRA Version 22.0.

FIG. 78

| System Organ Class Preferred Term | Severity | TRM-201 12.5 mg (N=24) | TRM-201 17.5 mg (N=24) | TRM-201 20 mg (N=24) | TRM-201 25 mg (N=24) |
|---|---|---|---|---|---|
| Subjects with at least one TEAE | Mild | 1 (4.2) | 0 | 0 | 2 (8.3) |
|  | Moderate | 0 | 0 | 0 | 0 |
|  | Severe | 0 | 0 | 0 | 0 |
| Ear and labyrinth disorders | Mild | 0 | 0 | 0 | 1 (4.2) |
|  | Moderate | 0 | 0 | 0 | 0 |
|  | Severe | 0 | 0 | 0 | 0 |
| Ear discomfort | Mild | 0 | 0 | 0 | 1 (4.2) |
|  | Moderate | 0 | 0 | 0 | 0 |
|  | Severe | 0 | 0 | 0 | 0 |
| Gastrointestinal disorders | Mild | 1 (4.2) | 0 | 0 | 0 |
|  | Moderate | 0 | 0 | 0 | 0 |
|  | Severe | 0 | 0 | 0 | 0 |

FIG. 79

| | | | | | |
|---|---|---|---|---|---|
| Constipation | Mild | 1 (4.2) | 0 | 0 | 0 |
| | Moderate | 0 | 0 | 0 | 0 |
| | Severe | 0 | 0 | 0 | 0 |
| Nervous system disorders | Mild | 0 | 0 | 0 | 1 (4.2) |
| | Moderate | 0 | 0 | 0 | 0 |
| | Severe | 0 | 0 | 0 | 0 |
| Headache | Mild | 0 | 0 | 0 | 1 (4.2) |
| | Moderate | 0 | 0 | 0 | 0 |
| | Severe | 0 | 0 | 0 | 0 |

For each subject, multiple adverse events of the same system organ class and/or preferred term will be counted only once within each system organ class and preferred term at the highest severity. Adverse events are listed in descending order of frequency within system organ class and preferred term.

All adverse events are coded using MedDRA Version 22.0.

DOSAGE FORMS OF ROFECOXIB AND RELATED METHODS

This application claims the benefit of and priority to U.S. Provisional Application No. 63/018,136 filed Apr. 30, 2020, and U.S. Provisional Application No. 62/934,898 filed Nov. 13, 2019, each of which is incorporated herein by reference.

All patents, patent applications and publications cited herein are hereby incorporated by reference in their entirety. The disclosures of these publications in their entireties are hereby incorporated by reference into this application.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Rofecoxib is a selective COX-2 inhibitor, nonsteroidal anti-inflammatory drug (NSAID), that was marketed under the brand name "VIOXX" until it was withdrawn from the market in at least 2004 over safety concerns. Before being withdrawn from the market, "VIOXX" was approved in the United States for the following indications: signs and symptoms of osteoarthritis (OA); signs and symptoms of rheumatoid arthritis (RA) in adults; signs and symptoms of pauciarticular or polyarticular course Juvenile Rheumatoid Arthritis; management of acute pain in adults; treatment of primary dysmenorrhea; and treatment of migraine attacks with or without aura in adults.

"VIOXX" was formulated in 12.5 mg, 25 mg, and 50 mg tablet dosage forms for oral administration. Rapid and complete absorption is important to the therapeutic efficacy of a drug. The bioavailability of solid oral dosages of drugs can be limited by poor dissolution into aqueous bodily fluids. The bioavailability of "VIOXX" was previously reported to be 93%, as provided in the FDA-approved label for the product. As rofecoxib, the active ingredient in "VIOXX", is a poorly water-soluble molecule, the reported 93% bioavailability was an exceptionally high value for an oral solid dosage form.

SUMMARY OF THE INVENTION

In certain aspects, the subject matter disclosed herein provides a solid dosage formulation comprising 17.5 mg of rofecoxib and a pharmaceutically acceptable carrier.

In some embodiments, the rofecoxib formulation reaches a median time to Cmax plasma concentration in 4 hours or less following a single administration of the formulation to human subjects less than 65 years of age. In some embodiments, the rofecoxib formulation reaches a median time to Cmax plasma concentration in 3.5 hours or less following a single administration of the formulation to human subjects less than 65 years of age. In some embodiments, the rofecoxib formulation reaches a median time to Cmax plasma concentration in 3 hours or less following a single administration of the formulation to human subjects less than 65 years of age. In some embodiments, the rofecoxib formulation reaches a median time to Cmax plasma concentration in 2.5 hours or less following a single administration of the formulation to human subjects less than 65 years of age.

In certain aspects, the subject matter disclosed herein provides a solid dosage formulation comprising 17.5 mg of rofecoxib and a pharmaceutically acceptable carrier, wherein the formulation achieves a mean Cmax plasma concentration of more than 100 ng/ml following a single administration of the formulation to human subjects less than 65 years of age.

In some embodiments, the rofecoxib formulation achieves a mean Cmax plasma concentration of more than 150 ng/ml, 167 ng/ml, or 190 ng/ml. In some embodiments, the rofecoxib formulation achieves a mean Cmax plasma concentration of more than 200 ng/ml. In some embodiments, the rofecoxib formulation achieves a mean Cmax plasma concentration of more than 220 ng/ml. In some embodiments, the rofecoxib formulation achieves a mean Cmax plasma concentration of more than 250 ng/ml.

In certain aspects, the subject matter disclosed herein provides a solid dosage formulation comprising 17.5 mg of rofecoxib and a pharmaceutically acceptable carrier, wherein the formulation achieves a mean $AUC_{0-\infty}$ of more than 1750 h*ng/ml following a single administration of the formulation to human subjects less than 65 years of age.

In some embodiments, the rofecoxib formulation achieves a mean $AUC_{0-\infty}$ of more than 2000 h*ng/ml following a single administration of the formulation to human subjects less than 65 years of age. In some embodiments, the rofecoxib formulation achieves a mean $AUC_{0-\infty}$ of more than 2500 h*ng/ml following a single administration of the formulation to human subjects less than 65 years of age. In some embodiments, the rofecoxib formulation achieves a mean $AUC_{0-\infty}$ of more than 3000 h*ng/ml following a single administration of the formulation to human subjects less than 65 years of age. In some embodiments, the rofecoxib formulation achieves a mean $AUC_{0-\infty}$ of more than 3100 h*ng/ml following a single administration of the formulation to human subjects less than 65 years of age. In some embodiments, the rofecoxib formulation achieves a mean $AUC_{0-\infty}$ of more than 3500 h*ng/ml following a single administration of the formulation to human subjects less than 65 years of age.

In some embodiments, the rofecoxib formulation further comprises a granular component and an extragranular component, wherein the granular component comprises an intragranular component comprising the rofecoxib and one or more disintegrants, and wherein the extragranular component comprises one or more disintegrants. In some embodiments, the rofecoxib in the formulation has a d90 particle size from about 10-12 μm, a d50 particle size from about 3-4 μm, and a d10 particle size from about 0.5-1.0 μm.

In certain aspects, the subject matter disclosed herein provides a solid dosage formulation comprising 20 mg of rofecoxib and a pharmaceutically acceptable carrier.

In some embodiments, the formulation reaches a median time to Cmax plasma concentration in 4 hours or less following a single administration of the formulation to human subjects less than 65 years of age. In some embodiments, the formulation reaches a median time to Cmax plasma concentration in 3 hours or less following administration. In some embodiments, the formulation reaches a mean Cmax plasma concentration in less than 3 hours following administration. In some embodiments, the formulation reaches a median time to Cmax plasma concentration in 2.5 hours or less following administration.

In certain aspects, the subject matter disclosed herein provides a solid dosage formulation comprising 20 mg of rofecoxib and a pharmaceutically acceptable carrier, wherein the formulation achieves a mean Cmax plasma concentration of more than 150 ng/ml following a single administration of the formulation to human subjects less than 65 years of age.

In some embodiments, the rofecoxib formulation achieves a mean Cmax plasma concentration of more than 191 ng/ml, 200 ng/ml, 215 ng/ml, or 225 ng/ml following a single administration of the formulation to human subjects less than 65 years of age. In some embodiments, the rofecoxib formulation achieves a mean Cmax plasma concentration of more than 250 ng/ml following a single administration of the formulation to human subjects less than 65 years of age. In some embodiments, the rofecoxib formulation achieves a mean Cmax plasma concentration of more than 258 ng/ml following a single administration of the formulation to human subjects less than 65 years of age. In some embodiments, the rofecoxib formulation achieves a mean Cmax plasma concentration of more than 300 ng/ml following a single administration of the formulation to human subjects less than 65 years of age.

In certain aspects, the subject matter disclosed herein provides a solid dosage formulation comprising 20 mg of rofecoxib and a pharmaceutically acceptable carrier, wherein the formulation achieves a mean $AUC_{0-\infty}$ of more than 2000 h*ng/ml following a single administration of the formulation to human subjects less than 65 years of age.

In some embodiments, the formulation achieves a mean $AUC_{0-\infty}$ of more than 2500 h*ng/ml following a single administration of the formulation to human subjects less than 65 years of age. In some embodiments, the formulation achieves a mean $AUC_{0-\infty}$ of more than 3000 h*ng/ml following a single administration of the formulation to human subjects less than 65 years of age. In some embodiments, the formulation achieves a mean $AUC_{0-\infty}$ of more than 3400 h*ng/ml following a single administration of the formulation to human subjects less than 65 years of age. In some embodiments, the formulation achieves a mean $AUC_{0-\infty}$ of more than 3500 h*ng/ml following a single administration of the formulation to human subjects less than 65 years of age. In some embodiments, the formulation achieves a mean $AUC_{0-\infty}$ of more than 3550 h*ng/ml following a single administration of the formulation to human subjects less than 65 years of age.

In some embodiments, the formulation further comprises a granular component and an extragranular component, wherein the granular component comprises an intragranular component comprising the rofecoxib and one or more disintegrants, and wherein the extragranular component comprises one or more disintegrants. In some embodiments, the rofecoxib in the formulation has a d90 particle size from about 10-12 µm, a d50 particle size from about 3-4 µm, and a d10 particle size from about 0.5-1.0 µm.

In certain aspects, the subject matter disclosed herein provides a method for treating pain, fever, or inflammation in a subject by administering a 25 mg solid dosage formulation of rofecoxib or a pharmaceutically acceptable salt thereof, wherein the formulation achieves a mean Cmax plasma concentration in less than 3 hours following a single administration of the formulation to human subjects less than 65 years of age.

In some embodiments, the rofecoxib formulation achieves a median time to Cmax plasma concentration in 2.5 hours or less following administration of the formulation to human subjects less than 65 years of age.

In certain aspects, the subject matter disclosed herein provides a method for treating pain, fever, or inflammation in a subject by administering a 25 mg solid dosage formulation of rofecoxib or a pharmaceutically acceptable salt thereof, wherein the formulation achieves a mean Cmax plasma concentration of more than 250 ng/ml following a single administration of the formulation to human subjects less than 65 years of age.

In some embodiments, the formulation achieves a mean Cmax plasma concentration of more than 300 ng/ml following administration of the formulation to human subjects less than 65 years of age. In some embodiments, the formulation achieves a mean Cmax plasma concentration of more than 320 ng/ml following administration of the formulation to human subjects less than 65 years of age. In some embodiments, the formulation achieves a mean Cmax plasma concentration of more than 350 ng/ml following administration of the formulation to human subjects less than 65 years of age.

In certain aspects, the subject matter disclosed herein provides a method for treating pain, fever, or inflammation in a subject by administering a 25 mg solid dosage formulation of rofecoxib or a pharmaceutically acceptable salt thereof, wherein the formulation achieves a mean $AUC_{0-\infty}$ of more than 4250 h*ng/ml following a single administration of the formulation to human subjects less than 65 years of age.

In some embodiments, the formulation achieves a mean $AUC_{0-\infty}$ of more than 4500 h*ng/ml following administration of the formulation to human subjects less than 65 years of age. In some embodiments, the formulation achieves a mean $AUC_{0-\infty}$ of more than 4700 h*ng/ml following administration of the formulation to human subjects less than 65 years of age. In some embodiments, the formulation achieves a mean $AUC_{0-\infty}$ of more than 5000 h*ng/ml following administration of the formulation to human subjects less than 65 years of age. In some embodiments, the formulation further comprises a granular component and an extragranular component, wherein the granular component comprises an intragranular component comprising the rofecoxib and one or more disintegrants, and wherein the extragranular component comprises one or more disintegrants.

In some embodiments, the rofecoxib in the formulation has a d90 particle size from about 10-12 µm, a d50 particle size from about 3-4 µm, and a d10 particle size from about 0.5-1.0 µm.

In certain aspects, the subject matter disclosed herein provides a method for treating pain, fever, or inflammation in a subject by administering a 25 mg solid dosage formulation of rofecoxib or a pharmaceutically acceptable salt thereof, wherein a single administration of the formulation to human subjects achieves a mean Cmax plasma concentration of more than 240 ng/ml in less than 3 hours following administration with a mean $AUC_{0-\infty}$ of more than 4250 h*ng/ml.

In certain aspects, the subject matter disclosed herein provides a method for treating pain, fever, or inflammation in a subject by administering a 17.5 mg solid dosage formulation of rofecoxib or a pharmaceutically acceptable salt thereof.

In some embodiments, the rofecoxib formulation achieves a median time to Cmax plasma concentration in 4 hours or less following a single administration of the formulation to human subjects less than 65 years of age. In some embodiments, the rofecoxib formulation achieves a median time to Cmax plasma concentration in 3.5 hours or less following administration. In some embodiments, the rofecoxib formulation achieves a median time to Cmax plasma concentration in 3 hours or less following administration. In some embodiments, the rofecoxib formulation achieves a median time to Cmax plasma concentration in 2.5 hours or less following administration.

In certain aspects, the subject matter disclosed herein provides a method for treating pain, fever, or inflammation in a subject by administering a 17.5 mg solid dosage formulation of rofecoxib or a pharmaceutically acceptable salt thereof, wherein a single administration of the formulation to human subjects less than 65 years of age achieves a mean Cmax plasma concentration of more than 100 ng/ml.

In some embodiments, the rofecoxib formulation achieves a mean Cmax plasma concentration of more than 150 ng/ml, 167 ng/ml, or 190 ng/ml. In some embodiments, the rofecoxib formulation achieves a mean Cmax plasma concentration of more than 200 ng/ml. In some embodiments, the rofecoxib formulation achieves a mean Cmax plasma concentration of more than 220 ng/ml. In some embodiments, the rofecoxib formulation achieves a mean Cmax plasma concentration of more than 250 ng/ml.

In certain aspects, the subject matter disclosed herein provides a method for treating pain, fever, or inflammation in a subject by administering a 17.5 mg solid dosage formulation of rofecoxib or a pharmaceutically acceptable salt thereof, wherein a single administration of the formulation to human subjects less than 65 years of age achieves a mean $AUC_{0-\infty}$ of more than 1750 h*ng/ml.

In some embodiments, the rofecoxib formulation achieves a mean $AUC_{0-\infty}$ of more than 2000 h*ng/ml. In some embodiments, the rofecoxib formulation achieves a mean $AUC_{0-\infty}$ of more than 2500 h*ng/ml. In some embodiments, the rofecoxib formulation achieves a mean $AUC_{0-\infty}$ of more than 3000 h*ng/ml. In some embodiments, the rofecoxib formulation achieves a mean $AUC_{0-\infty}$ of more than 3100 h*ng/ml. In some embodiments, the rofecoxib formulation achieves a mean $AUC_{0-\infty}$ of more than 3500 h*ng/ml.

In certain aspects, the subject matter disclosed herein provides a method for treating pain, fever, or inflammation in a subject by administering a 17.5 mg solid dosage formulation of rofecoxib or a pharmaceutically acceptable salt thereof, wherein a single administration of the formulation to human subjects less than 65 years of age achieves a mean Cmax plasma concentration within 80% to 125% of 224 ng/ml.

In certain aspects, the subject matter disclosed herein provides a method for treating pain, fever, or inflammation in a subject by administering a 17.5 mg solid dosage formulation of rofecoxib or a pharmaceutically acceptable salt thereof, wherein the formulation reaches a Cmax plasma concentration of least 170 ng/ml in the subject.

In some embodiments, the formulation reaches a Cmax plasma concentration level of at least 175 ng/ml. In some embodiments, the formulation reaches a Cmax plasma concentration level of at least 180 ng/ml. In some embodiments, the formulation reaches a Cmax plasma concentration level of at least 185 ng/ml. In some embodiments, the formulation reaches a Cmax plasma concentration level of at least 190 ng/ml.

In certain aspects, the subject matter disclosed herein provides a method for treating pain, fever, or inflammation in a subject by administering a 17.5 mg solid dosage formulation of rofecoxib or a pharmaceutically acceptable salt thereof, wherein the formulation reaches an $AUC_{0-\infty}$ of more than 2600 h*ng/ml in the subject.

In some embodiments, the rofecoxib formulation reaches an $AUC_{0-\infty}$ of more than 2750 h*ng/ml. In some embodiments, the rofecoxib formulation reaches an $AUC_{0-\infty}$ of more than 2900 h*ng/ml. In some embodiments, the rofecoxib formulation reaches an $AUC_{0-\infty}$ of more than 3050 h*ng/ml. In some embodiments, the rofecoxib formulation reaches an $AUC_{0-\infty}$ of more than 3200 h*ng/ml. In some embodiments, the rofecoxib formulation reaches an $AUC_{0-\infty}$ of more than 3350 h*ng/ml.

In certain aspects, the subject matter disclosed herein provides a method for treating pain, fever, or inflammation in a subject by administering a 20 mg solid dosage formulation of rofecoxib or a pharmaceutically acceptable salt thereof.

In some embodiments, the rofecoxib formulation achieves a median time to Cmax plasma concentration in 4 hours or less following a single administration of the formulation to human subjects. In some embodiments, the rofecoxib formulation achieves a median time to Cmax plasma concentration in 3.5 hours or less following administration. In some embodiments, the rofecoxib formulation achieves a median time to Cmax plasma concentration in 3 hours or less following administration. In some embodiments, the rofecoxib formulation achieves a median time to Cmax plasma concentration in 2.5 hours or less following administration.

In certain aspects, the subject matter disclosed herein provides a method for treating pain, fever, or inflammation in a subject by administering a 20 mg solid dosage formulation of rofecoxib or a pharmaceutically acceptable salt thereof, wherein a single administration of the formulation to human subjects less than 65 years of age achieves a mean Cmax plasma concentration of more than 150 ng/ml.

In some embodiments, the rofecoxib formulation achieves a mean Cmax plasma concentration of more than 191 ng/ml, 200 ng/ml, 215 ng/ml, or 225 ng/ml. In some embodiments, the rofecoxib formulation achieves a mean Cmax plasma concentration of more than 250 ng/ml. In some embodiments, the rofecoxib formulation achieves a mean Cmax plasma concentration of more than 258 ng/ml. In some embodiments, the formulation achieves a mean Cmax plasma concentration of more than 300 ng/ml.

In certain aspects, the subject matter disclosed herein provides a method for treating pain, fever, or inflammation in a subject by administering a 20 mg solid dosage formulation of rofecoxib or a pharmaceutically acceptable salt thereof, wherein a single administration of the formulation to human subjects less than 65 years of age achieves a mean $AUC_{0-\infty}$ of more than 2000 h*ng/ml.

In some embodiments, the rofecoxib formulation achieves a mean $AUC_{0-\infty}$ of more than 2500 h*ng/ml. In some embodiments, the rofecoxib formulation achieves a mean $AUC_{0-\infty}$ of more than 3000 h*ng/ml. In some embodiments, the rofecoxib formulation achieves a mean $AUC_{0-\infty}$ of more than 3400 h*ng/ml. In some embodiments, the rofecoxib formulation achieves a mean $AUC_{0-\infty}$ of more than 3500 h*ng/ml.

In certain aspects, the subject matter disclosed herein provides a method for treating pain, fever, or inflammation in a subject by administering a 20 mg solid dosage formulation of rofecoxib or a pharmaceutically acceptable salt thereof, wherein a single administration of the formulation to human subjects less than 65 years of age achieves a mean Cmax plasma concentration within 80% to 125% of 259 ng/ml.

In certain aspects, the subject matter disclosed herein provides a method for treating pain, fever, or inflammation in a subject by administering a 20 mg solid dosage formulation of rofecoxib or a pharmaceutically acceptable salt thereof, wherein the formulation reaches a Cmax plasma concentration of least 170 ng/ml in the subject.

In some embodiments, the rofecoxib formulation reaches a Cmax plasma concentration level of at least 190 ng/ml. In some embodiments, the rofecoxib formulation reaches a Cmax plasma concentration level of at least 205 ng/ml. In some embodiments, the rofecoxib formulation reaches a Cmax plasma concentration level of at least 220 ng/ml. In some embodiments, the rofecoxib formulation reaches a Cmax plasma concentration level of at least 235 ng/ml. In some embodiments, the rofecoxib formulation reaches a Cmax plasma concentration level of at least 250 ng/ml.

In certain aspects, the subject matter disclosed herein provides a method for treating pain, fever, or inflammation in a subject by administering a 20 mg solid dosage formulation of rofecoxib or a pharmaceutically acceptable salt thereof, wherein the formulation reaches an $AUC_{0-\infty}$ of more than 3000 h*ng/ml in the subject.

In some embodiments, the rofecoxib formulation reaches an $AUC_{0-\infty}$ of more than 3200 h*ng/ml. In some embodiments, the rofecoxib formulation reaches an $AUC_{0-\infty}$ of more than 3300 h*ng/ml. In some embodiments, the rofecoxib formulation reaches an $AUC_{0-\infty}$ of more than 3500 h*ng/ml. In some embodiments, the rofecoxib formulation reaches an $AUC_{0-\infty}$ of more than 3500 h*ng/ml. In some embodiments, the rofecoxib formulation reaches an $AUC_{0-\infty}$ of more than 3525 h*ng/ml. In some embodiments, the rofecoxib formulation reaches an $AUC_{0-\infty}$ of 3550 h*ng/ml or more. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In certain aspects, the subject matter disclosed herein provides a pharmaceutically acceptable formulation comprising a granular component and an extragranular component, wherein the granular component comprises an intragranular component comprising rofecoxib or a pharmaceutically acceptable salt thereof and one or more disintegrants, and wherein the extragranular component comprises one or more disintegrants.

In some embodiments, the one or more disintegrants in the granular component is selected from starches, clays, celluloses, algins, gums, cross-linked polymers, and combinations thereof. In some embodiments, the one or more disintegrants in the granular component is selected from croscarmellose, crospovidone, sodium starch glycolate, and combinations thereof. In some embodiments, one or more disintegrants in the granular component is croscarmellose sodium. In some embodiments, the one or more disintegrants in the granular component is about 1% (w/w) to about 8% (w/w) of the formulation. In some embodiments, the one or more disintegrants in the granular component is about 1% (w/w) to about 6% (w/w) of the formulation. In some embodiments, the one or more disintegrants in the granular component is about 1% (w/w) to about 4% (w/w) of the formulation. In some embodiments, the one or more disintegrants in the extragranular component is selected from starches, clays, celluloses, algins, gums, cross-linked polymers, and combinations thereof. In some embodiments, the one or more disintegrants in the extragranular component is selected from croscarmellose, crospovidone, sodium starch glycolate, and combinations thereof. In some embodiments, the one or more disintegrants in the extragranular component is croscarmellose sodium.

In some embodiments, the disintegrant in the extragranular component is about 1% (w/w) to about 8% (w/w) of the formulation. In some embodiments, the disintegrant in the extragranular component is about 1% (w/w) to about 6% (w/w) of the formulation. In some embodiments, the disintegrant in the extragranular component is about 1% (w/w) to about 4% (w/w) of the formulation. In some embodiments, the disintegrant in the granular component and the disintegrant in the extragranular component are together about 2% (w/w) to about 12% (w/w) of the formulation. In some embodiments, the disintegrant in the granular component and the disintegrant in the extragranular component are together about 2% (w/w) to about 10% (w/w) of the formulation. In some embodiments, the disintegrant in the granular component and the disintegrant in the extragranular component are together about 2% (w/w) to about 8% (w/w) of the formulation. In some embodiments, the ratio of granular disintegrant to extragranular disintegrant is about 40% to about 60% (w/w). In some embodiments, the ratio of granular disintegrant to extragranular disintegrant is about 45% to about 55% (w/w). In some embodiments, the ratio of granular disintegrant to extragranular disintegrant is about 50% to about 50% (w/w). In some embodiments, the ratio of granular disintegrant to extragranular disintegrant is about 55% to about 45% (w/w). In some embodiments, the ratio of granular disintegrant to extragranular disintegrant is about 60% to about 40% (w/w).

In some embodiments, the pharmaceutically acceptable formulation form further comprises one or more of a diluent, a binder, a coloring agent, and a lubricant. In some embodiments, at least a portion of the diluent is in the granular component. In some embodiments, the diluent is selected from dicalcium phosphate, calcium sulfate, lactose, cellulose, kaolin, mannitol, sodium chloride, dry starch, powdered sugar, sorbitol, sucrose, inositol, and combinations thereof. In some embodiments, the diluent is selected from lactose, cellulose, or a combination thereof. In some embodiments, the diluent is selected from lactose monohydrate, microcrystalline cellulose, or a combination thereof.

In some embodiments, the lactose monohydrate is about 35% (w/w) to about 45% (w/w) of the formulation. In some embodiments, the lactose monohydrate is about 37% (w/w) to about 42% (w/w) of the formulation. In some embodiments, the lactose monohydrate is about 39% (w/w) to about 40% (w/w) of the formulation. In some embodiments, the microcrystalline cellulose is about 35% (w/w) to about 45% (w/w) of the formulation. In some embodiments, the microcrystalline cellulose is about 37% (w/w) to about 42% (w/w) of the formulation. In some embodiments, the microcrystalline cellulose is about 39% (w/w) to about 40% (w/w) of the formulation. In some embodiments, the diluent is about 75% (w/w) to about 85% (w/w) of the formulation. In some embodiments, the diluent is about 77% (w/w) to about 82% (w/w) of the formulation. In some embodiments, the diluent is about 78% (w/w) to about 80% (w/w) of the formulation.

In some embodiments, at least a portion of the binder is in the granular component. In some embodiments, the binder is selected from starches, gelatins, sugars, gums, waxes, water, alcohols, celluloses, and combinations thereof. In some embodiments, the binder is selected from acacia gum, tragacanth, corn starch, methyl cellulose, panwar gum, ghatti gum, mucilage of isapol husks, carboxymethylcellulose, methylcellulose, polyvinylpyrrolidone, sucrose, glucose, dextrose, molasses, lactose, and combinations thereof. In some embodiments, the binder is hydroxypropyl cellulose.

In some embodiments, the binder is about 1% (w/w) to about 5% (w/w) of the formulation. In some embodiments, the binder is about 2% (w/w) to about 4% (w/w) of the formulation. In some embodiments, the binder is about 2.5% (w/w) to about 3.5% (w/w) of the formulation.

In some embodiments, at least a portion of the coloring agent is in the extragranular component. In some embodiments, the coloring agent is pigment blend yellow. In some embodiments, the coloring agent is about 0.30% (w/w) to about 0.60% (w/w) of the formulation.

In some embodiments, at least a portion of the lubricant is in the extragranular component. In some embodiments, the lubricant is selected from talc, magnesium stearate, calcium stearate, stearic acid, metallic stearate, hydrogenated vegetable oils, and polyethylene glycol, corn starch, boric acids, sodium chloride, sodium lauryl sulphate. In some embodiments, the lubricant is magnesium stearate. In some embodiments, the lubricant is about 0.10% (w/w) to about 1% (w/w) of the formulation. In some embodiments, the lubricant is about 0.50% (w/w) of the formulation.

In some embodiments, the rofecoxib or pharmaceutically acceptable salt thereof is about 5% (w/w) to about 30% (w/w) of the formulation. In some embodiments, the rofecoxib or pharmaceutically acceptable salt thereof is about 10% (w/w) to about 20% (w/w) of the formulation. In some embodiments, the rofecoxib or pharmaceutically acceptable salt thereof is about 12% (w/w) to about 13% (w/w) of the formulation.

In some embodiments, the formulation comprises about 10 mg of the rofecoxib or pharmaceutically acceptable salt thereof. In some embodiments, the formulation comprises about 12.5 mg of the rofecoxib or pharmaceutically acceptable salt thereof. In some embodiments, the formulation comprises about 17.5 mg of the rofecoxib or pharmaceutically acceptable salt thereof. In some embodiments, the formulation comprises about 20 mg of the rofecoxib or pharmaceutically acceptable salt thereof. In some embodiments, the formulation comprises about 25 mg of the rofecoxib or pharmaceutically acceptable salt thereof.

In some embodiments, the rofecoxib is substantially pure. In some embodiments, the rofecoxib is highly pure. In some embodiments, the highly pure rofecoxib comprises less than about 0.1% total impurities. In some embodiments, the highly pure rofecoxib comprises less than about 0.075% total impurities. In some embodiments, the highly pure rofecoxib comprises less than about 0.050% total impurities. In some embodiments, the highly pure rofecoxib comprises less than about 0.025% total impurities. In some embodiments, the highly pure rofecoxib comprises less than about 0.001% total impurities.

In some embodiments, the rofecoxib is substantially pure or highly pure. In some embodiments, the highly pure rofecoxib comprises less than about 0.10%, 0.05%, 0.02%, or 0.01% of 4-[4-(methylsulphonyl)phenyl]-3-phenyl-2,5-furandione. In some embodiments, the highly pure rofecoxib comprises less than about 0.10%, 0.05%, 0.02%, or 0.01% of 4-[4-(methylsulfonyl)phenyl]-3-phenyl-5-hydroxyfuran-2-one. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylsulfinyl)phenyl]-3-phenyl-2(5H)-furanone.

In some embodiments, the formulation is suitable for oral administration. In some embodiments, the formulation is a solid dosage form. In some embodiments, the solid dosage form is an oral tablet.

In some embodiments, the oral tablet provides a dissolution rate of at least about 80% of the rofecoxib or pharmaceutically acceptable salt thereof by about 15 minutes. In some embodiments, the oral tablet provides a dissolution rate of at least about 85% of the rofecoxib or pharmaceutically acceptable salt thereof by about 15 minutes. In some embodiments, the oral tablet provides a dissolution rate of at least about 90% of the rofecoxib or pharmaceutically acceptable salt thereof by about 15 minutes. In some embodiments, the oral tablet provides a dissolution rate of at least about 95% of the rofecoxib or pharmaceutically acceptable salt thereof by about 15 minutes. In some embodiments, the oral tablet provides a dissolution rate of at least about 100% of the rofecoxib or pharmaceutically acceptable salt thereof by about 15 minutes.

In some embodiments, the dissolution rate is measured in about 1% SDS at a paddle speed of about 50 rpm and at a temperature of about $37.0°$ C.$\pm 0.5°$ C. In some embodiments, the dissolution rate is measured in about 1% SDS at a paddle speed of about 75 rpm and at a temperature of about $37.0°$ C.$\pm 0.5°$ C. In some embodiments, the dissolution rate is measured in about 1.5% SDS at a paddle speed of about 50 rpm and at a temperature of about $37.0°$ C.$\pm 0.5°$ C. In some embodiments, the dissolution rate is measured in about 1.5% SDS at a paddle speed of about 75 rpm and at a temperature of about $37.0°$ C.$\pm 0.5°$ C. In some embodiments, the dissolution rate is measured in about 2% SDS at a paddle speed of about 50 rpm and at a temperature of about $37.0°$ C.$\pm 0.5°$ C. In some embodiments, the dissolution rate is measured in about 2% SDS at a paddle speed of about 75 rpm and at a temperature of about $37.0°$ C.$\pm 0.5°$ C.

In some embodiments, the rofecoxib or pharmaceutically acceptable salt thereof is formulated into granules and at least about 35% of the granules are less than about 75 μm. In some embodiments, the rofecoxib or pharmaceutically acceptable salt thereof is formulated into granules and at least about 55% of the granules are less than about 150 μm. In some embodiments, the rofecoxib or pharmaceutically acceptable salt thereof is formulated into granules and at least about 75% of the granules are less than about 250 μm. In some embodiments, the rofecoxib or pharmaceutically acceptable salt thereof is formulated into granules and at least about 85% of the granules are less than about 425 μm. In some embodiments, the rofecoxib or pharmaceutically acceptable salt thereof is formulated into granules and at least about 90% of the granules are less than about 1000 μm.

In some embodiments, the formulation is a solid dosage formulation comprising 12.5 mg, 17.5 mg, 20 mg, or 25 mg of rofecoxib, and wherein the formulation reaches a median time to Cmax plasma concentration in 3 hours or less following a single administration of the formulation to human subjects less than 65 years of age.

In some embodiments, the formulation reaches a mean Cmax plasma concentration in less than 3 hours following administration. In some embodiments, the formulation reaches a mean Cmax plasma concentration in less than 2.5 hours following administration. In some embodiments, the formulation reaches a mean Cmax plasma concentration in less than 2 hours following administration. In some embodiments, the formulation is a solid dosage formulation comprising 25 mg of rofecoxib, and wherein a single administration of the formulation to human subjects less than 65 years of age achieves a mean Cmax plasma concentration of more than 240 ng/ml. In some embodiments, the formulation achieves a mean Cmax plasma concentration of more than 300 ng/ml. In some embodiments, the formulation achieves a mean Cmax plasma concentration of more than 320 ng/ml. In some embodiments, the formulation achieves a mean Cmax plasma concentration of more than 350 ng/ml.

In some embodiments, the formulation is a solid dosage formulation comprising 25 mg of rofecoxib, and wherein a single administration of the formulation to human subjects less than 65 years of age achieves a mean $AUC_{0-\infty}$ of more than 4500 h*ng/ml. In some embodiments, the formulation achieves a mean $AUC_{0-\infty}$ of more than 4700 h*ng/ml. In some embodiments, the formulation achieves a mean $AUC_{0-\infty}$ of more than 5000 h*ng/ml.

In some embodiments, the formulation is a solid dosage formulation comprising 25 mg of rofecoxib, and wherein a single administration of the formulation in human subjects less than 65 years of age reaches a mean Cmax plasma concentration of more than 240 ng/ml in less than 3 hours following administration with a mean $AUC_{0-\infty}$ of more than 4250 h*ng/ml.

In certain aspects, the subject matter disclosed herein provides a solid dosage formulation comprising 10 mg to 50 mg of rofecoxib and a pharmaceutically acceptable carrier, wherein a single administration of the formulation in human subjects less than 65 years of age achieves a mean Cmax plasma concentration from 9.8 ng/ml to 16 ng/ml for each 1 mg of rofecoxib in the formulation.

In some embodiments, the formulation achieves a mean Cmax plasma concentration from 10 ng/ml to 14 ng/ml for each 1 mg of rofecoxib in the formulation. In some embodiments, the formulation achieves a mean Cmax plasma concentration from 10 ng/ml to 13 ng/ml for each 1 mg of rofecoxib in the formulation. In some embodiments, the formulation achieves a mean Cmax plasma concentration from 80% to 125% of 12.8 ng/ml. In some embodiments, the formulation achieves a mean Cmax plasma concentration that is bioequivalent to 12.8 ng/ml. In some embodiments, the formulation achieves a mean Cmax plasma concentration that is 80% to 125% of 12.8 ng/ml.

In certain aspects, the subject matter disclosed herein provides a solid dosage formulation comprising 10 mg to 50 mg of rofecoxib and a pharmaceutically acceptable carrier, wherein a single administration of the formulation in human subjects less than 65 years of age achieves a mean $AUC_{0-\infty}$ of 170 h*ng/ml to 235 h*ng/ml for each 1 mg of rofecoxib in the formulation.

In some embodiments, the formulation achieves a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the formulation achieves a mean $AUC_{0-\infty}$ of 190 h*ng/ml to 215 h*ng/ml for each 1 mg of rofecoxib in the formulation.

In certain aspects, the subject matter disclosed herein provides a method of inhibiting COX-2 in a subject by administering the formulations described herein.

In certain aspects, the subject matter disclosed herein provides a method of inhibiting COX-2 in a subject by administering a solid dosage formulation comprising 17.5 mg of rofecoxib.

In some embodiments, the formulation is a solid dosage formulation comprising 17.5 mg of rofecoxib, wherein a single administration of the formulation to human subjects less than 65 years of age achieves a mean Cmax that is equal to or greater than that reported by Schwartz, J. I., et al. Clin. Drug Invent. 2003, 23 (8): 503-509 for a rofecoxib 25 mg tablet. In some embodiments, the formulation is a solid dosage formulation comprising 17.5 mg of rofecoxib, wherein a single administration of the formulation to human subjects less than 65 years of age achieves a mean Cmax that is equal to or greater than that reported in the FDA-approved label for VIOXX for a single 25-mg dose of VIOXX. In some embodiments, the formulation is a solid dosage formulation comprising 20 mg of rofecoxib, where a single administration of the formulation to human subjects less than 65 years of age achieves a mean $AUC_{0-\infty}$ that is equal to or greater than that reported by Schwartz, J. I., et al. Clin. Drug Invent. 2003, 23 (8): 503-509 for a rofecoxib 25 mg tablet. In some embodiments, the formulation is a solid dosage formulation comprising 20 mg of rofecoxib, where a single administration of the formulation to human subjects less than 65 years of age achieves a mean Cmax that is equal to or greater than that reported by Schwartz, J. I., et al. Clin. Drug Invent. 2003, 23 (8): 503-509 for a rofecoxib 25 mg tablet. In some embodiments, the formulation is a solid dosage formulation comprising 20 mg of rofecoxib, wherein a single administration of the formulation to human subjects less than 65 years of age achieves a mean $AUC_{0-\infty}$ that is equal to or greater than that reported in the FDA-approved label for VIOXX for a single 25-mg dose of VIOXX. In some embodiments, the formulation is a solid dosage formulation comprising 20 mg of rofecoxib, wherein a single administration of the formulation to human subjects less than 65 years of age achieves a mean Cmax that is equal to or greater than that reported in the FDA-approved label for VIOXX for a single 25-mg dose of VIOXX.

In some embodiments, the patient is age 2 or older.

In certain aspects, the subject matter disclosed herein provides a method for treating pain, fever, or inflammation in a patient by administering the formulations as described herein.

In some embodiments, the human subjects are healthy human subjects. In some embodiments, the patient is age 2 or older.

In certain aspects, the subject matter disclosed herein provides a method for treating pain, fever or inflammation in a patient population comprising providing a solid dosage formulation comprising 10 mg to 50 mg of rofecoxib to the patient population for inhibiting COX-2, wherein the formulation achieves a mean Cmax plasma concentration of between 80 to 125% of 12.8 ng/ml for each 1 mg of rofecoxib in the formulation following single administration of the formulation in the patient population. In some embodiments, the formulation achieves a mean Cmax plasma concentration that is bioequivalent to 12.8 ng/ml for each 1 mg of rofecoxib in the formulation. In some embodiments, the formulation achieves a mean Cmax plasma concentration that is between 80 to 125% of 12.8 ng/ml for each 1 mg of rofecoxib in the formulation.

In some embodiments, the subject matter disclosed herein provides a formulation comprising 12.5 mg to 25 mg of rofecoxib and a pharmaceutically acceptable carrier, wherein a single administration of the formulation in human female subjects less than 65 years of age achieves a mean Cmax plasma concentration that is at least 5%, 10%, 15%, 20%, 25%, or 30% greater than that achieved following a single administration of the formulation to human male subjects less than 65 years of age. In some embodiments, the subject matter disclosed herein provides a formulation comprising 12.5 mg to 25 mg of rofecoxib and a pharmaceutically acceptable carrier, wherein a single administration of the formulation in human female subjects less than 65 years of age achieves a mean $AUC_{0-\infty}$ that is at least 5%, 10%, 15%, 20%, 25%, or 30% greater than that achieved following a single administration of the formulation to human male subjects less than 65 years of age.

In some embodiments, the subject matter disclosed herein provides a formulation comprising 12.5 mg to 25 mg of rofecoxib and a pharmaceutically acceptable carrier, wherein a single administration of the formulation in Caucasian subjects less than 65 years of age achieves a mean $AUC_{0-\infty}$ that is greater than that achieved following a single administration of the formulation to African American subjects less than 65 years of age. In some embodiments, the formulation achieves a mean $AUC_{0-\infty}$ in Caucasian subjects that is at least 1%, 2%, 5%, 9%, or 10% greater than that achieved following a single administration of the formulation to African American subjects less than 65 years of age.

In some embodiments, the subject matter herein provides a solid dosage formulation comprising 12.5 mg of rofecoxib, wherein the formulation achieves a mean plasma concentration of at least about 0.2 ng/ml, 0.3 ng/ml, 0.4 ng/ml, or 0.5 ng/ml at 15 minutes following single administration of the formulation to human subjects less than 65 years of age. In some embodiments, the subject matter herein provides a solid dosage formulation comprising 12.5 mg of rofecoxib, wherein the formulation achieves an arithmetic mean plasma concentration of at least about 0.8 ng/ml, 0.9 ng/ml, or 1.0 ng/ml at 15 minutes following single administration of the formulation to human subjects less than 65 years of age. In some embodiments, the subject matter herein provides a solid dosage formulation comprising 17.5 mg of rofecoxib, wherein the formulation achieves a mean plasma concentration of at least about 0.3 ng/ml, 0.4 ng/ml, 0.5 ng/ml, or 0.6 ng/ml at 15 minutes following single administration of the formulation to human subjects less than 65 years of age. In some embodiments, the subject matter herein provides a solid dosage formulation comprising 17.5 mg of rofecoxib, wherein the formulation achieves an arithmetic mean plasma concentration of at least about 1.8 ng/ml, 2.0 ng/ml, 2.2 ng/ml, or 2.4 ng/ml at 15 minutes following single administration of the formulation to human subjects less than 65 years of age. In some embodiments, the subject matter herein provides a solid dosage formulation comprising 20 mg of rofecoxib, wherein the formulation achieves a mean plasma concentration of at least about 0.8 ng/ml, 0.9 ng/ml, 1.0 ng/ml, 1.1 ng/ml, or 1.16 ng/ml at 15 minutes following single administration of the formulation to human subjects less than 65 years of age. In some embodiments, the subject matter herein provides a solid dosage formulation comprising 20 mg of rofecoxib, wherein the formulation achieves an arithmetic mean plasma concentration of at least about 4.6 ng/ml, 5.0 ng/ml, 5.4 ng/ml, or 5.7 ng/ml at 15 minutes following single administration of the formulation to human subjects less than 65 years of age. In some embodiments, the subject matter herein provides a solid dosage formulation comprising a solid dosage formulation comprising 25 mg of rofecoxib, wherein the formulation achieves a mean plasma concentration of at least about 1.0 ng/ml, 1.1 ng/ml, 1.2 ng/ml, or 1.3 ng/ml at 15 minutes following single administration of the formulation to human subjects less than 65 years of age. In some embodiments, the subject matter herein provides a solid dosage formulation comprising a solid dosage formulation comprising 25 mg of rofecoxib, wherein the formulation achieves an arithmetic mean plasma concentration of at least about 4.6 ng/ml, 5.0 ng/ml, 5.4 ng/ml, or 5.6 ng/ml at 15 minutes following single administration of the formulation to human subjects less than 65 years of age. In some embodiments, the subject matter herein provides a solid dosage formulation comprising 12.5 mg of rofecoxib, wherein the formulation achieves a mean plasma concentration of at least about 27 ng/ml, 29 ng/ml, 31 ng/ml, or 33 ng/ml at 45 minutes following single administration of the formulation to human subjects less than 65 years of age. In some embodiments, the subject matter herein provides a solid dosage formulation comprising 12.5 mg of rofecoxib, wherein the formulation achieves an arithmetic mean plasma concentration of at least about 45 ng/ml, 48 ng/ml, 51 ng/ml, 54 ng/ml, or 56 ng/ml at 45 minutes following single administration of the formulation to human subjects less than 65 years of age. In some embodiments, the subject matter herein provides a solid dosage formulation comprising a solid dosage formulation comprising 17.5 mg of rofecoxib, wherein the formulation achieves a mean plasma concentration of at least about 45 ng/ml, 47 ng/ml, 49 ng/ml, or 51 ng/ml at 45 minutes following single administration of the formulation to human subjects less than 65 years of age. In some embodiments, the subject matter herein provides a solid dosage formulation comprising a solid dosage formulation comprising 17.5 mg of rofecoxib, wherein the formulation achieves an arithmetic mean plasma concentration of at least about 74 ng/ml, 79 ng/ml, 84 ng/ml, 89 ng/ml, or 93 ng/ml at 45 minutes following single administration of the formulation to human subjects less than 65 years of age. In some embodiments, the subject matter herein provides a solid dosage formulation comprising 20 mg of rofecoxib, wherein the formulation achieves a mean plasma concentration of at least about 58 ng/ml, 62 ng/ml, 66 ng/ml, 70 ng/ml, or 72 ng/ml at 45 minutes following single administration of the formulation to human subjects less than 65 years of age. In some embodiments, the subject matter herein provides a solid dosage formulation comprising 20 mg of rofecoxib, wherein the formulation achieves an arithmetic mean plasma concentration of at least about 112 ng/ml, 116 ng/ml, or 121 ng/ml at 45 minutes following single administration of the formulation to human subjects less than 65 years of age. In some embodiments, the subject matter herein provides a solid dosage formulation comprising 25 mg of rofecoxib, wherein the formulation achieves a mean plasma concentration of at least about 78 ng/ml, 85 ng/ml, 92 ng/ml, or 97 ng/ml, at 45 minutes following single administration of the formulation to human subjects less than 65 years of age. In some embodiments, the subject matter herein provides a solid dosage formulation comprising 25 mg of rofecoxib, wherein the formulation achieves an arithmetic mean plasma concentration of at least about 133 ng/ml, 139 ng/ml, 145 ng/ml, 151 ng/ml, or 159 ng/ml at 45 minutes following single administration of the formulation to human subjects less than 65 years of age.

In some embodiments, the formulation and methods set forth herein achieve the recited median time to Cmax, mean Cmax plasma concentration, and mean $AUC_{0-\infty}$ values following the administration of the formulation to human subjects less than 65 years of age in a single dose pharmacokinetic study. In any of the embodiments described herein, the human subjects may be in a fasting state. In any of the embodiments described herein, the human subjects may be less than 60 years of age. In any of the embodiments described herein, the human subjects may be a population of healthy adults less than 65 years or 60 years of age.

BRIEF DESCRIPTION OF FIGURES

The patent application contains at least one drawing in color.

FIGS. 1A-B show two embodiments of the composition of a 25-mg rofecoxib tablet.

FIG. 1A shows the composition of a 25-mg rofecoxib tablet in prototype batches 1-8. FIG. 1B shows the composition of a 25-mg rofecoxib tablet.

FIG. 2 shows process conditions for Process $A_{1-3}$ in manufacturing of batches 1-4.

FIG. 3A shows dissolution of rofecoxib tablets in 0.1N HCl. FIG. 3B shows dissolution of rofecoxib tablets in at least 2% SDS.

FIG. 4A shows dissolution of rofecoxib tablets in 0.1N HCl. FIG. 4B shows dissolution of rofecoxib tablets in at least 2% SDS.

FIG. 5 shows process conditions for batches 5-8.

FIG. 6A shows dissolution of rofecoxib tablets in batches 5 and 6. FIG. 6B shows dissolution of rofecoxib tablets in batches 7 and 8.

FIG. 8 shows composition of 25-mg rofecoxib tablet in prototype batches 5-6.

FIG. 9 shows processes description for the manufacture of prototype 25-mg rofecoxib tablets.

FIG. 10A shows manufacture of rofecoxib granules. FIG. 10B shows manufacture of rofecoxib tablets.

FIGS. 11A-B show a flow diagram for rofecoxib tablet manufacturing Process $A_2$.

FIG. 11A shows manufacture of rofecoxib granules. FIG. 11B shows manufacture of rofecoxib tablets.

FIG. 12A shows manufacture of rofecoxib granules. FIG. 12B shows manufacture of rofecoxib tablets.

FIG. 13A shows manufacture of rofecoxib granules. FIG. 13B shows manufacture of rofecoxib tablets.

FIG. 15A shows dissolution of rofecoxib tablets in 0.1N HCl for batches 1 and 2. FIG. 15B shows dissolution of rofecoxib tablets in at least 2% SDS for batches 1 and 2.

FIG. 16A shows dissolution of rofecoxib tablets in 0.1N HCl for batches 3 and 4. FIG. 16B shows dissolution of rofecoxib tablets in at least 2% SDS for batches 3 and 4.

FIG. 19A shows dissolution of rofecoxib tablets in at least 2% SDS for batches 5 and 6. FIG. 19B shows dissolution of rofecoxib tablets in at least 2% SDS for batches 7 and 8.

FIG. 20A shows dissolution of rofecoxib tablets in at least 2% SDS for batches 5 and 6. FIG. 20B shows dissolution of rofecoxib tablets in at least 2% SDS for batches 5 and 6.

FIG. 22A shows dissolution of rofecoxib tablets in at least 2% SDS for batches 5 and 6 at 75 rpm. FIG. 22B shows dissolution of rofecoxib tablets in at least 2% SDS for batches 5 and 6 at 50 rpm.

FIG. 23A shows dissolution of rofecoxib tablets in 1.5% SDS for batches 5 and 6 at 75 rpm. FIG. 23B shows dissolution of rofecoxib tablets in 1.5% SDS for batches 5 and 6 at 50 rpm.

FIG. 24A shows dissolution of rofecoxib tablets in 1.0% SDS for batches 5 and 6 at 75 rpm. FIG. 24B shows dissolution of rofecoxib tablets in 1.0% SDS for batches 5 and 6 at 50 rpm.

FIG. 25 shows a summary of fasted $AUC_{0-\infty}$ and Cmax in the PK 101 (Example 4) pharmacokinetic study.

FIG. 28 shows an analysis of $AUC_{0-\infty}$ and Cmax compared to historical data (101 study only).

FIG. 31 shows extrapolated pharmacokinetic AUC and Cmax values for dosages other than 25 mg of rofecoxib.

FIG. 33 shows demographic and baseline characteristics—safety (102 study only).

FIG. 34 shows demographic and baseline characteristics—safety, BMI (102 study only).

FIG. 35 shows demographic and baseline characteristics—PK (102 study only).

FIG. 36 shows demographic and baseline characteristics—PK, BMI (102 study only).

FIG. 37 shows a summary of fasted plasma rofecoxib concentration (ng/mL)—PK, time points 0.00, 0.25, 0.5 hr (102 study only).

FIG. 38 shows a summary of fasted plasma rofecoxib concentration (ng/mL)—PK, time points 0.75, 1, 1.5 hr (102 study only).

FIG. 39 shows a summary of fasted plasma rofecoxib concentration (ng/mL)—PK, time points 2, 3, 4 hr (102 study only).

FIG. 40 shows a summary of fasted plasma rofecoxib concentration (ng/mL)—PK, time points 5, 6, 7.5 hr (102 study only).

FIG. 41 shows a summary of fasted plasma rofecoxib concentration (ng/mL)—PK, time points 9, 12, 15 hr (102 study only).

FIG. 42 shows a summary of fasted plasma rofecoxib concentration (ng/mL)—PK, time points 18, 21, 24 hr (102 study only).

FIG. 43 shows a summary of fasted plasma rofecoxib concentration (ng/mL)—PK, time points 27, 30, 33 hr (102 study only).

FIG. 44 shows a summary of fasted plasma rofecoxib concentration (ng/mL)—PK, time points 36, 39, 42 hr (102 study only).

FIG. 45 shows a summary of fasted plasma rofecoxib concentration (ng/mL)—PK, time points 48, 52, 60 hr (102 study only).

FIG. 46 shows a summary of fasted plasma rofecoxib concentration (ng/mL)—PK, time points 72, 96, 120 hr (102 study only).

FIG. 47 shows a summary of fasted $AUC_{0-\infty}$ and $C_{max}$ (101 and 102 studies)—PK.

FIG. 48 shows a summary of fasted $AUC_{0-\infty}$ (102 study only)—PK.

FIG. 49 shows a summary of fasted $C_{max}$ (102 study only)—PK.

FIG. 50 shows a summary of fasted $AUC_{0-\infty}$ and $C_{max}$ by gender (102 study only)—12.5 mg PK.

FIG. 51 shows a summary of fasted $AUC_{0-\infty}$ and $C_{max}$ by gender (102 study only)—17.5 mg PK.

FIG. 52 shows a summary of fasted $AUC_{0-\infty}$ and $C_{max}$ by gender (102 study only)—20 mg PK.

FIG. 53 shows a summary of fasted $AUC_{0-\infty}$ and $C_{max}$ by gender (102 study only)—25 mg PK.

FIG. 54 shows a summary of fasted $AUC_{0-\infty}$ and $C_{max}$ by age (102 study only)—12.5 mg PK.

FIG. 55 shows a summary of fasted $AUC_{0-\infty}$ and $C_{max}$ by age (102 study only)—17.5 mg PK.

FIG. 56 shows a summary of fasted $AUC_{0-\infty}$ and $C_{max}$ by age (102 study only)—20 mg PK.

FIG. 57 shows a summary of fasted $AUC_{0-\infty}$ and $C_{max}$ by age (102 study only)—25 mg PK.

FIG. 58 shows a summary of fasted $AUC_{0-\infty}$ and $C_{max}$ by race (102 study only)—12.5 mg PK.

FIG. 59 shows a summary of fasted $AUC_{0-\infty}$ and $C_{max}$ by race (102 study only)—17.5 mg PK.

FIG. 60 shows a summary of fasted $AUC_{0-\infty}$ and $C_{max}$ by race (102 study only)—20 mg PK.

FIG. 61 shows a summary of fasted $AUC_{0-\infty}$ and $C_{max}$ by race (102 study only)—25 mg PK.

FIG. 62 shows a summary of fasted $AUC_{0-\infty}$ and $C_{max}$ by body weight (102 study only)—12.5 mg PK.

FIG. 63 shows a summary of fasted $AUC_{0-\infty}$ and $C_{max}$ by body weight (102 study only)—17.5 mg PK.

FIG. 64 shows a summary of fasted $AUC_{0-\infty}$ and $C_{max}$ by body weight (102 study only)—20 mg PK.

FIG. 65 shows a summary of fasted $AUC_{0-\infty}$ and $C_{max}$ by body weight (102 study only)—25 mg PK.

FIG. 66 shows a summary of fasted $AUC_{0-\infty}$ and $C_{max}$ by ethnicity (102 study only)—12.5 mg PK.

FIG. 67 shows a summary of fasted $AUC_{0-\infty}$ and $C_{max}$ by ethnicity (102 study only)—17.5 mg PK.

FIG. 68 shows a summary of fasted $AUC_{0-\infty}$ and $C_{max}$ by ethnicity (102 study only)—20 mg PK.

FIG. 69 shows a summary of fasted $AUC_{0-\infty}$ and $C_{max}$ by ethnicity (102 study only)—25 mg PK.

FIG. 70 shows a sensitivity analysis of fasted $AUC_{0-\infty}$ and $C_{max}$ compared to historical data—PK (102 study only).

FIG. 71 shows a summary of fasted $T_{max}$ and $t_{1/2}$ (101 and 102 studies combined)—PK.

FIG. 72 shows a summary of fasted CL/F and $V_d$/F (102 study only)—PK.

FIG. 73 shows an exploratory analysis of fasted $AUC_{0-\infty}$ and $C_{max}$ to estimate the dose that yields values equal to those observed in the historical data (102 study only)—PK.

FIG. 74 shows a summary of treatment-emergent adverse events—safety (102 study only).

FIG. 75 shows incidence of treatment-emergent adverse events by system organ class and preferred term—safety (102 study only).

FIG. 76 shows incidence of related treatment-emergent adverse events by system organ class and preferred term—safety (102 study only).

FIG. 77 shows incidence of serious treatment-emergent adverse events by system organ class and preferred term—safety (102 study only).

FIG. 78 shows incidence of treatment adverse events leading to study discontinuation by system organ class and preferred term (102 study only).

FIG. 79 shows incidence of treatment-emergent adverse events by system organ class, preferred term, and severity—safety (102 study only).

Figure 104:
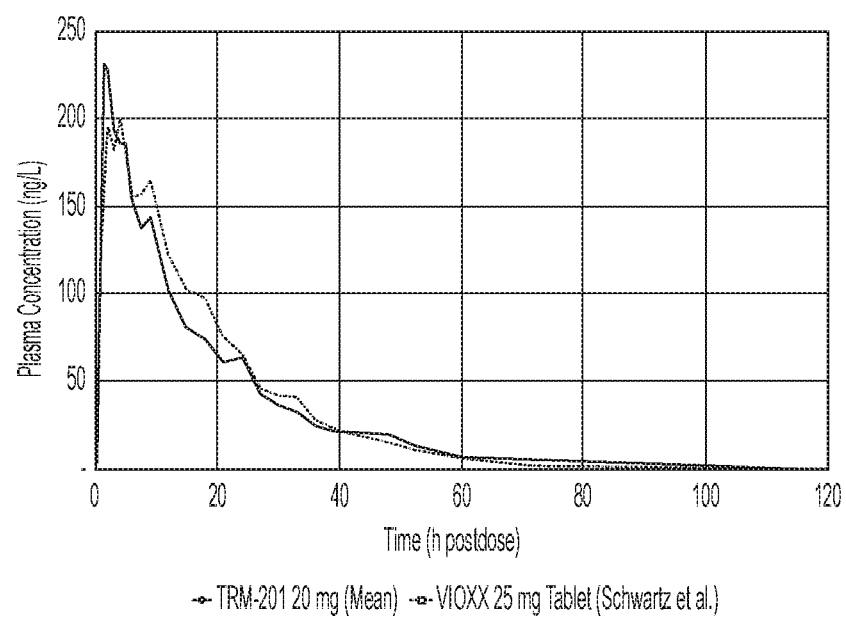

FIG. 104 shows a comparison of the mean plasma concentration (ng/L) versus time for TRM-201 20 mg and the 25 mg "VIOXX" tablet reported in Schwartz, J. I., et al. Clin. Drug Invent. 2003, 23 (8): 503-509.

DETAILED DESCRIPTION

Definitions

The following are definitions of terms used in the present specification. The initial definition provided for a group or term herein applies to that group or term throughout the present specification individually or as part of another group, unless otherwise indicated. Unless otherwise defined, all technical and scientific terms used herein have the same meaning as commonly understood by one of ordinary skill in the art.

As used herein, "dissolution rate" refers to the proportion of drug which enters a solution in a given amount of time.

As used herein, "rofecoxib" refers to the active ingredient 4-[4-(methylsulfonyl)phenyl]-3-phenyl-2(5H)-furanone or a pharmaceutically acceptable salt, solvate, or co-crystal thereof. The rofecoxib as described herein may be in amorphous or crystalline form. The purity of rofecoxib is determined as a percent (%) area basis, typically as quantified by analytical chromatography, such as using HPLC, UHPLC or UPLC.

In some embodiments, the highly pure rofecoxib comprises less than or equal to about 0.10%, 0.075%, 0.050%, 0.025%, 0.020%, or 0.001% area basis total impurities. In some embodiments, the highly pure rofecoxib comprises less than about 0.10%, 0.05%, 0.02%, or 0.01% of 4-[4-(methylsulphonyl)phenyl]-3-phenyl-2,5-furandione. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylsulfinyl)phenyl]-3-phenyl-2(5H)-furanone.

As used herein, "highly pure" means, with respect to an active ingredient, having less than or equal to about 0.10% area basis total impurities.

As used herein, "substantially pure" means, with respect to an active ingredient, having less than or equal to about 0.50% area basis total impurities.

As used herein, "essentially free" means, with respect to an impurity, having less than about 0.10% area basis of the impurity.

As used herein, "free of" means, with respect to an impurity having an amount of the impurity that is below the limitation of detection i.e. less than 0.02% area basis of the impurity.

The term "disintegrant" as used herein includes auxiliary agents which promote the disintegration of tablets or granulates, upon contact with liquids.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The term "pharmaceutically acceptable salt," as used herein, refers to the relatively non-toxic, inorganic and organic acid salts of compounds of the subject matter described herein.

As used herein, the term "subject" refers to a vertebrate animal. In one embodiment, the subject is a mammal or a mammalian species. In one embodiment, the subject is a human. In one embodiment, the subject is a healthy human adult. In other embodiments, the subject is a non-human vertebrate animal, including, without limitation, non-human primates, laboratory animals, livestock, racehorses, domesticated animals, and non-domesticated animals. In one embodiment, the term "human subjects" means a population of healthy human adults.

As used herein, the term "patient" refers to a human or animal.

The term "mammal" includes, but is not limited to, a human, mouse, rat, guinea pig, dog, cat, horse, cow, pig, or non-human primate, such as a monkey, chimpanzee, baboon or rhesus. In one embodiment, the mammal is a human.

As used herein, the term "effective amount" means an amount of a pharmaceutically active compound, i.e. a drug active, e.g. a quinolone carboxylic acid antimicrobial agent or pharmaceutically acceptable salt or ester thereof, given to a recipient patient sufficient to elicit biological activity, for example, anti-infective activity, e.g., anti-microbial activity.

As used herein, the term "a mean" refers to a geometric mean unless expressly indicated otherwise. The pharmacokinetic parameters such as "a mean Cmax" or "a mean AUC" refers to the geometric mean value of a Cmax or an AUC, unless expressly indicated otherwise.

The expression "bioequivalent" or "bioequivalence" is a term of art and is intended to be defined in accordance with 21 C.F.R. § 320.1 and prevailing guidelines from the FDA. Bioequivalence of different formulation of the same drug substance involves equivalence with respect to the rate and extent of drug absorption. The extent and rate of absorption of the test formulation is compared to a reference formulation in order to determine whether the two formulations are bioequivalent. In practice, two products are considered bioequivalent if the 90% confidence interval of the ratio of a log-transformed exposure measure (AUC and/or Cmax) falls completely within the range 80-125%.

Compositions of the Present Subject Matter

In certain aspects, the subject matter disclosed herein provides a solid dosage formulation comprising 17.5 mg of rofecoxib and a pharmaceutically acceptable carrier.

In some embodiments, the rofecoxib formulation reaches a median time to Cmax plasma concentration in 4 hours or less following a single administration of the formulation to human subjects less than 65 years of age. In some embodiments, the rofecoxib formulation reaches a median time to Cmax plasma concentration in 3.5 hours or less following a single administration of the formulation to human subjects less than 65 years of age. In some embodiments, the rofecoxib formulation reaches a median time to Cmax plasma concentration in 3 hours or less following a single administration of the formulation to human subjects less than 65 years of age. In some embodiments, the rofecoxib formulation reaches a median time to Cmax plasma concentration in 2.5 hours or less following a single administration of the formulation to human subjects less than 65 years of age.

In certain aspects, the subject matter disclosed herein provides a solid dosage formulation comprising 17.5 mg of rofecoxib and a pharmaceutically acceptable carrier, wherein the formulation achieves a mean Cmax plasma concentration of more than 100 ng/ml following a single administration of the formulation to human subjects less than 65 years of age.

In some embodiments, the rofecoxib formulation achieves a mean Cmax plasma concentration of more than 150 ng/ml, 167 ng/ml, or 190 ng/ml. In some embodiments, the rofecoxib formulation achieves a mean Cmax plasma concentration of more than 200 ng/ml. In some embodiments, the rofecoxib formulation achieves a mean Cmax plasma concentration of more than 220 ng/ml. In some embodiments, the rofecoxib formulation achieves a mean Cmax plasma concentration of more than 250 ng/ml.

In certain aspects, the subject matter disclosed herein provides a solid dosage formulation comprising 17.5 mg of rofecoxib and a pharmaceutically acceptable carrier, wherein the formulation achieves a mean $AUC_{0-\infty}$ of more than 1750 h*ng/ml following a single administration of the formulation to human subjects less than 65 years of age.

In some embodiments, the rofecoxib formulation achieves a mean $AUC_{0-\infty}$ of more than 2000 h*ng/ml following a single administration of the formulation to human subjects less than 65 years of age. In some embodiments, the rofecoxib formulation achieves a mean $AUC_{0-\infty}$ of more than 2500 h*ng/ml following a single administration of the formulation to human subjects less than 65 years of age. In some embodiments, the rofecoxib formulation achieves a mean $AUC_{0-\infty}$ of more than 3000 h*ng/ml following a single administration of the formulation to human subjects less than 65 years of age. In some embodiments, the rofecoxib formulation achieves a mean $AUC_{0-\infty}$ of more than 3100 h*ng/ml following a single administration of the formulation to human subjects less than 65 years of age. In some embodiments, the rofecoxib formulation achieves a mean $AUC_{0-\infty}$ of more than 3500 h*ng/ml following a single administration of the formulation to human subjects less than 65 years of age.

In some embodiments, the rofecoxib formulation further comprises a granular component and an extragranular component, wherein the granular component comprises an intragranular component comprising the rofecoxib and one or more disintegrants, and wherein the extragranular component comprises one or more disintegrants. In some embodiments, the rofecoxib in the formulation has a d90 particle size from about 10-12 μm, a d50 particle size from about 3-4 μm, and a d10 particle size from about 0.5-1.0 μm.

In certain aspects, the subject matter disclosed herein provides a solid dosage formulation comprising 20 mg of rofecoxib and a pharmaceutically acceptable carrier.

In some embodiments, the formulation reaches a median time to Cmax plasma concentration in 4 hours or less following a single administration of the formulation to human subjects less than 65 years of age. In some embodiments, the formulation reaches a median time to Cmax plasma concentration in 3 hours or less following administration. In some embodiments, the formulation reaches a mean Cmax plasma concentration in less than 3 hours following administration. In some embodiments, the formulation reaches a median time to Cmax plasma concentration in 2.5 hours or less following administration.

In certain aspects, the subject matter disclosed herein provides a solid dosage formulation comprising 20 mg of rofecoxib and a pharmaceutically acceptable carrier, wherein the formulation achieves a mean Cmax plasma concentration of more than 150 ng/ml following a single administration of the formulation to human subjects less than 65 years of age.

In some embodiments, the rofecoxib formulation achieves a mean Cmax plasma concentration of more than 191 ng/ml, 200 ng/ml, 215 ng/ml, or 225 ng/ml following a single administration of the formulation to human subjects less than 65 years of age. In some embodiments, the rofecoxib formulation achieves a mean Cmax plasma concentration of more than 250 ng/ml following a single administration of the formulation to human subjects less than 65 years of age. In some embodiments, the rofecoxib formulation achieves a mean Cmax plasma concentration of more than 258 ng/ml following a single administration of the formulation to human subjects less than 65 years of age. In some embodiments, the rofecoxib formulation achieves a mean Cmax plasma concentration of more than 300 ng/ml following a single administration of the formulation to human subjects less than 65 years of age.

In certain aspects, the subject matter disclosed herein provides a solid dosage formulation comprising 20 mg of rofecoxib and a pharmaceutically acceptable carrier, wherein the formulation achieves a mean $AUC_{0-\infty}$ of more than 2000 h*ng/ml following a single administration of the formulation to human subjects less than 65 years of age.

In some embodiments, the formulation achieves a mean $AUC_{0-\infty}$ of more than 2500 h*ng/ml following a single administration of the formulation to human subjects less than 65 years of age. In some embodiments, the formulation achieves a mean $AUC_{0-\infty}$ of more than 3000 h*ng/ml following a single administration of the formulation to human subjects less than 65 years of age. In some embodiments, the formulation achieves a mean $AUC_{0-\infty}$ of more than 3400 h*ng/ml following a single administration of the formulation to human subjects less than 65 years of age. In some embodiments, the formulation achieves a mean $AUC_{0-\infty}$ of more than 3500 h*ng/ml following a single administration of the formulation to human subjects less than 65 years of age. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In some embodiments, the formulation further comprises a granular component and an extragranular component, wherein the granular component comprises an intragranular component comprising the rofecoxib and one or more disintegrants, and wherein the extragranular component comprises one or more disintegrants. In some embodiments, the rofecoxib in the formulation has a d90 particle size from about 10-12 μm, a d50 particle size from about 3-4 μm, and a d10 particle size from about 0.5-1.0 μm.

In certain aspects, the subject matter disclosed herein provides a method for treating pain, fever, or inflammation in a subject by administering a 25 mg solid dosage formulation of rofecoxib or a pharmaceutically acceptable salt thereof, wherein the formulation achieves a mean Cmax plasma concentration in less than 3 hours following a single administration of the formulation to human subjects less than 65 years of age.

In some embodiments, the rofecoxib formulation achieves a median time to Cmax plasma concentration in 2.5 hours or less following administration of the formulation to human subjects less than 65 years of age.

In certain aspects, the subject matter disclosed herein provides a method for treating pain, fever, or inflammation in a subject by administering a 25 mg solid dosage formulation of rofecoxib or a pharmaceutically acceptable salt thereof, wherein the formulation achieves a mean Cmax plasma concentration of more than 250 ng/ml following a single administration of the formulation to human subjects less than 65 years of age.

In some embodiments, the formulation achieves a mean Cmax plasma concentration of more than 300 ng/ml following administration of the formulation to human subjects less than 65 years of age. In some embodiments, the formulation achieves a mean Cmax plasma concentration of more than 320 ng/ml following administration of the formulation to human subjects less than 65 years of age. In some embodiments, the formulation achieves a mean Cmax plasma concentration of more than 350 ng/ml following administration of the formulation to human subjects less than 65 years of age.

In certain aspects, the subject matter disclosed herein provides a method for treating pain, fever, or inflammation in a subject by administering a 25 mg solid dosage formulation of rofecoxib or a pharmaceutically acceptable salt thereof, wherein the formulation achieves a mean $AUC_{0-\infty}$ of more than 4250 h*ng/ml following a single administration of the formulation to human subjects less than 65 years of age.

In some embodiments, the formulation achieves a mean $AUC_{0-\infty}$ of more than 4500 h*ng/ml following administration of the formulation to human subjects less than 65 years of age. In some embodiments, the formulation achieves a mean $AUC_{0-\infty}$ of more than 4700 h*ng/ml following administration of the formulation to human subjects less than 65 years of age. In some embodiments, the formulation achieves a mean $AUC_{0-\infty}$ of more than 5000 h*ng/ml following administration of the formulation to human subjects less than 65 years of age. In some embodiments, the formulation further comprises a granular component and an extragranular component, wherein the granular component comprises an intragranular component comprising the rofecoxib and one or more disintegrants, and wherein the extragranular component comprises one or more disintegrants.

In some embodiments, the rofecoxib in the formulation has a d90 particle size from about 10-12 μm, a d50 particle size from about 3-4 μm, and a d10 particle size from about 0.5-1.0 μm.

In certain aspects, the subject matter disclosed herein provides a method for treating pain, fever, or inflammation in a subject by administering a 25 mg solid dosage formulation of rofecoxib or a pharmaceutically acceptable salt thereof, wherein a single administration of the formulation to human subjects achieves a mean Cmax plasma concentration of more than 240 ng/ml in less than 3 hours following administration with a mean $AUC_{0-\infty}$ of more than 4250 h*ng/ml.

In certain aspects, the subject matter disclosed herein provides a method for treating pain, fever, or inflammation in a subject by administering a 17.5 mg solid dosage formulation of rofecoxib or a pharmaceutically acceptable salt thereof.

In some embodiments, the rofecoxib formulation achieves a median time to Cmax plasma concentration in 4 hours or less following a single administration of the formulation to human subjects less than 65 years of age. In some embodiments, the rofecoxib formulation achieves a median time to Cmax plasma concentration in 3.5 hours or less following administration. In some embodiments, the rofecoxib formulation achieves a median time to Cmax plasma concentration in 3 hours or less following administration. In some embodiments, the rofecoxib formulation achieves a median time to Cmax plasma concentration in 2.5 hours or less following administration.

In certain aspects, the subject matter disclosed herein provides a method for treating pain, fever, or inflammation in a subject by administering a 17.5 mg solid dosage formulation of rofecoxib or a pharmaceutically acceptable salt thereof, wherein a single administration of the formulation to human subjects less than 65 years of age achieves a mean Cmax plasma concentration of more than 100 ng/ml.

In some embodiments, the rofecoxib formulation achieves a mean Cmax plasma concentration of more than 150 ng/ml, 167 ng/ml, or 190 ng/ml. In some embodiments, the rofecoxib formulation achieves a mean Cmax plasma concentration of more than 200 ng/ml. In some embodiments, the rofecoxib formulation achieves a mean Cmax plasma concentration of more than 220 ng/ml. In some embodiments, the rofecoxib formulation achieves a mean Cmax plasma concentration of more than 250 ng/ml.

In certain aspects, the subject matter disclosed herein provides a method for treating pain, fever, or inflammation in a subject by administering a 17.5 mg solid dosage formulation of rofecoxib or a pharmaceutically acceptable salt thereof, wherein a single administration of the formulation to human subjects less than 65 years of age achieves a mean $AUC_{0-\infty}$ of more than 1750 h*ng/ml.

In some embodiments, the rofecoxib formulation achieves a mean $AUC_{0-\infty}$ of more than 2000 h*ng/ml. In some embodiments, the rofecoxib formulation achieves a mean $AUC_{0-\infty}$ of more than 2500 h*ng/ml. In some embodiments, the rofecoxib formulation achieves a mean $AUC_{0-\infty}$ of more than 3000 h*ng/ml. In some embodiments, the rofecoxib formulation achieves a mean $AUC_{0-\infty}$ of more than 3100 h*ng/ml. In some embodiments, the rofecoxib formulation achieves a mean $AUC_{0-\infty}$ of more than 3500 h*ng/ml.

In certain aspects, the subject matter disclosed herein provides a method for treating pain, fever, or inflammation in a subject by administering a 17.5 mg solid dosage formulation of rofecoxib or a pharmaceutically acceptable salt thereof, wherein a single administration of the formulation to human subjects less than 65 years of age achieves a mean Cmax plasma concentration within 80% to 125% of 224 ng/ml.

In certain aspects, the subject matter disclosed herein provides a method for treating pain, fever, or inflammation in a subject by administering a 17.5 mg solid dosage formulation of rofecoxib or a pharmaceutically acceptable salt thereof, wherein the formulation reaches a Cmax plasma concentration of least 170 ng/ml in the subject.

In some embodiments, the formulation reaches a Cmax plasma concentration level of at least 175 ng/ml. In some embodiments, the formulation reaches a Cmax plasma concentration level of at least 180 ng/ml. In some embodiments, the formulation reaches a Cmax plasma concentration level of at least 185 ng/ml. In some embodiments, the formulation reaches a Cmax plasma concentration level of at least 190 ng/ml.

In certain aspects, the subject matter disclosed herein provides a method for treating pain, fever, or inflammation in a subject by administering a 17.5 mg solid dosage formulation of rofecoxib or a pharmaceutically acceptable salt thereof, wherein the formulation reaches an $AUC_{0-\infty}$ of more than 2600 h*ng/ml in the subject.

In some embodiments, the rofecoxib formulation reaches an $AUC_{0-\infty}$ of more than 2750 h*ng/ml. In some embodiments, the rofecoxib formulation reaches an $AUC_{0-\infty}$ of more than 2900 h*ng/ml. In some embodiments, the rofecoxib formulation reaches an $AUC_{0-\infty}$ of more than 3050 h*ng/ml. In some embodiments, the rofecoxib formulation reaches an $AUC_{0-\infty}$ of more than 3200 h*ng/ml. In some embodiments, the rofecoxib formulation reaches an $AUC_{0-\infty}$ of more than 3350 h*ng/ml.

In certain aspects, the subject matter disclosed herein provides a method for treating pain, fever, or inflammation in a subject by administering a 20 mg solid dosage formulation of rofecoxib or a pharmaceutically acceptable salt thereof.

In some embodiments, the rofecoxib formulation achieves a median time to Cmax plasma concentration in 4 hours or less following a single administration of the formulation to human subjects. In some embodiments, the rofecoxib formulation achieves a median time to Cmax plasma concentration in 3.5 hours or less following administration. In some embodiments, the rofecoxib formulation achieves a median time to Cmax plasma concentration in 3 hours or less following administration. In some embodiments, the rofecoxib formulation achieves a median time to Cmax plasma concentration in 2.5 hours or less following administration.

In certain aspects, the subject matter disclosed herein provides a method for treating pain, fever, or inflammation in a subject by administering a 20 mg solid dosage formulation of rofecoxib or a pharmaceutically acceptable salt thereof, wherein a single administration of the formulation to human subjects less than 65 years of age achieves a mean Cmax plasma concentration of more than 150 ng/ml.

In some embodiments, the rofecoxib formulation achieves a mean Cmax plasma concentration of more than 191 ng/ml, 200 ng/ml, 215 ng/ml, or 225 ng/ml. In some embodiments, the rofecoxib formulation achieves a mean Cmax plasma concentration of more than 250 ng/ml. In some embodiments, the rofecoxib formulation achieves a mean Cmax plasma concentration of more than 258 ng/ml. In some embodiments, the formulation achieves a mean Cmax plasma concentration of more than 300 ng/ml.

In certain aspects, the subject matter disclosed herein provides a method for treating pain, fever, or inflammation in a subject by administering a 20 mg solid dosage formulation of rofecoxib or a pharmaceutically acceptable salt thereof, wherein a single administration of the formulation to human subjects less than 65 years of age achieves a mean $AUC_{0-\infty}$ of more than 2000 h*ng/ml.

In some embodiments, the rofecoxib formulation achieves a mean $AUC_{0-\infty}$ of more than 2500 h*ng/ml. In some embodiments, the rofecoxib formulation achieves a mean $AUC_{0-\infty}$ of more than 3000 h*ng/ml. In some embodiments, the rofecoxib formulation achieves a mean $AUC_{0-\infty}$ of more than 3400 h*ng/ml. In some embodiments, the rofecoxib formulation achieves a mean $AUC_{0-\infty}$ of more than 3500 h*ng/ml.

In certain aspects, the subject matter disclosed herein provides a method for treating pain, fever, or inflammation in a subject by administering a 20 mg solid dosage formulation of rofecoxib or a pharmaceutically acceptable salt thereof, wherein a single administration of the formulation to human subjects less than 65 years of age achieves a mean Cmax plasma concentration within 80% to 125% of 259 ng/ml. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In certain aspects, the subject matter disclosed herein provides a method for treating pain, fever, or inflammation in a subject by administering a 20 mg solid dosage formulation of rofecoxib or a pharmaceutically acceptable salt thereof, wherein the formulation reaches a Cmax plasma concentration of least 170 ng/ml in the subject.

In some embodiments, the rofecoxib formulation reaches a Cmax plasma concentration level of at least 190 ng/ml. In some embodiments, the rofecoxib formulation reaches a Cmax plasma concentration level of at least 205 ng/ml. In some embodiments, the rofecoxib formulation reaches a Cmax plasma concentration level of at least 220 ng/ml. In some embodiments, the rofecoxib formulation reaches a Cmax plasma concentration level of at least 235 ng/ml. In some embodiments, the rofecoxib formulation reaches a Cmax plasma concentration level of at least 250 ng/ml.

In certain aspects, the subject matter disclosed herein provides a method for treating pain, fever, or inflammation in a subject by administering a 20 mg solid dosage formulation of rofecoxib or a pharmaceutically acceptable salt thereof, wherein the formulation reaches an $AUC_{0-\infty}$ of more than 3000 h*ng/ml in the subject.

In some embodiments, the rofecoxib formulation reaches an $AUC_{0-\infty}$ of more than 3200 h*ng/ml. In some embodiments, the rofecoxib formulation reaches an $AUC_{0-\infty}$ of more than 3300 h*ng/ml. In some embodiments, the rofecoxib formulation reaches an $AUC_{0-\infty}$ of more than 3400 h*ng/ml. In some embodiments, the rofecoxib formulation reaches an $AUC_{0-\infty}$ of more than 3500 h*ng/ml. In some embodiments, the rofecoxib formulation reaches an $AUC_{0-\infty}$ of more than 3525 h*ng/ml. In some embodiments, the rofecoxib formulation reaches an $AUC_{0-\infty}$ of 3550 h*ng/ml or more. In some embodiments, the rofecoxib formulation achieves a mean Cmax plasma concentration within 80% to 125% of 259 ng/ml and a mean $AUC_{0-\infty}$ within 80% to 125% of 3550 h*ng/ml.

In certain aspects, the subject matter disclosed herein provides a pharmaceutically acceptable formulation comprising a granular component and an extragranular component, wherein the granular component comprises an intragranular component comprising rofecoxib or a pharmaceutically acceptable salt thereof and one or more disintegrants, and wherein the extragranular component comprises one or more disintegrants.

In some embodiments, the one or more disintegrants in the granular component is selected from starches, clays, celluloses, algins, gums, cross-linked polymers, and combinations thereof. In some embodiments, the one or more disintegrants in the granular component is selected from croscarmellose, crospovidone, sodium starch glycolate, and combinations thereof. In some embodiments, one or more disintegrants in the granular component is croscarmellose sodium. In some embodiments, the one or more disintegrants in the granular component is about 1% (w/w) to about 8% (w/w) of the formulation. In some embodiments, the one or more disintegrants in the granular component is about 1% (w/w) to about 6% (w/w) of the formulation. In some embodiments, the one or more disintegrants in the granular component is about 1% (w/w) to about 4% (w/w) of the formulation. In some embodiments, the one or more disintegrants in the extragranular component is selected from starches, clays, celluloses, algins, gums, cross-linked polymers, and combinations thereof. In some embodiments, the one or more disintegrants in the extragranular component is selected from croscarmellose, crospovidone, sodium starch glycolate, and combinations thereof. In some embodiments, the one or more disintegrants in the extragranular component is croscarmellose sodium.

In some embodiments, the disintegrant in the extragranular component is about 1% (w/w) to about 8% (w/w) of the formulation. In some embodiments, the disintegrant in the extragranular component is about 1% (w/w) to about 6% (w/w) of the formulation. In some embodiments, the disintegrant in the extragranular component is about 1% (w/w) to about 4% (w/w) of the formulation. In some embodiments, the disintegrant in the granular component and the disintegrant in the extragranular component are together about 2% (w/w) to about 12% (w/w) of the formulation. In some embodiments, the disintegrant in the granular component and the disintegrant in the extragranular component are together about 2% (w/w) to about 10% (w/w) of the formulation. In some embodiments, the disintegrant in the granular component and the disintegrant in the extragranular component are together about 2% (w/w) to about 8% (w/w) of the formulation. In some embodiments, the ratio of granular disintegrant to extragranular disintegrant is about 40% to about 60% (w/w). In some embodiments, the ratio of granular disintegrant to extragranular disintegrant is about 45% to about 55% (w/w). In some embodiments, the ratio of granular disintegrant to extragranular disintegrant is about 50% to about 50% (w/w). In some embodiments, the ratio of granular disintegrant to extragranular disintegrant is about 55% to about 45% (w/w). In some embodiments, the ratio of granular disintegrant to extragranular disintegrant is about 60% to about 40% (w/w).

In some embodiments, the pharmaceutically acceptable formulation form further comprises one or more of a diluent, a binder, a coloring agent, and a lubricant. In some embodiments, at least a portion of the diluent is in the granular component. In some embodiments, the diluent is selected from dicalcium phosphate, calcium sulfate, lactose, cellulose, kaolin, mannitol, sodium chloride, dry starch, powdered sugar, sorbitol, sucrose, inositol, and combinations thereof. In some embodiments, the diluent is selected from lactose, cellulose, or a combination thereof. In some embodiments, the diluent is selected from lactose monohydrate, microcrystalline cellulose, or a combination thereof.

In some embodiments, the lactose monohydrate is about 35% (w/w) to about 45% (w/w) of the formulation. In some embodiments, the lactose monohydrate is about 37% (w/w) to about 42% (w/w) of the formulation. In some embodiments, the lactose monohydrate is about 39% (w/w) to about 40% (w/w) of the formulation. In some embodiments, the microcrystalline cellulose is about 35% (w/w) to about 45% (w/w) of the formulation. In some embodiments, the microcrystalline cellulose is about 37% (w/w) to about 42% (w/w) of the formulation. In some embodiments, the microcrystalline cellulose is about 39% (w/w) to about 40% (w/w) of the formulation. In some embodiments, the diluent is about 75% (w/w) to about 85% (w/w) of the formulation. In some embodiments, the diluent is about 77% (w/w) to about 82% (w/w) of the formulation. In some embodiments, the diluent is about 78% (w/w) to about 80% (w/w) of the formulation.

In some embodiments, at least a portion of the binder is in the granular component. In some embodiments, the binder is selected from starches, gelatins, sugars, gums, waxes, water, alcohols, celluloses, and combinations thereof. In some embodiments, the binder is selected from acacia gum, tragacanth, corn starch, methyl cellulose, panwar gum, ghatti gum, mucilage of isapol husks, carboxymethylcellulose, methylcellulose, polyvinylpyrrolidone, sucrose, glucose, dextrose, molasses, lactose, and combinations thereof. In some embodiments, the binder is hydroxypropyl cellulose.

In some embodiments, the binder is about 1% (w/w) to about 5% (w/w) of the formulation. In some embodiments, the binder is about 2% (w/w) to about 4% (w/w) of the formulation. In some embodiments, the binder is about 2.5% (w/w) to about 3.5% (w/w) of the formulation.

In some embodiments, at least a portion of the coloring agent is in the extragranular component. In some embodiments, the coloring agent is pigment blend yellow. In some embodiments, the coloring agent is about 0.30% (w/w) to about 0.60% (w/w) of the formulation.

In some embodiments, at least a portion of the lubricant is in the extragranular component. In some embodiments, the lubricant is selected from talc, magnesium stearate, calcium stearate, stearic acid, metallic stearate, hydrogenated vegetable oils, and polyethylene glycol, corn starch, boric acids, sodium chloride, sodium lauryl sulphate. In some embodiments, the lubricant is magnesium stearate. In some embodiments, the lubricant is about 0.10% (w/w) to about 1% (w/w) of the formulation. In some embodiments, the lubricant is about 0.50% (w/w) of the formulation.

In some embodiments, the rofecoxib or pharmaceutically acceptable salt thereof is about 5% (w/w) to about 30% (w/w) of the formulation. In some embodiments, the rofecoxib or pharmaceutically acceptable salt thereof is about 10% (w/w) to about 20% (w/w) of the formulation. In some embodiments, the rofecoxib or pharmaceutically acceptable salt thereof is about 12% (w/w) to about 13% (w/w) of the formulation.

In some embodiments, the formulation comprises about 10 mg of the rofecoxib or pharmaceutically acceptable salt thereof. In some embodiments, the formulation comprises about 12.5 mg of the rofecoxib or pharmaceutically acceptable salt thereof. In some embodiments, the formulation comprises about 17.5 mg of the rofecoxib or pharmaceutically acceptable salt thereof. In some embodiments, the formulation comprises about 20 mg of the rofecoxib or pharmaceutically acceptable salt thereof. In some embodiments, the formulation comprises about 25 mg of the rofecoxib or pharmaceutically acceptable salt thereof.

In some embodiments, the rofecoxib is substantially pure. In some embodiments, the rofecoxib is highly pure. In some embodiments, the highly pure rofecoxib comprises less than about 0.1% total impurities. In some embodiments, the highly pure rofecoxib comprises less than about 0.075% total impurities. In some embodiments, the highly pure rofecoxib comprises less than about 0.050% total impurities. In some embodiments, the highly pure rofecoxib comprises less than about 0.025% total impurities. In some embodiments, the highly pure rofecoxib comprises less than about 0.001% total impurities.

In some embodiments, the rofecoxib is substantially pure or highly pure. In some embodiments, the highly pure rofecoxib comprises less than about 0.10%, 0.05%, 0.02%, or 0.01% of 4-[4-(methylsulphonyl)phenyl]-3-phenyl-2,5-furandione. In some embodiments, the highly pure rofecoxib comprises less than about 0.10%, 0.05%, 0.02%, or 0.01% of 4-[4-(methylsulfonyl)phenyl]-3-phenyl-5-hydroxyfuran-2-one. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylsulfinyl)phenyl]-3-phenyl-2(5H)-furanone.

In some embodiments, the formulation is suitable for oral administration. In some embodiments, the formulation is a solid dosage form. In some embodiments, the solid dosage form is an oral tablet.

In some embodiments, the oral tablet provides a dissolution rate of at least about 80% of the rofecoxib or pharmaceutically acceptable salt thereof by about 15 minutes. In some embodiments, the oral tablet provides a dissolution rate of at least about 85% of the rofecoxib or pharmaceutically acceptable salt thereof by about 15 minutes. In some embodiments, the oral tablet provides a dissolution rate of at least about 90% of the rofecoxib or pharmaceutically acceptable salt thereof by about 15 minutes. In some embodiments, the oral tablet provides a dissolution rate of at least about 95% of the rofecoxib or pharmaceutically acceptable salt thereof by about 15 minutes. In some embodiments, the oral tablet provides a dissolution rate of at least about 100% of the rofecoxib or pharmaceutically acceptable salt thereof by about 15 minutes.

In some embodiments, the dissolution rate is measured in about 1% SDS at a paddle speed of about 50 rpm and at a temperature of about 37.0° C.±0.5° C. In some embodiments, the dissolution rate is measured in about 1% SDS at a paddle speed of about 75 rpm and at a temperature of about 37.0° C.±0.5° C. In some embodiments, the dissolution rate is measured in about 1.5% SDS at a paddle speed of about 50 rpm and at a temperature of about 37.0° C.±0.5° C. In some embodiments, the dissolution rate is measured in about 1.5% SDS at a paddle speed of about 75 rpm and at a temperature of about 37.0° C.±0.5° C. In some embodiments, the dissolution rate is measured in about 2% SDS at a paddle speed of about 50 rpm and at a temperature of about 37.0° C.±0.5° C. In some embodiments, the dissolution rate is measured in about 2% SDS at a paddle speed of about 75 rpm and at a temperature of about 37.0° C.±0.5° C.

In some embodiments, the rofecoxib or pharmaceutically acceptable salt thereof is formulated into granules and at least about 35% of the granules are less than about 75 μm. In some embodiments, the rofecoxib or pharmaceutically acceptable salt thereof is formulated into granules and at least about 55% of the granules are less than about 150 μm. In some embodiments, the rofecoxib or pharmaceutically acceptable salt thereof is formulated into granules and at least about 75% of the granules are less than about 250 μm. In some embodiments, the rofecoxib or pharmaceutically acceptable salt thereof is formulated into granules and at least about 85% of the granules are less than about 425 μm. In some embodiments, the rofecoxib or pharmaceutically acceptable salt thereof is formulated into granules and at least about 90% of the granules are less than about 1000 μm.

In some embodiments, the formulation is a solid dosage formulation comprising 12.5 mg, 17.5 mg, 20 mg, or 25 mg of rofecoxib, and wherein the formulation reaches a median time to Cmax plasma concentration in 3 hours or less following a single administration of the formulation to human subjects less than 65 years of age.

In some embodiments, the formulation reaches a mean Cmax plasma concentration in less than 3 hours following administration. In some embodiments, the formulation reaches a mean Cmax plasma concentration in less than 2.5 hours following administration. In some embodiments, the formulation reaches a mean Cmax plasma concentration in less than 2 hours following administration. In some embodiments, the formulation is a solid dosage formulation comprising 25 mg of rofecoxib, and wherein a single administration of the formulation to human subjects less than 65 years of age achieves a mean Cmax plasma concentration of more than 240 ng/ml. In some embodiments, the formulation achieves a mean Cmax plasma concentration of more than 300 ng/ml. In some embodiments, the formulation achieves a mean Cmax plasma concentration of more than 320 ng/ml. In some embodiments, the formulation achieves a mean Cmax plasma concentration of more than 350 ng/ml.

In some embodiments, the formulation is a solid dosage formulation comprising 25 mg of rofecoxib, and wherein a single administration of the formulation to human subjects less than 65 years of age achieves a mean $AUC_{0-\infty}$ of more than 4500 h*ng/ml. In some embodiments, the formulation achieves a mean $AUC_{0-\infty}$ of more than 4700 h*ng/ml. In some embodiments, the formulation achieves a mean $AUC_{0-\infty}$ of more than 5000 h*ng/ml.

In some embodiments, the formulation is a solid dosage formulation comprising 25 mg of rofecoxib, and wherein a single administration of the formulation in human subjects less than 65 years of age reaches a mean Cmax plasma concentration of more than 240 ng/ml in less than 3 hours following administration with a mean $AUC_{0-\infty}$ of more than 4250 h*ng/ml.

In certain aspects, the subject matter disclosed herein provides a solid dosage formulation comprising 10 mg to 50 mg of rofecoxib and a pharmaceutically acceptable carrier, wherein a single administration of the formulation in human subjects less than 65 years of age achieves a mean Cmax plasma concentration from 9.8 ng/ml to 16 ng/ml for each 1 mg of rofecoxib in the formulation.

In some embodiments, the formulation achieves a mean Cmax plasma concentration from 10 ng/ml to 14 ng/ml for each 1 mg of rofecoxib in the formulation. In some embodiments, the formulation achieves a mean Cmax plasma concentration from 10 ng/ml to 13 ng/ml for each 1 mg of rofecoxib in the formulation. In some embodiments, the formulation achieves a mean Cmax plasma concentration from 80% to 125% of 12.8 ng/ml.

In certain aspects, the subject matter disclosed herein provides a solid dosage formulation comprising 10 mg to 50 mg of rofecoxib and a pharmaceutically acceptable carrier, wherein a single administration of the formulation in human subjects less than 65 years of age achieves a mean $AUC_{0-\infty}$ of 170 h*ng/ml to 235 h*ng/ml for each 1 mg of rofecoxib in the formulation.

In some embodiments, the formulation achieves a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the formulation achieves a mean $AUC_{0-\infty}$ of 190 h*ng/ml to 215 h*ng/ml for each 1 mg of rofecoxib in the formulation.

In certain aspects, the subject matter disclosed herein provides a method of inhibiting COX-2 in a subject by administering the formulations described herein.

In certain aspects, the subject matter disclosed herein provides a method of inhibiting COX-2 in a subject by administering a solid dosage formulation comprising 17.5 mg of rofecoxib.

In some embodiments, the formulation is a solid dosage formulation comprising 17.5 mg of rofecoxib, wherein a single administration of the formulation to human subjects less than 65 years of age achieves a mean Cmax that is equal to or greater than that reported by Schwartz, J. I., et al. Clin. Drug Invent. 2003, 23 (8): 503-509 for a rofecoxib 25 mg tablet. In some embodiments, the formulation is a solid dosage formulation comprising 17.5 mg of rofecoxib, wherein a single administration of the formulation to human subjects less than 65 years of age achieves a mean Cmax that is equal to or greater than that reported in the FDA-approved label for VIOXX for a single 25-mg dose of VIOXX. In some embodiments, the formulation is a solid dosage formulation comprising 20 mg of rofecoxib, where a single administration of the formulation to human subjects less than 65 years of age achieves a mean $AUC_{0-\infty}$ that is equal to or greater than that reported by Schwartz, J. I., et al. Clin. Drug Invent. 2003, 23 (8): 503-509 for a rofecoxib 25 mg tablet. In some embodiments, the formulation is a solid dosage formulation comprising 20 mg of rofecoxib, where a single administration of the formulation to human subjects less than 65 years of age achieves a mean Cmax that is equal to or greater than that reported by Schwartz, J. I., et al. Clin. Drug Invent. 2003, 23 (8): 503-509 for a rofecoxib 25 mg tablet. In some embodiments, the formulation is a solid dosage formulation comprising 20 mg of rofecoxib, wherein a single administration of the formulation to human subjects less than 65 years of age achieves a mean $AUC_{0-\infty}$ that is equal to or greater than that reported in the FDA-approved label for VIOXX for a single 25-mg dose of VIOXX. In some embodiments, the formulation is a solid dosage formulation comprising 20 mg of rofecoxib, wherein a single administration of the formulation to human subjects less than 65 years of age achieves a mean Cmax that is equal to or greater than that reported in the FDA-approved label for VIOXX for a single 25-mg dose of VIOXX.

In some embodiments, the patient is age 2 or older.

In certain aspects, the subject matter disclosed herein provides a method for treating pain, fever, or inflammation in a patient by administering the formulations as described herein.

In some embodiments, the human subjects are healthy human subjects. In some embodiments, the patient is age 2 or older.

In certain aspects, the subject matter disclosed herein provides a method for treating pain, fever, or inflammation in a patient population comprising providing a solid dosage formulation comprising 10 mg to 50 mg of rofecoxib to the patient population for inhibiting COX-2, wherein the formulation achieves a mean Cmax plasma concentration of between 80 to 125% of 12.8 ng/ml for each 1 mg of rofecoxib in the formulation following single administration of the formulation in the patient population.

Further Embodiments of the Present Subject Matter

In certain aspects, the subject matter disclosed herein provides a pharmaceutically acceptable formulation comprising granules. In some embodiments, the pharmaceutically acceptable formulation comprises a granular component and an extragranular component, wherein the granular component comprises an intragranular component comprising rofecoxib or a pharmaceutically acceptable salt thereof and one or more disintegrants, and wherein the extragranular component comprises one or more disintegrants.

In some embodiments, the one or more disintegrants in the granular component is selected from starches, clays, celluloses, algins, gums, cross-linked polymers, and combinations thereof. In some embodiments, the one or more disintegrants in the granular component is selected from croscarmellose, crospovidone, sodium starch glycolate, and combinations thereof.

In some embodiments, the one or more disintegrants in the granular component is croscarmellose sodium. In some embodiments, the one or more disintegrants in the granular component is about 1% (w/w) to about 8% (w/w) of the formulation. In some embodiments, the one or more disintegrants in the granular component is about 1% (w/w) to about 6% (w/w) of the formulation. In some embodiments, the one or more disintegrants in the granular component is about 1% (w/w) to about 4% (w/w) of the formulation.

In some embodiments, the one or more disintegrants in the extragranular component is selected from starches, clays, celluloses, algins, gums, cross-linked polymers, and combinations thereof. In some embodiments, the one or more disintegrants in the extragranular component is selected from croscarmellose, crospovidone, sodium starch glycolate, and combinations thereof. In some embodiments, the one or more disintegrants in the extragranular component is croscarmellose sodium. In some embodiments, the disintegrant in the extragranular component is about 1% (w/w) to about 8% (w/w) of the formulation. In some embodiments, the disintegrant in the extragranular component is about 1% (w/w) to about 6% (w/w) of the formulation. In some embodiments, the disintegrant in the extragranular component is about 1% (w/w) to about 4% (w/w) of the formulation.

In some embodiments, the disintegrant in the granular component and the disintegrant in the extragranular component are together about 2% (w/w) to about 12% (w/w) of the formulation. In some embodiments, the disintegrant in the granular component and the disintegrant in the extragranular component are together about 2% (w/w) to about 10% (w/w) of the formulation. In some embodiments, the disintegrant in the granular component and the disintegrant in the extragranular component are together about 2% (w/w) to about 8% (w/w) of the formulation.

In some embodiments, the ratio of granular disintegrant to extragranular disintegrant is about 40% (w/w) to about 60% (w/w). In some embodiments, the ratio of granular disintegrant to extragranular disintegrant is about 45% (w/w) to about 55% (w/w). In some embodiments, the ratio of granular disintegrant to extragranular disintegrant is about 50% (w/w) to about 50% (w/w). In some embodiments the ratio of granular disintegrant to extragranular disintegrant is about 55% (w/w) to about 45% (w/w). In some embodiments the ratio of granular disintegrant to extragranular disintegrant is about 60% (w/w) to about 40% (w/w).

In some embodiments, the pharmaceutically acceptable formulation further comprising one or more of a diluent, a binder, a coloring agent, and a lubricant. In some embodiments, at least a portion of the diluent is in the granular component. In some embodiments, the diluent is selected from dicalcium phosphate, calcium sulfate, lactose, cellulose, kaolin, mannitol, sodium chloride, dry starch, powdered sugar, sorbitol, sucrose, inositol, and combinations thereof. In some embodiments, the diluent is selected from lactose, cellulose, or a combination thereof. In some embodiments, the diluent is selected from lactose monohydrate, microcrystalline cellulose, or a combination thereof.

In some embodiments, the lactose monohydrate is about 35% (w/w) to about 45% (w/w) of the formulation. In some embodiments, the lactose monohydrate is about 37% (w/w) to about 42% (w/w) of the formulation. In some embodiments, the lactose monohydrate is about 39% (w/w) to about 40% (w/w) of the formulation.

In some embodiments, the microcrystalline cellulose is about 35% (w/w) to about 45% (w/w) of the formulation. In some embodiments, the microcrystalline cellulose is about 37% (w/w) to about 42% (w/w) of the formulation. In some embodiments, the microcrystalline cellulose is about 39% (w/w) to about 40% (w/w) of the formulation.

In some embodiments, the diluent is about 75% (w/w) to about 85% (w/w) of the formulation. In some embodiments, diluent is about 77% (w/w) to about 82% (w/w) of the formulation. In some embodiments, the diluent is about 78% (w/w) to about 80% (w/w) of the formulation.

In some embodiments, at least a portion of the binder is in the granular component. In some embodiments, the binder is selected from starches, gelatins, sugars, gums, waxes, water, alcohols, celluloses, and combinations thereof. In some embodiments, the binder is selected from acacia gum, tragacanth, corn starch, methyl cellulose, panwar gum, ghatti gum, mucilage of isapol husks, carboxymethylcellulose, methylcellulose, polyvinylpyrrolidone, sucrose, glucose, dextrose, molasses, lactose, and combinations thereof. In some embodiments, the binder is hydroxypropyl cellulose. In some embodiments, the binder is about 1% (w/w) to about 5% (w/w) of the formulation. In some embodiments, binder is about 2% (w/w) to about 4% (w/w) of the formulation. In some embodiments, the binder is about 2.5% (w/w) to about 3.5% (w/w) of the formulation.

In some embodiments, at least a portion of the coloring agent is in the extragranular component. In some embodiments, the coloring agent is pigment blend yellow. In some embodiments, the coloring agent is about 0.30% (w/w) to about 0.60% (w/w) of the formulation.

In some embodiments, at least a portion of the lubricant is in the extragranular component. In some embodiments, the lubricant is selected from talc, magnesium stearate, calcium stearate, stearic acid, metallic stearate, hydrogenated vegetable oils, and polyethylene glycol, corn starch, boric acids, sodium chloride, sodium lauryl sulphate. In some embodiments, the lubricant is magnesium stearate. In some embodiments, the lubricant is about 0.10% (w/w) to about 1% (w/w) of the formulation. In some embodiments, the lubricant is about 0.50% (w/w) of the formulation.

In some embodiments, the rofecoxib or pharmaceutically acceptable salt thereof is about 5% (w/w) to about 30% (w/w) of the formulation. In some embodiments, the rofecoxib or pharmaceutically acceptable salt thereof is about 10% (w/w) to about 20% (w/w) of the formulation. In some embodiments, the rofecoxib or pharmaceutically acceptable salt thereof is about 12% (w/w) to about 13% (w/w) of the formulation. In some embodiments, the formulation comprises about 10 mg of the rofecoxib or pharmaceutically acceptable salt thereof. In some embodiments, the formulation comprises about 10.5 mg of the rofecoxib or pharmaceutically acceptable salt thereof. In some embodiments, the formulation comprises about 11 mg of the rofecoxib or pharmaceutically acceptable salt thereof. In some embodiments, the formulation comprises about 11.5 mg of the rofecoxib or pharmaceutically acceptable salt thereof. In some embodiments, the formulation comprises about 12 mg of the rofecoxib or pharmaceutically acceptable salt thereof. In some embodiments, the formulation comprises about 12.5 mg of the rofecoxib or pharmaceutically acceptable salt thereof. In some embodiments, the formulation comprises about 17.5 mg of the rofecoxib or pharmaceutically acceptable salt thereof. In some embodiments, the formulation comprises about 20 mg of the rofecoxib or pharmaceutically acceptable salt thereof. In some embodiments, the formulation comprises about 21 mg of the rofecoxib or pharmaceutically acceptable salt thereof. In some embodiments, the formulation comprises about 22 mg of the rofecoxib or pharmaceutically acceptable salt thereof. In some embodiments, the formulation comprises about 22.5 mg of the rofecoxib or pharmaceutically acceptable salt thereof. In some embodiments, the formulation comprises about 25 mg of the rofecoxib or pharmaceutically acceptable salt thereof. In some embodiments, the formulation comprises about 50 mg of the rofecoxib or pharmaceutically acceptable salt thereof.

In some embodiments, the rofecoxib is highly pure. In some embodiments, the highly pure rofecoxib comprises less than about 0.1% total impurities. In some embodiments, the highly pure rofecoxib comprises less than about 0.075% total impurities. In some embodiments, the highly pure rofecoxib comprises less than about 0.050% total impurities. In some embodiments, the highly pure rofecoxib comprises less than about 0.025% total impurities. In some embodiments, the highly pure rofecoxib comprises less than about 0.001% total impurities.

In some embodiments, the highly pure rofecoxib comprises less than about 0.10%, 0.05%, 0.02%, or 0.01% of 4-[4-(methylsulphonyl)phenyl]-3-phenyl-2,5-furandione. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylsulfinyl)phenyl]-3-phenyl-2(5H)-furanone.

In some embodiments, the formulation is suitable for oral administration. In some embodiments, the formulation is a solid dosage form. In some embodiments, the solid dosage form is an oral tablet. In some embodiments, the oral tablet provides a dissolution rate of at least about 80% of the rofecoxib or pharmaceutically acceptable salt thereof by about 15 minutes. In some embodiments, the oral tablet provides a dissolution rate of at least about 85% of the rofecoxib or pharmaceutically acceptable salt thereof by about 15 minutes. In some embodiments, the oral tablet provides a dissolution rate of at least about 90% of the rofecoxib or pharmaceutically acceptable salt thereof by about 15 minutes. In some embodiments, the oral tablet provides a dissolution rate of at least about 95% of the rofecoxib or pharmaceutically acceptable salt thereof by about 15 minutes. In some embodiments, the oral tablet provides a dissolution rate of at least about 100% of the rofecoxib or pharmaceutically acceptable salt thereof by about 15 minutes.

In some embodiments, the dissolution rate is measured in about 1% SDS at a paddle speed of about 50 rpm and at a temperature of about 37.0° C.±0.5° C. In some embodiments, the dissolution rate is measured in about 1% SDS at a paddle speed of about 75 rpm and at a temperature of about 37.0° C.±0.5° C. In some embodiments, the dissolution rate is measured in about 1.5% SDS at a paddle speed of about 50 rpm and at a temperature of about 37.0° C.±0.5° C. In some embodiments, the dissolution rate is measured in about 1.5% SDS at a paddle speed of about 75 rpm and at a temperature of about 37.0° C.±0.5° C. In some embodiments, the dissolution rate is measured in about 2% SDS at a paddle speed of about 50 rpm and at a temperature of about 37.0° C.±0.5° C. In some embodiments, the dissolution rate is measured in about 2% SDS at a paddle speed of about 75 rpm and at a temperature of about 37.0° C.±0.5° C.

In some embodiments, the rofecoxib or pharmaceutically acceptable salt thereof is formulated into granules and at least about 35% of the granules are less than about 75 µm. In some embodiments, the rofecoxib or pharmaceutically acceptable salt thereof is formulated into granules and at least about 55% of the granules are less than about 150 µm. In some embodiments, the rofecoxib or pharmaceutically acceptable salt thereof is formulated into granules and at least about 75% of the granules are less than about 250 µm. In some embodiments, the rofecoxib or pharmaceutically acceptable salt thereof is formulated into granules and at least about 85% of the granules are less than about 425 µm. In some embodiments, the rofecoxib or pharmaceutically acceptable salt thereof is formulated into granules and at least about 90% of the granules are less than about 1000 µm.

In some embodiments, a 17.5 mg solid dosage formulation of rofecoxib reaches a median time to Cmax plasma concentration in 4 hours or less following single administration of the formulation to human subjects. In some embodiments, a 17.5 mg solid dosage formulation of rofecoxib reaches a median time to Cmax plasma concentration in 3 hours or less following administration. In some embodiments, a 17.5 mg solid dosage formulation of rofecoxib reaches a mean Cmax plasma concentration 2.5 hours following administration. In some embodiments, a 17.5 mg solid dosage formulation of rofecoxib reaches a median time to Cmax plasma concentration in 2 hours or less following administration. In some embodiments, a 17.5 mg solid dosage formulation of rofecoxib has a mean Cmax plasma concentration of more than 100 ng/ml. In some embodiments, a 17.5 mg solid dosage formulation of rofecoxib has a mean Cmax plasma concentration of more than 150 ng/ml, 167 ng/ml, or 190 ng/ml. In some embodiments, a 17.5 mg solid dosage formulation of rofecoxib has a mean Cmax plasma concentration of more than 200 ng/ml. In some embodiments, a 17.5 mg solid dosage formulation of rofecoxib has a mean Cmax plasma concentration of more than 220 ng/ml. In some embodiments, a 17.5 mg solid dosage formulation of rofecoxib has a mean Cmax plasma concentration of more than 250 ng/ml. In some embodiments, a 17.5 mg solid dosage formulation of rofecoxib has a mean Cmax plasma concentration of more than 280 ng/ml. In some embodiments, a 17.5 mg solid dosage formulation of rofecoxib has a mean $AUC_{0-\infty}$ of more than 1750 h*ng/ml. In some embodiments, a 17.5 mg solid dosage formulation of rofecoxib has a mean $AUC_{0-\infty}$ of more than 2000 h*ng/ml. In some embodiments, a 17.5 mg solid dosage formulation of rofecoxib has a mean $AUC_{0-\infty}$ of more than 2500 h*ng/ml. In some embodiments, a 17.5 mg solid dosage formulation of rofecoxib has a mean $AUC_{0-\infty}$ of more than 3000 h*ng/ml. In some embodiments, a 17.5 mg solid dosage formulation of rofecoxib has a mean $AUC_{0-\infty}$ of more than 3100 h*ng/ml. In some embodiments, a 17.5 mg solid dosage formulation of rofecoxib has a mean $AUC_{0-\infty}$ of more than 3500 h*ng/ml. In some embodiments, a 17.5 mg solid dosage formulation of rofecoxib has a mean $AUC_{0-\infty}$ of more than 4000 h*ng/ml. In some embodiments, a 17.5 mg solid dosage formulation of rofecoxib has a mean $AUC_{0-\infty}$ of more than 4500 h*ng/ml. In some embodiments, a 17.5 mg solid dosage formulation of rofecoxib reaches a Cmax plasma concentration of least 167 ng/ml, 170 ng/ml, 175 ng/ml, 180 ng/ml, or higher following single administration of the formulation to a human subject. In some embodiments, a 17.5 mg solid dosage formulation of rofecoxib reaches an $AUC_{0-\infty}$ of at least 2600 h*ng/ml, 2750 h*ng/ml, 2900 h*ng/ml, 3050 h*ng/ml, 3100 h*ng/ml, 3200 h*ng/ml, 3350 h*ng/ml, 3500 h*ng/ml, 3650 h*ng/ml or higher following single administration of the formulation to a human subject.

In some embodiments, a 20 mg solid dosage formulation of rofecoxib reaches a median time to Cmax plasma concentration in 4 hours or less following single administration of the formulation to human subjects. In some embodiments, a 20 mg solid dosage formulation of rofecoxib reaches a median time to Cmax plasma concentration in 3 hours or less following administration. In some embodiments, a 20 mg solid dosage formulation of rofecoxib reaches a median time to Cmax plasma concentration in 2.5 hours or less following administration. In some embodiments, a 20 mg solid dosage formulation of rofecoxib reaches a median time to Cmax plasma concentration in 2 hours or less following administration. In some embodiments, a 20 mg solid dosage formulation of rofecoxib has a mean Cmax plasma concentration of more than 150 ng/ml. In some embodiments, a 20 mg solid dosage formulation of rofecoxib has a mean Cmax plasma concentration of more than 191 ng/ml, 200 ng/ml, 215 ng/ml, or 225 ng/ml. In some embodiments, a 20 mg solid dosage formulation of rofecoxib has a mean Cmax plasma concentration of more than 250 ng/ml. In some embodiments, a 20 mg solid dosage formulation of rofecoxib has a mean Cmax plasma concentration of more than 258 ng/ml. In some embodiments, a 20 mg solid dosage formulation of rofecoxib has a mean Cmax plasma concentration of more than 300 ng/ml. In some embodiments, a 20 mg solid dosage formulation of rofecoxib has a mean $AUC_{0-\infty}$ of more than 2000 h*ng/ml. In some embodiments, a 20 mg solid dosage formulation of rofecoxib has a mean $AUC_{0-\infty}$ of more than 2500 h*ng/ml. In some embodiments, a 20 mg solid dosage formulation of rofecoxib has a mean $AUC_{0-\infty}$ of more than 3000 h*ng/ml. In some embodiments, a 20 mg solid dosage formulation of rofecoxib has a mean $AUC_{0-\infty}$ of more than 3400 h*ng/ml. In some embodiments, a 20 mg solid dosage formulation of rofecoxib has a mean $AUC_{0-\infty}$ of more than 3500 h*ng/ml. In some embodiments, a 20 mg solid dosage formulation of rofecoxib has a mean $AUC_{0-\infty}$ of more than 4000 h*ng/ml. In some embodiments, a 20 mg solid dosage formulation of rofecoxib reaches a Cmax plasma concentration of least 190 ng/ml, 205 ng/ml, 220 ng/ml, 235 ng/ml, 250 ng/ml, or higher following single administration of the formulation to a human subject. In some embodiments, a 20 mg solid dosage formulation of rofecoxib reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In some embodiments, a 25 mg solid dosage formulation of rofecoxib reaches a mean Cmax plasma concentration in less than 3 hours following single administration of the formulation to human subjects. In some embodiments, a 25 mg solid dosage formulation of rofecoxib reaches a mean Cmax plasma concentration in less than 2.5 hours following administration. In some embodiments, a 25 mg solid dosage formulation of rofecoxib reaches a mean Cmax plasma concentration in less than 2 hours following administration. In some embodiments, a 25 mg solid dosage formulation of rofecoxib has a mean Cmax plasma concentration of more than 240 ng/ml. In some embodiments, a 25 mg solid dosage formulation of rofecoxib has a mean Cmax plasma concentration of more than 300 ng/ml. In some embodiments, a 25 mg solid dosage formulation of rofecoxib has a mean Cmax plasma concentration of more than 320 ng/ml. In some embodiments, a 25 mg solid dosage formulation of rofecoxib has a mean Cmax plasma concentration of more than 350 ng/ml. In some embodiments, a 25 mg solid dosage formulation of rofecoxib has a mean $AUC_{0-\infty}$ of more than 4250 h*ng/ml. In some embodiments, a 25 mg solid dosage formulation of rofecoxib has a mean $AUC_{0-\infty}$ of more than 4500 h*ng/ml. In some embodiments, a 25 mg solid dosage formulation of rofecoxib has a mean $AUC_{0-\infty}$ of more than 4550 h*ng/ml. In some embodiments, a 25 mg solid dosage formulation of rofecoxib has a mean $AUC_{0-\infty}$ of more than 4700 h*ng/ml. In some embodiments, a 25 mg solid dosage formulation of rofecoxib reaches a mean Cmax plasma concentration of more than 240 ng/ml in median time of about 3 hours or less following administration with an $AUC_{0-\infty}$ of more than 4250 h*ng/ml.

In some embodiments, a solid dosage formulation of 10 mg to 50 mg of rofecoxib achieves a mean Cmax plasma concentration from 9.8 ng/ml to 16 ng/ml for each 1 mg of rofecoxib in the formulation following single administration of the formulation to human subjects. In some embodiments, the solid dosage formulation of rofecoxib achieves a mean Cmax plasma concentration from 10 ng/ml to 14 ng/ml for each 1 mg of rofecoxib in the formulation. In some embodiments, the solid dosage formulation of rofecoxib achieves a mean Cmax plasma concentration from 10 ng/ml to 13 ng/ml for each 1 mg of rofecoxib in the formulation. In some embodiments, the solid dosage formulation of rofecoxib achieves a mean Cmax plasma concentration from 80% to 125% of 12.8 ng/ml. In some embodiments, the solid dosage formulation of rofecoxib reaches a mean $AUC_{0-\infty}$ of 170 h*ng/ml to 235 h*ng/ml for each 1 mg of rofecoxib in the formulation. In some embodiments, the solid dosage formulation of rofecoxib reaches a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the solid dosage formulation of rofecoxib reaches a mean $AUC_{0-\infty}$ of 190 h*ng/ml to 215 h*ng/ml for each 1 mg of rofecoxib in the formulation.

In certain aspects, the subject matter disclosed herein provides a method for treating pain, fever, or inflammation in a subject by administering a solid dosage formulation comprising 17.5 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 100 ng/ml. In some embodiments, the formulation achieves a mean Cmax plasma concentration of more than 150 ng/ml, 167 ng/ml, or 190 ng/ml. In some embodiments, the formulation achieves a mean Cmax plasma concentration of more than 200 ng/ml. In some embodiments, the formulation achieves a mean Cmax plasma concentration of more than 220 ng/ml. In some embodiments, the formulation achieves a mean Cmax plasma concentration of more than 250 ng/ml. In some embodiments, the formulation achieves a mean Cmax plasma concentration of more than 280 ng/ml. In some embodiments, the formulation achieves a mean $AUC_{0-\infty}$ of more than 1750 h*ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3100 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation achieves a mean $AUC_{0-\infty}$ of more than 4500 h*ng/ml. In some embodiments, the formulation reaches a Cmax plasma concentration of least 167 ng/ml, 170 ng/ml, 175 ng/ml, 180 ng/ml, or higher following single administration of the formulation to a human subject. In some embodiments, the formulation reaches an $AUC_{0-\infty}$ of at least 2600 h*ng/ml, 2750 h*ng/ml, 2900 h*ng/ml, 3050 h*ng/ml, 3200 h*ng/ml, 3350 h*ng/ml, 3500 h*ng/ml, 3650 h*ng/ml or higher following single administration of the formulation to a human subject.

In certain aspects, the subject matter disclosed herein provides a method for treating pain, fever, or inflammation in a subject by administering a solid dosage formulation comprising 20 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 150 ng/ml. In some embodiments, the formulation achieves a mean Cmax plasma concentration of more than 191 ng/ml, 200 ng/ml, 215 ng/ml, or 225 ng/ml. In some embodiments, the formulation achieves a mean Cmax plasma concentration of more than 250 ng/ml. In some embodiments, the formulation achieves a mean Cmax plasma concentration of more than 258 ng/ml. In some embodiments, the formulation achieves a mean Cmax plasma concentration of more than 300 ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3400 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation reaches a Cmax plasma concentration of at least 190 ng/ml, 205 ng/ml, 220 ng/ml, 235 ng/ml, 250 ng/ml, or higher following single administration of the formulation to a human subject. In some embodiments, the formulation reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In certain aspects, the subject matter disclosed herein provides a method for treating pain, fever, or inflammation in a subject by administering a solid dosage formulation comprising 25 mg of rofecoxib or a pharmaceutically acceptable salt thereof. In some embodiments, the formulation achieves a mean Cmax plasma concentration in less than 3 hours following single administration of the formulation to human subjects. In some embodiments, the formulation achieves a mean Cmax plasma concentration in less than 2.5 hours following administration. In some embodiments, the formulation achieves a mean Cmax plasma concentration in less than 2 hours following administration. In some embodiments, the formulation achieves a mean Cmax plasma concentration of more than 240 ng/ml. In some embodiments, the formulation achieves a mean Cmax plasma concentration of more than 250 ng/ml. In some embodiments, the formulation achieves a mean Cmax plasma concentration of more than 300 ng/ml. In some embodiments, the formulation achieves a mean Cmax plasma concentration of more than 320 ng/ml. In some embodiments, the formulation achieves a mean $AUC_{0-\infty}$ of more than 4250 h*ng/ml. In some embodiments, the formulation achieves a mean $AUC_{0-\infty}$ of more than 4500 h*ng/ml. In some embodiments, the formulation achieves a mean $AUC_{0-\infty}$ of more than 4550 h*ng/ml. In some embodiments, the formulation achieves a mean $AUC_{0-\infty}$ of more than 4700 h*ng/ml. In some embodiments, the formulation achieves a mean Cmax plasma concentration of more than 240 ng/ml in less than 3 hours following administration with a mean $AUC_{0-\infty}$ of more than 4250 h*ng/ml.

In some embodiments, the subject matter disclosed herein provides a method for treating pain, fever, or inflammation in a subject by administering a solid dosage formulation of 10 mg to 50 mg of rofecoxib that achieves a mean Cmax plasma concentration from 9.8 ng/ml to 16 ng/ml for each 1 mg of rofecoxib in the formulation following single administration of the formulation to human subjects. In some embodiments, the solid dosage formulation of rofecoxib achieves a mean Cmax plasma concentration from 10 ng/ml to 14 ng/ml for each 1 mg of rofecoxib in the formulation. In some embodiments, the solid dosage formulation of rofecoxib achieves a mean Cmax plasma concentration from 10 ng/ml to 13 ng/ml for each 1 mg of rofecoxib in the formulation. In some embodiments, the solid dosage formulation of rofecoxib achieves a mean Cmax plasma concentration from 80% to 125% of 12.8 ng/ml. In some embodiments, the solid dosage formulation of rofecoxib reaches a mean $AUC_{0-\infty}$ of 170 h*ng/ml to 235 h*ng/ml for each 1 mg of rofecoxib in the formulation. In some embodiments, the solid dosage formulation of rofecoxib reaches a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the solid dosage formulation of rofecoxib reaches a mean $AUC_{0-\infty}$ of 190 h*ng/ml to 215 h*ng/ml for each 1 mg of rofecoxib in the formulation.

In some embodiments, the subject matter disclosed herein provides a method for treating pain, fever, or inflammation in a subject by administering a solid dosage formulation of 10 mg to 50 mg of rofecoxib, wherein a single administration of the formulation in human female subjects less than 65 years of age achieves a mean Cmax plasma concentration that is at least 10% greater than that achieved following a single administration of the formulation to human male subjects less than 65 years of age. In some embodiments, the formulation achieves a mean Cmax plasma concentration in human female subjects that is at least 20% greater than that achieved in human male subjects. In some embodiments, the formulation achieves a mean Cmax plasma concentration in human female subjects that is at least 25% greater than that achieved in human male subjects. In some embodiments, the formulation comprises 17.5 mg to 25 mg of rofecoxib. In some embodiments, the formulation comprises 17.5 mg of rofecoxib. In some embodiments, the formulation comprises 20 mg of rofecoxib. In some embodiments, the formulation comprises 25 mg of rofecoxib. In some embodiments, the human female and/or male subjects meet the eligibility criteria of the PK-101 and/or PK-102 studies set forth in Examples 4 and 6.

In some embodiments, the subject matter disclosed herein provides a method for treating pain, fever, or inflammation in a subject by administering a solid dosage formulation of 10 mg to 50 mg of rofecoxib, wherein a single administration of the formulation in Caucasian subjects less than 65 years of age achieves a mean $AUC_{0-\infty}$ that is greater than that achieved following a single administration of the formulation to African American subjects less than 65 years of age. In some embodiments, the formulation achieves a mean $AUC_{0-\infty}$ in Caucasian subjects that is at least 1%, 2%, 5%, 9%, or 10% greater than that achieved following a single administration of the formulation to African American subjects less than 65 years of age. In some embodiments, the formulation comprises 17.5 mg to 25 mg of rofecoxib. In some embodiments, the formulation comprises 17.5 mg of rofecoxib. In some embodiments, the formulation comprises 20 mg of rofecoxib. In some embodiments, the formulation comprises 25 mg of rofecoxib. In some embodiments, the Caucasian and/or African American subjects meet the eligibility criteria of the PK-101 and/or PK-102 studies set forth in Examples 4 and 6.

In some embodiments, the subject matter disclosed herein provides a method for treating pain, fever, or inflammation in a subject by administering a solid dosage formulation comprising 12.5 mg of rofecoxib, wherein the formulation achieves a mean plasma concentration of at least about 0.2 ng/ml, 0.3 ng/ml, 0.4 ng/ml, or 0.5 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 12.5 mg of rofecoxib, wherein the formulation achieves an arithmetic mean plasma concentration of at least about 0.8 ng/ml, 0.9 ng/ml, or 1.0 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 17.5 mg of rofecoxib, wherein the formulation achieves a mean plasma concentration of at least about 0.3 ng/ml, 0.4 ng/ml, 0.5 ng/ml, or 0.6 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 17.5 mg of rofecoxib, wherein the formulation achieves an arithmetic mean plasma concentration of at least about 1.8 ng/ml, 2.0 ng/ml, 2.2 ng/ml, or 2.4 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 20 mg of rofecoxib, wherein the formulation achieves a mean plasma concentration of at least about 0.8 ng/ml, 0.9 ng/ml, 1.0 ng/ml, 1.1 ng/ml, or 1.16 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 20 mg of rofecoxib, wherein the formulation achieves an arithmetic mean plasma concentration of at least about 4.6 ng/ml, 5.0 ng/ml, 5.4 ng/ml, or 5.7 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 25 mg of rofecoxib, wherein the formulation achieves a mean plasma concentration of at least about 1.0 ng/ml, 1.1 ng/ml, 1.2 ng/ml, or 1.3 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 25 mg of rofecoxib, wherein the formulation achieves an arithmetic mean plasma concentration of at least about 4.6 ng/ml, 5.0 ng/ml, 5.4 ng/ml, or 5.6 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 12.5 mg of rofecoxib, wherein the formulation achieves a mean plasma concentration of at least about 27 ng/ml, 29 ng/ml, 31 ng/ml, or 33 ng/ml at 45 minutes following single administration of the formulation to human subjects less than 65 years of age. In some embodiments, the subject matter disclosed herein provides a method for treating pain, fever, or inflammation in a subject by administering a solid dosage formulation comprising 12.5 mg of rofecoxib, wherein the formulation achieves an arithmetic mean plasma concentration of at least about 45 ng/ml, 48 ng/ml, 51 ng/ml, 54 ng/ml, or 56 ng/ml at 45 minutes following single administration of the formulation to human subjects less than 65 years of age. In some embodiments, the subject matter disclosed herein provides a method for treating pain, fever, or inflammation in a subject by administering a solid dosage formulation comprising 17.5 mg of rofecoxib, wherein the formulation achieves a mean plasma concentration of at least about 45 ng/ml, 47 ng/ml, 49 ng/ml, or 51 ng/ml at 45 minutes following single administration of the formulation to human subjects less than 65 years of age. In some embodiments, the subject matter disclosed herein provides a method for treating pain, fever, or inflammation in a subject by administering a solid dosage formulation comprising 17.5 mg of rofecoxib, wherein the formulation achieves an arithmetic mean plasma concentration of at least about 74 ng/ml, 79 ng/ml, 84 ng/ml, 89 ng/ml, or 93 ng/ml at 45 minutes following single administration of the formulation to human subjects less than 65 years of age. In some embodiments, the subject matter disclosed herein provides a method for treating pain, fever, or inflammation in a subject by administering a solid dosage formulation comprising 20 mg of rofecoxib, wherein the formulation achieves a mean plasma concentration of at least about 58 ng/ml, 62 ng/ml, 66 ng/ml, 70 ng/ml, or 72 ng/ml at 45 minutes following single administration of the formulation to human subjects less than 65 years of age. In some embodiments, the subject matter disclosed herein provides a method for treating pain, fever, or inflammation in a subject by administering a solid dosage formulation comprising 20 mg of rofecoxib, wherein the formulation achieves an arithmetic mean plasma concentration of at least about 112 ng/ml, 116 ng/ml, or 121 ng/ml at 45 minutes following single administration of the formulation to human subjects less than 65 years of age. In some embodiments, the subject matter disclosed herein provides a method for treating pain, fever, or inflammation in a subject by administering a solid dosage formulation comprising 25 mg of rofecoxib, wherein the formulation achieves a mean plasma concentration of at least about 78 ng/ml, 85 ng/ml, 92 ng/ml, or 97 ng/ml, at 45 minutes following single administration of the formulation to human subjects less than 65 years of age. In some embodiments, the subject matter disclosed herein provides a method for treating pain, fever, or inflammation in a subject by administering a solid dosage formulation comprising 25 mg of rofecoxib, wherein the formulation achieves an arithmetic mean plasma concentration of at least about 133 ng/ml, 139 ng/ml, 145 ng/ml, 151 ng/ml, or 159 ng/ml at 45 minutes following single administration of the formulation to human subjects less than 65 years of age.

In certain aspects, the subject matter disclosed herein provides a solid oral dosage form of a pharmaceutically acceptable formulation comprising a granular component and an extragranular component, wherein the granular component comprises an intragranular component comprising rofecoxib or a pharmaceutically acceptable salt thereof and one or more disintegrants, and wherein the extragranular component comprises one or more disintegrants.

In some embodiments, the one or more disintegrants in the granular component is selected from starches, clays, celluloses, algins, gums, cross-linked polymers, and combinations thereof. In some embodiments, the one or more disintegrants in the granular component is selected from croscarmellose, crospovidone, sodium starch glycolate, and combinations thereof. In some embodiments, the one or more disintegrants in the granular component is croscarmellose sodium. In some embodiments, the one or more disintegrants in the granular component is about 1% (w/w) to about 8% (w/w) of the formulation. In some embodiments, the one or more disintegrants in the granular component is about 1% (w/w) to about 6% (w/w) of the formulation. In some embodiments, the one or more disintegrants in the granular component is about 1% (w/w) to about 4% (w/w) of the formulation.

In some embodiments, the one or more disintegrants in the extragranular component is selected from starches, clays, celluloses, algins, gums, cross-linked polymers, and combinations thereof. In some embodiments, the one or more disintegrants in the extragranular component is selected from croscarmellose, crospovidone, sodium starch glycolate, and combinations thereof. In some embodiments, the one or more disintegrants in the extragranular component is croscarmellose sodium. In some embodiments, the disintegrant in the extragranular component is about 1% (w/w) to about 8% (w/w) of the formulation. In some embodiments, the disintegrant in the extragranular component is about 1% (w/w) to about 6% (w/w) of the formulation. In some embodiments, the disintegrant in the extragranular component is about 1% (w/w) to about 4% (w/w) of the formulation.

In some embodiments, the disintegrant in the granular component and the disintegrant in the extragranular component are together about 2% (w/w) to about 12% (w/w) of the formulation. In some embodiments, the disintegrant in the granular component and the disintegrant in the extragranular component are together about 2% (w/w) to about 10% (w/w) of the formulation. In some embodiments, the disintegrant in the granular component and the disintegrant in the extragranular component are together about 2% (w/w) to about 8% (w/w) of the formulation.

In some embodiments, the ratio of granular disintegrant to extragranular disintegrant is about 40% (w/w) to about 60% (w/w). In some embodiments, the ratio of granular disintegrant to extragranular disintegrant is about 45% (w/w) to about 55% (w/w). In some embodiments the ratio of granular disintegrant to extragranular disintegrant is about 50% (w/w) to about 50% (w/w). In some embodiments the ratio of granular disintegrant to extragranular disintegrant is about 55% (w/w) to about 45% (w/w). In some embodiments the ratio of granular disintegrant to extragranular disintegrant is about 60% (w/w) to about 40% (w/w).

In some embodiments, the solid oral dosage form of the pharmaceutically acceptable formulation further comprising one or more of a diluent, a binder, a coloring agent, and a lubricant. In some embodiments, at least a portion of the diluent is in the granular component. In some embodiments, the diluent is selected from dicalcium phosphate, calcium sulfate, lactose, cellulose, kaolin, mannitol, sodium chloride, dry starch, powdered sugar, sorbitol, sucrose, inositol, and combinations thereof. In some embodiments, the diluent is selected from lactose, cellulose, or a combination thereof. In some embodiments, the diluent is selected from lactose monohydrate, microcrystalline cellulose, or a combination thereof.

In some embodiments, the lactose monohydrate is about 35% (w/w) to about 45% (w/w) of the formulation. In some embodiments, the lactose monohydrate is about 37% (w/w) to about 42% (w/w) of the formulation. In some embodiments, the lactose monohydrate is about 39% (w/w) to about 40% (w/w) of the formulation.

In some embodiments, the microcrystalline cellulose is about 35% (w/w) to about 45% (w/w) of the formulation. In some embodiments, the microcrystalline cellulose is about 37% (w/w) to about 42% (w/w) of the formulation. In some embodiments, the microcrystalline cellulose is about 39% (w/w) to about 40% (w/w) of the formulation.

In some embodiments, the diluent is about 75% (w/w) to about 85% (w/w) of the formulation. In some embodiments, diluent is about 77% (w/w) to about 82% (w/w) of the formulation. In some embodiments, the diluent is about 78% (w/w) to about 80% (w/w) of the formulation.

In some embodiments, at least a portion of the binder is in the granular component. In some embodiments, the binder is selected from starches, gelatins, sugars, gums, waxes, water, alcohols, celluloses, and combinations thereof. In some embodiments, the binder is selected from acacia gum, tragacanth, corn starch, methyl cellulose, panwar gum, ghatti gum, mucilage of isapol husks, carboxymethylcellulose, methylcellulose, polyvinylpyrrolidone, sucrose, glucose, dextrose, molasses, lactose, and combinations thereof. In some embodiments, the binder is hydroxypropyl cellulose. In some embodiments, the binder is about 1% (w/w) to about 5% (w/w) of the formulation. In some embodiments, binder is about 2% (w/w) to about 4% (w/w) of the formulation. In some embodiments, the binder is about 2.5% (w/w) to about 3.5% (w/w) of the formulation.

In some embodiments, at least a portion of the coloring agent is in the extragranular component. In some embodiments, at least a portion of the coloring agent is in the intragranular component. In some embodiments, the coloring agent is pigment blend yellow. In some embodiments, the coloring agent is about 0.30% (w/w) to about 0.60% (w/w) of the formulation.

In some embodiments, at least a portion of the lubricant is in the extragranular component. In some embodiments, the lubricant is selected from talc, magnesium stearate, calcium stearate, stearic acid, metallic stearate, hydrogenated vegetable oils, and polyethylene glycol, corn starch, boric acids, sodium chloride, sodium lauryl sulphate. In some embodiments, the lubricant is magnesium stearate. In some embodiments, the lubricant is about 0.10% (w/w) to about 1% (w/w) of the formulation. In some embodiments, the lubricant is about 0.50% (w/w) of the formulation.

In some embodiments, the rofecoxib or pharmaceutically acceptable salt thereof is about 5% (w/w) to about 30% (w/w) of the formulation. In some embodiments, the rofecoxib or pharmaceutically acceptable salt thereof is about 10% (w/w) to about 20% (w/w) of the formulation. In some embodiments, the rofecoxib or pharmaceutically acceptable salt thereof is about 12% (w/w) to about 13% (w/w) of the formulation. In some embodiments, the formulation comprises about 10 mg of the rofecoxib or pharmaceutically acceptable salt thereof. In some embodiments, the formulation comprises about 10.5 mg of the rofecoxib or pharmaceutically acceptable salt thereof. In some embodiments, the formulation comprises about 11 mg of the rofecoxib or pharmaceutically acceptable salt thereof. In some embodiments, the formulation comprises about 11.5 mg of the rofecoxib or pharmaceutically acceptable salt thereof. In some embodiments, the formulation comprises about 12 mg of the rofecoxib or pharmaceutically acceptable salt thereof. In some embodiments, the formulation comprises about 12.5 mg of the rofecoxib or pharmaceutically acceptable salt thereof. In some embodiments, the formulation comprises about 17.5 mg of the rofecoxib or pharmaceutically acceptable salt thereof. In some embodiments, the formulation comprises about 20 mg of the rofecoxib or pharmaceutically acceptable salt thereof. In some embodiments, the formulation comprises about 21 mg of the rofecoxib or pharmaceutically acceptable salt thereof. In some embodiments, the formulation comprises about 22 mg of the rofecoxib or pharmaceutically acceptable salt thereof. In some embodiments, the formulation comprises about 22.5 mg of the rofecoxib or pharmaceutically acceptable salt thereof. In some embodiments, the formulation comprises about 25 mg of the rofecoxib or pharmaceutically acceptable salt thereof. In some embodiments, the formulation comprises about 50 mg of the rofecoxib or pharmaceutically acceptable salt thereof.

In some embodiments, the rofecoxib is highly pure. In some embodiments, the highly pure rofecoxib comprises less than about 0.1% total impurities. In some embodiments, the highly pure rofecoxib comprises less than about 0.075% total impurities. In some embodiments, the highly pure rofecoxib comprises less than about 0.050% total impurities. In some embodiments, the highly pure rofecoxib comprises less than about 0.025% total impurities. In some embodiments, the highly pure rofecoxib comprises less than about 0.001% total impurities.

In some embodiments, the highly pure rofecoxib comprises less than about 0.10%, 0.05%, 0.02%, or 0.01% of 4-[4-(methylsulphonyl)phenyl]-3-phenyl-2,5-furandione. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylsulfinyl)phenyl]-3-phenyl-2(5H)-furanone.

In some embodiments, the solid oral dosage form is an oral tablet. In some embodiments, the oral tablet provides a dissolution rate of at least about 80% of the rofecoxib or pharmaceutically acceptable salt thereof by about 15 minutes. In some embodiments, the oral tablet provides a dissolution rate of at least about 85% of the rofecoxib or pharmaceutically acceptable salt thereof by about 15 minutes. In some embodiments, the oral tablet provides a dissolution rate of at least about 90% of the rofecoxib or pharmaceutically acceptable salt thereof by about 15 minutes. In some embodiments, the oral tablet provides a dissolution rate of at least about 95% of the rofecoxib or pharmaceutically acceptable salt thereof by about 15 minutes. In some embodiments, the oral tablet provides a dissolution rate of at least about 100% of the rofecoxib or pharmaceutically acceptable salt thereof by about 15 minutes.

In some embodiments, the dissolution rate is measured in about 1% SDS at a paddle speed of about 50 rpm and at a temperature of about 37.0° C.±0.5° C. In some embodiments, the dissolution rate is measured in about 1% SDS at a paddle speed of about 75 rpm and at a temperature of about 37.0° C.±0.5° C. In some embodiments, the dissolution rate is measured in about 1.5% SDS at a paddle speed of about 50 rpm and at a temperature of about 37.0° C.±0.5° C. In some embodiments, the dissolution rate is measured in about 1.5% SDS at a paddle speed of about 75 rpm and at a temperature of about 37.0° C.±0.5° C. In some embodiments, the dissolution rate is measured in about 2% SDS at a paddle speed of about 50 rpm and at a temperature of about 37.0° C.±0.5° C. In some embodiments, the dissolution rate is measured in about 2% SDS at a paddle speed of about 75 rpm and at a temperature of about 37.0° C.±0.5° C.

In some embodiments, the rofecoxib or pharmaceutically acceptable salt thereof is formulated into granules and at least about 35% of the granules are less than about 75 μm. In some embodiments, the rofecoxib or pharmaceutically acceptable salt thereof is formulated into granules and at least about 55% of the granules are less than about 150 μm. In some embodiments, the rofecoxib or pharmaceutically acceptable salt thereof is formulated into granules and at least about 75% of the granules are less than about 250 μm. In some embodiments, the rofecoxib or pharmaceutically acceptable salt thereof is formulated into granules and at least about 85% of the granules are less than about 425 μm. In some embodiments, the rofecoxib or pharmaceutically acceptable salt thereof is formulated into granules and at least about 90% of the granules are less than about 1000 μm.

In some embodiments, a 17.5 mg solid dosage formulation of rofecoxib reaches a median time to Cmax plasma concentration in 4 hours or less following single administration of the formulation to human subjects. In some embodiments, a 17.5 mg solid dosage formulation of rofecoxib reaches a median time to Cmax plasma concentration in 3 hours or less following administration. In some embodiments, a 17.5 mg solid dosage formulation of rofecoxib reaches a median time to Cmax plasma concentration in 2.5 hours or less following administration. In some embodiments, a 17.5 mg solid dosage formulation of rofecoxib reaches a median time to Cmax plasma concentration in 2 hours or less following administration. In some embodiments, a 17.5 mg solid dosage formulation of rofecoxib has a mean Cmax plasma concentration of more than 100 ng/ml. In some embodiments, a 17.5 mg solid dosage formulation of rofecoxib has a mean Cmax plasma concentration of more than 150 ng/ml, 167 ng/ml, or 190 ng/ml. In some embodiments, a 17.5 mg solid dosage formulation of rofecoxib has a mean Cmax plasma concentration of more than 200 ng/ml. In some embodiments, a 17.5 mg solid dosage formulation of rofecoxib has a mean Cmax plasma concentration of more than 220 ng/ml. In some embodiments, a 17.5 mg solid dosage formulation of rofecoxib has a mean Cmax plasma concentration of more than 250 ng/ml. In some embodiments, a 17.5 mg solid dosage formulation of rofecoxib has a mean Cmax plasma concentration of more than 280 ng/ml. In some embodiments, a 17.5 mg solid dosage formulation of rofecoxib has a mean $AUC_{0-\infty}$ of more than 1750 h*ng/ml. In some embodiments, a 17.5 mg solid dosage formulation of rofecoxib has a mean $AUC_{0-\infty}$ of more than 2000 h*ng/ml. In some embodiments, a 17.5 mg solid dosage formulation of rofecoxib has a mean $AUC_{0-\infty}$ of more than 2500 h*ng/ml. In some embodiments, a 17.5 mg solid dosage formulation of rofecoxib has a mean $AUC_{0-\infty}$ of more than 3000 h*ng/ml. In some embodiments, a 17.5 mg solid dosage formulation of rofecoxib has a mean $AUC_{0-\infty}$ of more than 3500 h*ng/ml. In some embodiments, a 17.5 mg solid dosage formulation of rofecoxib has a mean $AUC_{0-\infty}$ of more than 4000 h*ng/ml. In some embodiments, a 17.5 mg solid dosage formulation of rofecoxib has a mean $AUC_{0-\infty}$ of more than 4500 h*ng/ml. In some embodiments, a 17.5 mg solid dosage formulation of rofecoxib reaches a Cmax plasma concentration of least 167 ng/ml, 170 ng/ml, 175 ng/ml, 180 ng/ml, or higher following single administration of the formulation to a human subject. In some embodiments, a 17.5 mg solid dosage formulation of rofecoxib reaches an $AUC_{0-\infty}$ of at least 2600 h*ng/ml, 2750 h*ng/ml, 2900 h*ng/ml, 3050 h*ng/ml, 3200 h*ng/ml, 3350 h*ng/ml, 3500 h*ng/ml, 3650 h*ng/ml or higher following single administration of the formulation to a human subject.

In some embodiments, a 20 mg solid dosage formulation of rofecoxib reaches a median time to Cmax plasma concentration in 4 hours or less following single administration of the formulation to human subjects. In some embodiments, a 20 mg solid dosage formulation of rofecoxib reaches a median time to Cmax plasma concentration in 3 hours or less following administration. In some embodiments, a 20 mg solid dosage formulation of rofecoxib reaches a median time to Cmax plasma concentration in 2.5 hours or less following administration. In some embodiments, a 20 mg solid dosage formulation of rofecoxib reaches a median time to Cmax plasma concentration in 2 hours or less following administration. In some embodiments, a 20 mg solid dosage formulation of rofecoxib has a mean Cmax plasma concentration of more than 150 ng/ml. In some embodiments, a 20 mg solid dosage formulation of rofecoxib has a mean Cmax plasma concentration of more than 191 ng/ml, 200 ng/ml, 215 ng/ml, or 225 ng/ml. In some embodiments, a 20 mg solid dosage formulation of rofecoxib has a mean Cmax plasma concentration of more than 250 ng/ml. In some embodiments, a 20 mg solid dosage formulation of rofecoxib has a mean Cmax plasma concentration of more than 258 ng/ml. In some embodiments, a 20 mg solid dosage formulation of rofecoxib has a mean Cmax plasma concentration of more than 300 ng/ml. In some embodiments, a 20 mg solid dosage formulation of rofecoxib has a mean $AUC_{0-\infty}$ of more than 2000 h*ng/ml. In some embodiments, a 20 mg solid dosage formulation of rofecoxib has a mean $AUC_{0-\infty}$ of more than 2500 h*ng/ml. In some embodiments, a 20 mg solid dosage formulation of rofecoxib has a mean $AUC_{0-\infty}$ of more than 3000 h*ng/ml. In some embodiments, a 20 mg solid dosage formulation of rofecoxib has a mean $AUC_{0-\infty}$ of more than 3400 h*ng/ml. In some embodiments, a 20 mg solid dosage formulation of rofecoxib has a mean $AUC_{0-\infty}$ of more than 3500 h*ng/ml. In some embodiments, a 20 mg solid dosage formulation of rofecoxib has a mean $AUC_{0-\infty}$ of more than 4500 h*ng/ml. In some embodiments, a 20 mg solid dosage formulation of rofecoxib reaches a Cmax plasma concentration of least 190 ng/ml, 205 ng/ml, 220 ng/ml, 235 ng/ml, 250 ng/ml, or higher following single administration of the formulation to a human subject. In some embodiments, a 20 mg solid dosage formulation of rofecoxib reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In some embodiments, a 25 mg solid dosage formulation of rofecoxib reaches a mean Cmax plasma concentration in less than 3 hours following single administration of the formulation to human subjects. In some embodiments, a 25 mg solid dosage formulation of rofecoxib reaches a mean Cmax plasma concentration in less than 2.5 hours following administration. In some embodiments, a 25 mg solid dosage formulation of rofecoxib reaches a mean Cmax plasma concentration in less than 2 hours following administration. In some embodiments, a 25 mg solid dosage formulation of rofecoxib has a mean Cmax plasma concentration of more than 240 ng/ml. In some embodiments, a 25 mg solid dosage formulation of rofecoxib has a mean Cmax plasma concentration of more than 250 ng/ml. In some embodiments, a 25 mg solid dosage formulation of rofecoxib has a mean Cmax plasma concentration of more than 300 ng/ml. In some embodiments, a 25 mg solid dosage formulation of rofecoxib has a mean Cmax plasma concentration of more than 320 ng/ml. In some embodiments, a 25 mg solid dosage formulation of rofecoxib has a mean $AUC_{0-\infty}$ of more than 4250 h*ng/ml. In some embodiments, a 25 mg solid dosage formulation of rofecoxib has a mean $AUC_{0-\infty}$ of more than 4500 h*ng/ml. In some embodiments, a 25 mg solid dosage formulation of rofecoxib has a mean $AUC_{0-\infty}$ of more than 4550 h*ng/ml. In some embodiments, a 25 mg solid dosage formulation of rofecoxib has a mean $AUC_{0-\infty}$ of more than 4700 h*ng/ml. In some embodiments, a 25 mg solid dosage formulation of rofecoxib reaches a mean Cmax plasma concentration of more than 240 ng/ml in a median time of about 3 hours or less following administration with an $AUC_{0-\infty}$ of more than 4250 h*ng/ml.

In some embodiments, a solid dosage formulation of 10 mg to 50 mg of rofecoxib achieves a mean Cmax plasma concentration from 9.8 ng/ml to 16 ng/ml for each 1 mg of rofecoxib in the formulation following single administration of the formulation to human subjects. In some embodiments, the solid dosage formulation of rofecoxib achieves a mean Cmax plasma concentration from 10 ng/ml to 14 ng/ml for each 1 mg of rofecoxib in the formulation. In some embodiments, the solid dosage formulation of rofecoxib achieves a mean Cmax plasma concentration from 10 ng/ml to 13 ng/ml for each 1 mg of rofecoxib in the formulation. In some embodiments, the solid dosage formulation of rofecoxib achieves a mean Cmax plasma concentration from 80% to 125% of 12.8 ng/ml. In some embodiments, the solid dosage formulation of rofecoxib reaches a mean $AUC_{0-\infty}$ of 170 h*ng/ml to 235 h*ng/ml for each 1 mg of rofecoxib in the formulation. In some embodiments, the solid dosage formulation of rofecoxib reaches a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the solid dosage formulation of rofecoxib reaches a mean $AUC_{0-\infty}$ of 190 h*ng/ml to 215 h*ng/ml for each 1 mg of rofecoxib in the formulation.

In certain aspects, the subject matter disclosed herein provides a solid oral dosage form of a pharmaceutically acceptable formulation comprising a granular component and an extragranular component, wherein the granular component comprises an intragranular component comprising 17.5 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 100 ng/ml. In some embodiments, the formulation achieves a mean Cmax plasma concentration of more than 150 ng/ml, 167 ng/ml, or 190 ng/ml. In some embodiments, the formulation achieves a mean Cmax plasma concentration of more than 200 ng/ml. In some embodiments, the formulation achieves a mean Cmax plasma concentration of more than 220 ng/ml. In some embodiments, the formulation achieves a mean Cmax plasma concentration of more than 250 ng/ml. In some embodiments, the formulation achieves a mean Cmax plasma concentration of more than 280 ng/ml. In some embodiments, the formulation achieves a mean $AUC_{0-\infty}$ of more than 1750 h*ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3100 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation achieves a mean $AUC_{0-\infty}$ of more than 4500 h*ng/ml. In some embodiments, the formulation reaches a Cmax plasma concentration of least 167 ng/ml, 170 ng/ml, 175 ng/ml, 180 ng/ml, or higher following single administration of the formulation to a human subject. In some embodiments, the formulation reaches an $AUC_{0-\infty}$ of at least 2600 h*ng/ml, 2750 h*ng/ml, 2900 h*ng/ml, 3050 h*ng/ml, 3100 h*ng/ml, 3200 h*ng/ml, 3350 h*ng/ml, 3500 h*ng/ml, 3650 h*ng/ml or higher following single administration of the formulation to a human subject.

In certain aspects, the subject matter disclosed herein provides a solid oral dosage form of a pharmaceutically acceptable formulation comprising a granular component and an extragranular component, wherein the granular component comprises an intragranular component comprising 20 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 150 ng/ml. In some embodiments, the formulation achieves a mean Cmax plasma concentration of more than 191 ng/ml, 200 ng/ml, 215 ng/ml, or 225 ng/ml. In some embodiments, the formulation achieves a mean Cmax plasma concentration of more than 250 ng/ml. In some embodiments, the formulation achieves a mean Cmax plasma concentration of more than 258 ng/ml. In some embodiments, the formulation achieves a mean Cmax plasma concentration of more than 300 ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3400 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation reaches a Cmax plasma concentration of least 190 ng/ml, 205 ng/ml, 220 ng/ml, 235 ng/ml, 250 ng/ml, or higher following single administration of the formulation to a human subject. In some embodiments, the formulation reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In certain aspects, the subject matter disclosed herein provides a solid oral dosage form of a pharmaceutically acceptable formulation comprising a granular component and an extragranular component, wherein the granular component comprises an intragranular component comprising 25 mg of rofecoxib or a pharmaceutically acceptable salt thereof. In some embodiments, the formulation achieves a mean Cmax plasma concentration in less than 3 hours following single administration of the formulation to human subjects. In some embodiments, the formulation achieves a mean Cmax plasma concentration in less than 2.5 hours following administration. In some embodiments, the formulation achieves a mean Cmax plasma concentration in less than 2 hours following administration. In some embodiments, the formulation achieves a mean Cmax plasma concentration of more than 240 ng/ml. In some embodiments, the formulation achieves a mean Cmax plasma concentration of more than 300 ng/ml. In some embodiments, the formulation achieves a mean Cmax plasma concentration of more than 320 ng/ml. In some embodiments, the formulation achieves a mean $AUC_{0-\infty}$ of more than 4250 h*ng/ml. In some embodiments, the formulation achieves a mean $AUC_{0-\infty}$ of more than 4500 h*ng/ml. In some embodiments, the formulation achieves a mean $AUC_{0-\infty}$ of more than 4550 h*ng/ml. In some embodiments, the formulation achieves a mean $AUC_{0-\infty}$ of more than 4700 h*ng/ml. In some embodiments, the formulation achieves a Cmax plasma concentration of more than 240 ng/ml in about 3 hours following administration with an $AUC_{0-\infty}$ of more than 4250 h*ng/ml.

The subject matter disclosed herein provides a solid oral dosage form of a pharmaceutically acceptable formulation comprising a granular component and an extragranular component, wherein the granular component comprises an intragranular component comprising 10 mg to 50 mg of rofecoxib or a pharmaceutically acceptable salt thereof that achieves a mean Cmax plasma concentration from 9.8 ng/ml to 16 ng/ml for each 1 mg of rofecoxib in the formulation following single administration of the formulation to human subjects. In some embodiments, the solid dosage formulation of rofecoxib achieves a mean Cmax plasma concentration from 10 ng/ml to 14 ng/ml for each 1 mg of rofecoxib in the formulation. In some embodiments, the solid dosage formulation of rofecoxib achieves a mean Cmax plasma concentration from 10 ng/ml to 13 ng/ml for each 1 mg of rofecoxib in the formulation. In some embodiments, the solid dosage formulation of rofecoxib achieves a mean Cmax plasma concentration from 80% to 125% of 12.8 ng/ml. In some embodiments, the solid dosage formulation of rofecoxib reaches a mean $AUC_{0-\infty}$ of 170 h*ng/ml to 235 h*ng/ml for each 1 mg of rofecoxib in the formulation. In some embodiments, the solid dosage formulation of rofecoxib reaches a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the solid dosage formulation of rofecoxib reaches a mean $AUC_{0-\infty}$ of 190 h*ng/ml to 215 h*ng/ml for each 1 mg of rofecoxib in the formulation.

A method for inhibiting COX-2 in a subject in need thereof, the method comprising administering to the subject a pharmaceutically acceptable formulation comprising a granular component and an extragranular component, wherein the granular component comprises an intragranular component comprising rofecoxib or a pharmaceutically acceptable salt thereof and one or more disintegrants, and wherein the extragranular component comprises one or more disintegrants.

In some embodiments, the one or more disintegrants in the granular component is selected from starches, clays, celluloses, algins, gums, cross-linked polymers, and combinations thereof. In some embodiments, the one or more disintegrants in the granular component is selected from croscarmellose, crospovidone, sodium starch glycolate, and combinations thereof. In some embodiments, the one or more disintegrants in the granular component is croscarmellose sodium. In some embodiments, the one or more disintegrants in the granular component is about 1% (w/w) to about 8% (w/w) of the formulation. In some embodiments, the one or more disintegrants in the granular component is about 1% (w/w) to about 6% (w/w) of the formulation. In some embodiments, the one or more disintegrants in the granular component is about 1% (w/w) to about 4% (w/w) of the formulation.

In some embodiments, the one or more disintegrants in the extragranular component is selected from starches, clays, celluloses, algins, gums, cross-linked polymers, and combinations thereof. In some embodiments, the one or more disintegrants in the extragranular component is selected from croscarmellose, crospovidone, sodium starch glycolate, and combinations thereof. In some embodiments, the one or more disintegrants in the extragranular component is croscarmellose sodium. In some embodiments, the disintegrant in the extragranular component is about 1% (w/w) to about 8% (w/w) of the formulation. In some embodiments, the disintegrant in the extragranular component is about 1% (w/w) to about 6% (w/w) of the formulation. In some embodiments, the disintegrant in the extragranular component is about 1% (w/w) to about 4% (w/w) of the formulation.

In some embodiments, the disintegrant in the granular component and the disintegrant in the extragranular component are together about 2% (w/w) to about 12% (w/w) of the formulation. In some embodiments, the disintegrant in the granular component and the disintegrant in the extragranular component are together about 2% (w/w) to about 10% (w/w) of the formulation. In some embodiments, the disintegrant in the granular component and the disintegrant in the extragranular component are together about 2% (w/w) to about 8% (w/w) of the formulation.

In some embodiments, the ratio of granular disintegrant to extragranular disintegrant is about 40% (w/w) to about 60% (w/w). In some embodiments, the ratio of granular disintegrant to extragranular disintegrant is about 45% (w/w) to about 55% (w/w). In some embodiments, the ratio of granular disintegrant to extragranular disintegrant is about 50% (w/w) to about 50% (w/w). In some embodiments, the ratio of granular disintegrant to extragranular disintegrant is about 55% (w/w) to about 45% (w/w). In some embodiments the ratio of granular disintegrant to extragranular disintegrant is about 60% (w/w) to about 40% (w/w).

In some embodiments, the pharmaceutically acceptable formulation further comprises one or more of a diluent, a binder, a coloring agent, and a lubricant. In some embodiments, at least a portion of the diluent is in the granular component. In some embodiments, the diluent is selected from dicalcium phosphate, calcium sulfate, lactose, cellulose, kaolin, mannitol, sodium chloride, dry starch, powdered sugar, sorbitol, sucrose, inositol, and combinations thereof. In some embodiments, the diluent is selected from lactose, cellulose, or a combination thereof. In some embodiments, the diluent is selected from lactose monohydrate, microcrystalline cellulose, or a combination thereof.

In some embodiments, the lactose monohydrate is about 35% (w/w) to about 45% (w/w) of the formulation. In some embodiments, the lactose monohydrate is about 37% (w/w) to about 42% (w/w) of the formulation. In some embodiments, the lactose monohydrate is about 39% (w/w) to about 40% (w/w) of the formulation.

In some embodiments, the microcrystalline cellulose is about 35% (w/w) to about 45% (w/w) of the formulation. In some embodiments, the microcrystalline cellulose is about 37% (w/w) to about 42% (w/w) of the formulation. In some embodiments, the microcrystalline cellulose is about 39% (w/w) to about 40% (w/w) of the formulation.

In some embodiments, the diluent is about 75% (w/w) to about 85% (w/w) of the formulation. In some embodiments, diluent is about 77% (w/w) to about 82% (w/w) of the formulation. In some embodiments, the diluent is about 78% (w/w) to about 80% (w/w) of the formulation.

In some embodiments, at least a portion of the binder is in the granular component. In some embodiments, the binder is selected from starches, gelatins, sugars, gums, waxes, water, alcohols, celluloses, and combinations thereof. In some embodiments, the binder is selected from acacia gum, tragacanth, corn starch, methyl cellulose, panwar gum, ghatti gum, mucilage of isapol husks, carboxymethylcellulose, methylcellulose, polyvinylpyrrolidone, sucrose, glucose, dextrose, molasses, lactose, and combinations thereof. In some embodiments, the binder is hydroxypropyl cellulose. In some embodiments, the binder is about 1% (w/w) to about 5% (w/w) of the formulation. In some embodiments, binder is about 2% (w/w) to about 4% (w/w) of the formulation. In some embodiments, the binder is about 2.5% (w/w) to about 3.5% (w/w) of the formulation.

In some embodiments, at least a portion of the coloring agent is in the extragranular component. In some embodiments, the coloring agent is pigment blend yellow. In some embodiments, the coloring agent is about 0.30% (w/w) to about 0.60% (w/w) of the formulation.

In some embodiments, at least a portion of the lubricant is in the extragranular component. In some embodiments, the lubricant is selected from talc, magnesium stearate, calcium stearate, stearic acid, metallic stearate, hydrogenated vegetable oils, and polyethylene glycol, corn starch, boric acids, sodium chloride, sodium lauryl sulphate. In some embodiments, the lubricant is magnesium stearate. In some embodiments, the lubricant is about 0.10% (w/w) to about 1% (w/w) of the formulation. In some embodiments, the lubricant is about 0.50% (w/w) of the formulation.

In some embodiments, the rofecoxib or pharmaceutically acceptable salt thereof is about 5% (w/w) to about 30% (w/w) of the formulation. In some embodiments, the rofecoxib or pharmaceutically acceptable salt thereof is about 10% (w/w) to about 20% (w/w) of the formulation. In some embodiments, the rofecoxib or pharmaceutically acceptable salt thereof is about 12% (w/w) to about 13% (w/w) of the formulation. In some embodiments, the formulation comprises about 10 mg of the rofecoxib or pharmaceutically acceptable salt thereof. In some embodiments, the formulation comprises about 10.5 mg of the rofecoxib or pharmaceutically acceptable salt thereof. In some embodiments, the formulation comprises about 11 mg of the rofecoxib or pharmaceutically acceptable salt thereof. In some embodiments, the formulation comprises about 11.5 mg of the rofecoxib or pharmaceutically acceptable salt thereof. In some embodiments, the formulation comprises about 12 mg of the rofecoxib or pharmaceutically acceptable salt thereof. In some embodiments, the formulation comprises about 12.5 mg of the rofecoxib or pharmaceutically acceptable salt thereof. In some embodiments, the formulation comprises about 17.5 mg of the rofecoxib or pharmaceutically acceptable salt thereof. In some embodiments, the formulation comprises about 20 mg of the rofecoxib or pharmaceutically acceptable salt thereof. In some embodiments, the formulation comprises about 21 mg of the rofecoxib or pharmaceutically acceptable salt thereof. In some embodiments, the formulation comprises about 22 mg of the rofecoxib or pharmaceutically acceptable salt thereof. In some embodiments, the formulation comprises about 22.5 mg of the rofecoxib or pharmaceutically acceptable salt thereof. In some embodiments, the formulation comprises about 25 mg of the rofecoxib or pharmaceutically acceptable salt thereof. In some embodiments, the formulation comprises about 50 mg of the rofecoxib or pharmaceutically acceptable salt thereof.

In some embodiments, the rofecoxib is highly pure. In some embodiments, the highly pure rofecoxib comprises less than about 0.1% total impurities. In some embodiments, the highly pure rofecoxib comprises less than about 0.075% total impurities. In some embodiments, the highly pure rofecoxib comprises less than about 0.050% total impurities. In some embodiments, the highly pure rofecoxib comprises less than about 0.025% total impurities. In some embodiments, the highly pure rofecoxib comprises less than about 0.001% total impurities.

In some embodiments, the highly pure rofecoxib comprises less than about 0.10%, 0.05%, 0.02%, or 0.01% of 4-[4-(methylsulphonyl)phenyl]-3-phenyl-2,5-furandione. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylsulfinyl)phenyl]-3-phenyl-2(5H)-furanone.

In some embodiments, the formulation is suitable for oral administration. In some embodiments, the formulation is a solid dosage form. In some embodiments, the solid dosage form is an oral tablet. In some embodiments, the oral tablet provides a dissolution rate of at least about 80% of the rofecoxib or pharmaceutically acceptable salt thereof by about 15 minutes. In some embodiments, the oral tablet provides a dissolution rate of at least about 85% of the rofecoxib or pharmaceutically acceptable salt thereof by about 15 minutes. In some embodiments, the oral tablet provides a dissolution rate of at least about 90% of the rofecoxib or pharmaceutically acceptable salt thereof by about 15 minutes. In some embodiments, the oral tablet provides a dissolution rate of at least about 95% of the rofecoxib or pharmaceutically acceptable salt thereof by about 15 minutes. In some embodiments, the oral tablet provides a dissolution rate of at least about 100% of the rofecoxib or pharmaceutically acceptable salt thereof by about 15 minutes.

In some embodiments, the dissolution rate is measured in about 1% SDS at a paddle speed of about 50 rpm and at a temperature of about 37.0° C.±0.5° C. In some embodiments, the dissolution rate is measured in about 1% SDS at a paddle speed of about 75 rpm and at a temperature of about 37.0° C.±0.5° C. In some embodiments, the dissolution rate is measured in about 1.5% SDS at a paddle speed of about 50 rpm and at a temperature of about 37.0° C.±0.5° C. In some embodiments, the dissolution rate is measured in about 1.5% SDS at a paddle speed of about 75 rpm and at a temperature of about 37.0° C.±0.5° C. In some embodiments, the dissolution rate is measured in about 2% SDS at a paddle speed of about 50 rpm and at a temperature of about 37.0° C.±0.5° C. In some embodiments, the dissolution rate is measured in about 2% SDS at a paddle speed of about 75 rpm and at a temperature of about 37.0° C.±0.5° C.

In some embodiments, the rofecoxib or pharmaceutically acceptable salt thereof is formulated into granules and at least about 35% of the granules are less than about 75 µm. In some embodiments, the rofecoxib or pharmaceutically acceptable salt thereof is formulated into granules and at least about 55% of the granules are less than about 150 µm. In some embodiments, the rofecoxib or pharmaceutically acceptable salt thereof is formulated into granules and at least about 75% of the granules are less than about 250 µm. In some embodiments, the rofecoxib or pharmaceutically acceptable salt thereof is formulated into granules and at least about 85% of the granules are less than about 425 µm. In some embodiments, the rofecoxib or pharmaceutically acceptable salt thereof is formulated into granules and at least about 90% of the granules are less than about 1000 µm.

In some embodiments, a 17.5 mg solid dosage formulation of rofecoxib reaches a median time to Cmax plasma concentration in 4 hours or less following single administration of the formulation to human subjects. In some embodiments, a 17.5 mg solid dosage formulation of rofecoxib reaches a median time to Cmax plasma concentration in 3 hours or less following administration. In some embodiments, a 17.5 mg solid dosage formulation of rofecoxib reaches a median time to Cmax plasma concentration in 2.5 hours or less following administration. In some embodiments, a 17.5 mg solid dosage formulation of rofecoxib reaches a median time to Cmax plasma concentration in 2 hours or less following administration. In some embodiments, a 17.5 mg solid dosage formulation of rofecoxib has a mean Cmax plasma concentration of more than 100 ng/ml. In some embodiments, a 17.5 mg solid dosage formulation of rofecoxib has a mean Cmax plasma concentration of more than 150 ng/ml, 167 ng/ml, or 190 ng/ml. In some embodiments, a 17.5 mg solid dosage formulation of rofecoxib has a mean Cmax plasma concentration of more than 200 ng/ml. In some embodiments, a 17.5 mg solid dosage formulation of rofecoxib has a mean Cmax plasma concentration of more than 220 ng/ml. In some embodiments, a 17.5 mg solid dosage formulation of rofecoxib has a mean Cmax plasma concentration of more than 250 ng/ml. In some embodiments, a 17.5 mg solid dosage formulation of rofecoxib has a mean Cmax plasma concentration of more than 280 ng/ml. In some embodiments, a 17.5 mg solid dosage formulation of rofecoxib has a mean $AUC_{0-\infty}$ of more than 1750 h*ng/ml. In some embodiments, a 17.5 mg solid dosage formulation of rofecoxib has a mean $AUC_{0-\infty}$ of more than 2000 h*ng/ml. In some embodiments, a 17.5 mg solid dosage formulation of rofecoxib has a mean $AUC_{0-\infty}$ of more than 2500 h*ng/ml. In some embodiments, a 17.5 mg solid dosage formulation of rofecoxib has a mean $AUC_{0-\infty}$ of more than 3000 h*ng/ml. In some embodiments, a 17.5 mg solid dosage formulation of rofecoxib has a mean $AUC_{0-\infty}$ of more than 3100 h*ng/ml. In some embodiments, a 17.5 mg solid dosage formulation of rofecoxib has a mean $AUC_{0-\infty}$ of more than 3500 h*ng/ml. In some embodiments, a 17.5 mg solid dosage formulation of rofecoxib has a mean $AUC_{0-\infty}$ of more than 4000 h*ng/ml. In some embodiments, a 17.5 mg solid dosage formulation of rofecoxib has a mean $AUC_{0-\infty}$ of more than 4500 h*ng/ml. In some embodiments, a 17.5 mg solid dosage formulation of rofecoxib reaches a Cmax plasma concentration of least 167 ng/ml, 170 ng/ml, 175 ng/ml, 180 ng/ml, or higher following single administration of the formulation to a human subject. In some embodiments, a 17.5 mg solid dosage formulation of rofecoxib reaches an $AUC_{0-\infty}$ of at least 2600 h*ng/ml, 2750 h*ng/ml, 2900 h*ng/ml, 3050 h*ng/ml, 3100 h*ng/ml, 3200 h*ng/ml, 3350 h*ng/ml, 3500 h*ng/ml, 3650 h*ng/ml or higher following single administration of the formulation to a human subject.

In some embodiments, a 20 mg solid dosage formulation of rofecoxib reaches a median time to Cmax plasma concentration in 4 hours or less following single administration of the formulation to human subjects. In some embodiments, a 20 mg solid dosage formulation of rofecoxib reaches a median time to Cmax plasma concentration in 3 hours or less following administration. In some embodiments, a 20 mg solid dosage formulation of rofecoxib reaches a median time to Cmax plasma concentration in 2.5 hours or less following administration. In some embodiments, a 20 mg solid dosage formulation of rofecoxib reaches a median time to Cmax plasma concentration in 2 hours or less following administration. In some embodiments, a 20 mg solid dosage formulation of rofecoxib has a mean Cmax plasma concentration of more than 150 ng/ml. In some embodiments, a 20 mg solid dosage formulation of rofecoxib has a mean Cmax plasma concentration of more than 191 ng/ml, 200 ng/ml, 215 ng/ml, or 225 ng/ml. In some embodiments, a 20 mg solid dosage formulation of rofecoxib has a mean Cmax plasma concentration of more than 250 ng/ml. In some embodiments, a 20 mg solid dosage formulation of rofecoxib has a mean Cmax plasma concentration of more than 258 ng/ml. In some embodiments, a 20 mg solid dosage formulation of rofecoxib has a mean Cmax plasma concentration of more than 300 ng/ml. In some embodiments, a 20 mg solid dosage formulation of rofecoxib has a mean $AUC_{0-\infty}$ of more than 2000 h*ng/ml. In some embodiments, a 20 mg solid dosage formulation of rofecoxib has a mean $AUC_{0-\infty}$ of more than 2500 h*ng/ml. In some embodiments, a 20 mg solid dosage formulation of rofecoxib has a mean $AUC_{0-\infty}$ of more than 3000 h*ng/ml. In some embodiments, a 20 mg solid dosage formulation of rofecoxib has a mean $AUC_{0-\infty}$ of more than 3400 h*ng/ml. In some embodiments, a 20 mg solid dosage formulation of rofecoxib has a mean $AUC_{0-\infty}$ of more than 3500 h*ng/ml. In some embodiments, a 20 mg solid dosage formulation of rofecoxib has a mean $AUC_{0-\infty}$ of more than 4000 h*ng/ml. In some embodiments, a 20 mg solid dosage formulation of rofecoxib reaches a Cmax plasma concentration of least 190 ng/ml, 205 ng/ml, 220 ng/ml, 235 ng/ml, 250 ng/ml, or higher following single administration of the formulation to a human subject. In some embodiments, a 20 mg solid dosage formulation of rofecoxib reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In some embodiments, a 25 mg solid dosage formulation of rofecoxib reaches a mean Cmax plasma concentration in less than 3 hours following single administration of the formulation to human subjects. In some embodiments, a 25 mg solid dosage formulation of rofecoxib reaches a mean Cmax plasma concentration in less than 2.5 hours following administration. In some embodiments, a 25 mg solid dosage formulation of rofecoxib reaches a mean Cmax plasma concentration in less than 2 hours following administration. In some embodiments, a 25 mg solid dosage formulation of rofecoxib has a mean Cmax plasma concentration of more than 240 ng/ml. In some embodiments, a 25 mg solid dosage formulation of rofecoxib has a mean Cmax plasma concentration of more than 250 ng/ml. In some embodiments, a 25 mg solid dosage formulation of rofecoxib has a mean Cmax plasma concentration of more than 300 ng/ml. In some embodiments, a 25 mg solid dosage formulation of rofecoxib has a mean Cmax plasma concentration of more than 320 ng/ml. In some embodiments, a 25 mg solid dosage formulation of rofecoxib has a mean $AUC_{0-\infty}$ of more than 4250 h*ng/ml. In some embodiments, a 25 mg solid dosage formulation of rofecoxib has a mean $AUC_{0-\infty}$ of more than 4500 h*ng/ml. In some embodiments, a 25 mg solid dosage formulation of rofecoxib has a mean $AUC_{0-\infty}$ of more than 4700 h*ng/ml. In some embodiments, a 25 mg solid dosage formulation of rofecoxib has a mean $AUC_{0-\infty}$ of more than 5000 h*ng/ml. In some embodiments, a 25 mg solid dosage formulation of rofecoxib reaches a Cmax plasma concentration of more than 240 ng/ml in a median time of about 3 hours or less following administration with an $AUC_{0-\infty}$ of more than 4250 h*ng/ml.

In some embodiments, a 10 mg to 50 mg solid dosage formulation of rofecoxib achieves a mean Cmax plasma concentration from 9.8 ng/ml to 16 ng/ml for each 1 mg of rofecoxib in the formulation following single administration of the formulation to human subjects. In some embodiments, the solid dosage formulation of rofecoxib achieves a mean Cmax plasma concentration from 10 ng/ml to 14 ng/ml for each 1 mg of rofecoxib in the formulation. In some embodiments, the solid dosage formulation of rofecoxib achieves a mean Cmax plasma concentration from 10 ng/ml to 13 ng/ml for each 1 mg of rofecoxib in the formulation. In some embodiments, the solid dosage formulation of rofecoxib achieves a mean Cmax plasma concentration from 80% to 125% of 12.8 ng/ml. In some embodiments, the solid dosage formulation of rofecoxib reaches a mean $AUC_{0-\infty}$ of 170 h*ng/ml to 235 h*ng/ml for each 1 mg of rofecoxib in the formulation. In some embodiments, the solid dosage formulation of rofecoxib reaches a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the solid dosage formulation of rofecoxib reaches a mean $AUC_{0-\infty}$ of 190 h*ng/ml to 215 h*ng/ml for each 1 mg of rofecoxib in the formulation.

In certain aspects, the subject matter disclosed herein provides a method for inhibiting COX-2 in a subject in need thereof, the method comprising administering to the subject a solid dosage formulation comprising 17.5 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 100 ng/ml. In some embodiments, the formulation achieves a mean Cmax plasma concentration of more than 150 ng/ml, 167 ng/ml, or 190 ng/ml. In some embodiments, the formulation achieves a mean Cmax plasma concentration of more than 200 ng/ml. In some embodiments, the formulation achieves a mean Cmax plasma concentration of more than 220 ng/ml. In some embodiments, the formulation achieves a mean Cmax plasma concentration of more than 250 ng/ml. In some embodiments, the formulation achieves a mean Cmax plasma concentration of more than 280 ng/ml. In some embodiments, the formulation achieves a mean $AUC_{0-\infty}$ of more than 1750 h*ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation achieves a mean $AUC_{0-\infty}$ of more than 4500 h*ng/ml. In some embodiments, a 17.5 mg solid dosage formulation of rofecoxib reaches a Cmax plasma concentration of least 167 ng/ml, 170 ng/ml, 175 ng/ml, 180 ng/ml, or higher following single administration of the formulation to a human subject. In some embodiments, a 17.5 mg solid dosage formulation of rofecoxib reaches an $AUC_{0-\infty}$ of at least 2600 h*ng/ml, 2750 h*ng/ml, 2900 h*ng/ml, 3050 h*ng/ml, 3200 h*ng/ml, 3350 h*ng/ml, 3500 h*ng/ml, 3650 h*ng/ml or higher following single administration of the formulation to a human subject.

In certain aspects, the subject matter disclosed herein provides a method for inhibiting COX-2 in a subject in need thereof, the method comprising administering to the subject a solid dosage formulation comprising 20 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a mean Cmax plasma concentration in less than 3 hours following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 150 ng/ml. In some embodiments, the formulation achieves a mean Cmax plasma concentration of more than 191 ng/ml, 200 ng/ml, 215 ng/ml, or 225 ng/ml. In some embodiments, the formulation achieves a mean Cmax plasma concentration of more than 250 ng/ml. In some embodiments, the formulation achieves a mean Cmax plasma concentration of more than 258 ng/ml. In some embodiments, the formulation achieves a mean Cmax plasma concentration of more than 300 ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3400 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation reaches a Cmax plasma concentration of least 190 ng/ml, 205 ng/ml, 220 ng/ml, 235 ng/ml, 250 ng/ml, or higher following single administration of the formulation to a human subject. In some embodiments, the formulation reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject.

In certain aspects, the subject matter disclosed herein provides a method for inhibiting COX-2 in a subject in need thereof, the method comprising administering to the subject a solid dosage formulation comprising 25 mg of rofecoxib or a pharmaceutically acceptable salt thereof. In some embodiments, the formulation achieves a mean Cmax plasma concentration in less than 3 hours following single administration of the formulation to human subjects. In some embodiments, the formulation achieves a mean Cmax plasma concentration in less than 2.5 hours following administration. In some embodiments, the formulation achieves a mean Cmax plasma concentration in less than 2 hours following administration. In some embodiments, the formulation achieves a mean Cmax plasma concentration of more than 240 ng/ml. In some embodiments, the formulation achieves a mean Cmax plasma concentration of more than 250 ng/ml. In some embodiments, the formulation achieves a mean Cmax plasma concentration of more than 300 ng/ml. In some embodiments, the formulation achieves a mean Cmax plasma concentration of more than 320 ng/ml. In some embodiments, the formulation achieves a mean $AUC_{0-\infty}$ of more than 4250 h*ng/ml. In some embodiments, the formulation achieves a mean $AUC_{0-\infty}$ of more than 4500 h*ng/ml. In some embodiments, the formulation achieves a mean $AUC_{0-\infty}$ of more than 4550 h*ng/ml. In some embodiments, the formulation achieves a mean $AUC_{0-\infty}$ of more than 4700 h*ng/ml. In some embodiments, the formulation achieves a Cmax plasma concentration of more than 240 ng/ml about 3 hours following administration with an $AUC_{0-\infty}$ of more than 4250 h*ng/ml.

In certain aspects, the subject matter disclosed herein provides a method for inhibiting COX-2 in a subject in need thereof, the method comprising administering to the subject a solid dosage formulation comprising 10 mg to 50 mg of rofecoxib or a pharmaceutically acceptable salt thereof. In some embodiments, the formulation achieves a mean Cmax plasma concentration from 9.8 ng/ml to 16 ng/ml for each 1 mg of rofecoxib in the formulation following single administration of the formulation to human subjects. In some embodiments, the formulation of rofecoxib achieves a mean Cmax plasma concentration from 10 ng/ml to 14 ng/ml for each 1 mg of rofecoxib in the formulation. In some embodiments, the formulation of rofecoxib achieves a mean Cmax plasma concentration from 10 ng/ml to 13 ng/ml for each 1 mg of rofecoxib in the formulation. In some embodiments, the solid dosage formulation of rofecoxib achieves a mean Cmax plasma concentration from 80% to 125% of 12.8 ng/ml. In some embodiments, the formulation of rofecoxib reaches a mean $AUC_{0-\infty}$ of 170 h*ng/ml to 235 h*ng/ml for each 1 mg of rofecoxib in the formulation. In some embodiments, the formulation of rofecoxib reaches a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the formulation of rofecoxib reaches a mean $AUC_{0-\infty}$ of 190 h*ng/ml to 215 h*ng/ml for each 1 mg of rofecoxib in the formulation.

In certain aspects, a method is provided for inhibiting COX-2 in patients within a patient population, the method comprising providing a solid dosage formulation comprising 10 mg to 50 mg of rofecoxib to the patient population, wherein the formulation achieves a mean Cmax plasma concentration from 9.8 ng/ml to 16 ng/ml for each 1 mg of rofecoxib in the formulation following single administration of the formulation to the patients within the patient population. In some embodiments, the solid dosage formulation of rofecoxib achieves a mean Cmax plasma concentration from 10 ng/ml to 14 ng/ml for each 1 mg of rofecoxib in the formulation. In some embodiments, the solid dosage formulation of rofecoxib achieves a mean Cmax plasma concentration from 10 ng/ml to 13 ng/ml for each 1 mg of rofecoxib in the formulation. In some embodiments, the solid dosage formulation of rofecoxib achieves a mean Cmax plasma concentration from 80% to 125% of 12.8 ng/ml. In some embodiments, the solid dosage formulation of rofecoxib reaches a mean $AUC_{0-\infty}$ of 170 h*ng/ml to 235 h*ng/ml for each 1 mg of rofecoxib in the formulation. In some embodiments, the solid dosage formulation of rofecoxib reaches a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the solid dosage formulation of rofecoxib reaches a mean $AUC_{0-\infty}$ of 190 h*ng/ml to 215 h*ng/ml for each 1 mg of rofecoxib in the formulation.

A method for inhibiting COX-2 in a subject in need thereof, the method comprising administering to the subject a solid dosage form comprising a granular component and an extragranular component, wherein the granular component comprises an intragranular component comprising rofecoxib or a pharmaceutically acceptable salt thereof and one or more disintegrants, and wherein the extragranular component comprises one or more disintegrants.

In some embodiments, the one or more disintegrants in the granular component is selected from starches, clays, celluloses, algins, gums, cross-linked polymers, and combinations thereof. In some embodiments, the one or more disintegrants in the granular component is selected from croscarmellose, crospovidone, sodium starch glycolate, and combinations thereof.

In some embodiments, the one or more disintegrants in the granular component is croscarmellose sodium. In some embodiments, the one or more disintegrants in the granular component is about 1% (w/w) to about 8% (w/w) of the solid dosage form. In some embodiments, the one or more disintegrants in the granular component is about 1% (w/w) to about 6% (w/w) of the solid dosage form. In some embodiments, the one or more disintegrants in the granular component is about 1% (w/w) to about 4% (w/w) of the solid dosage form.

In some embodiments, the one or more disintegrants in the extragranular component is selected from starches, clays, celluloses, algins, gums, cross-linked polymers, and combinations thereof. In some embodiments, the one or more disintegrants in the extragranular component is selected from croscarmellose, crospovidone, sodium starch glycolate, and combinations thereof. In some embodiments, the one or more disintegrants in the extragranular component is croscarmellose sodium. In some embodiments, the disintegrant in the extragranular component is about 1% (w/w) to about 8% (w/w) of the solid dosage form. In some embodiments, the disintegrant in the extragranular component is about 1% (w/w) to about 6% (w/w) of the solid dosage form. In some embodiments, the disintegrant in the extragranular component is about 1% (w/w) to about 4% (w/w) of the solid dosage form.

In some embodiments, the disintegrant in the granular component and the disintegrant in the extragranular component are together about 2% (w/w) to about 12% (w/w) of the solid dosage form. In some embodiments, the disintegrant in the granular component and the disintegrant in the extragranular component are together about 2% (w/w) to about 10% (w/w) of the solid dosage form. In some embodiments, the disintegrant in the granular component and the disintegrant in the extragranular component are together about 2% (w/w) to about 8% (w/w) of the solid dosage form.

In some embodiments, the ratio of granular disintegrant to extragranular disintegrant is about 40% (w/w) to about 60% (w/w). In some embodiments, the ratio of granular disintegrant to extragranular disintegrant is about 45% (w/w) to about 55% (w/w). In some embodiments, the ratio of granular disintegrant to extragranular disintegrant is about 50% (w/w) to about 50% (w/w). In some embodiments, the ratio of granular disintegrant to extragranular disintegrant is about 55% (w/w) to about 45% (w/w). In some embodiments, the ratio of granular disintegrant to extragranular disintegrant is about 60% (w/w) to about 40% (w/w).

In some embodiments, the solid dosage form further comprising one or more of a diluent, a binder, a coloring agent, and a lubricant. In some embodiments, at least a portion of the diluent is in the granular component. In some embodiments, the diluent is selected from dicalcium phosphate, calcium sulfate, lactose, cellulose, kaolin, mannitol, sodium chloride, dry starch, powdered sugar, sorbitol, sucrose, inositol, and combinations thereof. In some embodiments, the diluent is selected from lactose, cellulose, or a combination thereof. In some embodiments, the diluent is selected from lactose monohydrate, microcrystalline cellulose, or a combination thereof.

In some embodiments, the lactose monohydrate is about 35% (w/w) to about 45% (w/w) of the solid dosage form. In some embodiments, the lactose monohydrate is about 37% (w/w) to about 42% (w/w) of the solid dosage form. In some embodiments, the lactose monohydrate is about 39% (w/w) to about 40% (w/w) of the solid dosage form.

In some embodiments, the microcrystalline cellulose is about 35% (w/w) to about 45% (w/w) of the solid dosage form. In some embodiments, the microcrystalline cellulose is about 37% (w/w) to about 42% (w/w) of the solid dosage form. In some embodiments, the microcrystalline cellulose is about 39% (w/w) to about 40% (w/w) of the solid dosage form.

In some embodiments, the diluent is about 75% (w/w) to about 85% (w/w) of the solid dosage form. In some embodiments, diluent is about 77% (w/w) to about 82% (w/w) of the solid dosage form. In some embodiments, the diluent is about 78% (w/w) to about 80% (w/w) of the solid dosage form.

In some embodiments, at least a portion of the binder is in the granular component. In some embodiments, the binder is selected from starches, gelatins, sugars, gums, waxes, water, alcohols, celluloses, and combinations thereof. In some embodiments, the binder is selected from acacia gum, tragacanth, corn starch, methyl cellulose, panwar gum, ghatti gum, mucilage of isapol husks, carboxymethylcellulose, methylcellulose, polyvinylpyrrolidone, sucrose, glucose, dextrose, molasses, lactose, and combinations thereof. In some embodiments, the binder is hydroxypropyl cellulose. In some embodiments, the binder is about 1% (w/w) to about 5% (w/w) of the solid dosage form. In some embodiments, binder is about 2% (w/w) to about 4% (w/w) of the solid dosage form. In some embodiments, the binder is about 2.5% (w/w) to about 3.5% (w/w) of the solid dosage form.

In some embodiments, at least a portion of the coloring agent is in the extragranular component. In some embodiments, the coloring agent is pigment blend yellow. In some embodiments, the coloring agent is about 0.30% (w/w) to about 0.60% (w/w) of the solid dosage form.

In some embodiments, at least a portion of the lubricant is in the extragranular component. In some embodiments, the lubricant is selected from talc, magnesium stearate, calcium stearate, stearic acid, metallic stearate, hydrogenated vegetable oils, and polyethylene glycol, corn starch, boric acids, sodium chloride, sodium lauryl sulphate. In some embodiments, the lubricant is magnesium stearate. In some embodiments, the lubricant is about 0.10% (w/w) to about 1% (w/w) of the solid dosage form. In some embodiments, the lubricant is about 0.50% (w/w) of the solid dosage form.

In some embodiments, the rofecoxib or pharmaceutically acceptable salt thereof is about 5% (w/w) to about 30% (w/w) of the solid dosage form. In some embodiments, the rofecoxib or pharmaceutically acceptable salt thereof is about 10% (w/w) to about 20% (w/w) of the solid dosage form. In some embodiments, the rofecoxib or pharmaceutically acceptable salt thereof is about 12% (w/w) to about 13% (w/w) of the solid dosage form. In some embodiments, the solid dosage form comprises about 10 mg of the rofecoxib or pharmaceutically acceptable salt thereof. In some embodiments, the solid dosage form comprises about 10.5 mg of the rofecoxib or pharmaceutically acceptable salt thereof. In some embodiments, the solid dosage form comprises about 11 mg of the rofecoxib or pharmaceutically acceptable salt thereof. In some embodiments, the solid dosage form comprises about 11.5 mg of the rofecoxib or pharmaceutically acceptable salt thereof. In some embodiments, the solid dosage form comprises about 12 mg of the rofecoxib or pharmaceutically acceptable salt thereof. In some embodiments, the solid dosage form comprises about 12.5 mg of the rofecoxib or pharmaceutically acceptable salt thereof. In some embodiments, the solid dosage form comprises about 17.5 mg of the rofecoxib or pharmaceutically acceptable salt thereof. In some embodiments, the solid dosage form comprises about 20 mg of the rofecoxib or pharmaceutically acceptable salt thereof. In some embodiments, the solid dosage form comprises about 21 mg of the rofecoxib or pharmaceutically acceptable salt thereof. In some embodiments, the solid dosage form comprises about 22 mg of the rofecoxib or pharmaceutically acceptable salt thereof. In some embodiments, the solid dosage form comprises about 22.5 mg of the rofecoxib or pharmaceutically acceptable salt thereof. In some embodiments, the solid dosage form comprises about 25 mg of the rofecoxib or pharmaceutically acceptable salt thereof. In some embodiments, the solid dosage form comprises about 50 mg of the rofecoxib or pharmaceutically acceptable salt thereof.

In some embodiments, the rofecoxib is highly pure. In some embodiments, the highly pure rofecoxib comprises less than about 0.1% total impurities. In some embodiments, the highly pure rofecoxib comprises less than about 0.075% total impurities. In some embodiments, the highly pure rofecoxib comprises less than about 0.050% total impurities. In some embodiments, the highly pure rofecoxib comprises less than about 0.025% total impurities. In some embodiments, the highly pure rofecoxib comprises less than about 0.001% total impurities.

In some embodiments, the highly pure rofecoxib comprises less than about 0.10%, 0.05%, 0.02%, or 0.01% of 4-[4-(methylsulphonyl)phenyl]-3-phenyl-2,5-furandione. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylsulfinyl)phenyl]-3-phenyl-2(5H)-furanone.

In some embodiments, the solid dosage form is suitable for oral administration. In some embodiments, the solid dosage form is an oral tablet. In some embodiments, the oral tablet provides a dissolution rate of at least about 80% of the rofecoxib or pharmaceutically acceptable salt thereof by about 15 minutes. In some embodiments, the oral tablet provides a dissolution rate of at least about 85% of the rofecoxib or pharmaceutically acceptable salt thereof by about 15 minutes. In some embodiments, the oral tablet provides a dissolution rate of at least about 90% of the rofecoxib or pharmaceutically acceptable salt thereof by about 15 minutes. In some embodiments, the oral tablet provides a dissolution rate of at least about 95% of the rofecoxib or pharmaceutically acceptable salt thereof by about 15 minutes. In some embodiments, the oral tablet provides a dissolution rate of at least about 100% of the rofecoxib or pharmaceutically acceptable salt thereof by about 15 minutes.

In some embodiments, the dissolution rate is measured in about 1% SDS at a paddle speed of about 50 rpm and at a temperature of about 37.0° C.±0.5° C. In some embodiments, the dissolution rate is measured in about 1% SDS at a paddle speed of about 75 rpm and at a temperature of about 37.0° C.±0.5° C. In some embodiments, the dissolution rate is measured in about 1.5% SDS at a paddle speed of about 50 rpm and at a temperature of about 37.0° C.±0.5° C. In some embodiments, the dissolution rate is measured in about 1.5% SDS at a paddle speed of about 75 rpm and at a temperature of about 37.0° C.±0.5° C. In some embodiments, the dissolution rate is measured in about 2% SDS at a paddle speed of about 50 rpm and at a temperature of about 37.0° C.±0.5° C. In some embodiments, the dissolution rate is measured in about 2% SDS at a paddle speed of about 75 rpm and at a temperature of about 37.0° C.±0.5° C.

In some embodiments, the rofecoxib or pharmaceutically acceptable salt thereof is formulated into granules and at least about 35% of the granules are less than about 75 µm. In some embodiments, the rofecoxib or pharmaceutically acceptable salt thereof is formulated into granules and at least about 55% of the granules are less than about 150 µm. In some embodiments, the rofecoxib or pharmaceutically acceptable salt thereof is formulated into granules and at least about 75% of the granules are less than about 250 µm. In some embodiments, the rofecoxib or pharmaceutically acceptable salt thereof is formulated into granules and at least about 85% of the granules are less than about 425 µm. In some embodiments, the rofecoxib or pharmaceutically acceptable salt thereof is formulated into granules and at least about 90% of the granules are less than about 1000 µm.

In some embodiments, a 17.5 mg solid dosage formulation of rofecoxib reaches a median time to Cmax plasma concentration in 4 hours or less following single administration of the formulation to human subjects. In some embodiments, a 17.5 mg solid dosage formulation of rofecoxib reaches a median time to Cmax plasma concentration in 3 hours or less following administration. In some embodiments, a 17.5 mg solid dosage formulation of rofecoxib reaches a median time to Cmax plasma concentration in 2.5 hours or less following administration. In some embodiments, a 17.5 mg solid dosage formulation of rofecoxib reaches a median time to Cmax plasma concentration in 2 hours or less following administration. In some embodiments, a 17.5 mg solid dosage formulation of rofecoxib has a mean Cmax plasma concentration of more than 100 ng/ml. In some embodiments, a 17.5 mg solid dosage formulation of rofecoxib has a mean Cmax plasma concentration of more than 150 ng/ml, 167 ng/ml, or 190 ng/ml. In some embodiments, a 17.5 mg solid dosage formulation of rofecoxib has a mean Cmax plasma concentration of more than 200 ng/ml. In some embodiments, a 17.5 mg solid dosage formulation of rofecoxib has a mean Cmax plasma concentration of more than 220 ng/ml. In some embodiments, a 17.5 mg solid dosage formulation of rofecoxib has a mean Cmax plasma concentration of more than 250 ng/ml. In some embodiments, a 17.5 mg solid dosage formulation of rofecoxib has a mean Cmax plasma concentration of more than 280 ng/ml. In some embodiments, a 17.5 mg solid dosage formulation of rofecoxib has a mean $AUC_{0-\infty}$ of more than 1750 h*ng/ml. In some embodiments, a 17.5 mg solid dosage formulation of rofecoxib has a mean $AUC_{0-\infty}$ of more than 2000 h*ng/ml. In some embodiments, a 17.5 mg solid dosage formulation of rofecoxib has a mean $AUC_{0-\infty}$ of more than 2500 h*ng/ml. In some embodiments, a 17.5 mg solid dosage formulation of rofecoxib has a mean $AUC_{0-\infty}$ of more than 3000 h*ng/ml. In some embodiments, a 17.5 mg solid dosage formulation of rofecoxib has a mean $AUC_{0-\infty}$ of more than 3100 h*ng/ml. In some embodiments, a 17.5 mg solid dosage formulation of rofecoxib has a mean $AUC_{0-\infty}$ of more than 3500 h*ng/ml. In some embodiments, a 17.5 mg solid dosage formulation of rofecoxib has a mean $AUC_{0-\infty}$ of more than 4000 h*ng/ml. In some embodiments, a 17.5 mg solid dosage formulation of rofecoxib has a mean $AUC_{0-\infty}$ of more than 4500 h*ng/ml. In some embodiments, a 17.5 mg solid dosage formulation of rofecoxib reaches a Cmax plasma concentration of least 167 ng/ml, 170 ng/ml, 175 ng/ml, 180 ng/ml, or higher following single administration of the formulation to a human subject. In some embodiments, a 17.5 mg solid dosage formulation of rofecoxib reaches an $AUC_{0-\infty}$ of at least 2600 h*ng/ml, 2750 h*ng/ml, 2900 h*ng/ml, 3050 h*ng/ml, 3100 h*ng/ml, 3200 h*ng/ml, 3350 h*ng/ml, 3500 h*ng/ml, 3650 h*ng/ml or higher following single administration of the formulation to a human subject.

In some embodiments, a 20 mg solid dosage formulation of rofecoxib reaches a median time to Cmax plasma concentration in 4 hours or less following single administration of the formulation to human subjects. In some embodiments, a 20 mg solid dosage formulation of rofecoxib reaches a median time to Cmax plasma concentration in 3 hours or less following administration. In some embodiments, a 20 mg solid dosage formulation of rofecoxib reaches a median time to Cmax plasma concentration in 2.5 hours or less following administration. In some embodiments, a 20 mg solid dosage formulation of rofecoxib reaches a median time to Cmax plasma concentration in 2 hours or less following administration. In some embodiments, a 20 mg solid dosage formulation of rofecoxib has a mean Cmax plasma concentration of more than 150 ng/ml. In some embodiments, a 20 mg solid dosage formulation of rofecoxib has a mean Cmax plasma concentration of more than 191 ng/ml, 200 ng/ml, 215 ng/ml, or 225 ng/ml. In some embodiments, a 20 mg solid dosage formulation of rofecoxib has a mean Cmax plasma concentration of more than 250 ng/ml. In some embodiments, a 20 mg solid dosage formulation of rofecoxib has a mean Cmax plasma concentration of more than 258 ng/ml. In some embodiments, a 20 mg solid dosage formulation of rofecoxib has a mean Cmax plasma concentration of more than 300 ng/ml. In some embodiments, a 20 mg solid dosage formulation of rofecoxib has a mean $AUC_{0-\infty}$ of more than 2000 h*ng/ml. In some embodiments, a 20 mg solid dosage formulation of rofecoxib has a mean $AUC_{0-\infty}$ of more than 2500 h*ng/ml. In some embodiments, a 20 mg solid dosage formulation of rofecoxib has a mean $AUC_{0-\infty}$ of more than 3000 h*ng/ml. In some embodiments, a 20 mg solid dosage formulation of rofecoxib has a mean $AUC_{0-\infty}$ of more than 3400 h*ng/ml. In some embodiments, a 20 mg solid dosage formulation of rofecoxib has a mean $AUC_{0-\infty}$ of more than 3500 h*ng/ml. In some embodiments, a 20 mg solid dosage formulation of rofecoxib has a mean $AUC_{0-\infty}$ of more than 4000 h*ng/ml. In some embodiments, a 20 mg solid dosage formulation of rofecoxib reaches a Cmax plasma concentration of least 190 ng/ml, 205 ng/ml, 220 ng/ml, 235 ng/ml, 250 ng/ml, or higher following single administration of the formulation to a human subject. In some embodiments, a 20 mg solid dosage formulation of rofecoxib reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In some embodiments, a 25 mg solid dosage formulation of rofecoxib reaches a mean Cmax plasma concentration in less than 3 hours following single administration of the formulation to human subjects. In some embodiments, a 25 mg solid dosage formulation of rofecoxib reaches a mean Cmax plasma concentration in less than 2.5 hours following administration. In some embodiments, a 25 mg solid dosage formulation of rofecoxib reaches a mean Cmax plasma concentration in less than 2 hours following administration. In some embodiments, a 25 mg solid dosage formulation of rofecoxib has a mean Cmax plasma concentration of more than 240 ng/ml. In some embodiments, a 25 mg solid dosage formulation of rofecoxib has a mean Cmax plasma concentration of more than 250 ng/ml. In some embodiments, a 25 mg solid dosage formulation of rofecoxib has a mean Cmax plasma concentration of more than 300 ng/ml. In some embodiments, a 25 mg solid dosage formulation of rofecoxib has a mean Cmax plasma concentration of more than 320 ng/ml. In some embodiments, a 25 mg solid dosage formulation of rofecoxib has a mean $AUC_{0-\infty}$ of more than 4250 h*ng/ml. In some embodiments, a 25 mg solid dosage formulation of rofecoxib has a mean $AUC_{0-\infty}$ of more than 4500 h*ng/ml. In some embodiments, a 25 mg solid dosage formulation of rofecoxib has a mean $AUC_{0-\infty}$ of more than 4700 h*ng/ml. In some embodiments, a 25 mg solid dosage formulation of rofecoxib has a mean $AUC_{0-\infty}$ of more than 5000 h*ng/ml. In some embodiments, a 25 mg solid dosage formulation of rofecoxib reaches a mean Cmax plasma concentration of more than 240 ng/ml in a median time of about 3 hours or less following administration with an $AUC_{0-\infty}$ of more than 4250 h*ng/ml.

In some embodiments, a 10 mg to 50 mg solid dosage formulation of rofecoxib achieves a mean Cmax plasma concentration from 9.8 ng/ml to 16 ng/ml for each 1 mg of rofecoxib in the formulation following single administration of the formulation to human subjects. In some embodiments, the solid dosage formulation achieves a mean Cmax plasma concentration from 10 ng/ml to 14 ng/ml for each 1 mg of rofecoxib in the formulation. In some embodiments, the solid dosage formulation achieves a mean Cmax plasma concentration from 10 ng/ml to 13 ng/ml for each 1 mg of rofecoxib in the formulation. In some embodiments, the solid dosage formulation achieves a mean Cmax plasma concentration from 80% to 125% of 12.8 ng/ml. In some embodiments, the solid dosage formulation reaches a mean $AUC_{0-\infty}$ of 170 h*ng/ml to 235 h*ng/ml for each 1 mg of rofecoxib in the formulation. In some embodiments, the solid dosage formulation reaches a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the solid dosage formulation reaches a mean $AUC_{0-\infty}$ of 190 h*ng/ml to 215 h*ng/ml for each 1 mg of rofecoxib in the formulation.

In certain aspects, the subject matter disclosed herein provides a method for inhibiting COX-2 in a subject in need thereof, the method comprising administering to the subject a solid dosage formulation comprising 17.5 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 100 ng/ml. In some embodiments, the formulation achieves a mean Cmax plasma concentration of more than 150 ng/ml, 167 ng/ml, or 190 ng/ml. In some embodiments, the formulation achieves a mean Cmax plasma concentration of more than 200 ng/ml. In some embodiments, the formulation achieves a mean Cmax plasma concentration of more than 220 ng/ml. In some embodiments, the formulation achieves a mean Cmax plasma concentration of more than 250 ng/ml. In some embodiments, the formulation achieves a mean Cmax plasma concentration of more than 280 ng/ml. In some embodiments, the formulation achieves a mean $AUC_{0-\infty}$ of more than 1750 h*ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3100 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation achieves a mean $AUC_{0-\infty}$ of more than 4500 h*ng/ml. In some embodiments, the formulation reaches a Cmax plasma concentration of least 167 ng/ml, 170 ng/ml, 175 ng/ml, 180 ng/ml, or higher following single administration of the formulation to a human subject. In some embodiments, the formulation reaches an $AUC_{0-\infty}$ of at least 2600 h*ng/ml, 2750 h*ng/ml, 2900 h*ng/ml, 3050 h*ng/ml, 3200 h*ng/ml, 3350 h*ng/ml, 3500 h*ng/ml, 3650 h*ng/ml or higher following single administration of the formulation to a human subject.

In certain aspects, the subject matter disclosed herein provides a method for inhibiting COX-2 in a subject in need thereof, the method comprising administering to the subject a solid dosage formulation comprising 20 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 150 ng/ml. In some embodiments, the formulation achieves a mean Cmax plasma concentration of more than 191 ng/ml, 200 ng/ml, 215 ng/ml, or 225 ng/ml. In some embodiments, the formulation achieves a mean Cmax plasma concentration of more than 250 ng/ml. In some embodiments, a 20 mg solid dosage formulation of rofecoxib has a mean Cmax plasma concentration of more than 258 ng/ml. In some embodiments, the formulation achieves a mean Cmax plasma concentration of more than 300 ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3400 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation reaches a Cmax plasma concentration of least 190 ng/ml, 205 ng/ml, 220 ng/ml, 235 ng/ml, 250 ng/ml, or higher following single administration of the formulation to a human subject. In some embodiments, the formulation reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In certain aspects, the subject matter disclosed herein provides a method for inhibiting COX-2 in a subject in need thereof, the method comprising administering to the subject a solid dosage formulation comprising 25 mg of rofecoxib or a pharmaceutically acceptable salt thereof. In some embodiments, the formulation achieves a mean Cmax plasma concentration in less than 3 hours following single administration of the formulation to human subjects. In some embodiments, the formulation achieves a mean Cmax plasma concentration in less than 2.5 hours following administration. In some embodiments, the formulation achieves a mean Cmax plasma concentration in less than 2 hours following administration. In some embodiments, the formulation achieves a mean Cmax plasma concentration of more than 240 ng/ml. In some embodiments, the formulation achieves a mean Cmax plasma concentration of more than 250 ng/ml. In some embodiments, the formulation achieves a mean Cmax plasma concentration of more than 300 ng/ml. In some embodiments, the formulation achieves a mean Cmax plasma concentration of more than 320 ng/ml. In some embodiments, the formulation achieves a mean $AUC_{0-\infty}$ of more than 4250 h*ng/ml. In some embodiments, the formulation achieves a mean $AUC_{0-\infty}$ of more than 4500 h*ng/ml. In some embodiments, the formulation achieves a mean $AUC_{0-\infty}$ of more than 4550 h*ng/ml. In some embodiments, the formulation achieves a mean $AUC_{0-\infty}$ of more than 4700 h*ng/ml. In some embodiments, the formulation achieves a Cmax plasma concentration of more than 240 ng/ml about 3 hours following administration with an $AUC_{0-\infty}$ of more than 4250 h*ng/ml.

In certain aspects, the subject matter disclosed herein provides a method for inhibiting COX-2 in a subject in need thereof, the method comprising administering to the subject a solid dosage formulation comprising 10 mg to 50 mg of rofecoxib or a pharmaceutically acceptable salt thereof. In some embodiments, the formulation achieves a mean Cmax plasma concentration from 9.8 ng/ml to 16 ng/ml for each 1 mg of rofecoxib in the formulation following single administration of the formulation to human subjects. In some embodiments, the formulation achieves a mean Cmax plasma concentration from 10 ng/ml to 14 ng/ml for each 1 mg of rofecoxib in the formulation. In some embodiments, the formulation achieves a mean Cmax plasma concentration from 10 ng/ml to 13 ng/ml for each 1 mg of rofecoxib in the formulation. In some embodiments, the formulation achieves a mean Cmax plasma concentration from 80% to 125% of 12.8 ng/ml. In some embodiments, the formulation reaches a mean $AUC_{0-\infty}$ of 170 h*ng/ml to 235 h*ng/ml for each 1 mg of rofecoxib in the formulation. In some embodiments, the formulation reaches a mean $AUC_{0-\infty}$ of 177 h*ng/ml to 225 h*ng/ml for each 1 mg of rofecoxib in the formulation. In some embodiments, the formulation reaches a mean $AUC_{0-\infty}$ of 190 h*ng/ml to 215 h*ng/ml for each 1 mg of rofecoxib in the formulation.

A method for treating one or more conditions in a subject in need thereof, the method comprising administering to the subject a pharmaceutically acceptable formulation comprising a granular component and an extragranular component, wherein the granular component comprises an intragranular component comprising rofecoxib or a pharmaceutically acceptable salt thereof and one or more disintegrants, and wherein the extragranular component comprises one or more disintegrants.

In some embodiments, the one or more disintegrants in the granular component is selected from starches, clays, celluloses, algins, gums, cross-linked polymers, and combinations thereof. In some embodiments, the one or more disintegrants in the granular component is selected from croscarmellose, crospovidone, sodium starch glycolate, and combinations thereof.

In some embodiments, the one or more disintegrants in the granular component is croscarmellose sodium. In some embodiments, the one or more disintegrants in the granular component is about 1% (w/w) to about 8% (w/w) of the formulation. In some embodiments, the one or more disintegrants in the granular component is about 1% (w/w) to about 6% (w/w) of the formulation. In some embodiments, the one or more disintegrants in the granular component is about 1% (w/w) to about 4% (w/w) of the formulation.

In some embodiments, the one or more disintegrants in the extragranular component is selected from starches, clays, celluloses, algins, gums, cross-linked polymers, and combinations thereof. In some embodiments, the one or more disintegrants in the extragranular component is selected from croscarmellose, crospovidone, sodium starch glycolate, and combinations thereof. In some embodiments, the one or more disintegrants in the extragranular component is croscarmellose sodium. In some embodiments, the disintegrant in the extragranular component is about 1% (w/w) to about 8% (w/w) of the formulation. In some embodiments, the disintegrant in the extragranular component is about 1% (w/w) to about 6% (w/w) of the formulation. In some embodiments, the disintegrant in the extragranular component is about 1% (w/w) to about 4% (w/w) of the formulation.

In some embodiments, the disintegrant in the granular component and the disintegrant in the extragranular component are together about 2% (w/w) to about 12% (w/w) of the formulation. In some embodiments, the disintegrant in the granular component and the disintegrant in the extragranular component are together about 2% (w/w) to about 10% (w/w) of the formulation. In some embodiments, the disintegrant in the granular component and the disintegrant in the extragranular component are together about 2% (w/w) to about 8% (w/w) of the formulation.

In some embodiments, the ratio of granular disintegrant to extragranular disintegrant is about 40% (w/w) to about 60% (w/w). In some embodiments, the ratio of granular disintegrant to extragranular disintegrant is about 45% (w/w) to about 55% (w/w). In some embodiments, the ratio of granular disintegrant to extragranular disintegrant is about 50% (w/w) to about 50% (w/w). In some embodiments, the ratio of granular disintegrant to extragranular disintegrant is about 55% (w/w) to about 45% (w/w). In some embodiments, the ratio of granular disintegrant to extragranular disintegrant is about 60% (w/w) to about 40% (w/w).

In some embodiments, the pharmaceutically acceptable formulation further comprising one or more of a diluent, a binder, a coloring agent, and a lubricant. In some embodiments, at least a portion of the diluent is in the granular component. In some embodiments, the diluent is selected from dicalcium phosphate, calcium sulfate, lactose, cellulose, kaolin, mannitol, sodium chloride, dry starch, powdered sugar, sorbitol, sucrose, inositol, and combinations thereof. In some embodiments, the diluent is selected from lactose, cellulose, or a combination thereof. In some embodiments, the diluent is selected from lactose monohydrate, microcrystalline cellulose, or a combination thereof.

In some embodiments, the lactose monohydrate is about 35% (w/w) to about 45% (w/w) of the formulation. In some embodiments, the lactose monohydrate is about 37% (w/w) to about 42% (w/w) of the formulation. In some embodiments, the lactose monohydrate is about 39% (w/w) to about 40% (w/w) of the formulation.

In some embodiments, the microcrystalline cellulose is about 35% (w/w) to about 45% (w/w) of the formulation. In some embodiments, the microcrystalline cellulose is about 37% (w/w) to about 42% (w/w) of the formulation. In some embodiments, the microcrystalline cellulose is about 39% (w/w) to about 40% (w/w) of the formulation.

In some embodiments, the diluent is about 75% (w/w) to about 85% (w/w) of the formulation. In some embodiments, diluent is about 77% (w/w) to about 82% (w/w) of the formulation. In some embodiments, the diluent is about 78% (w/w) to about 80% (w/w) of the formulation.

In some embodiments, at least a portion of the binder is in the granular component. In some embodiments, the binder is selected from starches, gelatins, sugars, gums, waxes, water, alcohols, celluloses, and combinations thereof. In some embodiments, the binder is selected from acacia gum, tragacanth, corn starch, methyl cellulose, panwar gum, ghatti gum, mucilage of isapol husks, carboxymethylcellulose, methylcellulose, polyvinylpyrrolidone, sucrose, glucose, dextrose, molasses, lactose, and combinations thereof. In some embodiments, the binder is hydroxypropyl cellulose. In some embodiments, the binder is about 1% (w/w) to about 5% (w/w) of the formulation. In some embodiments, binder is about 2% (w/w) to about 4% (w/w) of the formulation. In some embodiments, the binder is about 2.5% (w/w) to about 3.5% (w/w) of the formulation.

In some embodiments, at least a portion of the coloring agent is in the extragranular component. In some embodiments, the coloring agent is pigment blend yellow. In some embodiments, the coloring agent is about 0.30% (w/w) to about 0.60% (w/w) of the formulation.

In some embodiments, at least a portion of the lubricant is in the extragranular component. In some embodiments, the lubricant is selected from talc, magnesium stearate, calcium stearate, stearic acid, metallic stearate, hydrogenated vegetable oils, and polyethylene glycol, corn starch, boric acids, sodium chloride, sodium lauryl sulphate. In some embodiments, the lubricant is magnesium stearate. In some embodiments, the lubricant is about 0.10% (w/w) to about 1% (w/w) of the formulation. In some embodiments, the lubricant is about 0.50% (w/w) of the formulation.

In some embodiments, the rofecoxib or pharmaceutically acceptable salt thereof is about 5% (w/w) to about 30% (w/w) of the formulation. In some embodiments, the rofecoxib or pharmaceutically acceptable salt thereof is about 10% (w/w) to about 20% (w/w) of the formulation. In some embodiments, the rofecoxib or pharmaceutically acceptable salt thereof is about 12% (w/w) to about 13% (w/w) of the formulation. In some embodiments, the formulation comprises about 10 mg of the rofecoxib or pharmaceutically acceptable salt thereof. In some embodiments, the formulation comprises about 10.5 mg of the rofecoxib or pharmaceutically acceptable salt thereof. In some embodiments, the formulation comprises about 11 mg of the rofecoxib or pharmaceutically acceptable salt thereof. In some embodiments, the formulation comprises about 11.5 mg of the rofecoxib or pharmaceutically acceptable salt thereof. In some embodiments, the formulation comprises about 12 mg of the rofecoxib or pharmaceutically acceptable salt thereof. In some embodiments, the formulation comprises about 12.5 mg of the rofecoxib or pharmaceutically acceptable salt thereof. In some embodiments, the formulation comprises about 17.5 mg of the rofecoxib or pharmaceutically acceptable salt thereof. In some embodiments, the formulation comprises about 20 mg of the rofecoxib or pharmaceutically acceptable salt thereof. In some embodiments, the formulation comprises about 21 mg of the rofecoxib or pharmaceutically acceptable salt thereof. In some embodiments, the formulation comprises about 22 mg of the rofecoxib or pharmaceutically acceptable salt thereof. In some embodiments, the formulation comprises about 22.5 mg of the rofecoxib or pharmaceutically acceptable salt thereof. In some embodiments, the formulation comprises about 25 mg of the rofecoxib or pharmaceutically acceptable salt thereof. In some embodiments, the formulation comprises about 50 mg of the rofecoxib or pharmaceutically acceptable salt thereof.

In some embodiments, the rofecoxib is highly pure. In some embodiments, the highly pure rofecoxib comprises less than about 0.1% total impurities. In some embodiments, the highly pure rofecoxib comprises less than about 0.075% total impurities. In some embodiments, the highly pure rofecoxib comprises less than about 0.050% total impurities. In some embodiments, the highly pure rofecoxib comprises less than about 0.025% total impurities. In some embodiments, the highly pure rofecoxib comprises less than about 0.001% total impurities.

In some embodiments, the highly pure rofecoxib comprises less than about 0.10%, 0.05%, 0.02%, or 0.01% of 4-[4-(methylsulphonyl)phenyl]-3-phenyl-2,5-furandione. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylsulfinyl)phenyl]-3-phenyl-2(5H)-furanone.

In some embodiments, the formulation is suitable for oral administration. In some embodiments, the formulation is a solid dosage form. In some embodiments, the solid dosage form is an oral tablet. In some embodiments, the oral tablet provides a dissolution rate of at least about 80% of the rofecoxib or pharmaceutically acceptable salt thereof by about 15 minutes. In some embodiments, the oral tablet provides a dissolution rate of at least about 85% of the rofecoxib or pharmaceutically acceptable salt thereof by about 15 minutes. In some embodiments, the oral tablet provides a dissolution rate of at least about 90% of the rofecoxib or pharmaceutically acceptable salt thereof by about 15 minutes. In some embodiments, the oral tablet provides a dissolution rate of at least about 95% of the rofecoxib or pharmaceutically acceptable salt thereof by about 15 minutes. In some embodiments, the oral tablet provides a dissolution rate of at least about 100% of the rofecoxib or pharmaceutically acceptable salt thereof by about 15 minutes.

In some embodiments, the dissolution rate is measured in about 1% SDS at a paddle speed of about 50 rpm and at a temperature of about 37.0° C.±0.5° C. In some embodiments, the dissolution rate is measured in about 1% SDS at a paddle speed of about 75 rpm and at a temperature of about 37.0° C.±0.5° C. In some embodiments, the dissolution rate is measured in about 1.5% SDS at a paddle speed of about 50 rpm and at a temperature of about 37.0° C.±0.5° C. In some embodiments, the dissolution rate is measured in about 1.5% SDS at a paddle speed of about 75 rpm and at a temperature of about 37.0° C.±0.5° C. In some embodiments, the dissolution rate is measured in about 2% SDS at a paddle speed of about 50 rpm and at a temperature of about 37.0° C.±0.5° C. In some embodiments, the dissolution rate is measured in about 2% SDS at a paddle speed of about 75 rpm and at a temperature of about 37.0° C.±0.5° C.

In some embodiments, the rofecoxib or pharmaceutically acceptable salt thereof is formulated into granules and at least about 35% of the granules are less than about 75 μm. In some embodiments, the rofecoxib or pharmaceutically acceptable salt thereof is formulated into granules and at least about 55% of the granules are less than about 150 μm. In some embodiments, the rofecoxib or pharmaceutically acceptable salt thereof is formulated into granules and at least about 75% of the granules are less than about 250 μm. In some embodiments, the rofecoxib or pharmaceutically acceptable salt thereof is formulated into granules and at least about 85% of the granules are less than about 425 μm. In some embodiments, the rofecoxib or pharmaceutically acceptable salt thereof is formulated into granules and at least about 90% of the granules are less than about 1000 μm.

In some embodiments, a 17.5 mg solid dosage formulation of rofecoxib reaches a median time to Cmax plasma concentration in 4 hours or less following single administration of the formulation to human subjects. In some embodiments, a 17.5 mg solid dosage formulation of rofecoxib reaches a median time to Cmax plasma concentration in 3 hours or less following administration. In some embodiments, a 17.5 mg solid dosage formulation of rofecoxib reaches a median time to Cmax plasma concentration in 2.5 hours or less following administration. In some embodiments, a 17.5 mg solid dosage formulation of rofecoxib reaches a median time to Cmax plasma concentration in 2 hours or less following administration. In some embodiments, a 17.5 mg solid dosage formulation of rofecoxib has a mean Cmax plasma concentration of more than 100 ng/ml. In some embodiments, a 17.5 mg solid dosage formulation of rofecoxib has a mean Cmax plasma concentration of more than 150 ng/ml, 167 ng/ml, or 190 ng/ml. In some embodiments, a 17.5 mg solid dosage formulation of rofecoxib has a mean Cmax plasma concentration of more than 200 ng/ml. In some embodiments, a 17.5 mg solid dosage formulation of rofecoxib has a mean Cmax plasma concentration of more than 220 ng/ml. In some embodiments, a 17.5 mg solid dosage formulation of rofecoxib has a mean Cmax plasma concentration of more than 250 ng/ml. In some embodiments, a 17.5 mg solid dosage formulation of rofecoxib has a mean Cmax plasma concentration of more than 280 ng/ml. In some embodiments, a 17.5 mg solid dosage formulation of rofecoxib has a mean $AUC_{0-\infty}$ of more than 1750 h*ng/ml. In some embodiments, a 17.5 mg solid dosage formulation of rofecoxib has a mean $AUC_{0-\infty}$ of more than 2000 h*ng/ml. In some embodiments, a 17.5 mg solid dosage formulation of rofecoxib has a mean $AUC_{0-\infty}$ of more than 2500 h*ng/ml. In some embodiments, a 17.5 mg solid dosage formulation of rofecoxib has a mean $AUC_{0-\infty}$ of more than 3000 h*ng/ml. In some embodiments, a 17.5 mg solid dosage formulation of rofecoxib has a mean $AUC_{0-\infty}$ of more than 3100 h*ng/ml. In some embodiments, a 17.5 mg solid dosage formulation of rofecoxib has a mean $AUC_{0-\infty}$ of more than 3500 h*ng/ml. In some embodiments, a 17.5 mg solid dosage formulation of rofecoxib has a mean $AUC_{0-\infty}$ of more than 4000 h*ng/ml. In some embodiments, a 17.5 mg solid dosage formulation of rofecoxib has a mean $AUC_{0-\infty}$ of more than 4500 h*ng/ml. In some embodiments, a 17.5 mg solid dosage formulation of rofecoxib reaches a Cmax plasma concentration of least 167 ng/ml, 170 ng/ml, 175 ng/ml, 180 ng/ml, or higher following single administration of the formulation to a human subject. In some embodiments, a 17.5 mg solid dosage formulation of rofecoxib reaches an $AUC_{0-\infty}$ of at least 2600 h*ng/ml, 2750 h*ng/ml, 2900 h*ng/ml, 3050 h*ng/ml, 3100 h*ng/ml, 3200 h*ng/ml, 3350 h*ng/ml, 3500 h*ng/ml, 3650 h*ng/ml or higher following single administration of the formulation to a human subject.

In some embodiments, a 20 mg solid dosage formulation of rofecoxib reaches a median time to Cmax plasma concentration in 4 hours or less following single administration of the formulation to human subjects. In some embodiments, a 20 mg solid dosage formulation of rofecoxib reaches a median time to Cmax plasma concentration in 3 hours or less following administration. In some embodiments, a 20 mg solid dosage formulation of rofecoxib reaches a median time to Cmax plasma concentration in 2.5 hours or less following administration. In some embodiments, a 20 mg solid dosage formulation of rofecoxib reaches a median time to Cmax plasma concentration in 2 hours or less following administration. In some embodiments, a 20 mg solid dosage formulation of rofecoxib has a mean Cmax plasma concentration of more than 150 ng/ml. In some embodiments, a 20 mg solid dosage formulation of rofecoxib has a mean Cmax plasma concentration of more than 191 ng/ml, 200 ng/ml, 215 ng/ml, or 225 ng/ml. In some embodiments, a 20 mg solid dosage formulation of rofecoxib has a mean Cmax plasma concentration of more than 250 ng/ml. In some embodiments, a 20 mg solid dosage formulation of rofecoxib has a mean Cmax plasma concentration of more than 258 ng/ml. In some embodiments, a 20 mg solid dosage formulation of rofecoxib has a mean Cmax plasma concentration of more than 300 ng/ml. In some embodiments, a 20 mg solid dosage formulation of rofecoxib has a mean $AUC_{0-\infty}$ of more than 2000 h*ng/ml. In some embodiments, a 20 mg solid dosage formulation of rofecoxib has a mean $AUC_{0-\infty}$ of more than 2500 h*ng/ml. In some embodiments, a 20 mg solid dosage formulation of rofecoxib has a mean $AUC_{0-\infty}$ of more than 3000 h*ng/ml. In some embodiments, a 20 mg solid dosage formulation of rofecoxib has a mean $AUC_{0-\infty}$ of more than 3400 h*ng/ml. In some embodiments, a 20 mg solid dosage formulation of rofecoxib has a mean $AUC_{0-\infty}$ of more than 3500 h*ng/ml. In some embodiments, a 20 mg solid dosage formulation of rofecoxib has a mean $AUC_{0-\infty}$ of more than 4000 h*ng/ml. In some embodiments, a 20 mg solid dosage formulation of rofecoxib reaches a Cmax plasma concentration of least 190 ng/ml, 205 ng/ml, 220 ng/ml, 235 ng/ml, 250 ng/ml, or higher following single administration of the formulation to a human subject. In some embodiments, a 20 mg solid dosage formulation of rofecoxib reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In some embodiments, a 25 mg solid dosage formulation of rofecoxib reaches a mean Cmax plasma concentration in less than 3 hours following single administration of the formulation to human subjects. In some embodiments, a 25 mg solid dosage formulation of rofecoxib reaches a mean Cmax plasma concentration in less than 2.5 hours following administration. In some embodiments, a 25 mg solid dosage formulation of rofecoxib reaches a mean Cmax plasma concentration in less than 2 hours following administration. In some embodiments, a 25 mg solid dosage formulation of rofecoxib has a mean Cmax plasma concentration of more than 240 ng/ml. In some embodiments, a 25 mg solid dosage formulation of rofecoxib has a mean Cmax plasma concentration of more than 250 ng/ml. In some embodiments, a 25 mg solid dosage formulation of rofecoxib has a mean Cmax plasma concentration of more than 300 ng/ml. In some embodiments, a 25 mg solid dosage formulation of rofecoxib has a mean Cmax plasma concentration of more than 320 ng/ml. In some embodiments, a 25 mg solid dosage formulation of rofecoxib has a mean $AUC_{0-\infty}$ of more than 4250 h*ng/ml. In some embodiments, a 25 mg solid dosage formulation of rofecoxib has a mean $AUC_{0-\infty}$ of more than 4500 h*ng/ml. In some embodiments, a 25 mg solid dosage formulation of rofecoxib has a mean $AUC_{0-\infty}$ of more than 4550 h*ng/ml. In some embodiments, a 25 mg solid dosage formulation of rofecoxib has a mean $AUC_{0-\infty}$ of more than 4700 h*ng/ml. In some embodiments, a 25 mg solid dosage formulation of rofecoxib reaches a Cmax plasma concentration of more than 240 ng/ml in a median time of about 3 hours or less following administration with an $AUC_{0-\infty}$ of more than 4250 h*ng/ml.

In some embodiments, a 10 mg to 50 mg solid dosage formulation of rofecoxib achieves a mean Cmax plasma concentration from 9.8 ng/ml to 16 ng/ml for each 1 mg of rofecoxib in the formulation following single administration of the formulation to human subjects. In some embodiments, a 10 mg to 50 mg solid dosage formulation achieves a mean Cmax plasma concentration from 10 ng/ml to 14 ng/ml for each 1 mg of rofecoxib in the formulation. In some embodiments, a 10 mg to 50 mg solid dosage formulation achieves a mean Cmax plasma concentration from 10 ng/ml to 13 ng/ml for each 1 mg of rofecoxib in the formulation. In some embodiments, a 10 mg to 50 mg solid dosage formulation achieves a mean Cmax plasma concentration from 80% to 125% of 12.8 ng/ml. In some embodiments, a 10 mg to 50 mg solid dosage formulation reaches a mean $AUC_{0-\infty}$ of 170 h*ng/ml to 235 h*ng/ml for each 1 mg of rofecoxib in the formulation. In some embodiments, a 10 mg to 50 mg solid dosage formulation reaches a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, a 10 mg to 50 mg solid dosage formulation reaches a mean $AUC_{0-\infty}$ of 190 h*ng/ml to 215 h*ng/ml for each 1 mg of rofecoxib in the formulation.

In certain aspects, the subject matter disclosed herein provides a method for treating one or more conditions in a subject in need thereof, the method comprising administering to the subject a pharmaceutically acceptable formulation comprising a granular component and an extragranular component, wherein the granular component comprises an intragranular component comprising a 17.5 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a mean Cmax plasma concentration in less than 2.5 hours following administration. In some embodiments, the formulation achieves a median time to Cmax plasma concentration in 2 hours or less following administration. In some embodiments, the formulation achieves a mean Cmax plasma concentration of more than 100 ng/ml. In some embodiments, the formulation achieves a mean Cmax plasma concentration of more than 150 ng/ml, 167 ng/ml, or 190 ng/ml. In some embodiments, the formulation achieves a mean Cmax plasma concentration of more than 200 ng/ml. In some embodiments, the formulation achieves a mean Cmax plasma concentration of more than 250 ng/ml. In some embodiments, the formulation achieves a mean Cmax plasma concentration of more than 280 ng/ml. In some embodiments, the formulation achieves a mean $AUC_{0-\infty}$ of more than 1750 h*ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3100 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation achieves a mean $AUC_{0-\infty}$ of more than 4500 h*ng/ml.

In certain aspects, the subject matter disclosed herein provides a method for treating one or more conditions in a subject in need thereof, the method comprising administering to the subject a pharmaceutically acceptable formulation comprising a granular component and an extragranular component, wherein the granular component comprises an intragranular component comprising 20 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 150 ng/ml. In some embodiments, the formulation achieves a mean Cmax plasma concentration of more than 191 ng/ml, 200 ng/ml, 215 ng/ml, or 225 ng/ml. In some embodiments, the formulation achieves a mean Cmax plasma concentration of more than 250 ng/ml. In some embodiments, the formulation achieves a mean Cmax plasma concentration of more than 258 ng/ml. In some embodiments, the formulation achieves a mean Cmax plasma concentration of more than 300 ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3400 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation reaches a Cmax plasma concentration of least 190 ng/ml, 205 ng/ml, 220 ng/ml, 235 ng/ml, 250 ng/ml, or higher following single administration of the formulation to a human subject. In some embodiments, the formulation reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In certain aspects, the subject matter disclosed herein provides a method for treating one or more conditions in a subject in need thereof, the method comprising administering to the subject a pharmaceutically acceptable formulation comprising a granular component and an extragranular component, wherein the granular component comprises an intragranular component comprising 25 mg of rofecoxib or a pharmaceutically acceptable salt thereof. In some embodiments, the formulation achieves a mean Cmax plasma concentration in less than 3 hours following single administration of the formulation to human subjects. In some embodiments, the formulation achieves a mean Cmax plasma concentration in less than 2.5 hours following administration. In some embodiments, the formulation achieves a mean Cmax plasma concentration in less than 2 hours following administration. In some embodiments, the formulation achieves a mean Cmax plasma concentration of more than 240 ng/ml. In some embodiments, the formulation achieves a mean Cmax plasma concentration of more than 250 ng/ml. In some embodiments, the formulation achieves a mean Cmax plasma concentration of more than 300 ng/ml. In some embodiments, the formulation achieves a mean Cmax plasma concentration of more than 350 ng/ml. In some embodiments, the formulation achieves a mean $AUC_{0-\infty}$ of more than 4250 h*ng/ml. In some embodiments, the formulation achieves a mean $AUC_{0-\infty}$ of more than 4500 h*ng/ml. In some embodiments, the formulation achieves a mean $AUC_{0-\infty}$ of more than 4550 h*ng/ml. In some embodiments, the formulation achieves a mean $AUC_{0-\infty}$ of more than 4700 h*ng/ml. In some embodiments, the formulation achieves a Cmax plasma concentration of more than 240 ng/ml in about 3 hours following administration with an $AUC_{0-\infty}$ of more than 4250 h*ng/ml.

In certain aspects, the subject matter disclosed herein provides a method for treating one or more conditions in a subject in need thereof, the method comprising administering to the subject a pharmaceutically acceptable formulation comprising a granular component and an extragranular component, wherein the granular component comprises an intragranular component comprising 10 mg to 50 mg of rofecoxib or a pharmaceutically acceptable salt thereof. In some embodiments, the formulation achieves a mean Cmax plasma concentration from 9.8 ng/ml to 16 ng/ml for each 1 mg of rofecoxib in the formulation following single administration of the formulation to human subjects. In some embodiments, the formulation achieves a mean Cmax plasma concentration from 10 ng/ml to 14 ng/ml for each 1 mg of rofecoxib in the formulation. In some embodiments, the formulation achieves a mean Cmax plasma concentration from 10 ng/ml to 13 ng/ml for each 1 mg of rofecoxib in the formulation. In some embodiments, the formulation achieves a mean Cmax plasma concentration from 80% to 125% of 12.8 ng/ml. In some embodiments, the formulation reaches a mean $AUC_{0-\infty}$ of 170 h*ng/ml to 235 h*ng/ml for each 1 mg of rofecoxib in the formulation. In some embodiments, the formulation reaches a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the formulation reaches a mean $AUC_{0-\infty}$ of 190 h*ng/ml to 215 h*ng/ml for each 1 mg of rofecoxib in the formulation.

A method for treating one or more conditions in a subject in need thereof, the method comprising administering to the subject a solid dosage form comprising a granular component and an extragranular component, wherein the granular component comprises an intragranular component comprising rofecoxib or a pharmaceutically acceptable salt thereof and one or more disintegrants, and wherein the extragranular component comprises one or more disintegrants.

In some embodiments, the one or more disintegrants in the granular component is selected from starches, clays, celluloses, algins, gums, cross-linked polymers, and combinations thereof. In some embodiments, the one or more disintegrants in the granular component is selected from croscarmellose, crospovidone, sodium starch glycolate, and combinations thereof.

In some embodiments, the one or more disintegrants in the granular component is croscarmellose sodium. In some embodiments, the one or more disintegrants in the granular component is about 1% (w/w) to about 8% (w/w) of the solid dosage form. In some embodiments, the one or more disintegrants in the granular component is about 1% (w/w) to about 6% (w/w) of the solid dosage form. In some embodiments, the one or more disintegrants in the granular component is about 1% (w/w) to about 4% (w/w) of the solid dosage form.

In some embodiments, the one or more disintegrants in the extragranular component is selected from starches, clays, celluloses, algins, gums, cross-linked polymers, and combinations thereof. In some embodiments, the one or more disintegrants in the extragranular component is selected from croscarmellose, crospovidone, sodium starch glycolate, and combinations thereof. In some embodiments, the one or more disintegrants in the extragranular component is croscarmellose sodium. In some embodiments, the disintegrant in the extragranular component is about 1% (w/w) to about 8% (w/w) of the solid dosage form. In some embodiments, the disintegrant in the extragranular component is about 1% (w/w) to about 6% (w/w) of the solid dosage form. In some embodiments, the disintegrant in the extragranular component is about 1% (w/w) to about 4% (w/w) of the solid dosage form.

In some embodiments, the disintegrant in the granular component and the disintegrant in the extragranular component are together about 2% (w/w) to about 12% (w/w) of the solid dosage form. In some embodiments, the disintegrant in the granular component and the disintegrant in the extragranular component are together about 2% (w/w) to about 10% (w/w) of the solid dosage form. In some embodiments, the disintegrant in the granular component and the disintegrant in the extragranular component are together about 2% (w/w) to about 8% (w/w) of the solid dosage form.

In some embodiments, the ratio of granular disintegrant to extragranular disintegrant is about 40% (w/w) to about 60% (w/w). In some embodiments, the ratio of granular disintegrant to extragranular disintegrant is about 45% (w/w) to about 55% (w/w). In some embodiments, the ratio of granular disintegrant to extragranular disintegrant is about 50% (w/w) to about 50% (w/w). In some embodiments the ratio of granular disintegrant to extragranular disintegrant is about 55% (w/w) to about 45% (w/w). In some embodiments the ratio of granular disintegrant to extragranular disintegrant is about 60% (w/w) to about 40% (w/w).

In some embodiments, the solid dosage form further comprises one or more of a diluent, a binder, a coloring agent, and a lubricant. In some embodiments, at least a portion of the diluent is in the granular component. In some embodiments, the diluent is selected from dicalcium phosphate, calcium sulfate, lactose, cellulose, kaolin, mannitol, sodium chloride, dry starch, powdered sugar, sorbitol, sucrose, inositol, and combinations thereof. In some embodiments, the diluent is selected from lactose, cellulose, or a combination thereof. In some embodiments, the diluent is selected from lactose monohydrate, microcrystalline cellulose, or a combination thereof.

In some embodiments, the lactose monohydrate is about 35% (w/w) to about 45% (w/w) of the solid dosage form. In some embodiments, the lactose monohydrate is about 37% (w/w) to about 42% (w/w) of the solid dosage form. In some embodiments, the lactose monohydrate is about 39% (w/w) to about 40% (w/w) of the solid dosage form.

In some embodiments, the microcrystalline cellulose is about 35% (w/w) to about 45% (w/w) of the solid dosage form. In some embodiments, the microcrystalline cellulose is about 37% (w/w) to about 42% (w/w) of the solid dosage form. In some embodiments, the microcrystalline cellulose is about 39% (w/w) to about 40% (w/w) of the solid dosage form.

In some embodiments, the diluent is about 75% (w/w) to about 85% (w/w) of the solid dosage form. In some embodiments, diluent is about 77% (w/w) to about 82% (w/w) of the solid dosage form. In some embodiments, the diluent is about 78% (w/w) to about 80% (w/w) of the solid dosage form.

In some embodiments, at least a portion of the binder is in the granular component. In some embodiments, the binder is selected from starches, gelatins, sugars, gums, waxes, water, alcohols, celluloses, and combinations thereof. In some embodiments, the binder is selected from acacia gum, tragacanth, corn starch, methyl cellulose, panwar gum, ghatti gum, mucilage of isapol husks, carboxymethylcellulose, methylcellulose, polyvinylpyrrolidone, sucrose, glucose, dextrose, molasses, lactose, and combinations thereof. In some embodiments, the binder is hydroxypropyl cellulose. In some embodiments, the binder is about 1% (w/w) to about 5% (w/w) of the solid dosage form. In some embodiments, binder is about 2% (w/w) to about 4% (w/w) of the solid dosage form. In some embodiments, the binder is about 2.5% (w/w) to about 3.5% (w/w) of the solid dosage form.

In some embodiments, at least a portion of the coloring agent is in the extragranular component. In some embodiments, the coloring agent is pigment blend yellow. In some embodiments, the coloring agent is about 0.30% (w/w) to about 0.60% (w/w) of the solid dosage form.

In some embodiments, at least a portion of the lubricant is in the extragranular component. In some embodiments, the lubricant is selected from talc, magnesium stearate, calcium stearate, stearic acid, metallic stearate, hydrogenated vegetable oils, and polyethylene glycol, corn starch, boric acids, sodium chloride, sodium lauryl sulphate. In some embodiments, the lubricant is magnesium stearate. In some embodiments, the lubricant is about 0.10% (w/w) to about 1% (w/w) of the solid dosage form. In some embodiments, the lubricant is about 0.50% (w/w) of the solid dosage form.

In some embodiments, the rofecoxib or pharmaceutically acceptable salt thereof is about 5% (w/w) to about 30% (w/w) of the solid dosage form. In some embodiments, the rofecoxib or pharmaceutically acceptable salt thereof is about 10% (w/w) to about 20% (w/w) of the solid dosage form. In some embodiments, the rofecoxib or pharmaceutically acceptable salt thereof is about 12% (w/w) to about 13% (w/w) of the solid dosage form. In some embodiments, the solid dosage form comprises about 10 mg of the rofecoxib or pharmaceutically acceptable salt thereof. In some embodiments, the solid dosage form comprises about 10.5 mg of the rofecoxib or pharmaceutically acceptable salt thereof. In some embodiments, the solid dosage form comprises about 11 mg of the rofecoxib or pharmaceutically acceptable salt thereof. In some embodiments, the solid dosage form comprises about 11.5 mg of the rofecoxib or pharmaceutically acceptable salt thereof. In some embodiments, the solid dosage form comprises about 12 mg of the rofecoxib or pharmaceutically acceptable salt thereof. In some embodiments, the solid dosage form comprises about 12.5 mg of the rofecoxib or pharmaceutically acceptable salt thereof. In some embodiments, the solid dosage form comprises about 20 mg of the rofecoxib or pharmaceutically acceptable salt thereof. In some embodiments, the solid dosage form comprises about 21 mg of the rofecoxib or pharmaceutically acceptable salt thereof. In some embodiments, the solid dosage form comprises about 22 mg of the rofecoxib or pharmaceutically acceptable salt thereof. In some embodiments, the solid dosage form comprises about 22.5 mg of the rofecoxib or pharmaceutically acceptable salt thereof. In some embodiments, the solid dosage form comprises about 25 mg of the rofecoxib or pharmaceutically acceptable salt thereof. In some embodiments, the solid dosage form comprises about 50 mg of the rofecoxib or pharmaceutically acceptable salt thereof.

In some embodiments, the rofecoxib is highly pure. In some embodiments, the highly pure rofecoxib comprises less than about 0.1% total impurities. In some embodiments, the highly pure rofecoxib comprises less than about 0.075% total impurities. In some embodiments, the highly pure rofecoxib comprises less than about 0.050% total impurities. In some embodiments, the highly pure rofecoxib comprises less than about 0.025% total impurities. In some embodiments, the highly pure rofecoxib comprises less than about 0.001% total impurities.

In some embodiments, the highly pure rofecoxib comprises less than about 0.10%, 0.05%, 0.02%, or 0.01% of 4-[4-(methylsulphonyl)phenyl]-3-phenyl-2,5-furandione. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylsulfinyl)phenyl]-3-phenyl-2(5H)-furanone.

In some embodiments, the solid dosage form is suitable for oral administration. In some embodiments, the solid dosage form is an oral tablet. In some embodiments, the oral tablet provides a dissolution rate of at least about 80% of the rofecoxib or pharmaceutically acceptable salt thereof by about 15 minutes. In some embodiments, the oral tablet provides a dissolution rate of at least about 85% of the rofecoxib or pharmaceutically acceptable salt thereof by about 15 minutes. In some embodiments, the oral tablet provides a dissolution rate of at least about 90% of the rofecoxib or pharmaceutically acceptable salt thereof by about 15 minutes. In some embodiments, the oral tablet provides a dissolution rate of at least about 95% of the rofecoxib or pharmaceutically acceptable salt thereof by about 15 minutes. In some embodiments, the oral tablet provides a dissolution rate of at least about 100% of the rofecoxib or pharmaceutically acceptable salt thereof by about 15 minutes.

In some embodiments, the dissolution rate is measured in about 1% SDS at a paddle speed of about 50 rpm and at a temperature of about 37.0° C.±0.5° C. In some embodiments, the dissolution rate is measured in about 1% SDS at a paddle speed of about 75 rpm and at a temperature of about 37.0° C.±0.5° C. In some embodiments, the dissolution rate is measured in about 1.5% SDS at a paddle speed of about 50 rpm and at a temperature of about 37.0° C.±0.5° C. In some embodiments, the dissolution rate is measured in about 1.5% SDS at a paddle speed of about 75 rpm and at a temperature of about 37.0° C.±0.5° C. In some embodiments, the dissolution rate is measured in about 2% SDS at a paddle speed of about 50 rpm and at a temperature of about 37.0° C.±0.5° C. In some embodiments, the dissolution rate is measured in about 2% SDS at a paddle speed of about 75 rpm and at a temperature of about 37.0° C.±0.5° C.

In some embodiments, the rofecoxib or pharmaceutically acceptable salt thereof is formulated into granules and at least about 35% of the granules are less than about 75 μm. In some embodiments, the rofecoxib or pharmaceutically acceptable salt thereof is formulated into granules and at least about 55% of the granules are less than about 150 μm. In some embodiments, the rofecoxib or pharmaceutically acceptable salt thereof is formulated into granules and at least about 75% of the granules are less than about 250 μm. In some embodiments, the rofecoxib or pharmaceutically acceptable salt thereof is formulated into granules and at least about 85% of the granules are less than about 425 μm. In some embodiments, the rofecoxib or pharmaceutically acceptable salt thereof is formulated into granules and at least about 90% of the granules are less than about 1000 μm.

In some embodiments, a 17.5 mg solid dosage formulation of rofecoxib reaches a median time to Cmax plasma concentration in 4 hours or less following single administration of the formulation to human subjects. In some embodiments, a 17.5 mg solid dosage formulation of rofecoxib reaches a median time to Cmax plasma concentration in 3 hours or less following administration. In some embodiments, a 17.5 mg solid dosage formulation of rofecoxib reaches a median time to Cmax plasma concentration in 2.5 hours or less following administration. In some embodiments, a 17.5 mg solid dosage formulation of rofecoxib reaches a median time to Cmax plasma concentration in 2 hours or less following administration. In some embodiments, a 17.5 mg solid dosage formulation of rofecoxib has a mean Cmax plasma concentration of more than 100 ng/ml. In some embodiments, a 17.5 mg solid dosage formulation of rofecoxib has a mean Cmax plasma concentration of more than 150 ng/ml, 167 ng/ml, or 190 ng/ml. In some embodiments, a 17.5 mg solid dosage formulation of rofecoxib has a mean Cmax plasma concentration of more than 200 ng/ml. In some embodiments, a 17.5 mg solid dosage formulation of rofecoxib has a mean Cmax plasma concentration of more than 220 ng/ml. In some embodiments, a 17.5 mg solid dosage formulation of rofecoxib has a mean Cmax plasma concentration of more than 250 ng/ml. In some embodiments, a 17.5 mg solid dosage formulation of rofecoxib has a mean Cmax plasma concentration of more than 280 ng/ml. In some embodiments, a 17.5 mg solid dosage formulation of rofecoxib has a mean $AUC_{0-\infty}$ of more than 1750 h*ng/ml. In some embodiments, a 17.5 mg solid dosage formulation of rofecoxib has a mean $AUC_{0-\infty}$ of more than 2000 h*ng/ml. In some embodiments, a 17.5 mg solid dosage formulation of rofecoxib has a mean $AUC_{0-\infty}$ of more than 2500 h*ng/ml. In some embodiments, a 17.5 mg solid dosage formulation of rofecoxib has a mean $AUC_{0-\infty}$ of more than 3000 h*ng/ml. In some embodiments, a 17.5 mg solid dosage formulation of rofecoxib has a mean $AUC_{0-\infty}$ of more than 3100 h*ng/ml. In some embodiments, a 17.5 mg solid dosage formulation of rofecoxib has a mean $AUC_{0-\infty}$ of more than 3500 h*ng/ml. In some embodiments, a 17.5 mg solid dosage formulation of rofecoxib has a mean $AUC_{0-\infty}$ of more than 4000 h*ng/ml. In some embodiments, a 17.5 mg solid dosage formulation of rofecoxib has a mean $AUC_{0-\infty}$ of more than 4500 h*ng/ml. In some embodiments, a 17.5 mg solid dosage formulation of rofecoxib reaches a Cmax plasma concentration of least 167 ng/ml, 170 ng/ml, 175 ng/ml, 180 ng/ml, or higher following single administration of the formulation to a human subject. In some embodiments, a 17.5 mg solid dosage formulation of rofecoxib reaches an $AUC_{0-\infty}$ of at least 2600 h*ng/ml, 2750 h*ng/ml, 2900 h*ng/ml, 3050 h*ng/ml, 3100 h*ng/ml, 3200 h*ng/ml, 3350 h*ng/ml, 3500 h*ng/ml, 3650 h*ng/ml or higher following single administration of the formulation to a human subject.

In some embodiments, a 20 mg solid dosage formulation of rofecoxib reaches a median time to Cmax plasma concentration in 4 hours or less following single administration of the formulation to human subjects. In some embodiments, a 20 mg solid dosage formulation of rofecoxib reaches a median time to Cmax plasma concentration in 3 hours or less following administration. In some embodiments, a 20 mg solid dosage formulation of rofecoxib reaches a median time to Cmax plasma concentration in 2.5 hours or less following administration. In some embodiments, a 20 mg solid dosage formulation of rofecoxib reaches a median time to Cmax plasma concentration in 2 hours or less following administration. In some embodiments, a 20 mg solid dosage formulation of rofecoxib has a mean Cmax plasma concentration of more than 150 ng/ml. In some embodiments, a 20 mg solid dosage formulation of rofecoxib has a mean Cmax plasma concentration of more than 191 ng/ml, 200 ng/ml, 215 ng/ml, or 225 ng/ml. In some embodiments, a 20 mg solid dosage formulation of rofecoxib has a mean Cmax plasma concentration of more than 250 ng/ml. In some embodiments, a 20 mg solid dosage formulation of rofecoxib has a mean Cmax plasma concentration of more than 300 ng/ml. In some embodiments, a 20 mg solid dosage formulation of rofecoxib has a mean $AUC_{0-\infty}$ of more than 2000 h*ng/ml. In some embodiments, a 20 mg solid dosage formulation of rofecoxib has a mean $AUC_{0-\infty}$ of more than 2500 h*ng/ml. In some embodiments, a 20 mg solid dosage formulation of rofecoxib has a mean $AUC_{0-\infty}$ of more than 3000 h*ng/ml. In some embodiments, a 20 mg solid dosage formulation of rofecoxib has a mean $AUC_{0-\infty}$ of more than 3400 h*ng/ml. In some embodiments, a 20 mg solid dosage formulation of rofecoxib has a mean $AUC_{0-\infty}$ of more than 3500 h*ng/ml. In some embodiments, a 20 mg solid dosage formulation of rofecoxib has a mean $AUC_{0-\infty}$ of more than 4000 h*ng/ml. In some embodiments, a 20 mg solid dosage formulation of rofecoxib reaches a Cmax plasma concentration of least 190 ng/ml, 205 ng/ml, 220 ng/ml, 235 ng/ml, 250 ng/ml, or higher following single administration of the formulation to a human subject. In some embodiments, a 20 mg solid dosage formulation of rofecoxib reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In some embodiments, a 25 mg solid dosage formulation of rofecoxib reaches a mean Cmax plasma concentration in less than 3 hours following single administration of the formulation to human subjects. In some embodiments, a 25 mg solid dosage formulation of rofecoxib reaches a mean Cmax plasma concentration in less than 2.5 hours following administration. In some embodiments, a 25 mg solid dosage formulation of rofecoxib reaches a mean Cmax plasma concentration in less than 2 hours following administration. In some embodiments, a 25 mg solid dosage formulation of rofecoxib has a mean Cmax plasma concentration of more than 240 ng/ml. In some embodiments, a 25 mg solid dosage formulation of rofecoxib has a mean Cmax plasma concentration of more than 250 ng/ml. In some embodiments, a 25 mg solid dosage formulation of rofecoxib has a mean Cmax plasma concentration of more than 300 ng/ml. In some embodiments, a 25 mg solid dosage formulation of rofecoxib has a mean Cmax plasma concentration of more than 320 ng/ml. In some embodiments, a 25 mg solid dosage formulation of rofecoxib has a mean $AUC_{0-\infty}$ of more than 4250 h*ng/ml. In some embodiments, a 25 mg solid dosage formulation of rofecoxib has a mean $AUC_{0-\infty}$ of more than 4500 h*ng/ml. In some embodiments, a 25 mg solid dosage formulation of rofecoxib has a mean $AUC_{0-\infty}$ of more than 4550 h*ng/ml. In some embodiments, a 25 mg solid dosage formulation of rofecoxib has a mean $AUC_{0-\infty}$ of more than 4700 h*ng/ml. In some embodiments, a 25 mg solid dosage formulation of rofecoxib reaches a mean Cmax plasma concentration of more than 240 ng/ml in a median time of about 3 hours or less following administration with an $AUC_{0-\infty}$ of more than 4250 h*ng/ml.

In certain aspects, a 10 mg to 50 mg solid dosage formulation of rofecoxib achieves a mean Cmax plasma concentration from 9.8 ng/ml to 16 ng/ml for each 1 mg of rofecoxib in the formulation following single administration of the formulation to human subjects. In some embodiments, the 10 mg to 50 mg solid dosage formulation of rofecoxib achieves a mean Cmax plasma concentration from 10 ng/ml to 14 ng/ml for each 1 mg of rofecoxib in the formulation. In some embodiments, the 10 mg to 50 mg solid dosage formulation of rofecoxib achieves a mean Cmax plasma concentration from 10 ng/ml to 13 ng/ml for each 1 mg of rofecoxib in the formulation. In some embodiments, the 10 mg to 50 mg solid dosage formulation achieves a mean Cmax plasma concentration from 80% to 125% of 12.8 ng/ml. In some embodiments, the 10 mg to 50 mg solid dosage formulation of rofecoxib reaches a mean $AUC_{0-\infty}$ of 170 h*ng/ml to 235 h*ng/ml for each 1 mg of rofecoxib in the formulation. In some embodiments, the 10 mg to 50 mg solid dosage formulation of rofecoxib reaches a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the 10 mg to 50 mg solid dosage formulation of rofecoxib reaches a mean $AUC_{0-\infty}$ of 190 h*ng/ml to 215 h*ng/ml for each 1 mg of rofecoxib in the formulation.

In certain aspects, the subject matter disclosed herein provides a method for treating one or more conditions in a subject in need thereof, the method comprising administering to the subject a solid dosage form comprising a granular component and an extragranular component, wherein the granular component comprises an intragranular component comprising 17.5 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 100 ng/ml. In some embodiments, the formulation achieves a mean Cmax plasma concentration of more than 150 ng/ml, 167 ng/ml, or 190 ng/ml. In some embodiments, the formulation achieves a mean Cmax plasma concentration of more than 200 ng/ml. In some embodiments, the formulation achieves a mean Cmax plasma concentration of more than 220 ng/ml. In some embodiments, the formulation achieves a mean Cmax plasma concentration of more than 250 ng/ml. In some embodiments, the formulation achieves a mean Cmax plasma concentration of more than 280 ng/ml. In some embodiments, the formulation achieves a mean $AUC_{0-\infty}$ of more than 1750 h*ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3100 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation achieves a mean $AUC_{0-\infty}$ of more than 4500 h*ng/ml. In some embodiments, the formulation reaches a Cmax plasma concentration of least 167 ng/ml, 170 ng/ml, 175 ng/ml, 180 ng/ml, or higher following single administration of the formulation to a human subject. In some embodiments, the formulation reaches an $AUC_{0-\infty}$ of at least 2600 h*ng/ml, 2750 h*ng/ml, 2900 h*ng/ml, 3050 h*ng/ml, 3100 h*ng/ml, 3200 h*ng/ml, 3350 h*ng/ml, 3500 h*ng/ml, 3650 h*ng/ml or higher following single administration of the formulation to a human subject.

In certain aspects, the subject matter disclosed herein provides a method for treating one or more conditions in a subject in need thereof, the method comprising administering to the subject a solid dosage form comprising a granular component and an extragranular component, wherein the granular component comprises an intragranular component comprising 20 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 150 ng/ml. In some embodiments, the formulation achieves a mean Cmax plasma concentration of more than 191 ng/ml, 200 ng/ml, 215 ng/ml, or 225 ng/ml. In some embodiments, the formulation achieves a mean Cmax plasma concentration of more than 250 ng/ml. In some embodiments, the formulation achieves a mean Cmax plasma concentration of more than 258 ng/ml. In some embodiments, the formulation achieves a mean Cmax plasma concentration of more than 300 ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3400 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation reaches a Cmax plasma concentration of least 190 ng/ml, 205 ng/ml, 220 ng/ml, 235 ng/ml, 250 ng/ml, or higher following single administration of the formulation to a human subject. In some embodiments, the formulation reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In certain aspects, the subject matter disclosed herein provides a method for treating one or more conditions in a subject in need thereof, the method comprising administering to the subject a solid dosage form comprising a granular component and an extragranular component, wherein the granular component comprises an intragranular component comprising 25 mg of rofecoxib or a pharmaceutically acceptable salt thereof. In some embodiments, the formulation achieves a mean Cmax plasma concentration in less than 3 hours following single administration of the formulation to human subjects. In some embodiments, the formulation achieves a mean Cmax plasma concentration in less than 2.5 hours following administration. In some embodiments, the formulation achieves a mean Cmax plasma concentration in less than 2 hours following administration. In some embodiments, the formulation achieves a mean Cmax plasma concentration of more than 240 ng/ml. In some embodiments, the formulation achieves a mean Cmax plasma concentration of more than 250 ng/ml. In some embodiments, the formulation achieves a mean Cmax plasma concentration of more than 300 ng/ml. In some embodiments, the formulation achieves a mean Cmax plasma concentration of more than 320 ng/ml. In some embodiments, the formulation achieves a mean $AUC_{0-\infty}$ of more than 4250 h*ng/ml. In some embodiments, the formulation achieves a mean $AUC_{0-\infty}$ of more than 4500 h*ng/ml. In some embodiments, the formulation achieves a mean $AUC_{0-\infty}$ of more than 4550 h*ng/ml. In some embodiments, the formulation achieves a mean $AUC_{0-\infty}$ of more than 4700 h*ng/ml. In some embodiments, the formulation achieves a Cmax plasma concentration of more than 240 ng/ml in about 3 hours following administration with an $AUC_{0-\infty}$ of more than 4250 h*ng/ml.

In certain aspects, the subject matter disclosed herein provides a method for treating one or more conditions in a subject in need thereof, the method comprising administering to the subject a solid dosage form comprising a granular component and an extragranular component, wherein the granular component comprises an intragranular component comprising 10 mg to 50 mg of rofecoxib or a pharmaceutically acceptable salt thereof. In some embodiments, the formulation achieves a mean Cmax plasma concentration from 9.8 ng/ml to 16 ng/ml for each 1 mg of rofecoxib in the formulation following single administration of the formulation to human subjects. In some embodiments, the formulation achieves a mean Cmax plasma concentration from 10 ng/ml to 14 ng/ml for each 1 mg of rofecoxib in the formulation. In some embodiments, the formulation achieves a mean Cmax plasma concentration from 10 ng/ml to 13 ng/ml for each 1 mg of rofecoxib in the formulation. In some embodiments, the formulation achieves a mean Cmax plasma concentration from 80% to 125% of 12.8 ng/ml. In some embodiments, the formulation reaches a mean $AUC_{0-\infty}$ of 170 h*ng/ml to 235 h*ng/ml for each 1 mg of rofecoxib in the formulation. In some embodiments, the formulation reaches a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the formulation reaches a mean $AUC_{0-\infty}$ of 190 h*ng/ml to 215 h*ng/ml for each 1 mg of rofecoxib in the formulation.

A method for enhancing the dissolution profile of a solid dosage form comprising rofecoxib or a pharmaceutically acceptable salt thereof, the method comprising providing a pharmaceutically acceptable formulation comprising a granular component and an extragranular component, wherein the granular component comprises an intragranular component comprising rofecoxib or a pharmaceutically acceptable salt thereof and one or more disintegrants, and wherein the extragranular component comprises one or more disintegrants.

In some embodiments, the one or more disintegrants in the granular component is selected from starches, clays, celluloses, algins, gums, cross-linked polymers, and combinations thereof. In some embodiments, the one or more disintegrants in the granular component is selected from croscarmellose, crospovidone, sodium starch glycolate, and combinations thereof. In some embodiments, the one or more disintegrants in the granular component is croscarmellose sodium. In some embodiments, the one or more disintegrants in the granular component is about 1% (w/w) to about 8% (w/w) of the formulation. In some embodiments, the one or more disintegrants in the granular component is about 1% (w/w) to about 6% (w/w) of the formulation. In some embodiments, the one or more disintegrants in the granular component is about 1% (w/w) to about 4% (w/w) of the formulation.

In some embodiments, the one or more disintegrants in the extragranular component is selected from starches, clays, celluloses, algins, gums, cross-linked polymers, and combinations thereof. In some embodiments, the one or more disintegrants in the extragranular component is selected from croscarmellose, crospovidone, sodium starch glycolate, and combinations thereof. In some embodiments, the one or more disintegrants in the extragranular component is croscarmellose sodium. In some embodiments, the disintegrant in the extragranular component is about 1% (w/w) to about 8% (w/w) of the formulation. In some embodiments, the disintegrant in the extragranular component is about 1% (w/w) to about 6% (w/w) of the formulation. In some embodiments, the disintegrant in the extragranular component is about 1% (w/w) to about 4% (w/w) of the formulation.

In some embodiments, the disintegrant in the granular component and the disintegrant in the extragranular component are together about 2% (w/w) to about 12% (w/w) of the formulation. In some embodiments, the disintegrant in the granular component and the disintegrant in the extragranular component are together about 2% (w/w) to about 10% (w/w) of the formulation. In some embodiments, the disintegrant in the granular component and the disintegrant in the extragranular component are together about 2% (w/w) to about 8% (w/w) of the formulation.

In some embodiments, the ratio of granular disintegrant to extragranular disintegrant is about 40% (w/w) to about 60% (w/w). In some embodiments, the ratio of granular disintegrant to extragranular disintegrant is about 45% (w/w) to about 55% (w/w). In some embodiments, the ratio of granular disintegrant to extragranular disintegrant is about 50% (w/w) to about 50% (w/w). In some embodiments, the ratio of granular disintegrant to extragranular disintegrant is about 55% (w/w) to about 45% (w/w). In some embodiments, the ratio of granular disintegrant to extragranular disintegrant is about 60% (w/w) to about 40% (w/w).

In some embodiments, the pharmaceutically acceptable formulation further comprising one or more of a diluent, a binder, a coloring agent, and a lubricant. In some embodiments, at least a portion of the diluent is in the granular component. In some embodiments, the diluent is selected from dicalcium phosphate, calcium sulfate, lactose, cellulose, kaolin, mannitol, sodium chloride, dry starch, powdered sugar, sorbitol, sucrose, inositol, and combinations thereof. In some embodiments, the diluent is selected from lactose, cellulose, or a combination thereof. In some embodiments, the diluent is selected from lactose monohydrate, microcrystalline cellulose, or a combination thereof.

In some embodiments, the lactose monohydrate is about 35% (w/w) to about 45% (w/w) of the formulation. In some embodiments, the lactose monohydrate is about 37% (w/w) to about 42% (w/w) of the formulation. In some embodiments, the lactose monohydrate is about 39% (w/w) to about 40% (w/w) of the formulation.

In some embodiments, the microcrystalline cellulose is about 35% (w/w) to about 45% (w/w) of the formulation. In some embodiments, the microcrystalline cellulose is about 37% (w/w) to about 42% (w/w) of the formulation. In some embodiments, the microcrystalline cellulose is about 39% (w/w) to about 40% (w/w) of the formulation.

In some embodiments, the diluent is about 75% (w/w) to about 85% (w/w) of the formulation. In some embodiments, diluent is about 77% (w/w) to about 82% (w/w) of the formulation. In some embodiments, the diluent is about 78% (w/w) to about 80% (w/w) of the formulation.

In some embodiments, at least a portion of the binder is in the granular component. In some embodiments, the binder is selected from starches, gelatins, sugars, gums, waxes, water, alcohols, celluloses, and combinations thereof. In some embodiments, the binder is selected from acacia gum, tragacanth, corn starch, methyl cellulose, panwar gum, ghatti gum, mucilage of isapol husks, carboxymethylcellulose, methylcellulose, polyvinylpyrrolidone, sucrose, glucose, dextrose, molasses, lactose, and combinations thereof. In some embodiments, the binder is hydroxypropyl cellulose. In some embodiments, the binder is about 1% (w/w) to about 5% (w/w) of the formulation. In some embodiments, binder is about 2% (w/w) to about 4% (w/w) of the formulation. In some embodiments, the binder is about 2.5% (w/w) to about 3.5% (w/w) of the formulation.

In some embodiments, at least a portion of the coloring agent is in the extragranular component. In some embodiments, the coloring agent is pigment blend yellow. In some embodiments, the coloring agent is about 0.30% (w/w) to about 0.60% (w/w) of the formulation.

In some embodiments, at least a portion of the lubricant is in the extragranular component. In some embodiments, the lubricant is selected from talc, magnesium stearate, calcium stearate, stearic acid, metallic stearate, hydrogenated vegetable oils, and polyethylene glycol, corn starch, boric acids, sodium chloride, sodium lauryl sulphate. In some embodiments, the lubricant is magnesium stearate. In some embodiments, the lubricant is about 0.10% (w/w) to about 1% (w/w) of the formulation. In some embodiments, the lubricant is about 0.50% (w/w) of the formulation.

In some embodiments, the rofecoxib or pharmaceutically acceptable salt thereof is about 5% (w/w) to about 30% (w/w) of the formulation. In some embodiments, the rofecoxib or pharmaceutically acceptable salt thereof is about 10% (w/w) to about 20% (w/w) of the formulation. In some embodiments, the rofecoxib or pharmaceutically acceptable salt thereof is about 12% (w/w) to about 13% (w/w) of the formulation. In some embodiments, the formulation comprises about 10 mg of the rofecoxib or pharmaceutically acceptable salt thereof. In some embodiments, the formulation comprises about 10.5 mg of the rofecoxib or pharmaceutically acceptable salt thereof. In some embodiments, the formulation comprises about 11 mg of the rofecoxib or pharmaceutically acceptable salt thereof. In some embodiments, the formulation comprises about 11.5 mg of the rofecoxib or pharmaceutically acceptable salt thereof. In some embodiments, the formulation comprises about 12 mg of the rofecoxib or pharmaceutically acceptable salt thereof. In some embodiments, the formulation comprises about 12.5 mg of the rofecoxib or pharmaceutically acceptable salt thereof. In some embodiments, the formulation comprises about 17.5 mg of the rofecoxib or pharmaceutically acceptable salt thereof. In some embodiments, the formulation comprises about 20 mg of the rofecoxib or pharmaceutically acceptable salt thereof. In some embodiments, the formulation comprises about 21 mg of the rofecoxib or pharmaceutically acceptable salt thereof. In some embodiments, the formulation comprises about 22 mg of the rofecoxib or pharmaceutically acceptable salt thereof. In some embodiments, the formulation comprises about 22.5 mg of the rofecoxib or pharmaceutically acceptable salt thereof. In some embodiments, the formulation comprises about 25 mg of the rofecoxib or pharmaceutically acceptable salt thereof. In some embodiments, the formulation comprises about 50 mg of the rofecoxib or pharmaceutically acceptable salt thereof.

In some embodiments, the rofecoxib is highly pure. In some embodiments, the highly pure rofecoxib comprises less than about 0.1% total impurities. In some embodiments, the highly pure rofecoxib comprises less than about 0.075% total impurities. In some embodiments, the highly pure rofecoxib comprises less than about 0.050% total impurities. In some embodiments, the highly pure rofecoxib comprises less than about 0.025% total impurities. In some embodiments, the highly pure rofecoxib comprises less than about 0.001% total impurities.

In some embodiments, the highly pure rofecoxib comprises less than about 0.10%, 0.05%, 0.02%, or 0.01% of 4-[4-(methylsulphonyl)phenyl]-3-phenyl-2,5-furandione. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylsulfinyl)phenyl]-3-phenyl-2(5H)-furanone.

In some embodiments, the formulation is suitable for oral administration. In some embodiments, the formulation is an oral tablet. In some embodiments, the oral tablet provides a dissolution rate of at least about 80% of the rofecoxib or pharmaceutically acceptable salt thereof by about 15 minutes. In some embodiments, the oral tablet provides a dissolution rate of at least about 85% of the rofecoxib or pharmaceutically acceptable salt thereof by about 15 minutes. In some embodiments, the oral tablet provides a dissolution rate of at least about 90% of the rofecoxib or pharmaceutically acceptable salt thereof by about 15 minutes. In some embodiments, the oral tablet provides a dissolution rate of at least about 95% of the rofecoxib or pharmaceutically acceptable salt thereof by about 15 minutes. In some embodiments, the oral tablet provides a dissolution rate of at least about 100% of the rofecoxib or pharmaceutically acceptable salt thereof by about 15 minutes.

In some embodiments, the dissolution rate is measured in about 1% SDS at a paddle speed of about 50 rpm and at a temperature of about 37.0° C.±0.5° C. In some embodiments, the dissolution rate is measured in about 1% SDS at a paddle speed of about 75 rpm and at a temperature of about 37.0° C.±0.5° C. In some embodiments, the dissolution rate is measured in about 1.5% SDS at a paddle speed of about 50 rpm and at a temperature of about 37.0° C.±0.5° C. In some embodiments, the dissolution rate is measured in about 1.5% SDS at a paddle speed of about 75 rpm and at a temperature of about 37.0° C.±0.5° C. In some embodiments, the dissolution rate is measured in about 2% SDS at a paddle speed of about 50 rpm and at a temperature of about 37.0° C.±0.5° C. In some embodiments, the dissolution rate is measured in about 2% SDS at a paddle speed of about 75 rpm and at a temperature of about 37.0° C.±0.5° C.

In some embodiments, the rofecoxib or pharmaceutically acceptable salt thereof is formulated into granules and at least about 35% of the granules are less than about 75 μm. In some embodiments, the rofecoxib or pharmaceutically acceptable salt thereof is formulated into granules and at least about 55% of the granules are less than about 150 μm. In some embodiments, the rofecoxib or pharmaceutically acceptable salt thereof is formulated into granules and at least about 75% of the granules are less than about 250 μm. In some embodiments, the rofecoxib or pharmaceutically acceptable salt thereof is formulated into granules and at least about 85% of the granules are less than about 425 μm. In some embodiments, the rofecoxib or pharmaceutically acceptable salt thereof is formulated into granules and at least about 90% of the granules are less than about 1000 μm.

In some embodiments, a 17.5 mg solid dosage formulation of rofecoxib reaches a median time to Cmax plasma concentration in 4 hours or less following single administration of the formulation to human subjects. In some embodiments, a 17.5 mg solid dosage formulation of rofecoxib reaches a median time to Cmax plasma concentration in 3 hours or less following administration. In some embodiments, a 17.5 mg solid dosage formulation of rofecoxib reaches a mean Cmax plasma concentration in less than 2.5 hours following administration. In some embodiments, a 17.5 mg solid dosage formulation of rofecoxib reaches a mean Cmax plasma concentration in less than 2.5 hours following administration. In some embodiments, a 17.5 mg solid dosage formulation of rofecoxib has a mean Cmax plasma concentration of more than 100 ng/ml. In some embodiments, a 17.5 mg solid dosage formulation of rofecoxib has a mean Cmax plasma concentration of more than 150 ng/ml, 167 ng/ml, or 190 ng/ml. In some embodiments, a 17.5 mg solid dosage formulation of rofecoxib has a mean Cmax plasma concentration of more than 200 ng/ml. In some embodiments, a 17.5 mg solid dosage formulation of rofecoxib has a mean Cmax plasma concentration of more than 220 ng/ml. In some embodiments, a 17.5 mg solid dosage formulation of rofecoxib has a mean Cmax plasma concentration of more than 250 ng/ml. In some embodiments, a 17.5 mg solid dosage formulation of rofecoxib has a mean Cmax plasma concentration of more than 280 ng/ml. In some embodiments, a 17.5 mg solid dosage formulation of rofecoxib has a mean $AUC_{0-\infty}$ of more than 1750 h*ng/ml. In some embodiments, a 17.5 mg solid dosage formulation of rofecoxib has a mean $AUC_{0-\infty}$ of more than 2000 h*ng/ml. In some embodiments, a 17.5 mg solid dosage formulation of rofecoxib has a mean $AUC_{0-\infty}$ of more than 2500 h*ng/ml. In some embodiments, a 17.5 mg solid dosage formulation of rofecoxib has a mean $AUC_{0-\infty}$ of more than 3000 h*ng/ml. In some embodiments, a 17.5 mg solid dosage formulation of rofecoxib has a mean $AUC_{0-\infty}$ of more than 3100 h*ng/ml. In some embodiments, a 17.5 mg solid dosage formulation of rofecoxib has a mean $AUC_{0-\infty}$ of more than 3500 h*ng/ml. In some embodiments, a 17.5 mg solid dosage formulation of rofecoxib has a mean $AUC_{0-\infty}$ of more than 4000 h*ng/ml. In some embodiments, a 17.5 mg solid dosage formulation of rofecoxib has a mean $AUC_{0-\infty}$ of more than 4500 h*ng/ml. In some embodiments, a 17.5 mg solid dosage formulation of rofecoxib reaches a Cmax plasma concentration of least 167 ng/ml, 170 ng/ml, 175 ng/ml, 180 ng/ml, or higher following single administration of the formulation to a human subject. In some embodiments, a 17.5 mg solid dosage formulation of rofecoxib reaches an $AUC_{0-\infty}$ of at least 2600 h*ng/ml, 2750 h*ng/ml, 2900 h*ng/ml, 3050 h*ng/ml, 3100 h*ng/ml, 3200 h*ng/ml, 3350 h*ng/ml, 3500 h*ng/ml, 3650 h*ng/ml or higher following single administration of the formulation to a human subject.

In some embodiments, a 20 mg solid dosage formulation of rofecoxib reaches a median time to Cmax plasma concentration in 4 hours or less following single administration of the formulation to human subjects. In some embodiments, a 20 mg solid dosage formulation of rofecoxib reaches a median time to Cmax plasma concentration in 3 hours or less following administration. In some embodiments, a 20 mg solid dosage formulation of rofecoxib reaches a median time to Cmax plasma concentration in 2.5 hours or less following administration. In some embodiments, a 20 mg solid dosage formulation of rofecoxib reaches a median time to Cmax plasma concentration in 2 hours or less following administration. In some embodiments, a 20 mg solid dosage formulation of rofecoxib has a mean Cmax plasma concentration of more than 150 ng/ml. In some embodiments, a 20 mg solid dosage formulation of rofecoxib has a mean Cmax plasma concentration of more than 191 ng/ml, 200 ng/ml, 215 ng/ml, or 225 ng/ml. In some embodiments, a 20 mg solid dosage formulation of rofecoxib has a mean Cmax plasma concentration of more than 250 ng/ml. In some embodiments, a 20 mg solid dosage formulation of rofecoxib has a mean Cmax plasma concentration of more than 258 ng/ml. In some embodiments, a 20 mg solid dosage formulation of rofecoxib has a mean Cmax plasma concentration of more than 300 ng/ml. In some embodiments, a 20 mg solid dosage formulation of rofecoxib has a mean $AUC_{0-\infty}$ of more than 2000 h*ng/ml. In some embodiments, a 20 mg solid dosage formulation of rofecoxib has a mean $AUC_{0-\infty}$ of more than 2500 h*ng/ml. In some embodiments, a 20 mg solid dosage formulation of rofecoxib has a mean $AUC_{0-\infty}$ of more than 3000 h*ng/ml. In some embodiments, a 20 mg solid dosage formulation of rofecoxib has a mean $AUC_{0-\infty}$ of more than 3400 h*ng/ml. In some embodiments, a 20 mg solid dosage formulation of rofecoxib has a mean $AUC_{0-\infty}$ of more than 3500 h*ng/ml. In some embodiments, a 20 mg solid dosage formulation of rofecoxib has a mean $AUC_{0-\infty}$ of more than 4000 h*ng/ml. In some embodiments, a 20 mg solid dosage formulation of rofecoxib reaches a Cmax plasma concentration of least 190 ng/ml, 205 ng/ml, 220 ng/ml, 235 ng/ml, 250 ng/ml, or higher following single administration of the formulation to a human subject. In some embodiments, a 20 mg solid dosage formulation of rofecoxib reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In some embodiments, a 25 mg solid dosage formulation of rofecoxib reaches a mean Cmax plasma concentration in less than 3 hours following single administration of the formulation to human subjects. In some embodiments, a 25 mg solid dosage formulation of rofecoxib has a mean Cmax plasma concentration of more than 240 ng/ml. In some embodiments, a 25 mg solid dosage formulation of rofecoxib has a mean Cmax plasma concentration of more than 250 ng/ml. In some embodiments, a 25 mg solid dosage formulation of rofecoxib has a mean Cmax plasma concentration of more than 300 ng/ml. In some embodiments, a 25 mg solid dosage formulation of rofecoxib has a mean Cmax plasma concentration of more than 320 ng/ml. In some embodiments, a 25 mg solid dosage formulation of rofecoxib has a mean $AUC_{0-\infty}$ of more than 4250 h*ng/ml. In some embodiments, a 25 mg solid dosage formulation of rofecoxib has a mean $AUC_{0-\infty}$ of more than 4500 h*ng/ml. In some embodiments, a 25 mg solid dosage formulation of rofecoxib has a mean $AUC_{0-\infty}$ of more than 4550 h*ng/ml. In some embodiments, a 25 mg solid dosage formulation of rofecoxib has a mean $AUC_{0-\infty}$ of more than 4700 h*ng/ml. In some embodiments, a 25 mg solid dosage formulation of rofecoxib reaches a mean Cmax plasma concentration of more than 240 ng/ml in about 3 hours following administration with an $AUC_{0-\infty}$ of more than 4250 h*ng/ml.

In certain aspects, a 10 mg to 50 mg solid dosage formulation of rofecoxib achieves a mean Cmax plasma concentration from 9.8 ng/ml to 16 ng/ml for each 1 mg of rofecoxib in the formulation following single administration of the formulation to human subjects. In some embodiments, a 10 mg to 50 mg solid dosage formulation of rofecoxib achieves a mean Cmax plasma concentration from 10 ng/ml to 14 ng/ml for each 1 mg of rofecoxib in the formulation. In some embodiments, a 10 mg to 50 mg solid dosage formulation of rofecoxib achieves a mean Cmax plasma concentration from 10 ng/ml to 13 ng/ml for each 1 mg of rofecoxib in the formulation. In some embodiments, a 10 mg to 50 mg solid dosage formulation of rofecoxib achieves a mean Cmax plasma concentration from 80% to 125% of 12.8 ng/ml. In some embodiments, a 10 mg to 50 mg solid dosage formulation of rofecoxib reaches a mean $AUC_{0-\infty}$ of 170 h*ng/ml to 235 h*ng/ml for each 1 mg of rofecoxib in the formulation. In some embodiments, a 10 mg to 50 mg solid dosage formulation of rofecoxib reaches a mean $AUC_{0-\infty}$ of 170 h*ng/ml to 225 h*ng/ml for each 1 mg of rofecoxib in the formulation. In some embodiments, a 10 mg to 50 mg solid dosage formulation achieves a mean $AUC_{0-\infty}$ of 177 h*ng/ml to 225 h*ng/ml for each 1 mg of rofecoxib in the formulation. In some embodiments, a 10 mg to 50 mg solid dosage formulation achieves a mean $AUC_{0-\infty}$ of 180 h*ng/ml to 225 h*ng/ml for each 1 mg of rofecoxib in the formulation. In some embodiments, a 10 mg to 50 mg solid dosage formulation of rofecoxib reaches a mean $AUC_{0-\infty}$ of 190 h*ng/ml to 215 h*ng/ml for each 1 mg of rofecoxib in the formulation.

In certain aspects, the subject matter disclosed herein provides a method for enhancing the dissolution profile of a solid dosage form comprising rofecoxib or a pharmaceutically acceptable salt thereof, the method comprising providing a pharmaceutically acceptable formulation comprising a granular component and an extragranular component, wherein the granular component comprises an intragranular component comprising 17.5 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 100 ng/ml. In some embodiments, the formulation achieves a mean Cmax plasma concentration of more than 150 ng/ml, 167 ng/ml, or 190 ng/ml. In some embodiments, the formulation achieves a mean Cmax plasma concentration of more than 200 ng/ml. In some embodiments, the formulation achieves a mean Cmax plasma concentration of more than 220 ng/ml. In some embodiments, the formulation achieves a mean Cmax plasma concentration of more than 250 ng/ml. In some embodiments, the formulation achieves a mean Cmax plasma concentration of more than 280 ng/ml. In some embodiments, the formulation achieves a mean $AUC_{0-\infty}$ of more than 1750 h*ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3100 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation achieves a mean $AUC_{0-\infty}$ of more than 4500 h*ng/ml. In some embodiments, the formulation reaches a Cmax plasma concentration of at least 167 ng/ml, 170 ng/ml, 175 ng/ml, 180 ng/ml, or higher following single administration of the formulation to a human subject. In some embodiments, the formulation reaches an $AUC_{0-\infty}$ of at least 2600 h*ng/ml, 2750 h*ng/ml, 2900 h*ng/ml, 3050 h*ng/ml, 3100 h*ng/ml, 3200 h*ng/ml, 3350 h*ng/ml, 3500 h*ng/ml, 3650 h*ng/ml or higher following single administration of the formulation to a human subject.

In certain aspects, the subject matter disclosed herein provides a method for enhancing the dissolution profile of a solid dosage form comprising rofecoxib or a pharmaceutically acceptable salt thereof, the method comprising providing a pharmaceutically acceptable formulation comprising a granular component and an extragranular component, wherein the granular component comprises an intragranular component comprising 20 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 150 ng/ml. In some embodiments, the formulation achieves a mean Cmax plasma concentration of more than 191 ng/ml, 200 ng/ml, 215 ng/ml, or 225 ng/ml. In some embodiments, the formulation achieves a mean Cmax plasma concentration of more than 250 ng/ml. In some embodiments, the formulation achieves a mean Cmax plasma concentration of more than 258 ng/ml. In some embodiments, the formulation achieves a mean Cmax plasma concentration of more than 300 ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3400 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation reaches a Cmax plasma concentration of at least 190 ng/ml, 205 ng/ml, 220 ng/ml, 235 ng/ml, 250 ng/ml, or higher following single administration of the formulation to a human subject. In some embodiments, the formulation reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject.

In certain aspects, the subject matter disclosed herein provides a method for enhancing the dissolution profile of a solid dosage form comprising rofecoxib or a pharmaceutically acceptable salt thereof, the method comprising providing a pharmaceutically acceptable formulation comprising a granular component and an extragranular component, wherein the granular component comprises an intragranular component comprising 25 mg solid dosage formulation of rofecoxib or a pharmaceutically acceptable salt thereof. In some embodiments, the formulation achieves a mean Cmax plasma concentration in less than 3 hours following single administration of the formulation to human subjects. In some embodiments, the formulation achieves a mean Cmax plasma concentration in less than 2.5 hours following administration. In some embodiments, the formulation achieves a mean Cmax plasma concentration in less than 2 hours following administration. In some embodiments, the formulation achieves a mean Cmax plasma concentration of more than 240 ng/ml. In some embodiments, the formulation achieves a mean Cmax plasma concentration of more than 250 ng/ml. In some embodiments, the formulation achieves a mean Cmax plasma concentration of more than 300 ng/ml. In some embodiments, the formulation achieves a mean Cmax plasma concentration of more than 320 ng/ml. In some embodiments, the formulation achieves a mean $AUC_{0-\infty}$ of more than 4250 h*ng/ml. In some embodiments, the formulation achieves a mean $AUC_{0-\infty}$ of more than 4500 h*ng/ml. In some embodiments, the formulation achieves a mean $AUC_{0-\infty}$ of more than 4550 h*ng/ml. In some embodiments, the formulation achieves a mean $AUC_{0-\infty}$ of more than 4700 h*ng/ml. In some embodiments, the formulation achieves a mean Cmax plasma concentration of more than 240 ng/ml in less than 3 hours following administration with an $AUC_{0-\infty}$ of more than 4250 h*ng/ml.

In certain aspects, the subject matter disclosed herein provides a method for enhancing the dissolution profile of a solid dosage form comprising rofecoxib or a pharmaceutically acceptable salt thereof, the method comprising providing a pharmaceutically acceptable formulation comprising a granular component and an extragranular component, wherein the granular component comprises an intragranular component comprising 10 mg to 50 mg of rofecoxib or a pharmaceutically acceptable salt thereof. In some embodiments, the formulation achieves a mean Cmax plasma concentration from 9.8 ng/ml to 16 ng/ml for each 1 mg of rofecoxib in the formulation following single administration of the formulation to human subjects. In some embodiments, the formulation achieves a mean Cmax plasma concentration from 10 ng/ml to 14 ng/ml for each 1 mg of rofecoxib in the formulation. In some embodiments, the formulation achieves a mean Cmax plasma concentration from 10 ng/ml to 13 ng/ml for each 1 mg of rofecoxib in the formulation. In some embodiments, the formulation achieves a mean Cmax plasma concentration from 80% to 125% of 12.8 ng/ml. In some embodiments, the formulation reaches a mean $AUC_{0-\infty}$ of 170 h*ng/ml to 235 h*ng/ml for each 1 mg of rofecoxib in the formulation. In some embodiments, the formulation reaches a mean $AUC_{0-\infty}$ of 170 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the formulation reaches a mean $AUC_{0-\infty}$ of 190 h*ng/ml to 215 h*ng/ml for each 1 mg of rofecoxib in the formulation.

A method for manufacturing a solid dosage form comprising rofecoxib or a pharmaceutically acceptable salt thereof, the method comprising providing a pharmaceutically acceptable formulation comprising a granular component and an extragranular component, wherein the granular component comprises an intragranular component comprising rofecoxib or a pharmaceutically acceptable salt thereof and one or more disintegrants, and wherein the extragranular component comprises one or more disintegrants.

In some embodiments, the one or more disintegrants in the granular component is selected from starches, clays, celluloses, algins, gums, cross-linked polymers, and combinations thereof. In some embodiments, the one or more disintegrants in the granular component is selected from croscarmellose, crospovidone, sodium starch glycolate, and combinations thereof. In some embodiments, the one or more disintegrants in the granular component is croscarmellose sodium. In some embodiments, the one or more disintegrants in the granular component is about 1% (w/w) to about 8% (w/w) of the formulation. In some embodiments, the one or more disintegrants in the granular component is about 1% (w/w) to about 6% (w/w) of the formulation. In some embodiments, the one or more disintegrants in the granular component is about 1% (w/w) to about 4% (w/w) of the formulation.

In some embodiments, the one or more disintegrants in the extragranular component is selected from starches, clays, celluloses, algins, gums, cross-linked polymers, and combinations thereof. In some embodiments, the one or more disintegrants in the extragranular component is selected from croscarmellose, crospovidone, sodium starch glycolate, and combinations thereof.

In some embodiments, the one or more disintegrants in the extragranular component is croscarmellose sodium. In some embodiments, the disintegrant in the extragranular component is about 1% (w/w) to about 8% (w/w) of the formulation. In some embodiments, the disintegrant in the extragranular component is about 1% (w/w) to about 6% (w/w) of the formulation. In some embodiments, the disintegrant in the extragranular component is about 1% (w/w) to about 4% (w/w) of the formulation.

In some embodiments, the disintegrant in the granular component and the disintegrant in the extragranular component are together about 2% (w/w) to about 12% (w/w) of the formulation. In some embodiments, the disintegrant in the granular component and the disintegrant in the extragranular component are together about 2% (w/w) to about 10% (w/w) of the formulation. In some embodiments, the disintegrant in the granular component and the disintegrant in the extragranular component are together about 2% (w/w) to about 8% (w/w) of the formulation.

In some embodiments, the ratio of granular disintegrant to extragranular disintegrant is about 40% (w/w) to about 60% (w/w). In some embodiments, the ratio of granular disintegrant to extragranular disintegrant is about 45% (w/w) to about 55% (w/w). In some embodiments, the ratio of granular disintegrant to extragranular disintegrant is about 50% (w/w) to about 50% (w/w). In some embodiments, the ratio of granular disintegrant to extragranular disintegrant is about 55% (w/w) to about 45% (w/w). In some embodiments, the ratio of granular disintegrant to extragranular disintegrant is about 60% (w/w) to about 40% (w/w).

In some embodiments, the pharmaceutically acceptable formulation further comprising one or more of a diluent, a binder, a coloring agent, and a lubricant. In some embodiments, at least a portion of the diluent is in the granular component. In some embodiments, the diluent is selected from dicalcium phosphate, calcium sulfate, lactose, cellulose, kaolin, mannitol, sodium chloride, dry starch, powdered sugar, sorbitol, sucrose, inositol, and combinations thereof. In some embodiments, the diluent is selected from lactose, cellulose, or a combination thereof. In some embodiments, the diluent is selected from lactose monohydrate, microcrystalline cellulose, or a combination thereof.

In some embodiments, the lactose monohydrate is about 35% (w/w) to about 45% (w/w) of the formulation. In some embodiments, the lactose monohydrate is about 37% (w/w) to about 42% (w/w) of the formulation. In some embodiments, the lactose monohydrate is about 39% (w/w) to about 40% (w/w) of the formulation.

In some embodiments, the microcrystalline cellulose is about 35% (w/w) to about 45% (w/w) of the formulation. In some embodiments, the microcrystalline cellulose is about 37% (w/w) to about 42% (w/w) of the formulation. In some embodiments, the microcrystalline cellulose is about 39% (w/w) to about 40% (w/w) of the formulation.

In some embodiments, the diluent is about 75% (w/w) to about 85% (w/w) of the formulation. In some embodiments, diluent is about 77% (w/w) to about 82% (w/w) of the formulation. In some embodiments, the diluent is about 78% (w/w) to about 80% (w/w) of the formulation.

In some embodiments, at least a portion of the binder is in the granular component. In some embodiments, the binder is selected from starches, gelatins, sugars, gums, waxes, water, alcohols, celluloses, and combinations thereof. In some embodiments, the binder is selected from acacia gum, tragacanth, corn starch, methyl cellulose, panwar gum, ghatti gum, mucilage of isapol husks, carboxymethylcellulose, methylcellulose, polyvinylpyrrolidone, sucrose, glucose, dextrose, molasses, lactose, and combinations thereof. In some embodiments, the binder is hydroxypropyl cellulose. In some embodiments, the binder is about 1% (w/w) to about 5% (w/w) of the formulation. In some embodiments, binder is about 2% (w/w) to about 4% (w/w) of the formulation. In some embodiments, the binder is about 2.5% (w/w) to about 3.5% (w/w) of the formulation.

In some embodiments, at least a portion of the coloring agent is in the extragranular component. In some embodiments, the coloring agent is pigment blend yellow. In some embodiments, the coloring agent is about 0.30% (w/w) to about 0.60% (w/w) of the formulation.

In some embodiments, at least a portion of the lubricant is in the extragranular component. In some embodiments, the lubricant is selected from talc, magnesium stearate, calcium stearate, stearic acid, metallic stearate, hydrogenated vegetable oils, and polyethylene glycol, corn starch, boric acids, sodium chloride, sodium lauryl sulphate. In some embodiments, the lubricant is magnesium stearate. In some embodiments, the lubricant is about 0.10% (w/w) to about 1% (w/w) of the formulation. In some embodiments, the lubricant is about 0.50% (w/w) of the formulation.

In some embodiments, the rofecoxib or pharmaceutically acceptable salt thereof is about 5% (w/w) to about 30% (w/w) of the formulation. In some embodiments, the rofecoxib or pharmaceutically acceptable salt thereof is about 10% (w/w) to about 20% (w/w) of the formulation. In some embodiments, the rofecoxib or pharmaceutically acceptable salt thereof is about 12% (w/w) to about 13% (w/w) of the formulation. In some embodiments, the formulation comprises about 10 mg of the rofecoxib or pharmaceutically acceptable salt thereof. In some embodiments, the formulation comprises about 10.5 mg of the rofecoxib or pharmaceutically acceptable salt thereof. In some embodiments, the formulation comprises about 11 mg of the rofecoxib or pharmaceutically acceptable salt thereof. In some embodiments, the formulation comprises about 11.5 mg of the rofecoxib or pharmaceutically acceptable salt thereof. In some embodiments, the formulation comprises about 12 mg of the rofecoxib or pharmaceutically acceptable salt thereof. In some embodiments, the formulation comprises about 12.5 mg of the rofecoxib or pharmaceutically acceptable salt thereof. In some embodiments, the formulation comprises about 17.5 mg of the rofecoxib or pharmaceutically acceptable salt thereof. In some embodiments, the formulation comprises about 20 mg of the rofecoxib or pharmaceutically acceptable salt thereof. In some embodiments, the formulation comprises about 21 mg of the rofecoxib or pharmaceutically acceptable salt thereof. In some embodiments, the formulation comprises about 22 mg of the rofecoxib or pharmaceutically acceptable salt thereof. In some embodiments, the formulation comprises about 22.5 mg of the rofecoxib or pharmaceutically acceptable salt thereof. In some embodiments, the formulation comprises about 25 mg of the rofecoxib or pharmaceutically acceptable salt thereof. In some embodiments, the formulation comprises about 50 mg of the rofecoxib or pharmaceutically acceptable salt thereof.

In some embodiments, the rofecoxib is highly pure. In some embodiments, the highly pure rofecoxib comprises less than about 0.1% total impurities. In some embodiments, the highly pure rofecoxib comprises less than about 0.075% total impurities. In some embodiments, the highly pure rofecoxib comprises less than about 0.050% total impurities. In some embodiments, the highly pure rofecoxib comprises less than about 0.025% total impurities. In some embodiments, the highly pure rofecoxib comprises less than about 0.001% total impurities.

In some embodiments, the highly pure rofecoxib comprises less than about 0.10%, 0.05%, 0.02%, or 0.01% of 4-[4-(methylsulphonyl)phenyl]-3-phenyl-2,5-furandione. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylsulfinyl)phenyl]-3-phenyl-2(5H)-furanone.

In some embodiments, the formulation is suitable for oral administration. In some embodiments, the formulation is an oral tablet. In some embodiments, the oral tablet provides a dissolution rate of at least about 80% of the rofecoxib or pharmaceutically acceptable salt thereof by about 15 minutes. In some embodiments, the oral tablet provides a dissolution rate of at least about 85% of the rofecoxib or pharmaceutically acceptable salt thereof by about 15 minutes. In some embodiments, the oral tablet provides a dissolution rate of at least about 90% of the rofecoxib or pharmaceutically acceptable salt thereof by about 15 minutes. In some embodiments, the oral tablet provides a dissolution rate of at least about 95% of the rofecoxib or pharmaceutically acceptable salt thereof by about 15 minutes. In some embodiments, the oral tablet provides a dissolution rate of at least about 100% of the rofecoxib or pharmaceutically acceptable salt thereof by about 15 minutes.

In some embodiments, the dissolution rate is measured in about 1% SDS at a paddle speed of about 50 rpm and at a temperature of about 37.0° C.±0.5° C. In some embodiments, the dissolution rate is measured in about 1% SDS at a paddle speed of about 75 rpm and at a temperature of about 37.0° C.±0.5° C. In some embodiments, the dissolution rate is measured in about 1.5% SDS at a paddle speed of about 50 rpm and at a temperature of about 37.0° C.±0.5° C. In some embodiments, the dissolution rate is measured in about 1.5% SDS at a paddle speed of about 75 rpm and at a temperature of about 37.0° C.±0.5° C. In some embodiments, the dissolution rate is measured in about 2% SDS at a paddle speed of about 50 rpm and at a temperature of about 37.0° C.±0.5° C. In some embodiments, the dissolution rate is measured in about 2% SDS at a paddle speed of about 75 rpm and at a temperature of about 37.0° C.±0.5° C.

In some embodiments, the rofecoxib or pharmaceutically acceptable salt thereof is formulated into granules and at least about 35% of the granules are less than about 75 μm. In some embodiments, the rofecoxib or pharmaceutically acceptable salt thereof is formulated into granules and at least about 55% of the granules are less than about 150 μm. In some embodiments, the rofecoxib or pharmaceutically acceptable salt thereof is formulated into granules and at least about 75% of the granules are less than about 250 μm. In some embodiments, the rofecoxib or pharmaceutically acceptable salt thereof is formulated into granules and at least about 85% of the granules are less than about 425 μm. In some embodiments, the rofecoxib or pharmaceutically acceptable salt thereof is formulated into granules and at least about 90% of the granules are less than about 1000 μm.

In some embodiments, a 17.5 mg solid dosage formulation of rofecoxib reaches a median time to Cmax plasma concentration in 4 hours or less following single administration of the formulation to human subjects. In some embodiments, a 17.5 mg solid dosage formulation of rofecoxib reaches a median time to Cmax plasma concentration in 3 hours or less following administration. In some embodiments, a 17.5 mg solid dosage formulation of rofecoxib reaches a median time to Cmax plasma concentration in 2.5 hours or less following administration. In some embodiments, a 17.5 mg solid dosage formulation of rofecoxib reaches a median time to Cmax plasma concentration in 2 hours or less following administration. In some embodiments, a 17.5 mg solid dosage formulation of rofecoxib has a mean Cmax plasma concentration of more than 150 ng/ml, 167 ng/ml, or 190 ng/ml. In some embodiments, a 17.5 mg solid dosage formulation of rofecoxib has a mean Cmax plasma concentration of more than 200 ng/ml. In some embodiments, a 17.5 mg solid dosage formulation of rofecoxib has a mean Cmax plasma concentration of more than 220 ng/ml. In some embodiments, a 17.5 mg solid dosage formulation of rofecoxib has a mean Cmax plasma concentration of more than 250 ng/ml. In some embodiments, a 17.5 mg solid dosage formulation of rofecoxib has a mean Cmax plasma concentration of more than 280 ng/ml. In some embodiments, a 17.5 mg solid dosage formulation of rofecoxib has a mean $AUC_{0-\infty}$ of more than 1750 h*ng/ml. In some embodiments, a 17.5 mg solid dosage formulation of rofecoxib has a mean $AUC_{0-\infty}$ of more than 2000 h*ng/ml. In some embodiments, a 17.5 mg solid dosage formulation of rofecoxib has a mean $AUC_{0-\infty}$ of more than 2500 h*ng/ml. In some embodiments, a 17.5 mg solid dosage formulation of rofecoxib has a mean $AUC_{0-\infty}$ of more than 3000 h*ng/ml. In some embodiments, a 17.5 mg solid dosage formulation of rofecoxib has a mean $AUC_{0-\infty}$ of more than 3100 h*ng/ml. In some embodiments, a 17.5 mg solid dosage formulation of rofecoxib has a mean $AUC_{0-\infty}$ of more than 3500 h*ng/ml. In some embodiments, a 17.5 mg solid dosage formulation of rofecoxib has a mean $AUC_{0-\infty}$ of more than 4000 h*ng/ml. In some embodiments, a 17.5 mg solid dosage formulation of rofecoxib has a mean $AUC_{0-\infty}$ of more than 4500 h*ng/ml. In some embodiments, a 17.5 mg solid dosage formulation of rofecoxib reaches a Cmax plasma concentration of least 167 ng/ml, 170 ng/ml, 175 ng/ml, 180 ng/ml, or higher following single administration of the formulation to a human subject. In some embodiments, a 17.5 mg solid dosage formulation of rofecoxib reaches an $AUC_{0-\infty}$ of at least 2600 h*ng/ml, 2750 h*ng/ml, 2900 h*ng/ml, 3050 h*ng/ml, 3100 h*ng/ml, 3200 h*ng/ml, 3350 h*ng/ml, 3500 h*ng/ml, 3650 h*ng/ml or higher following single administration of the formulation to a human subject.

In some embodiments, a 20 mg solid dosage formulation of rofecoxib reaches a median time to Cmax plasma concentration in 4 hours or less following single administration of the formulation to human subjects. In some embodiments, a 20 mg solid dosage formulation of rofecoxib reaches a median time to Cmax plasma concentration in 3 hours or less following administration. In some embodiments, a 20 mg solid dosage formulation of rofecoxib reaches a median time to Cmax plasma concentration in 2.5 hours or less following administration. In some embodiments, a 20 mg solid dosage formulation of rofecoxib reaches a median time to Cmax plasma concentration in 2 hours or less following administration. In some embodiments, a 20 mg solid dosage formulation of rofecoxib has a mean Cmax plasma concentration of more than 150 ng/ml. In some embodiments, a 20 mg solid dosage formulation of rofecoxib has a mean Cmax plasma concentration of more than 191 ng/ml, 200 ng/ml, 215 ng/ml, or 225 ng/ml. In some embodiments, a 20 mg solid dosage formulation of rofecoxib has a mean Cmax plasma concentration of more than 250 ng/ml. In some embodiments, a 20 mg solid dosage formulation of rofecoxib has a mean Cmax plasma concentration of more than 258 ng/ml. In some embodiments, a 20 mg solid dosage formulation of rofecoxib has a mean Cmax plasma concentration of more than 300 ng/ml. In some embodiments, a 20 mg solid dosage formulation of rofecoxib has a mean $AUC_{0-\infty}$ of more than 2000 h*ng/ml. In some embodiments, a 20 mg solid dosage formulation of rofecoxib has a mean $AUC_{0-\infty}$ of more than 2500 h*ng/ml. In some embodiments, a 20 mg solid dosage formulation of rofecoxib has a mean $AUC_{0-\infty}$ of more than 3000 h*ng/ml. In some embodiments, a 20 mg solid dosage formulation of rofecoxib has a mean $AUC_{0-\infty}$ of more than 3400 h*ng/ml. In some embodiments, a 20 mg solid dosage formulation of rofecoxib has a mean $AUC_{0-\infty}$ of more than 3500 h*ng/ml. In some embodiments, a 20 mg solid dosage formulation of rofecoxib has a mean $AUC_{0-\infty}$ of more than 4000 h*ng/ml. In some embodiments, a 20 mg solid dosage formulation of rofecoxib reaches a Cmax plasma concentration of least 190 ng/ml, 205 ng/ml, 220 ng/ml, 235 ng/ml, 250 ng/ml, or higher following single administration of the formulation to a human subject. In some embodiments, a 20 mg solid dosage formulation of rofecoxib reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In some embodiments, a 25 mg solid dosage formulation of rofecoxib reaches a mean Cmax plasma concentration in less than 3 hours following single administration of the formulation to human subjects. In some embodiments, a 25 mg solid dosage formulation of rofecoxib reaches a mean Cmax plasma concentration in less than 2.5 hours following administration. In some embodiments, a 25 mg solid dosage formulation of rofecoxib reaches a mean Cmax plasma concentration in less than 2 hours following administration. In some embodiments, a 25 mg solid dosage formulation of rofecoxib has a mean Cmax plasma concentration of more than 240 ng/ml. In some embodiments, a 25 mg solid dosage formulation of rofecoxib has a mean Cmax plasma concentration of more than 250 ng/ml. In some embodiments, a 25 mg solid dosage formulation of rofecoxib has a mean Cmax plasma concentration of more than 300 ng/ml. In some embodiments, a 25 mg solid dosage formulation of rofecoxib has a mean Cmax plasma concentration of more than 320 ng/ml. In some embodiments, a 25 mg solid dosage formulation of rofecoxib has a mean $AUC_{0-\infty}$ of more than 4250 h*ng/ml. In some embodiments, a 25 mg solid dosage formulation of rofecoxib has a mean $AUC_{0-\infty}$ of more than 4500 h*ng/ml. In some embodiments, a 25 mg solid dosage formulation of rofecoxib has a mean $AUC_{0-\infty}$ of more than 4550 h*ng/ml. In some embodiments, a 25 mg solid dosage formulation of rofecoxib has a mean $AUC_{0-\infty}$ of more than 4700 h*ng/ml. In some embodiments, a 25 mg solid dosage formulation of rofecoxib reaches a mean Cmax plasma concentration of more than 240 ng/ml in a median time of about 3 hours or less following administration with an $AUC_{0-\infty}$ of more than 4250 h*ng/ml.

In some embodiments, a 10 mg to 50 mg solid dosage formulation of rofecoxib achieves a mean Cmax plasma concentration from 9.8 ng/ml to 16 ng/ml for each 1 mg of rofecoxib in the formulation following single administration of the formulation to human subjects. In some embodiments, a 10 mg to 50 mg solid dosage formulation of rofecoxib achieves a mean Cmax plasma concentration from 10 ng/ml to 14 ng/ml for each 1 mg of rofecoxib in the formulation. In some embodiments, a 10 mg to 50 mg solid dosage formulation of rofecoxib achieves a mean Cmax plasma concentration from 10 ng/ml to 13 ng/ml for each 1 mg of rofecoxib in the formulation. In some embodiments, a 10 mg to 50 mg solid dosage formulation of rofecoxib achieves a mean Cmax plasma concentration from 80% to 125% of 12.8 ng/ml. In some embodiments, a 10 mg to 50 mg solid dosage formulation of rofecoxib reaches a mean $AUC_{0-\infty}$ of 170 h*ng/ml to 235 h*ng/ml for each 1 mg of rofecoxib in the formulation. In some embodiments, a 10 mg to 50 mg solid dosage formulation of rofecoxib reaches a mean $AUC_{0-\infty}$ of 170 h*ng/ml to 225 h*ng/ml for each 1 mg of rofecoxib in the formulation. In some embodiments, a 10 mg to 50 mg solid dosage formulation of rofecoxib achieves a mean $AUC_{0-\infty}$ of 177 h*ng/ml to 225 h*ng/ml for each 1 mg of rofecoxib in the formulation. In some embodiments, a 10 mg to 50 mg solid dosage formulation of rofecoxib achieves a mean $AUC_{0-\infty}$ of 180 h*ng/ml to 225 h*ng/ml for each 1 mg of rofecoxib in the formulation. In some embodiments, a 10 mg to 50 mg solid dosage formulation of rofecoxib reaches a mean $AUC_{0-\infty}$ of 190 h*ng/ml to 215 h*ng/ml for each 1 mg of rofecoxib in the formulation.

In certain aspects, the subject matter disclosed herein provides a method for manufacturing a solid dosage form comprising rofecoxib or a pharmaceutically acceptable salt thereof, the method comprising providing a pharmaceutically acceptable formulation comprising a granular component and an extragranular component, wherein the granular component comprises an intragranular component comprising 17.5 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 150 ng/ml, 167 ng/ml, or 190 ng/ml. In some embodiments, the formulation achieves a mean Cmax plasma concentration of more than 200 ng/ml. In some embodiments, the formulation achieves a mean Cmax plasma concentration of more than 220 ng/ml. In some embodiments, the formulation achieves a mean Cmax plasma concentration of more than 250 ng/ml. In some embodiments, the formulation achieves a mean Cmax plasma concentration of more than 280 ng/ml. In some embodiments, the formulation achieves a mean $AUC_{0-\infty}$ of more than 1750 h*ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3100 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation achieves a mean $AUC_{0-\infty}$ of more than 4500 h*ng/ml. In some embodiments, the formulation reaches a Cmax plasma concentration of least 167 ng/ml, 170 ng/ml, 175 ng/ml, 180 ng/ml, or higher following single administration of the formulation to a human subject. In some embodiments, the formulation reaches an $AUC_{0-\infty}$ of at least 2600 h*ng/ml, 2750 h*ng/ml, 2900 h*ng/ml, 3050 h*ng/ml, 3100 h*ng/ml, 3200 h*ng/ml, 3350 h*ng/ml, 3500 h*ng/ml, 3650 h*ng/ml or higher following single administration of the formulation to a human subject.

In certain aspects, the subject matter disclosed herein provides a method for manufacturing a solid dosage form comprising rofecoxib or a pharmaceutically acceptable salt thereof, the method comprising providing a pharmaceutically acceptable formulation comprising a granular component and an extragranular component, wherein the granular component comprises an intragranular component comprising 20 mg of rofecoxib or a pharmaceutically acceptable salt thereof. In some embodiments, the formulation achieves a median time to Cmax plasma concentration in 4 hours or less following single administration of the formulation to human subjects. In some embodiments, the formulation achieves a median time to Cmax plasma concentration in 3 hours or less following administration. In some embodiments, the formulation achieves a median time to Cmax plasma concentration in 2.5 hours or less following administration. In some embodiments, the formulation achieves a median time to Cmax plasma concentration in 2 hours or less following administration. In some embodiments, the formulation achieves a mean Cmax plasma concentration of more than 150 ng/ml. In some embodiments, the formulation achieves a mean Cmax plasma concentration of more than 191 ng/ml, 200 ng/ml, 215 ng/ml, or 225 ng/ml. In some embodiments, the formulation achieves a mean Cmax plasma concentration of more than 250 ng/ml. In some embodiments, the formulation achieves a mean Cmax plasma concentration of more than 258 ng/ml. In some embodiments, the formulation achieves a mean Cmax plasma concentration of more than 300 ng/ml. In some embodiments, the formulation achieves a mean $AUC_{0-\infty}$ of more than 2000 h*ng/ml. In some embodiments, the formulation achieves a mean $AUC_{0-\infty}$ of more than 2500 h*ng/ml. In some embodiments, the formulation achieves a mean $AUC_{0-\infty}$ of more than 3000 h*ng/ml. In some embodiments, the formulation achieves a mean $AUC_{0-\infty}$ of more than 3400 h*ng/ml. In some embodiments, the formulation achieves a mean $AUC_{0-\infty}$ of more than 3500 h*ng/ml. In some embodiments, the formulation achieves a mean $AUC_{0-\infty}$ of more than 4000 h*ng/ml. In some embodiments, the formulation reaches a Cmax plasma concentration of least 190 ng/ml, 205 ng/ml, 220 ng/ml, 235 ng/ml, 250 ng/ml, or higher following single administration of the formulation to a human subject. In some embodiments, the formulation reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject. In some embodiments, the rofecoxib formulation achieves a mean Cmax plasma concentration within 80% to 125% of 259 ng/ml and a mean $AUC_{0-\infty}$ within 80% to 125% of 3550 h*ng/ml. In some embodiments, the rofecoxib formulation achieves a mean plasma $AUC_{0-\infty}$ of about 2840-4438 h*ng/ml and a mean plasma Cmax of about 207-324 ng/ml following oral administration of a single dose of the formulation to a population of healthy adults less than 65 years of age in a fasted state. In some embodiments, the population of healthy adults are less than 60 years of age.

In certain aspects, the subject matter disclosed herein provides a method for manufacturing a solid dosage form comprising rofecoxib or a pharmaceutically acceptable salt thereof, the method comprising providing a pharmaceutically acceptable formulation comprising a granular component and an extragranular component, wherein the granular component comprises an intragranular component comprising 25 mg of rofecoxib or a pharmaceutically acceptable salt thereof. In some embodiments, the formulation achieves a mean Cmax plasma concentration in less than 3 hours following single administration of the formulation to human subjects. In some embodiments, the formulation achieves a mean Cmax plasma concentration in less than 2.5 hours following administration. In some embodiments, the formulation achieves a mean Cmax plasma concentration in less than 2 hours following administration. In some embodiments, the formulation achieves a mean Cmax plasma concentration of more than 240 ng/ml. In some embodiments, the formulation achieves a mean Cmax plasma concentration of more than 250 ng/ml. In some embodiments, the formulation achieves a mean Cmax plasma concentration of more than 300 ng/ml. In some embodiments, the formulation achieves a mean Cmax plasma concentration of more than 320 ng/ml. In some embodiments, the formulation achieves a mean $AUC_{0-\infty}$ of more than 4250 h*ng/ml. In some embodiments, the formulation achieves a mean $AUC_{0-\infty}$ of more than 4500 h*ng/ml. In some embodiments, the formulation achieves a mean $AUC_{0-\infty}$ of more than 4550 h*ng/ml. In some embodiments, the formulation achieves a mean $AUC_{0-\infty}$ of more than 4700 h*ng/ml. In some embodiments, the formulation achieves a Cmax plasma concentration of more than 240 ng/ml in about 3 hours following administration with an $AUC_{0-\infty}$ of more than 4250 h*ng/ml.

In certain aspects, the subject matter disclosed herein provides a method for manufacturing a solid dosage form comprising rofecoxib or a pharmaceutically acceptable salt thereof, the method comprising providing a pharmaceutically acceptable formulation comprising a granular component and an extragranular component, wherein the granular component comprises an intragranular component comprising 10 mg to 50 mg of rofecoxib or a pharmaceutically acceptable salt thereof. In some embodiments, the formulation achieves a mean Cmax plasma concentration from 9.8 ng/ml to 16 ng/ml for each 1 mg of rofecoxib in the formulation following single administration of the formulation to human subjects. In some embodiments, the formulation achieves a mean Cmax plasma concentration from 10 ng/ml to 14 ng/ml for each 1 mg of rofecoxib in the formulation. In some embodiments, the formulation achieves a mean Cmax plasma concentration from 10 ng/ml to 13 ng/ml for each 1 mg of rofecoxib in the formulation. In some embodiments, the formulation achieves a mean Cmax plasma concentration from 80% to 125% of 12.8 ng/ml. In some embodiments, the formulation reaches a mean $AUC_{0-\infty}$ of 170 h*ng/ml to 235 h*ng/ml for each 1 mg of rofecoxib in the formulation. In some embodiments, the formulation reaches a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the formulation reaches a mean $AUC_{0-\infty}$ of 190 h*ng/ml to 215 h*ng/ml for each 1 mg of rofecoxib in the formulation.

Methods for Manufacturing of Rofecoxib Tablets

In some embodiments, the subject matter disclosed herein provides for a method of manufacture of a 25-mg rofecoxib tablet. In some embodiments, the rofecoxib tablet is a 5-mg rofecoxib tablet, 10-mg rofecoxib tablet, 10.5-mg rofecoxib tablet, 11-mg rofecoxib tablet, 11.5-mg rofecoxib tablet, 12-mg rofecoxib tablet, 12.5-mg rofecoxib tablet, 13-mg rofecoxib tablet, 14-mg rofecoxib tablet, 15-mg rofecoxib tablet, 16-mg rofecoxib tablet, 17-mg rofecoxib tablet, 17.5-mg rofecoxib tablet, 18-mg rofecoxib tablet, 19-mg rofecoxib tablet, 20-mg rofecoxib tablet, 21-mg rofecoxib tablet, 22-mg rofecoxib tablet, 22.5-mg rofecoxib tablet, 25-mg rofecoxib tablet, 30-mg rofecoxib tablet, 40-mg rofecoxib tablet, 50-mg rofecoxib tablet, or 60-mg rofecoxib tablet.

In some embodiments, the composition of the 25-mg rofecoxib tablet and the function of each excipient are as provided in FIGS. 1A-B. In some embodiments, the manufacturing train includes high-shear wet granulation because the micronized drug substance could be prone to powder flow issues during scale-up if a direct compression process was used. Some of the different embodiments of the manufacturing process described herein are referred to as Process $A_1$, Process $A_2$, Process $A_3$ or Process $B_1$. Subscripted numbers denote small differences in the manufacturing process between embodiments. Letters denote major differences in the manufacturing process between embodiments.

Process $A_1$, Process $A_2$, and Process $A_3$

Figure 3A:
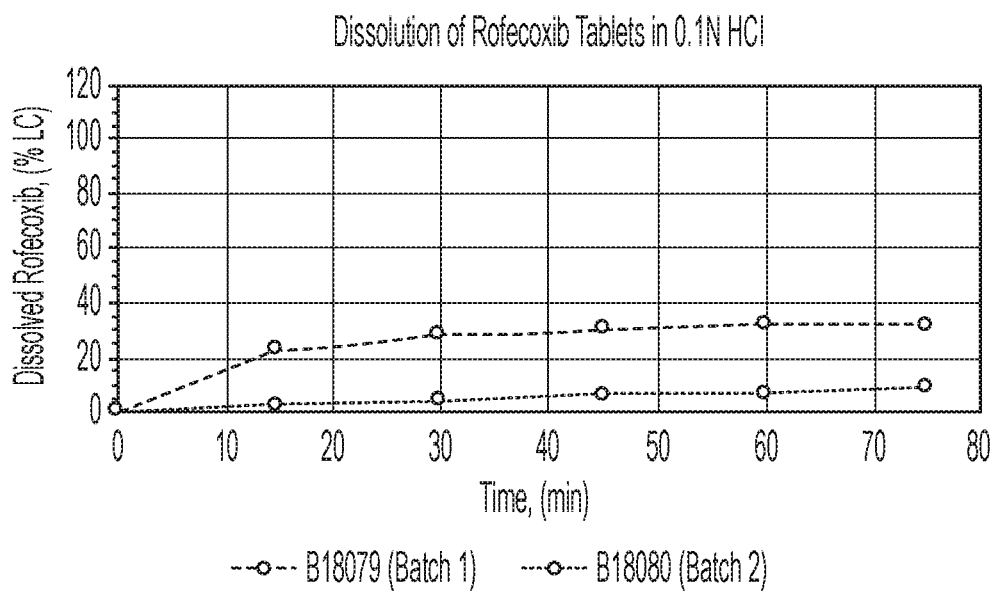
FIGS. 3A-B show dissolution profiles of rofecoxib tablets, batches 1 and 2.
Figure 3B:
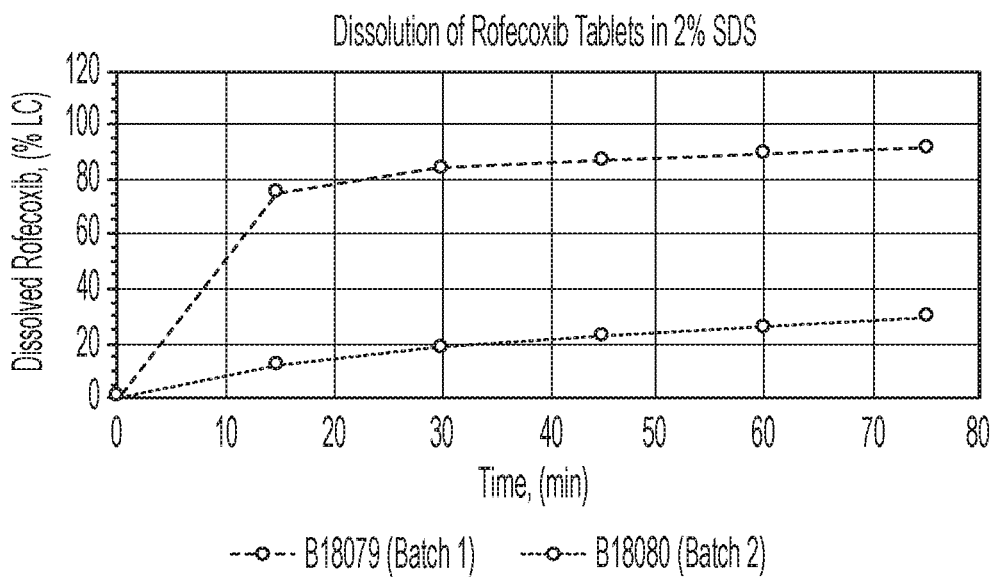
Figure 4A:
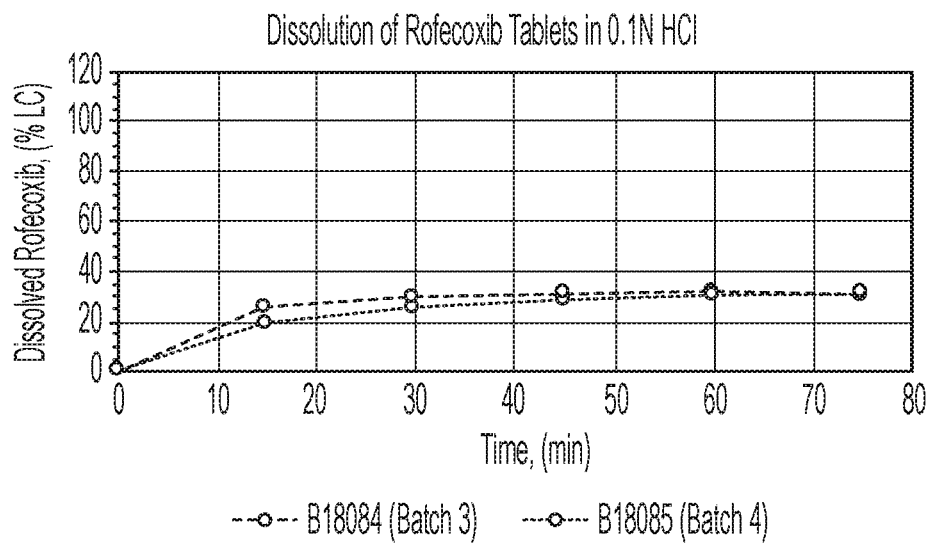
FIGS. 4A-B show dissolution profiles of rofecoxib tablets, batches 3 and 4.
Figure 4B:
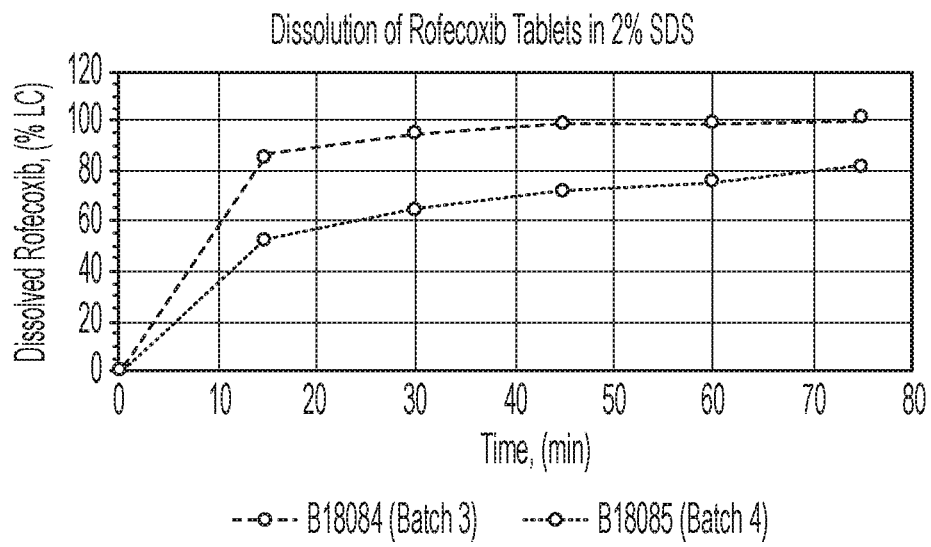

In some embodiments, the manufacturing process can be Process $A_1$, Process $A_2$, or Process $A_3$, each with processing conditions as described in FIG. 2. In some embodiments, Process $A_1$, Process $A_2$, or Process $A_3$ result in manufacture of batches 1-4. In some embodiments, dissolution testing of batches is performed in two media: 2% SDS and 0.1N HCl at 37.0±0.5° C. with a paddle speed of 75 rpm. Dissolution profiles for batches 1 and 2 are shown in FIGS. 3A-B. The points shown in the dissolution profiles are an average of three tablets, and the 75-minute point is an infinity spin in which the paddle speed was increased to 250 rpm for 15 minutes following the 60-minute time point. FIG. 3A shows dissolution of rofecoxib tablets in 0.1N HCl. FIG. 3B shows dissolution of rofecoxib tablets in at least 2% SDS. The results in both media indicate that dissolution may be incomplete after 60 minutes, with one exception being batch 3 in at least 2% SDS. Dissolution profiles for batches 3 and 4 are shown in FIGS. 4A-B. FIG. 4A shows dissolution of rofecoxib tablets in 0.1N HCl. FIG. 4B shows dissolution of rofecoxib tablets in at least 2% SDS.

Process $B_1$

Figure 6A:
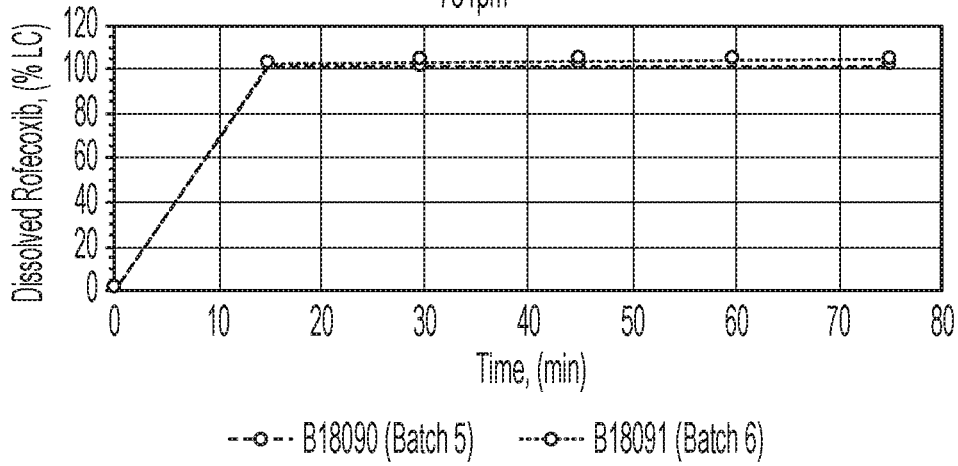
FIGS. 6A-B shows dissolution profiles for Process $B_1$ in manufacturing batches 5-8.
Figure 6B:
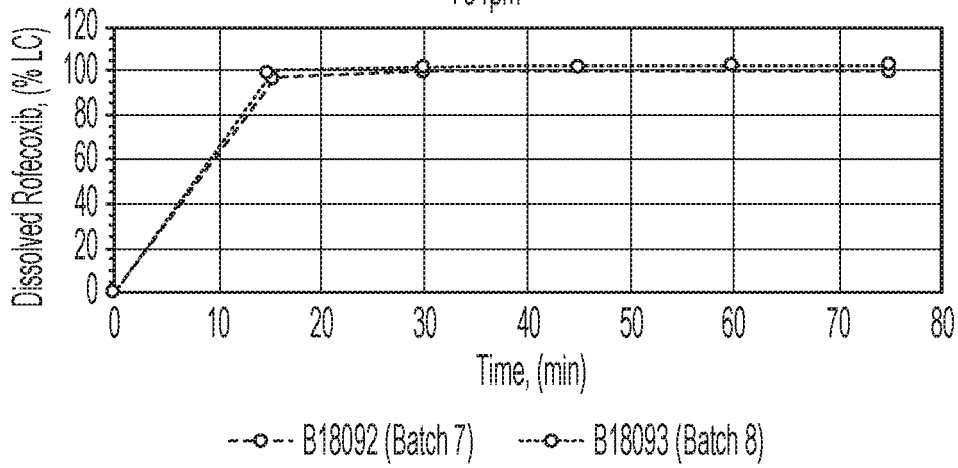
Figure 7:
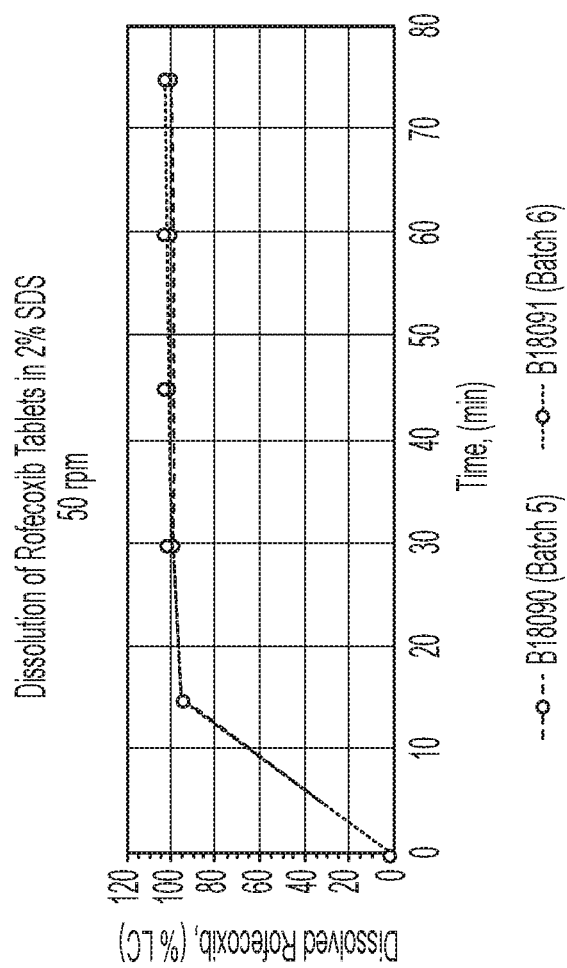
FIG. 7 shows dissolution profiles for batches 5 and 6

In some embodiments, the manufacturing process of the rofecoxib tablets is Process BL In some embodiments, Process $B_1$ includes croscarmellose sodium, a disintegrant, as an intragranular and extragranular component in order to achieve complete dissolution of rofecoxib. Batches 1-4 according to Process $A_{1-3}$ may include croscarmellose sodium as an extragranular component. In some embodiments, the processing conditions of Process $B_1$ are shown in FIG. 5. In Process $B_1$, as compared to Process $A_{1-3}$, the pigment amount can be increased from 0.30 to 0.60%, while the percentage of the diluents is decreased to accommodate increases in pigment or croscarmellose sodium; the ratio of lactose monohydrate to microcrystalline cellulose can remain at 1:1. In some embodiments, dissolution testing is performed in at least 2% SDS at 37.0±0.5° C. with a paddle speed of 75 rpm. Dissolution profiles for rofecoxib tablets manufactured using Process $B_1$ in batches 5-8 are shown in FIGS. 6A-B. The results indicate that intragranular disintegrant can improve the rate at which rofecoxib dissolves and the extent to which rofecoxib dissolves. The results also indicate that there is no advantage to having 8% total disintegrant in the tablet versus 4% total disintegrant. Therefore, in some embodiments, batches 5 and 6 are the lead formulations. Additional dissolution testing of batches 5 and 6 in at least 2% SDS at 37.0±0.5° C. with a slower paddle speed of 50 rpm indicate that 50 rpm is an appropriate paddle speed for the dissolution test as shown in FIG. 7.

Exemplary batch analysis and dissolution profile is presented in Table 1 below for 17.5 mg rofecoxib tablets.

TABLE 1

Batch Analysis for 17.5-mg Rofecoxib Tablets

| Lot No. | Uniformity of Dosage Forms | | | Dissolution, % Dissolved | | | | | |
|---|---|---|---|---|---|---|---|---|---|
| (manufacturing process) | Mean % w/w | Range % w/w | AV | 10 minutes | 15 minutes | 20 minutes | 30 minutes | 45 minutes | 60 minutes |
| B19056 (B$_1$) | 100.1 | 99.2-110.9 | 1.2 | 89 | 97 | 98 | 100 | 101 | 101 |

Exemplary batch analysis and dissolution profile is presented in Table 2 below for 20 mg rofecoxib tablets.

TABLE 2

Batch Analysis Data for 20-mg Rofecoxib Tablets

| Lot No. | Uniformity of Dosage Forms | | | Dissolution, % Dissolved | | | | | |
|---|---|---|---|---|---|---|---|---|---|
| (manufacturing process) | Mean % w/w | Range % w/w | AV | 10 minutes | 15 minutes | 20 minutes | 30 minutes | 45 minutes | 60 minutes |
| B19057 (B$_1$) | 99.7 | 99.8-100.3 | 1.2 | 88 | 95 | 97 | 99 | 100 | 100 |

Process B$_2$

In some embodiments, the manufacturing process of the rofecoxib tablets is Process B$_2$. Process B$_2$ differs from Process B$_1$ in that, in Process B$_2$, the pigment blend is added during granulation. As a result, the compositions of the 25-mg rofecoxib tablets manufactured using Processes B$_1$ and B$_2$ are identical, as only the manufacturing step during which pigment is added differs. Additional dose strengths can be manufactured by varying the quantities of the first three components, while keeping the tablet weight constant at 200 mg. The ratio of microcrystalline cellulose to lactose monohydrate is maintained at 1:1 in all dose strengths. Exemplary tablets manufactured according to Process B$_2$ are set forth in Tables 6B and 18.

Formulation and Process for the PK Study

In some embodiments, the amount of pigment in the clinical batch is 0.30%. For example, the color of batches 5-8 is only slightly darker than the color of batches 1-4, despite having a greater amount of pigment. Therefore, there may not be any aesthetic advantage to having 0.60% pigment in the tablet. Batches 5 and 6, even though they contain more pigment than the clinical batch, are considered representative of the clinical batch because all were manufactured using Process B1 and because the composition of the intragranular and extragranular disintegrant is the same as that for the clinical batch as shown in FIG. 8. Additional dose strengths can be manufactured by varying the quantities of the first three components, while keeping the tablet weight constant at 200 mg. The ratio of microcrystalline cellulose to lactose monohydrate is maintained at 1:1 in all dose strengths.

Figure 10A:
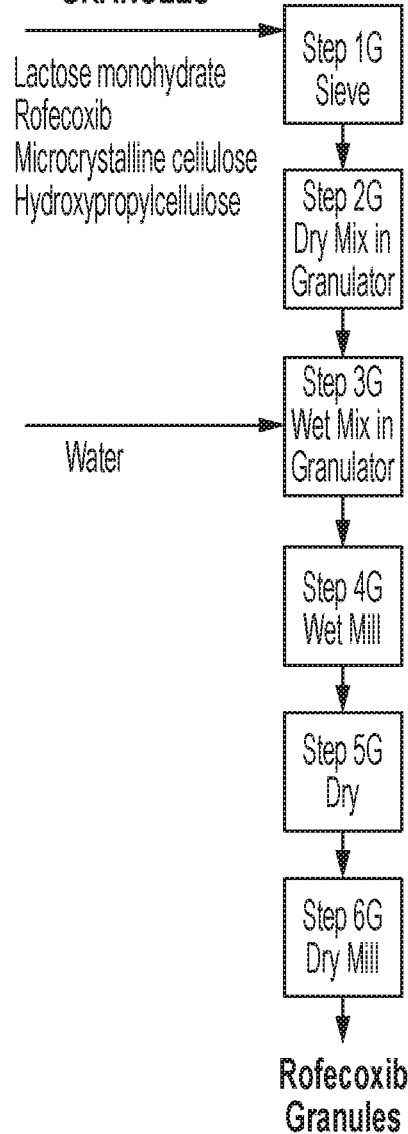
FIGS. 10A-B show a flow diagram for rofecoxib tablet manufacturing Process $A_1$.
Figure 10B:
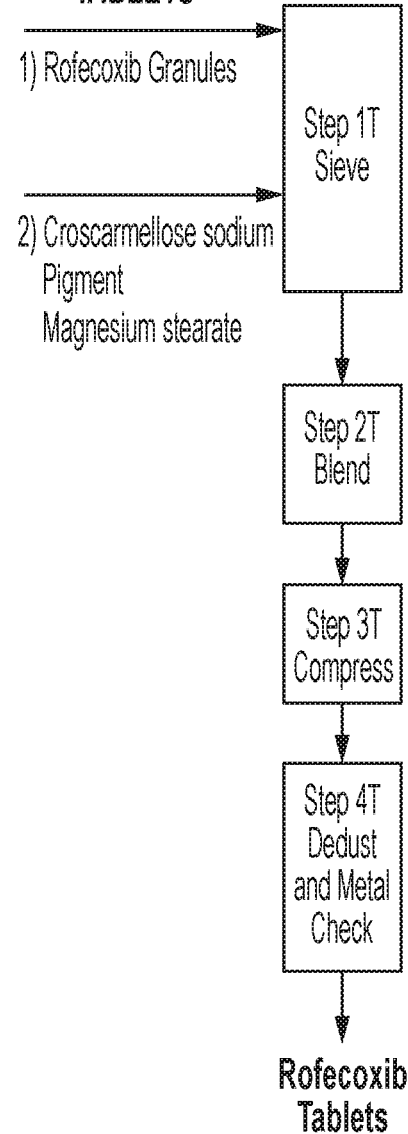
Figure 12A:
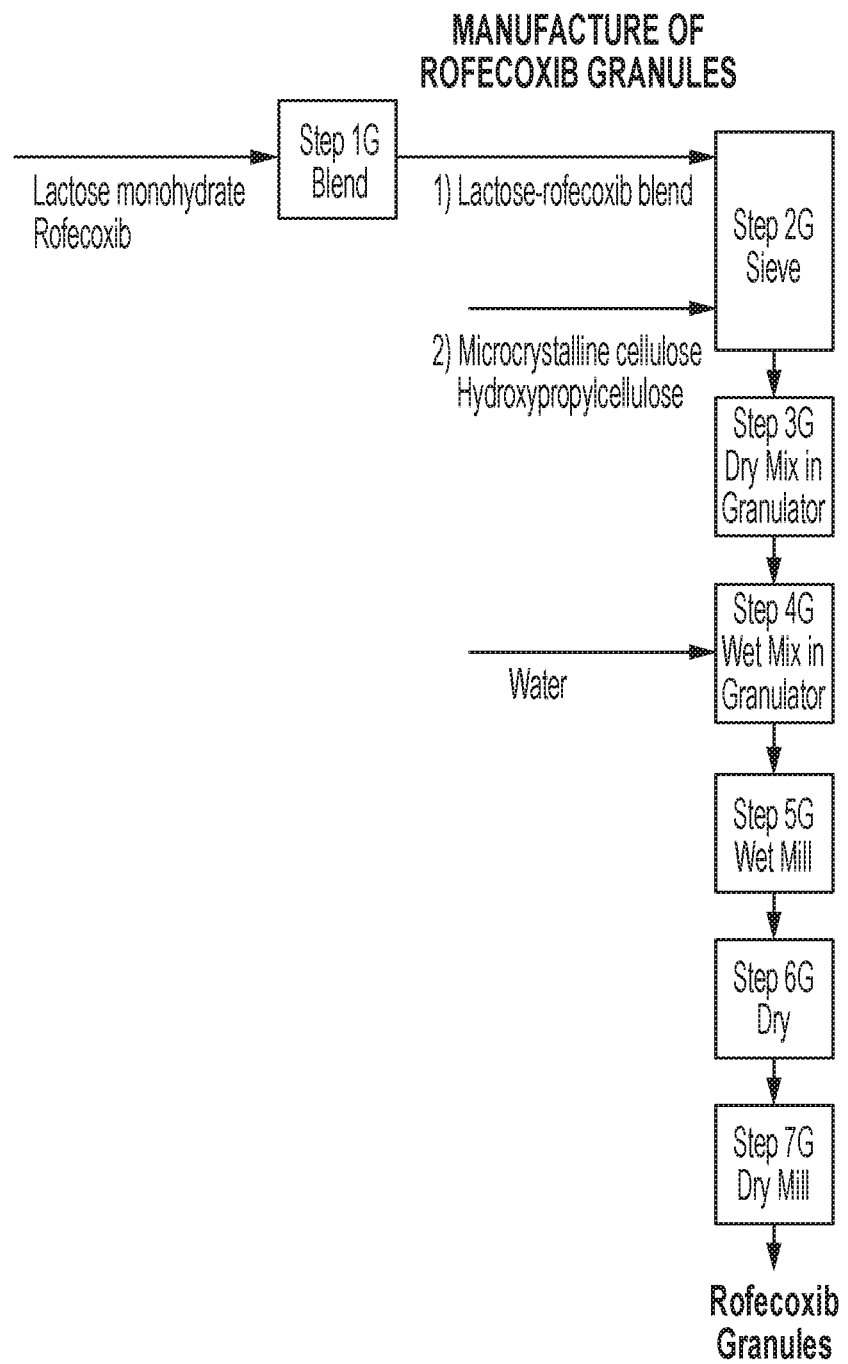
FIGS. 12A-B show a flow diagram for rofecoxib tablet manufacturing Process $A_3$.
Figure 12B:
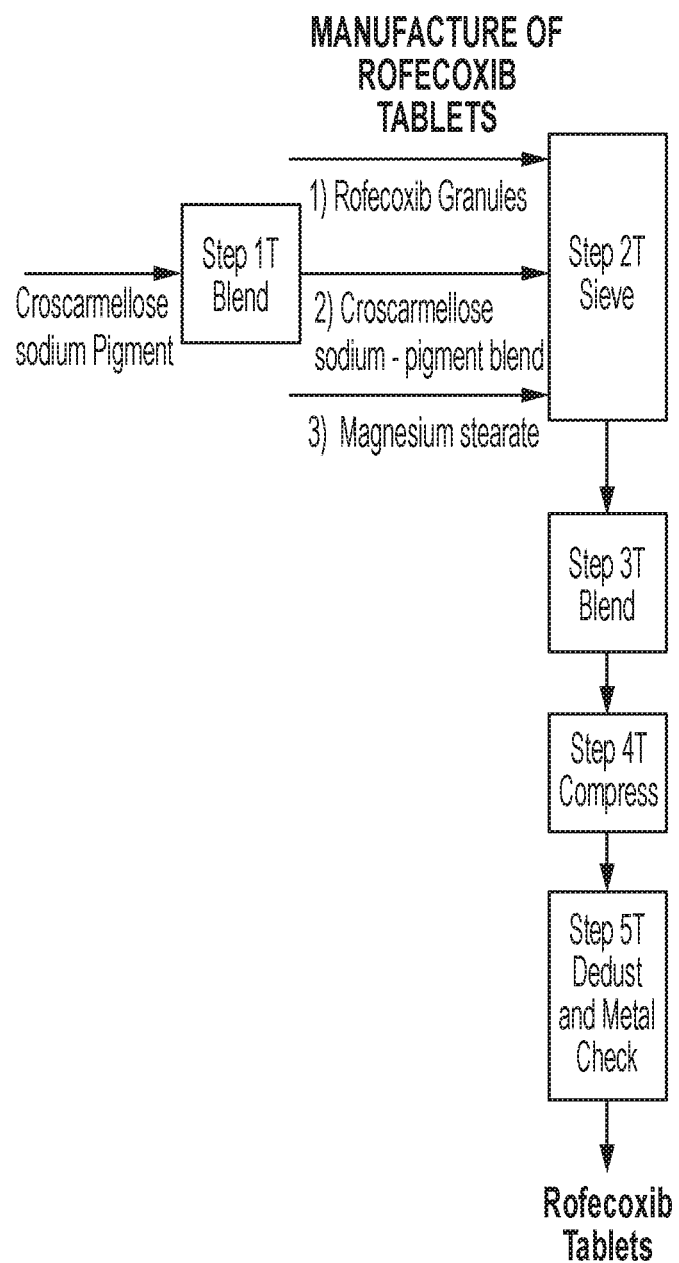
Figure 13A:
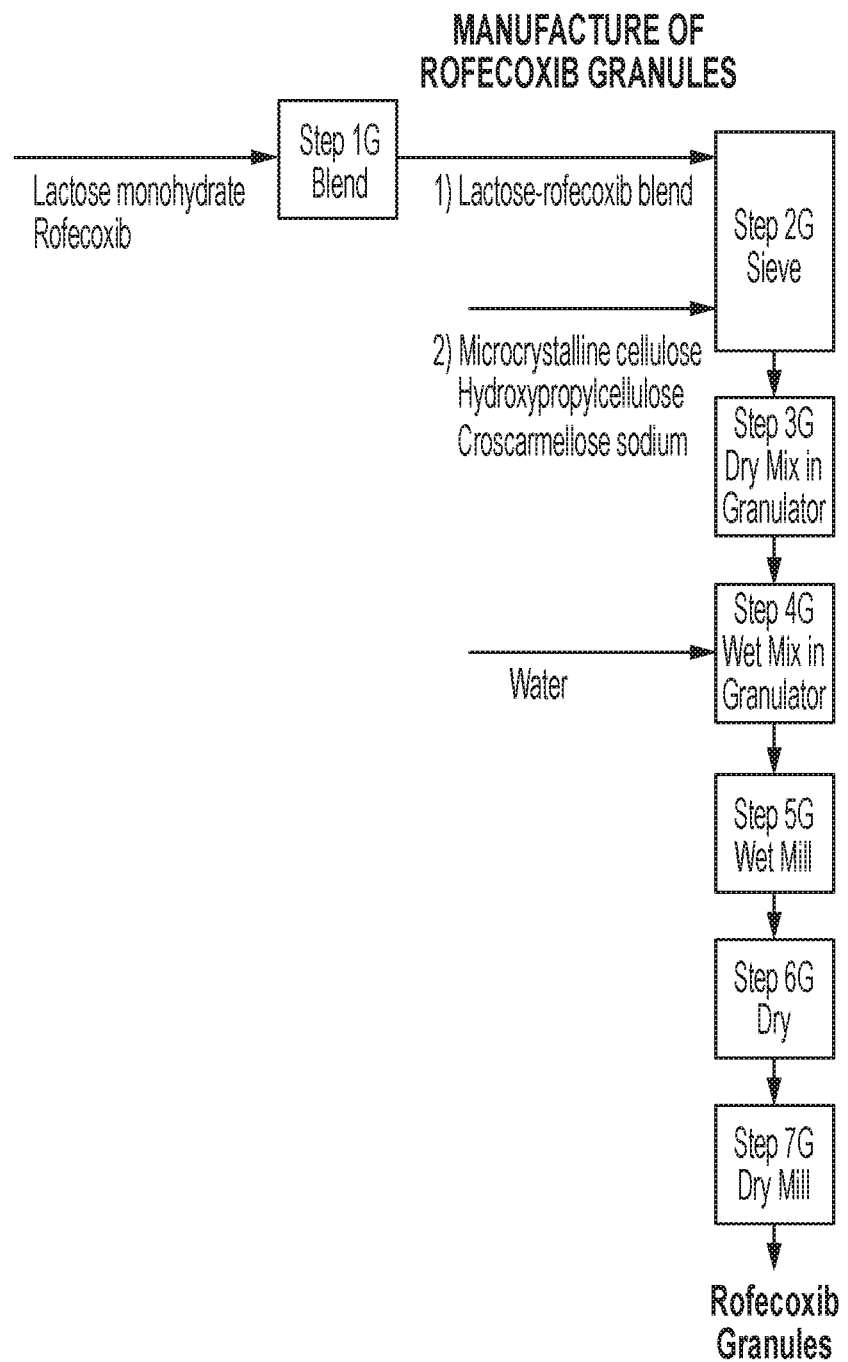
FIGS. 13A-B show a flow diagram for rofecoxib tablet manufacturing Process $B_1$.
Figure 13B:
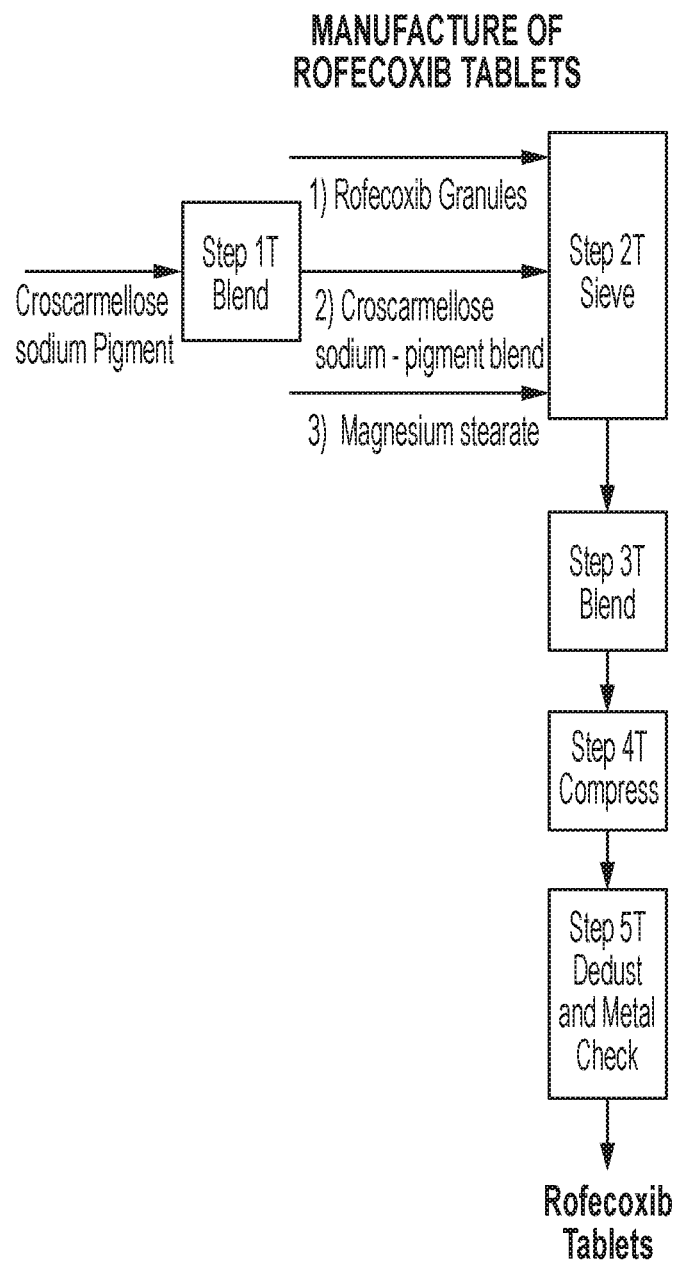

Process descriptions for the manufacture of prototype 25-mg rofecoxib tablets for Process A$_1$, Process A$_2$, or Process A$_3$, and Process B$_1$ are shown in FIG. 9. FIGS. 10A-B show a flow diagram for rofecoxib tablet manufacturing Process A$_1$. FIG. 10A shows manufacture of rofecoxib granules. FIG. 10B shows manufacture of rofecoxib tablets. FIGS. 11A-B show a flow diagram for rofecoxib tablet manufacturing Process A$_2$. FIG. 11A shows manufacture of rofecoxib granules. FIG. 11B shows manufacture of rofecoxib tablets. FIGS. 12A-B show a flow diagram for rofecoxib tablet manufacturing Process A$_3$. FIG. 12A shows manufacture of rofecoxib granules. FIG. 12B shows manufacture of rofecoxib tablets. FIGS. 13A-B show a flow diagram for rofecoxib tablet manufacturing Process B$_1$. FIG. 13A shows manufacture of rofecoxib granules. FIG. 13B shows manufacture of rofecoxib tablets.

In some embodiments, rofecoxib tablets are administered to patients at a clinical site and are packaged in multi-use HDPE bottles that are induction sealed and closed with child resistant caps. Each bottle may also contain rayon coil USP. In some embodiments, rofecoxib tablets are manufactured using a wet-granulation process.

In some embodiments, rofecoxib tablets are a solid oral dosage form that is manufactured using equipment with non-reactive surfaces. In some embodiments, rofecoxib is packaged in standard containers that do not present compatibility issues.

The batch formulae for representative 2.3-kg batches of rofecoxib tablets are shown in Table 3 below. In some embodiments, other batch sizes are possible.

TABLE 3

Batch Formula for 25-mg Rofecoxib Tablets

| | Amount, (g) | | | |
|---|---|---|---|---|
| Components | 25 mg | 20 mg | 17.5 mg | 12.5 mg |
| Rofecoxib$^a$ | 287.50 | 230.00 | 201.25 | 143.75 |
| Lactose monohydrate | 916.55 | 945.30 | 959.68 | 988.43 |
| Microcrystalline cellulose | 916.55 | 945.30 | 959.68 | 988.43 |
| Hydroxypropylcellulose | 69.00 | 69.00 | 69.00 | 69.00 |
| Croscarmellose sodium | 92.00 | 92.00 | 92.00 | 92.00 |
| Pigment blend yellow | 6.90 | 6.90 | 6.90 | 6.90 |

TABLE 3-continued

Batch Formula for 25-mg Rofecoxib Tablets

| | Amount, (g) | | | |
|---|---|---|---|---|
| Components | 25 mg | 20 mg | 17.5 mg | 12.5 mg |
| Magnesium stearate | 11.50 | 11.50 | 11.50 | 11.50 |
| Water | NA[b] | NA[b] | NA[b] | NA[b] |

[a]Note that the amount of rofecoxib may be adjusted for purity and moisture content. An adjustment can be made to the amounts of lactose monohydrate and microcrystalline cellulose used to maintain tablet weight.
[b]NA = not applicable. The amount of water for granulation may vary in order to achieve granules; water for granulation is removed upon drying of the wet mass.

Rofecoxib

Rofecoxib (also known as TRM-201; RXB-201; and 4-[4-(methylsulfonyl)phenyl]-3-phenyl-2(5H)-furanone) is a nonsteroidal anti-inflammatory drug that exhibits anti-inflammatory, analgesic, and antipyretic activities. Without being bound by theory, the mechanism of action of rofecoxib is believed to be due to inhibition of prostaglandin synthesis, via inhibition of cyclooxygenase-2 (COX-2). Additionally, at therapeutic concentrations in humans, rofecoxib does not inhibit the cyclooxygenase-1 (COX-1) isoenzyme.

Rofecoxib is a potent inhibitor of prostaglandin synthesis in vitro. Prostaglandins are mediators of inflammation. Rofecoxib concentrations reached during therapy have produced in vivo effects. Prostaglandins sensitize afferent nerves and potentiate the action of bradykinin in inducing pain in animal models. Because rofecoxib is an inhibitor of prostaglandin synthesis, its mode of action may be due to a decrease of prostaglandins in peripheral tissues.

In some embodiments, rofecoxib is indicated: for relief of the signs and symptoms of osteoarthritis, for relief of the signs and symptoms of rheumatoid arthritis in adults, for relief of the signs and symptoms of pauciarticular or polyarticular course Juvenile Rheumatoid Arthritis (JRA) in patients 2 years and older and who weigh 10 kg (22 lbs) or more, for the management of acute pain in adults, for the treatment of primary dysmenorrhea, for the acute treatment of migraine attacks with or without aura in adults. In some embodiments, rofecoxib is used to treat lower back pain, including chronic lower back pain, and psoriatic arthritis.

The chemical structure of rofecoxib is shown below. Rofecoxib bears no chiral centers and has a molecular weight of 314.355 g moL$^{-1}$.

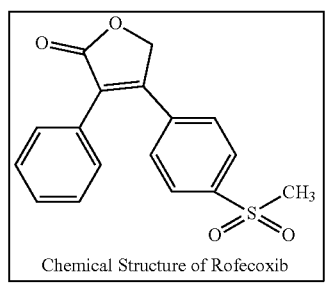 [SMILES: CS(=O)(=O)c1ccc(C2=C(c3ccccc3)C(=O)OC2)cc1]

Chemical Structure of Rofecoxib

In some embodiments, rofecoxib is a white to off-white to light yellow powder. In some embodiments, rofecoxib is sparingly soluble in acetone, slightly soluble in methanol and isopropyl acetate, very slightly soluble in ethanol, practically insoluble in octanol, and insoluble in water. In some embodiments, each tablet of rofecoxib for oral administration contains either 10 mg, 10.5 mg, 11 mg, 11.5 mg, 12 mg, 12.5 mg, 17.5 mg, 20 mg, 21 mg, 22 mg, 22.5 mg, 25 mg, or 50 mg of rofecoxib and the following inactive ingredients: croscarmellose sodium, hydroxypropyl cellulose, lactose, magnesium stearate, microcrystalline cellulose, and yellow ferric oxide. The 50 mg tablets may also contain red ferric oxide. In some embodiments, each 5 mL of the oral suspension contains 10 mg, 10.5 mg, 11 mg, 11.5 mg, 12 mg, 12.5 mg, 17.5 mg, 20 mg, 21 mg, 22 mg, 22.5 mg 25 mg, or 50 mg of rofecoxib and the following inactive ingredients: citric acid (monohydrate), sodium citrate (dihydrate), sorbitol solution, strawberry flavor, xanthan gum, and purified water. Added as preservatives are sodium methylparaben about 0.13% and sodium propylparaben about 0.02%.

In some embodiments, the rofecoxib or pharmaceutically acceptable salt thereof is about 1%, about 5% (w/w), about 10% (w/w), about 15% (w/w), about 20% (w/w), about 25% (w/w), about 30% (w/w), about 35% (w/w), or about 40% (w/w) of the formulation. In some embodiments, the formulation comprises about 5 mg, about 8 mg, about 10 mg, about 10.5 mg, about 11 mg, about 11.5 mg, about 12 mg, about 12.5 mg, about 15 mg, about 17.5 mg, or about 20 mg of the rofecoxib or pharmaceutically acceptable salt thereof. In some embodiments, the formulation comprises about 20 mg, 21 mg, 22 mg, 22.5 mg. In some embodiments, the formulation comprises about 23 mg, about 25 mg, about 27 mg, about 30 mg, about 35 mg, or about 40 mg of the rofecoxib or pharmaceutically acceptable salt thereof. In some embodiments, the formulation comprises about 45 mg, about 47 mg, about 50 mg, about 53 mg, about 55 mg, about 60 mg of the rofecoxib or pharmaceutically acceptable salt thereof.

In some embodiments, the pharmaceutically acceptable formulation as described here includes highly pure rofecoxib, which is essentially free or free of one or more of the impurities found in previously available rofecoxib bulk drug product: 4-[4-(methylsulfonyl)phenyl]-3-phenyl-5-hydroxyfuran-2-one; and 4-[4-(methylsulfonyl)phenyl]-3-phenyl-2,5-furandione. In some embodiments, the pharmaceutically acceptable formulation as described here includes one or more beneficial rofecoxib impurities, such as 4-[4-(methylsulfinyl)phenyl]-3-phenyl-2(5H)-furanone.

In some embodiments, the highly pure rofecoxib comprises less than about 0.1% total impurities. In some embodiments, the highly pure rofecoxib comprises less than about 0.075% total impurities. In some embodiments, the highly pure rofecoxib comprises less than about 0.050% total impurities. In some embodiments, the highly pure rofecoxib comprises less than about 0.025% total impurities. In some embodiments, the highly pure rofecoxib comprises less than about 0.001% total impurities.

In some embodiments, the highly pure rofecoxib comprises less than about 0.10%, 0.05%, 0.02%, or 0.01% of 4-[4-(methylsulphonyl)phenyl]-3-phenyl-2,5-furandione. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylthio)phenyl]-3-phenyl-2(5H)-furanone. In some embodiments, the highly pure rofecoxib comprises less than about 0.10%, 0.05%, 0.02%, or 0.01% of 4-[4-(methylsulfinyl)phenyl]-3-phenyl-2(5H)-furanone.

In some embodiments, the rofecoxib as provided herein contains less than about 0.25%, 0.20%, 0.15%, 0.10%, 0.05%, 0.02% or 0.01% of 4-[4-(methylthio)phenyl]-3-phenyl-2(5H)-furanone and/or 4-[4-(methylsulfinyl)phenyl]-3-phenyl-2(5H)-furanone as an impurity. In some embodiments, the rofecoxib as provided herein contains greater than or equal to about 0.001%, 0.005%, 0.01%, 0.02%, 0.05%, or 0.10%, but in all cases less than or equal to about 0.15%, of 4-[4-(methylthio)phenyl]-3-phenyl-2(5H)-furanone and/or 4-[4-(methylsulfinyl)phenyl]-3-phenyl-2(5H)-furanone as an impurity.

Purity of the resulting rofecoxib as described herein is determined as a percent area basis, typically as quantified by analytical chromatography, such as using HPLC, UHPLC, UPLC or other analytical means in the art. In some embodiments, the rofecoxib or pharmaceutically acceptable salt thereof as provided herein is micronized.

Rofecoxib Pharmacokinetics

It was surprisingly and unexpectedly discovered that the bioavailability of "VIOXX" was likely lower than 93%, contrary to the FDA-approved label, and that the formulations and methods described herein can achieve a comparable pharmacokinetic profile to the previously available "VIOXX" tablets after a single administration, despite containing 80% or less rofecoxib than the comparable "VIOXX" tablet.

In some embodiments, a 17.5 mg solid dosage formulation of rofecoxib reaches a median time to Cmax plasma concentration in 4 hours or less following single administration of the formulation to human subjects. In some embodiments, a 17.5 mg solid dosage formulation of rofecoxib reaches a median time to Cmax plasma concentration in 3 hours or less following administration. In some embodiments, a 17.5 mg solid dosage formulation of rofecoxib reaches a median time to Cmax plasma concentration in 2.5 hours or less following administration. In some embodiments, a 17.5 mg solid dosage formulation of rofecoxib reaches a median time to Cmax plasma concentration in 2 hours or less following administration. In some embodiments, a 17.5 mg solid dosage formulation of rofecoxib has a mean Cmax plasma concentration of more than 100 ng/ml. In some embodiments, a 17.5 mg solid dosage formulation of rofecoxib has a mean Cmax plasma concentration of more than 150 ng/ml, 167 ng/ml, or 190 ng/ml. In some embodiments, a 17.5 mg solid dosage formulation of rofecoxib has a mean Cmax plasma concentration of more than 200 ng/ml. In some embodiments, a 17.5 mg solid dosage formulation of rofecoxib has a mean Cmax plasma concentration of more than 220 ng/ml. In some embodiments, a 17.5 mg solid dosage formulation of rofecoxib has a mean Cmax plasma concentration of more than 250 ng/ml. In some embodiments, a 17.5 mg solid dosage formulation of rofecoxib has a mean Cmax plasma concentration of more than 280 ng/ml. In some embodiments, a 17.5 mg solid dosage formulation of rofecoxib has a mean $AUC_{0-\infty}$ of more than 1750 h*ng/ml. In some embodiments, a 17.5 mg solid dosage formulation of rofecoxib has a mean $AUC_{0-\infty}$ of more than 2000 h*ng/ml. In some embodiments, a 17.5 mg solid dosage formulation of rofecoxib has a mean $AUC_{0-\infty}$ of more than 2500 h*ng/ml. In some embodiments, a 17.5 mg solid dosage formulation of rofecoxib has a mean $AUC_{0-\infty}$ of more than 3000 h*ng/ml. In some embodiments, a 17.5 mg solid dosage formulation of rofecoxib has a mean $AUC_{0-\infty}$ of more than 3100 h*ng/ml. In some embodiments, a 17.5 mg solid dosage formulation of rofecoxib has a mean $AUC_{0-\infty}$ of more than 3500 h*ng/ml. In some embodiments, a 17.5 mg solid dosage formulation of rofecoxib has a mean $AUC_{0-\infty}$ of more than 4000 h*ng/ml. In some embodiments, a 17.5 mg solid dosage formulation of rofecoxib has a mean $AUC_{0-\infty}$ of more than 4500 h*ng/ml. In some embodiments, a 17.5 mg solid dosage form of rofecoxib achieves a mean Cmax plasma concentration within 80% to 125% of 224 ng/ml. In some embodiments, a 17.5 mg solid dosage form of rofecoxib achieves a mean $AUC_{0-\infty}$ within 80% to 125% of 3110 h*ng/ml. In some embodiments, a 17.5 mg solid dosage formulation of rofecoxib reaches a Cmax plasma concentration of least 167 ng/ml, 170 ng/ml, 175 ng/ml, 180 ng/ml, or higher following single administration of the formulation to a human subject. In some embodiments, a 17.5 mg solid dosage formulation of rofecoxib reaches an $AUC_{0-\infty}$ of at least 2600 h*ng/ml, 2750 h*ng/ml, 2900 h*ng/ml, 3050 h*ng/ml, 3100 h*ng/ml, 3200 h*ng/ml, 3350 h*ng/ml, 3500 h*ng/ml, 3650 h*ng/ml or higher following single administration of the formulation to a human subject.

In certain aspects, the subject matter disclosed herein provides a method of treating pain, fever, or inflammation in a subject by administering to the subject a solid dosage formulation comprising 17.5 mg of rofecoxib or a pharmaceutically acceptable salt thereof. In some embodiments, a 17.5 mg solid dosage formulation of rofecoxib reaches a mean Cmax plasma concentration in less than 4 hours following single administration of the formulation to human subjects. In some embodiments, a 17.5 mg solid dosage formulation of rofecoxib reaches a median time to Cmax plasma concentration in 3 hours or less following administration. In some embodiments, a 17.5 mg solid dosage formulation of rofecoxib reaches a mean Cmax plasma concentration in less than 2.5 hours following administration. In some embodiments, a 17.5 mg solid dosage formulation of rofecoxib reaches a mean Cmax plasma concentration in less than 2 hours following administration. In some embodiments, a 17.5 mg solid dosage formulation of rofecoxib has a mean Cmax plasma concentration of more than 150 ng/ml, 167 ng/ml, or 190 ng/ml. In some embodiments, a 17.5 mg solid dosage formulation of rofecoxib achieves a mean Cmax plasma concentration of more than 200 ng/ml. In some embodiments, a 17.5 mg solid dosage formulation of rofecoxib achieves a mean Cmax plasma concentration of more than 220 ng/ml. In some embodiments, a 17.5 mg solid dosage formulation of rofecoxib achieves a mean Cmax plasma concentration of more than 250 ng/ml. In some embodiments, a 17.5 mg solid dosage formulation of rofecoxib achieves a mean Cmax plasma concentration of more than 280 ng/ml. In some embodiments, a 17.5 mg solid dosage formulation of rofecoxib achieves a mean $AUC_{0-\infty}$ of more than 1750 h*ng/ml. In In some embodiments, a 17.5 mg solid dosage formulation of rofecoxib achieves a mean $AUC_{0-\infty}$ of more than 2000 h*ng/ml. In some embodiments, a 17.5 mg solid dosage formulation of rofecoxib achieves a mean $AUC_{0-\infty}$ of more than 2500 h*ng/ml. In some embodiments, a 17.5 mg solid dosage formulation of rofecoxib achieves a mean $AUC_{0-\infty}$ of more than 3000 h*ng/ml. In some embodiments, a 17.5 mg solid dosage formulation of rofecoxib achieves a mean $AUC_{0-\infty}$ of more than 3100 h*ng/ml. In some embodiments, a 17.5 mg solid dosage formulation of rofecoxib achieves a mean $AUC_{0-\infty}$ of more than 3500 h*ng/ml. In some embodiments, a 17.5 mg solid dosage formulation of rofecoxib achieves a mean Cmax plasma concentration of more than 200 ng/ml in less than 3.5 hours following administration with an $AUC_{0-\infty}$ of more than 3000 h*ng/ml. In some embodiments, a 17.5 mg solid dosage formulation of rofecoxib as described herein achieves a mean Cmax, Tmax, or $AUC_{0-\infty}$ that is bioequivalent to a 25 mg tablet of VIOXX. In some embodiments, a 17.5 mg solid dosage form of rofecoxib achieves a mean Cmax plasma concentration within 80% to 125% of 224 ng/ml. In some embodiments, a 17.5 mg solid dosage form of rofecoxib achieves a mean $AUC_{0-\infty}$ within 80% to 125% of 3110 h*ng/ml. In some embodiments, a 17.5 mg solid dosage formulation of rofecoxib reaches a Cmax plasma concentration of least 167 ng/ml, 170 ng/ml, 175 ng/ml, 180 ng/ml, or higher following single administration of the formulation to a human subject. In some embodiments, a 17.5 mg solid dosage formulation of rofecoxib reaches an $AUC_{0-\infty}$ of at least 2600 h*ng/ml, 2750 h*ng/ml, 2900 h*ng/ml, 3050 h*ng/ml, 3100 h*ng/ml, 3200 h*ng/ml, 3350 h*ng/ml, 3500 h*ng/ml, 3650 h*ng/ml or higher following single administration of the formulation to a human subject.

In some embodiments, a 20 mg solid dosage formulation of rofecoxib reaches a median time to Cmax plasma concentration in 4 hours or less following single administration of the formulation to human subjects. In some embodiments, a 20 mg solid dosage formulation of rofecoxib reaches a median time to Cmax plasma concentration in 3 hours or less following administration. In some embodiments, a 20 mg solid dosage formulation of rofecoxib reaches a median time to Cmax plasma concentration in 2.5 hours or less following administration. In some embodiments, a 20 mg solid dosage formulation of rofecoxib reaches a median time to Cmax plasma concentration in 2 hours or less following administration. In some embodiments, a 20 mg solid dosage formulation of rofecoxib has a mean Cmax plasma concentration of more than 150 ng/ml. In some embodiments, a 20 mg solid dosage formulation of rofecoxib has a mean Cmax plasma concentration of more than 191 ng/ml, 200 ng/ml, 215 ng/ml, or 225 ng/ml. In some embodiments, a 20 mg solid dosage formulation of rofecoxib has a mean Cmax plasma concentration of more than 250 ng/ml. In some embodiments, a 20 mg solid dosage formulation of rofecoxib has a mean Cmax plasma concentration of more than 258 ng/ml. In some embodiments, a 20 mg solid dosage formulation of rofecoxib has a mean Cmax plasma concentration of more than 300 ng/ml. In some embodiments, a 20 mg solid dosage formulation of rofecoxib has a mean $AUC_{0-\infty}$ of more than 2000 h*ng/ml. In some embodiments, a 20 mg solid dosage formulation of rofecoxib has a mean $AUC_{0-\infty}$ of more than 2500 h*ng/ml. In some embodiments, a 20 mg solid dosage formulation of rofecoxib has a mean $AUC_{0-\infty}$ of more than 3000 h*ng/ml. In some embodiments, a 20 mg solid dosage formulation of rofecoxib has a mean $AUC_{0-\infty}$ of more than 3400 h*ng/ml. In some embodiments, a 20 mg solid dosage formulation of rofecoxib has a mean $AUC_{0-\infty}$ of more than 3500 h*ng/ml. In some embodiments, a 20 mg solid dosage formulation of rofecoxib has a mean $AUC_{0-\infty}$ of more than 4000 h*ng/ml. In some embodiments, a 20 mg solid dosage form of rofecoxib achieves a mean Cmax plasma concentration within 80% to 125% of 259 ng/ml. In some embodiments, a 20 mg solid dosage form of rofecoxib achieves a mean $AUC_{0-\infty}$ within 80% to 125% of 3550 h*ng/ml. In some embodiments, a 20 mg solid dosage formulation of rofecoxib reaches a Cmax plasma concentration of least 190 ng/ml, 205 ng/ml, 220 ng/ml, 235 ng/ml, 250 ng/ml, or higher following single administration of the formulation to a human subject. In some embodiments, a 20 mg solid dosage formulation of rofecoxib reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject.

In certain aspects, the subject matter disclosed herein provides a method of treating pain, fever, or inflammation in a subject by administering to the subject a solid dosage formulation comprising 20 mg of rofecoxib or a pharmaceutically acceptable salt thereof. In some embodiments, a 20 mg solid dosage formulation of rofecoxib reaches a mean Cmax plasma concentration in less than 4 hours following single administration of the formulation to human subjects. In some embodiments, a 20 mg solid dosage formulation of rofecoxib reaches a median time to Cmax plasma concentration 3 hours or less following administration. In some embodiments, a 20 mg solid dosage formulation of rofecoxib reaches a mean Cmax plasma concentration in less than 2.5 hours following administration. In some embodiments, a 20 mg solid dosage formulation of rofecoxib reaches a mean Cmax plasma concentration in less than 2 hours following administration. In some embodiments, a 20 mg solid dosage formulation of rofecoxib has a mean Cmax plasma concentration of more than 150 ng/ml. In some embodiments, a 20 mg solid dosage formulation of rofecoxib achieves a mean Cmax plasma concentration of more than 191 ng/ml, 200 ng/ml, 215 ng/ml, or 225 ng/ml. In some embodiments, a 20 mg solid dosage formulation of rofecoxib achieves a mean Cmax plasma concentration of more than 250 ng/ml. In some embodiments, a 20 mg solid dosage formulation of rofecoxib achieves a mean Cmax plasma concentration of more than 258 ng/ml. In some embodiments, a 20 mg solid dosage formulation of rofecoxib achieves a mean Cmax plasma concentration of more than 300 ng/ml. In some embodiments, a 20 mg solid dosage formulation of rofecoxib achieves a mean $AUC_{0-\infty}$ of more than 2000 h*ng/ml. In some embodiments, a 20 mg solid dosage formulation of rofecoxib achieves a mean $AUC_{0-\infty}$ of more than 2500 h*ng/ml. In some embodiments, a 20 mg solid dosage formulation of rofecoxib achieves a mean $AUC_{0-\infty}$ of more than 3000 h*ng/ml. In some embodiments, a 20 mg solid dosage formulation of rofecoxib achieves a mean $AUC_{0-\infty}$ of more than 3400 h*ng/ml. In some embodiments, a 20 mg solid dosage formulation of rofecoxib achieves a mean $AUC_{0-\infty}$ of more than 3500 h*ng/ml. In some embodiments, a 20 mg solid dosage formulation of rofecoxib achieves a mean Cmax plasma concentration of more than 191 ng/ml, 200 ng/ml, 215 ng/ml, or 225 ng/ml in less than 3.5 hours following administration with an $AUC_{0-\infty}$ of more than 3000 h*ng/ml. In some embodiments, a 20 mg solid dosage formulation of rofecoxib as described herein achieves a mean Cmax, Tmax, or $AUC_{0-\infty}$ that is bioequivalent to a 25 mg tablet of VIOXX. In some embodiments, a 20 mg solid dosage form of rofecoxib achieves a mean Cmax plasma concentration within 80% to 125% of 259 ng/ml. In some embodiments, a 20 mg solid dosage form of rofecoxib achieves a mean $AUC_{0-\infty}$ within 80% to 125% of 3550 h*ng/ml. In some embodiments, a 20 mg solid dosage formulation of rofecoxib reaches a Cmax plasma concentration of least 190 ng/ml, 205 ng/ml, 220 ng/ml, 235 ng/ml, 250 ng/ml, or higher following single administration of the formulation to a human subject. In some embodiments, a 20 mg solid dosage formulation of rofecoxib reaches an $AUC_{0-\infty}$ of at least 3000 h*ng/ml, 3200 h*ng/ml, 3350 h*ng/ml, 3500 h*ng/ml, 3650 h*ng/ml, 3800 h*ng/ml, 3950 h*ng/ml, or higher following single administration of the formulation to a human subject.

In some embodiments, a 25 mg solid dosage formulation of rofecoxib reaches a mean Cmax plasma concentration in less than 3 hours following single administration of the formulation to human subjects. In some embodiments, a 25 mg solid dosage formulation of rofecoxib reaches a mean Cmax plasma concentration in less than 2.5 hours following administration. In some embodiments, a 25 mg solid dosage formulation of rofecoxib reaches a mean Cmax plasma concentration in less than 2 hours following administration. In some embodiments, a 25 mg solid dosage formulation of rofecoxib has a mean Cmax plasma concentration of more than 240 ng/ml. In some embodiments, a 25 mg solid dosage formulation of rofecoxib has a mean Cmax plasma concentration of more than 250 ng/ml. In some embodiments, a 25 mg solid dosage formulation of rofecoxib has a mean Cmax plasma concentration of more than 300 ng/ml. In some embodiments, a 25 mg solid dosage formulation of rofecoxib has a mean Cmax plasma concentration of more than 320 ng/ml. In some embodiments, a 25 mg solid dosage formulation of rofecoxib has a mean $AUC_{0-\infty}$ of more than 4250 h*ng/ml. In some embodiments, a 25 mg solid dosage formulation of rofecoxib has a mean $AUC_{0-\infty}$ of more than 4500 h*ng/ml. In some embodiments, a 25 mg solid dosage formulation of rofecoxib has a mean $AUC_{0-\infty}$ of more than 4550 h*ng/ml. In some embodiments, a 25 mg solid dosage formulation of rofecoxib has a mean $AUC_{0-\infty}$ of more than 4700 h*ng/ml. In some embodiments, a 25 mg solid dosage formulation of rofecoxib reaches a mean Cmax plasma concentration of more than 240 ng/ml in a median time of about 3 hours or less following administration with an $AUC_{0-\infty}$ of more than 4250 h*ng/ml. In some embodiments, a 25 mg solid dosage form of rofecoxib achieves a mean Cmax plasma concentration within 80% to 125% of 325 ng/ml. In some embodiments, a 25 mg solid dosage form of rofecoxib achieves a mean $AUC_{0-\infty}$ within 80% to 125% of 4590 h*ng/ml.

In certain aspects, the subject matter disclosed herein provides a method of treating pain, fever, or inflammation in a subject by administering to the subject a 25 mg solid dosage formulation of rofecoxib or a pharmaceutically acceptable salt thereof. In some embodiments, a 25 mg solid dosage formulation of rofecoxib reaches a mean Cmax plasma concentration in less than 3 hours following administration. In some embodiments, a 25 mg solid dosage formulation of rofecoxib reaches a mean Cmax plasma concentration in less than 2.5 hours following administration. In some embodiments, a 25 mg solid dosage formulation of rofecoxib reaches a mean Cmax plasma concentration in less than 2 hours following administration. In some embodiments, a 25 mg solid dosage formulation of rofecoxib has a mean Cmax plasma concentration of more than 240 ng/ml. In some embodiments, a 25 mg solid dosage formulation of rofecoxib achieves a mean Cmax plasma concentration of more than 250 ng/ml. In some embodiments, a 25 mg solid dosage formulation of rofecoxib has a mean Cmax plasma concentration of more than 300 ng/ml. In some embodiments, a 25 mg solid dosage formulation of rofecoxib achieves a mean Cmax plasma concentration of more than 320 ng/ml. In some embodiments, a 25 mg solid dosage formulation of rofecoxib achieves a mean $AUC_{0-\infty}$ of more than 4250 h*ng/ml. In some embodiments, a 25 mg solid dosage formulation of rofecoxib achieves a mean $AUC_{0-\infty}$ of more than 4500 h*ng/ml. In some embodiments, a 25 mg solid dosage formulation of rofecoxib achieves a mean $AUC_{0-\infty}$ of more than 4550 h*ng/ml. In some embodiments, a 25 mg solid dosage formulation of rofecoxib achieves a mean $AUC_{0-\infty}$ of more than 4700 h*ng/ml. In some embodiments, a 25 mg solid dosage formulation of rofecoxib achieves a Cmax plasma concentration of more than 240 ng/ml in about 3 hours following administration with an $AUC_{0-\infty}$ of more than 4250 h*ng/ml. In some embodiments, a 25 mg solid dosage formulation of rofecoxib as described herein achieves a mean Cmax, Tmax, or $AUC_{0-\infty}$ that is higher than a 25 mg tablet of VIOXX. In some embodiments, a 25 mg solid dosage form of rofecoxib achieves a mean Cmax plasma concentration within 80% to 125% of 325 ng/ml. In some embodiments, a 25 mg solid dosage form of rofecoxib achieves a mean $AUC_{0-\infty}$ within 80% to 125% of 4590 h*ng/ml.

In certain aspects, the subject matter disclosed herein provides a method of treating pain, fever, or inflammation in a subject by administering to the subject a solid dosage formulation comprising 10 mg to 50 mg of rofecoxib or a pharmaceutically acceptable salt thereof. In some embodiments, the formulation achieves a mean Cmax plasma concentration from 9.8 ng/ml to 16 ng/ml for each 1 mg of rofecoxib in the formulation. In some embodiments, the formulation achieves a mean Cmax plasma concentration from 10 ng/ml to 14 ng/ml for each 1 mg of rofecoxib in the formulation. In some embodiments, the formulation achieves a mean Cmax plasma concentration from 10 ng/ml to 13 ng/ml for each 1 mg of rofecoxib in the formulation. In some embodiments, the formulation achieves a mean Cmax plasma concentration from 80% to 125% of 12.8 ng/ml. In some embodiments, the formulation reaches a mean $AUC_{0-\infty}$ of 170 h*ng/ml to 235 h*ng/ml for each 1 mg of rofecoxib in the formulation. In some embodiments, the formulation reaches a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the formulation reaches a mean $AUC_{0-\infty}$ of 190 h*ng/ml to 215 h*ng/ml for each 1 mg of rofecoxib in the formulation.

In some embodiments, a method is provided for treating pain, fever, or inflammation in patients within a patient population, the method comprising providing a solid dosage formulation comprising 10 mg to 50 mg of rofecoxib, more specifically 17.5 mg to 25 mg, to the patient population, wherein the formulation achieves a mean Cmax plasma concentration from 9.8 ng/ml to 16 ng/ml for each 1 mg of rofecoxib in the formulation following single administration of the formulation to the patients within the patient population. In some embodiments, the solid dosage formulation of rofecoxib achieves a mean Cmax plasma concentration from 10 ng/ml to 14 ng/ml for each 1 mg of rofecoxib in the formulation. In some embodiments, the solid dosage formulation of rofecoxib achieves a mean Cmax plasma concentration from 10 ng/ml to 13 ng/ml for each 1 mg of rofecoxib in the formulation. In some embodiments, the solid dosage formulation of rofecoxib achieves a mean Cmax plasma concentration from 80% to 125% of 12.8 ng/ml. In some embodiments, the solid dosage formulation of rofecoxib reaches a mean $AUC_{0-\infty}$ of 170 h*ng/ml to 235 h*ng/ml for each 1 mg of rofecoxib in the formulation. In some embodiments, the solid dosage formulation of rofecoxib reaches a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 177 h*ng/ml to 225 h*ng/ml for each 1 mg of rofecoxib in the formulation. In some embodiments, the formulation achieves a mean $AUC_{0-\infty}$ of 180 h*ng/ml to 225 h*ng/ml for each 1 mg of rofecoxib in the formulation. In some embodiments, the solid dosage formulation of rofecoxib reaches a mean $AUC_{0-\infty}$ of 190 h*ng/ml to 215 h*ng/ml for each 1 mg of rofecoxib in the formulation.

In certain aspects, the subject matter disclosed herein provides a method of treating pain, fever, or inflammation in a male or female subject by administering to the subject a solid dosage formulation comprising 10 mg to 50 mg of rofecoxib or a pharmaceutically acceptable salt thereof. In some embodiments, a single administration of a solid dosage formulation comprising 12.5 mg to 25 mg of rofecoxib or a pharmaceutically acceptable salt thereof to healthy female subjects results in a mean Cmax plasma concentration that is at least 5%, 10%, 15%, 20%, 25%, or 30% greater than that resulting from a single administration of the same formulation to male subjects. In some embodiments, a single administration of a solid dosage formulation comprising 12.5 mg to 25 mg of rofecoxib or a pharmaceutically acceptable salt thereof to healthy female subjects results in a mean $AUC_{0-\infty}$ that is at least 5%, 10%, 15%, 20%, 25%, or 30% greater than that resulting from a single administration of the same formulation to male subjects.

In some embodiments, the subject matter disclosed herein provides a method for treating pain, fever, or inflammation in a subject by administering a solid dosage formulation of 10 mg to 50 mg of rofecoxib, wherein a single administration of the formulation in Caucasian subjects less than 65 years of age achieves a mean $AUC_{0-\infty}$ that is greater than that achieved following a single administration of the formulation to African American subjects less than 65 years of age. In some embodiments, a single administration of a solid dosage formulation comprising 12.5 mg to 25 mg of rofecoxib or a pharmaceutically acceptable salt thereof to Caucasian subjects results in a mean $AUC_{0-\infty}$ that is at least 1%, 2%, 5%, 9%, or 10% greater than that achieved following a single administration of the formulation to African American subjects less than 65 years of age. In some embodiments, the formulation comprises 17.5 mg to 25 mg of rofecoxib. In some embodiments, the formulation comprises 17.5 mg of rofecoxib. In some embodiments, the formulation comprises 20 mg of rofecoxib. In some embodiments, the formulation comprises 25 mg of rofecoxib.

In some embodiments, the subject matter disclosed herein provides a method for treating pain, fever, or inflammation in a subject by administering a solid dosage formulation comprising 12.5 mg of rofecoxib, wherein the formulation achieves a mean plasma concentration of at least about 0.2 ng/ml, 0.3 ng/ml, 0.4 ng/ml, or 0.5 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 12.5 mg of rofecoxib, wherein the formulation achieves an arithmetic mean plasma concentration of at least about 0.8 ng/ml, 0.9 ng/ml, or 1.0 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 17.5 mg of rofecoxib, wherein the formulation achieves a mean plasma concentration of at least about 0.3 ng/ml, 0.4 ng/ml, 0.5 ng/ml, or 0.6 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 17.5 mg of rofecoxib, wherein the formulation achieves an arithmetic mean plasma concentration of at least about 1.8 ng/ml, 2.0 ng/ml, 2.2 ng/ml, or 2.4 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 20 mg of rofecoxib, wherein the formulation achieves a mean plasma concentration of at least about 0.8 ng/ml, 0.9 ng/ml, 1.0 ng/ml, 1.1 ng/ml, or 1.16 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 20 mg of rofecoxib, wherein the formulation achieves an arithmetic mean plasma concentration of at least about 4.6 ng/ml, 5.0 ng/ml, 5.4 ng/ml, or 5.7 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 25 mg of rofecoxib, wherein the formulation achieves a mean plasma concentration of at least about 1.0 ng/ml, 1.1 ng/ml, 1.2 ng/ml, or 1.3 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 25 mg of rofecoxib, wherein the formulation achieves an arithmetic mean plasma concentration of at least about 4.6 ng/ml, 5.0 ng/ml, 5.4 ng/ml, or 5.6 ng/ml at 15 minutes following single administration of the formulation to human subjects less than 65 years of age. In some embodiments, the subject matter disclosed herein provides a method for treating pain, fever, or inflammation in a subject by administering a solid dosage formulation comprising 12.5 mg of rofecoxib, wherein the formulation achieves a mean plasma concentration of at least about 27 ng/ml, 29 ng/ml, 31 ng/ml, or 33 ng/ml at 45 minutes following single administration of the formulation to human subjects less than 65 years of age. In some embodiments, the subject matter disclosed herein provides a method for treating pain, fever, or inflammation in a subject by administering a solid dosage formulation comprising 12.5 mg of rofecoxib, wherein the formulation achieves an arithmetic mean plasma concentration of at least about 45 ng/ml, 48 ng/ml, 51 ng/ml, 54 ng/ml, or 56 ng/ml at 45 minutes following single administration of the formulation to human subjects less than 65 years of age. In some embodiments, the subject matter disclosed herein provides a method for treating pain, fever, or inflammation in a subject by administering a solid dosage formulation comprising 17.5 mg of rofecoxib, wherein the formulation achieves a mean plasma concentration of at least about 45 ng/ml, 47 ng/ml, 49 ng/ml, or 51 ng/ml at 45 minutes following single administration of the formulation to human subjects less than 65 years of age. In some embodiments, the subject matter disclosed herein provides a method for treating pain, fever, or inflammation in a subject by administering a solid dosage formulation comprising 17.5 mg of rofecoxib, wherein the formulation achieves an arithmetic mean plasma concentration of at least about 74 ng/ml, 79 ng/ml, 84 ng/ml, 89 ng/ml, or 93 ng/ml at 45 minutes following single administration of the formulation to human subjects less than 65 years of age. In some embodiments, the subject matter disclosed herein provides a method for treating pain, fever, or inflammation in a subject by administering a solid dosage formulation comprising 20 mg of rofecoxib, wherein the formulation achieves a mean plasma concentration of at least about 58 ng/ml, 62 ng/ml, 66 ng/ml, 70 ng/ml, or 72 ng/ml at 45 minutes following single administration of the formulation to human subjects less than 65 years of age. In some embodiments, the subject matter disclosed herein provides a method for treating pain, fever, or inflammation in a subject by administering a solid dosage formulation comprising 20 mg of rofecoxib, wherein the formulation achieves an arithmetic mean plasma concentration of at least about 112 ng/ml, 116 ng/ml, or 121 ng/ml at 45 minutes following single administration of the formulation to human subjects less than 65 years of age. In some embodiments, the subject matter disclosed herein provides a method for treating pain, fever, or inflammation in a subject by administering a solid dosage formulation comprising 25 mg of rofecoxib, wherein the formulation achieves a mean plasma concentration of at least about 78 ng/ml, 85 ng/ml, 92 ng/ml, or 97 ng/ml, at 45 minutes following single administration of the formulation to human subjects less than 65 years of age. In some embodiments, the subject matter disclosed herein provides a method for treating pain, fever, or inflammation in a subject by administering a solid dosage formulation comprising 25 mg of rofecoxib, wherein the formulation achieves an arithmetic mean plasma concentration of at least about 133 ng/ml, 139 ng/ml, 145 ng/ml, 151 ng/ml, or 159 ng/ml at 45 minutes following single administration of the formulation to human subjects less than 65 years of age.

Specific Compositions

In some embodiments, the subject matter discloses a drug product including an immediate-release tablet that contains either 12.5-, 17.5-, 20-, or 25-mg rofecoxib. In some embodiments, the tablets are 7.2-mm in diameter tablets. In some embodiments, the tablets are off-white to light yellow, round, and uncoated with no markings. In some embodiments, rofecoxib tablets disclosed herein are for oral administration. In some embodiments, the drug product does not comprise a liquisolid, orally disintegrating tablet, rapid dissolving tablets, or chewable.

In some embodiments, each rofecoxib tablet for oral administration contains either 12.5-, 17.5-, 20-, or 25-mg of rofecoxib. In some embodiments, each rofecoxib tablet also contains one or more of the following inactive ingredients: croscarmellose sodium, hydroxypropyl cellulose, lactose, magnesium stearate, microcrystalline cellulose, and pigment blend yellow. The quantitative composition of one embodiment of the 25-mg tablet and the function and compendial status of each component are listed in FIG. 1.

In some embodiments, the pigment blend is comprised of three compendial materials as listed in Table 4 below.

TABLE 4

Components of the Pigment Blend

| Components | Reference to Standards[a] |
|---|---|
| Titanium dioxide | USP-NF, Ph. Eur. |
| Iron oxide yellow | USP-NF |
| Iron oxide red | USP-NF |

USP = United States Pharmacopeia;
NF = National Formulary;
Ph. Eur. = European Pharmacopeia
[a]When referred to a Pharmacopeia, the current edition of this Pharmacopeia is applied.

Exemplary excipients used in the manufacture of rofecoxib are listed in Table 5 below. Water is used only as a granulation medium.

TABLE 5

Excipients for Rofecoxib Tablets

| Excipient | Compendial Reference |
|---|---|
| Croscarmellose sodium | USP-NF, Ph. Eur., JP |
| Hydroxypropylcellulose | USP-NF, Ph. Eur., JP |
| Lactose monohydrate | USP-NF, Ph. Eur., JP |
| Magnesium stearate | USP-NF, Ph. Eur., JP |
| Microcrystalline cellulose | USP-NF, Ph. Eur., JP |
| Pigment blend yellow | |
| Water | USP-NF, Ph. Eur. |

USP = United States Pharmacopeia;
NF = National Formulary;
Ph. Eur. = European Pharmacopeia;
JP = Japanese Pharmacopeia.

Tables 6A and 6B compare exemplary embodiments of the composition of each tablet dose strength. In some embodiments, the tablet weight is 200 mg for each dose strength. In some embodiments, tablet dose strengths are manufactured by varying the quantities of the first three components, while maintaining the 1:1 ratio of microcrystalline cellulose to lactose monohydrate.

TABLE 6A

Composition of Rofecoxib Tablets

| Components | 25-mg Tablet | | 20-mg Tablet | | 17.5-mg Tablet | | 12.5-mg Tablet | |
|---|---|---|---|---|---|---|---|---|
| | % (w/w) per tablet | mg per tablet | % (w/w) per tablet | mg per tablet | % (w/w) per tablet | mg per tablet | % (w/w) per tablet | mg per tablet |
| Intragranular | | | | | | | | |
| Rofecoxib[a] | 12.50 | 25.0 | 10.00 | 20.0 | 8.75 | 17.5 | 6.25 | 12.5 |
| Lactose monohydrate | 39.85 | 79.7 | 41.10 | 82.2 | 41.725 | 83.45 | 42.975 | 85.95 |
| Microcrystalline cellulose | 39.85 | 79.7 | 41.10 | 82.2 | 41.725 | 83.45 | 42.975 | 85.95 |
| Hydroxypropylcellulose | 3.00 | 6.0 | 3.00 | 6.00 | 3.00 | 6.0 | 3.00 | 6.0 |
| Croscarmellose sodium | 2.00 | 4.0 | 2.00 | 4.0 | 2.00 | 4.0 | 2.00 | 4.0 |
| Water | NA[b] | NA[b] | NA[b] | NA[b] | NA[b] | NA[b] | NA[b] | NA[b] |
| Extragranular | | | | | | | | |
| Pigment blend yellow | 0.30 | 0.6 | 0.30 | 0.6 | 0.30 | 0.6 | 0.30 | 0.6 |
| Croscarmellose sodium | 2.00 | 4.0 | 2.00 | 4.0 | 2.00 | 4.0 | 2.00 | 4.0 |
| Magnesium stearate | 0.50 | 1.0 | 0.50 | 1.0 | 0.50 | 1.0 | 0.50 | 1.0 |
| Totals | 100.00 | 200.0 | 100.00 | 200.0 | 100.00 | 200.0 | 100.00 | 200.0 |

[a]Note that the amount of rofecoxib may be adjusted for purity and moisture content. An adjustment will be made to the amounts of lactose monohydrate and microcrystalline cellulose used to maintain tablet weight.
[b]Water for granulation is removed upon drying of the wet mass.

TABLE 6B

Composition of Rofecoxib Tablets Manufactured by Process B$_2$

| Components | 25-mg Tablet | | 20-mg Tablet | | 17.5-mg Tablet | | 12.5-mg Tablet | |
|---|---|---|---|---|---|---|---|---|
| | % (w/w) per tablet | mg per tablet | % (w/w) per tablet | mg per tablet | % (w/w) per tablet | mg per tablet | % (w/w) per tablet | mg per tablet |
| Intragranular | | | | | | | | |
| Rofecoxib[a] | 12.50 | 25.0 | 10.00 | 20.0 | 8.75 | 17.5 | 6.25 | 12.5 |
| Lactose monohydrate | 39.85 | 79.7 | 41.10 | 82.2 | 41.725 | 83.45 | 42.975 | 85.95 |
| Microcrystalline cellulose | 39.85 | 79.7 | 41.10 | 82.2 | 41.725 | 83.45 | 42.975 | 85.95 |
| Hydroxypropylcellulose | 3.00 | 6.0 | 3.00 | 6.00 | 3.00 | 6.0 | 3.00 | 6.0 |
| Croscarmellose sodium | 2.00 | 4.0 | 2.00 | 4.0 | 2.00 | 4.0 | 2.00 | 4.0 |
| Water | NA[b] | NA[b] | NA[b] | NA[b] | NA[b] | NA[b] | NA[b] | NA[b] |
| Extragranular | | | | | | | | |
| Pigment blend yellow | 0.30 | 0.6 | 0.30 | 0.6 | 0.30 | 0.6 | 0.30 | 0.6 |
| Croscarmellose sodium | 2.00 | 4.0 | 2.00 | 4.0 | 2.00 | 4.0 | 2.00 | 4.0 |
| Magnesium stearate | 0.50 | 1.0 | 0.50 | 1.0 | 0.50 | 1.0 | 0.50 | 1.0 |
| Totals | 100.00 | 200.0 | 100.00 | 200.0 | 100.00 | 200.0 | 100.00 | 200.0 |

[a]Note that the amount of rofecoxib may be adjusted for purity and moisture content. An adjustment will be made to the amounts of lactose monohydrate and microcrystalline cellulose used to maintain tablet weight.
[b]Water for granulation is removed upon drying of the wet mass.

In some embodiments, rofecoxib is a single crystal form (Form A), the only structure reported in the Cambridge Structural Database (Groom C R, Bruno M P, Lightfoot S C, et al. The Cambridge Structural Database. Acta Cryst. 2016; B72:171-179. (Entry CAXMUJ: https://www.ccdc.cam.ac.uk/structures/Search?Compound=Rofecoxib&DatabaseToSearch=Published). Rofecoxib is practically insoluble in water (solubility<0.1 mg/mL). Rofecoxib has no ionizable moieties and cannot form salts; the solubility of rofecoxib cannot be increased by changing pH. Therefore, in some embodiments, rofecoxib is micronized in the final step of the manufacturing process in order to increase dissolution rate.

Description of Manufacturing Process and Process Controls for Rofecoxib Tablets

The specific process used to manufacture rofecoxib granules and subsequent rofecoxib tablets is Process B1, which is described below and illustrated in FIG. 1. The process nomenclature consists of a letter with a subscripted number. The letter is indexed when a major change is made to the process during development; the subscripted number is indexed when a minor change is made.

Exemplary Preparation of Rofecoxib Granules.

Step 1G: Blend lactose monohydrate and rofecoxib.

Step 2G: Pass the lactose-rofecoxib blend, microcrystalline cellulose, hydroxypropylcellulose, and croscarmellose sodium through an appropriate-sized sieve screen as the granulator is charged.

Step 3G: Mix the dry powder in the high-shear granulator.

Step 4G: Spray the water of granulation onto the contents of the high-shear granulator while mixing. The target amount of water of granulation is 32% relative to the mass of the dry powder in the granulator. The actual amount of water added may vary.

Step 5G: Discharge the wet granules from the granulator into a high-speed mill equipped with an appropriate-sized screen. Mill the wet granules.

Step 6G: Dry the wet-milled granules into a fluid-bed drier.

Step 7G: Mill the dried granules using a high-speed mill equipped with an appropriate-sized screen.

Exemplary Preparation of Rofecoxib Tablets:

Step 1T: Blend croscarmellose sodium and pigment.

Step 2T: Pass the rofecoxib granules, croscarmellose sodium-pigment blend, and magnesium stearate through an appropriate-sized sieve screen as the blender is charged. Note more than one granulation batch may be used in this step.

Step 3T: Blend the powders.

Step 4T: Compress the blended powder into tablets.

Step 5T: Dedust and metal check the tablets. FIGS. 13A-B show flow diagrams for rofecoxib tablet manufacturing Process B$_1$.

In some embodiments, e.g. the formation of those tablets described in Table 6B, the pigment may be added in preparation of the rofecoxib granules prior to formation of the tablets.

Disintegrants and Dissolution Rate

Disintegrants included in tablet or granulate formulations are auxiliary agents which can promote the disintegration of said tablets or granulates upon contact with liquids and bodily fluids. Disintegrants are essential excipients in solid formulations because they can lead to enhanced dissolution of tablets into coarse fragments and further into smaller particles. Disintegrants ultimately result in the active ingredients of solid drug formulations interacting sufficiently with liquids or bodily fluids and forming a solution. In general, higher tablet densities are associated with poorer solubility profiles. Therefore, the addition of disintegrants into tablets promotes their desired rapid dissolution, or disintegration and dissolution. In some embodiments, the formulation described herein further includes a granular component and an extragranular component, wherein the granular component includes an intragranular component including the rofecoxib and one or more disintegrants, and wherein the extragranular component includes one or more disintegrants. In some embodiments, the rofecoxib in the formulation has a d90 particle size from about 10-12 µm, a d50 particle size from about 3-4 µm, and a d10 particle size from about 0.5-1.0 µm.

In some embodiments of the pharmaceutically acceptable formulation described herein, the one or more disintegrants in the granular component of the formulation may include starches, clays, celluloses, algins, gums, cross-linked polymers, croscarmellose, croscarmellose sodium, crospovidone, sodium starch glycolate, and combinations thereof. In some embodiments, the one or more disintegrants in the granular component are about 0.5% (w/w) about 1% (w/w), about 2% (w/w), about 3% (w/w), about 4% (w/w), about 5% (w/w), about 6% (w/w), about 7% (w/w), about 8% (w/w), about 9% (w/w), or about 10% (w/w) of the formulation.

In some embodiments of the pharmaceutically acceptable formulation described herein, the one or more disintegrants in the extragranular component may include starches, clays, celluloses, algins, gums, cross-linked polymers, croscarmellose, croscarmellose sodium, crospovidone, sodium starch glycolate, and combinations thereof. In some embodiments, the one or more disintegrants in the extragranular component are about 0.5% (w/w), about 1% (w/w), about 2% (w/w), about 3% (w/w), about 4% (w/w), about 5% (w/w), about 6% (w/w), about 7% (w/w), about 8% (w/w), about 9% (w/w), about 10% (w/w) of the formulation.

In some embodiments, the disintegrant in the granular component and the disintegrant in the extragranular component are together about 1% (w/w), about 2% (w/w), about 3% (w/w), about 4% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w) of the formulation.

The dissolution rate of a solid formulation such as an oral tablet refers to the proportion of drug which enters a solution in a given amount of time. In some embodiments of the pharmaceutically acceptable formulations described herein, the oral tablet provides a dissolution rate of at least about 70%, at least about 75%, at least about 80%, at least about 85%, at least about 90%, at least about 95%, at least about 100% of the rofecoxib or pharmaceutically acceptable salt thereof by about 15 minutes.

In some embodiments, the dissolution rate is measured in about 1% SDS at a paddle speed of about 40 rpm, about 45 rpm, about 50 rpm, about 55 rpm, about 60 rpm, about 65 rpm, about 70 rpm, about 75 rpm, about 80 rpm, about 85 rpm, about 90 rpm, about 95 rpm and at a temperature of about 37.0° C.±0.5° C. In some embodiments, the dissolution rate is measured in about 1.5% SDS at a paddle speed of about 40 rpm, about 45 rpm, about 50 rpm, about 55 rpm, about 60 rpm, about 65 rpm, about 70 rpm, about 75 rpm, about 80 rpm, about 85 rpm, about 90 rpm, about 95 rpm and at a temperature of about 37.0° C.±0.5° C. In some embodiments, the dissolution rate is measured in about 2% SDS at a paddle speed of about 40 rpm, about 45 rpm, about 50 rpm, about 55 rpm, about 60 rpm, about 65 rpm, about 70 rpm, about 75 rpm, about 80 rpm, about 85 rpm, about 90 rpm, about 95 rpm and at a temperature of about 37.0° C.±0.5° C.

In some embodiments, the ratio of granular disintegrant to extragranular disintegrant is about 40% (w/w) to about 60% (w/w). In some embodiments, the ratio of granular disintegrant to extragranular disintegrant is about 45% (w/w) to about 55% (w/w). In some embodiments, the ratio of granular disintegrant to extragranular disintegrant is about 50% (w/w) to about 50% (w/w). In some embodiments, the ratio of granular disintegrant to extragranular disintegrant is about 55% (w/w) to about 45% (w/w). In some embodiments, the ratio of granular disintegrant to extragranular disintegrant is about 60% (w/w) to about 40% (w/w).

Granulation Process and Granules for Oral Formulations

Granulation is the process of forming of granules from powders or solid substances, producing a material which has the consistency or granules. This process is highly used in the pharmaceutical industry to produce tablets for oral administration of drugs. The process of granulation generally refers to the agglomeration of very fine particles into larger granules. The size of the produced granules depends on their intended subsequent use and can vary largely from 20 µm to 4 mm.

In the course of a granulation process, particles from one or more powder substances can be combined to form a granule. Bonds can be formed between these particles in the process of granulation by compression or by using a binding agent. Subsequently, this allows for tablets or pellets to be formed within specific pre-determined limits.

In some embodiments of the pharmaceutically acceptable formulation described herein, the rofecoxib or pharmaceutically acceptable salt thereof is formulated into granules and at least about 20%, at least about 25%, at least about 35%, or at least about 40% of the granules are less than about 75 µm. In some embodiments, the rofecoxib or pharmaceutically acceptable salt thereof is formulated into granules and at least about 40%, at least about 45%, at least about 50%, at least about 55%, or at least about 60% of the granules are less than about 150 µm. In some embodiments, the rofecoxib or pharmaceutically acceptable salt thereof is formulated into granules and at least about 60%, at least about 65%, at least about 70%, at least about 75%, or at least about 80% of the granules are less than about 250 µm. In some embodiments, the rofecoxib or pharmaceutically acceptable salt thereof is formulated into granules and at least about 70%, at least about 75%, at least about 80%, at least about 85%, or at least about 90% of the granules are less than about 425 µm. In some embodiments, the rofecoxib or pharmaceutically acceptable salt thereof is formulated into granules and at least about 80%, at least about 85%, at least about 90%, at least about 95%, or at least about 100% of the granules are less than about 1000 µm. Prior to being formulated into granules, the rofecoxib or pharmaceutically acceptable salt thereof may be micronized. In some embodiments, the particle size distribution of the rofecoxib or a pharmaceutically acceptable salt thereof used in the formulation is as follows: a) the d90 particle size is less than about 12 µm, 11 µm, 10 µm, 9 µm, 8 µm, 7 µm, 6 µm, 5 µm, or 4 µm; b) the d50 particle size is less than about 4 µm, 3 µm, 2 µm, or 1 µm; and c) the d10 particle size is less than about 1 µm, 0.9 µm, 0.8 µm, 0.7 µm, 0.6 µm, or 0.5 µm. In some embodiments, the particle size distribution of the rofecoxib or a pharmaceutically acceptable salt thereof used in the formulation is as follows: a) the d90 particle size is about 10-12 µm; b) the d50 particle size is about 3-4 µm; and c) the d10 particle size is about 0.5-1.0 µm.

Additional Components

The pharmaceutically acceptable formulations presented herein can further comprise one or more additional components selected from a wide variety of excipients known in the pharmaceutical formulation art. According to the desired properties of the tablet or capsule, any number of ingredients can be selected, alone or in combination, based upon their known uses in preparing the compositions of the present invention.

Diluents

Diluents function as fillers in solid formulations such as tablets. Fillers increase weight and improve content uniformity of the solid formulations. In some embodiments of the pharmaceutically acceptable formulations described herein, at least a portion of one or more diluents is in the granular component. The one or more diluents include dicalcium phosphate, calcium sulfate, lactose, cellulose, kaolin, mannitol, dry starch, powdered sugar, sorbitol, sucrose, inositol, monohydrate, microcrystalline cellulose, and combinations thereof.

In some embodiments, the lactose monohydrate diluent is about 25% (w/w), 30% (w/w), about 32% (w/w), about 34% (w/w), about 35% (w/w), about 37% (w/w), about 39% (w/w), about 40% (w/w), about 42% (w/w), about 44% (w/w) about 45% (w/w), about 47% (w/w), about 49% (w/w), or about 50% (w/w) of the formulation. In some embodiments, the microcrystalline cellulose diluent is about 30% (w/w), about 32% (w/w), about 34% (w/w), about 35% (w/w), about 37% (w/w), about 39% (w/w), about 40% (w/w), about 42% (w/w), about 44% (w/w), about 45% (w/w), about 47% (w/w), about 49% (w/w), or about 50% (w/w) of the formulation. In some embodiments, the diluent is about 70% (w/w), about 72% (w/w), about 74% (w/w), about 75% (w/w), about 77% (w/w), about 79% (w/w), about 80% (w/w), about 82% (w/w), about 84% (w/w), about 85% (w/w), about 87% (w/w), or about 89% (w/w) of the formulation.

Binders

Binders can be used in the formulation of solid oral dosage forms to hold the active pharmaceutical ingredient and inactive ingredients together in a cohesive mix. In some embodiments, at least a portion of the binder is in the granular component. In some embodiments, the one or more binder include starches, gelatins, sugars, gums, waxes, water, alcohols, celluloses, acacia gum, tragacanth, corn starch, methyl cellulose, panwar gum, ghatti gum, mucilage of isapol husks, carboxymethylcellulose, methylcellulose, polyvinylpyrrolidone, sucrose, glucose, dextrose, molasses, lactose, hydroxypropyl cellulose, and combinations thereof. In some embodiments, the binder is about 0.5% (w/w), about 1% (w/w), about 1.5% (w/w), about 2% (w/w), about 2.5% (w/w), about 3% (w/w), about 3.5% (w/w), about 4% (w/w) about 4.5% (w/w), about 5% (w/w), about 5.5% (w/w), about 6% (w/w) of the formulation.

Color Agents

One of the most important reasons for adding coloring agents to solid oral formulations is to prevent errors and confusion for patients between different medications. In some embodiments, at least a portion of the one or more coloring agent is in the extragranular component. The one or more coloring agents can include pigment blend yellow. In some embodiments, the coloring agent is about 0.20% (w/w), about 0.25% (w/w) about 0.30% (w/w), about 0.35% (w/w), about 0.40% (w/w), about 0.45% (w/w), about 0.50% (w/w), about 0.55% (w/w), about 0.60% (w/w), about 0.65% (w/w), or about 0.70% (w/w) of the formulation.

Lubricants

In some embodiments, at least a portion of the lubricant is in the extragranular component. In some embodiments, the one or more lubricants include talc, magnesium stearate, calcium stearate, stearic acid, metallic stearate, hydrogenated vegetable oils, and polyethylene glycol, corn starch, boric acids, sodium chloride, sodium lauryl sulphate, magnesium stearate, and any combination thereof. In some embodiments, the lubricant is about 0.05% (w/w), about 0.10% (w/w), about 0.20% (w/w), about 0.30% (w/w), about 0.40% (w/w), about 0.50% (w/w), about 0.60% (w/w), about 0.70% (w/w), about 0.80% (w/w), about 0.90% (w/w), about 1% (w/w), or about 1.2% (w/w), or about 2% (w/w), or about 3% (w/w) of the formulation.

Formulation

In certain aspects, the pharmaceutically acceptable formulation as provided herein can be formulated as a pharmaceutically acceptable salt or solvate thereof. In some embodiments, the pharmaceutically acceptable formulations as provided herein comprising highly pure rofecoxib or a pharmaceutically acceptable salt or solvate thereof as provided herein may include the excipients, and may otherwise be formulated, as described in U.S. Pat. No. 6,063,811, which is incorporated herein by reference in its entirety, including but not limited to the formulations specified in Examples 2, 2a, 2b, and 2c of U.S. Pat. No. 6,063,811. The term "pharmaceutically acceptable salt," as used herein, refers to the relatively non-toxic, inorganic and organic acid salts of compounds of the subject matter described herein. These salts can be prepared in situ during the final isolation and purification of the compounds of the subject matter described herein, or by separately reacting a purified compound of the subject matter described herein in its free base form with a suitable organic or inorganic acid, and isolating the salt thus formed. Representative salts include hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts, and the like. See, for example, Berge et al., (1977) "Pharmaceutical Salts", J. Pharm. Sci. 66:1-19.

The pharmaceutically acceptable salts of the compounds disclosed herein include but are not limited to the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, butionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In some embodiments, the compounds of the subject matter described herein may contain one or more acidic functional groups and, thus, are capable of forming pharmaceutically acceptable salts with pharmaceutically acceptable bases. The term "pharmaceutically-acceptable salts" in these instances refers to the relatively non-toxic, inorganic and organic base addition salts of compounds of the subject matter described herein. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like. See, for example, Berge el al., supra.

Formulations of the subject matter described herein include but are not limited to those suitable for oral administration. The formulations may conveniently be presented in unit dosage form and may be prepared by any methods well known in the art of pharmacy. The amount of active ingredient which can be combined with a carrier or excipient material to produce a single dosage form will vary depending upon the host being treated and the particular mode of administration. The amount of active ingredient, which can be combined with a carrier or excipient material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these pharmaceutically acceptable formulations or compositions include the step of bringing into association a compound of the subject matter described herein with the carrier or excipient and, optionally, one or more accessory ingredients. In general, the formulations are prepared by uniformly and intimately bringing into association a compound of the subject matter described herein with liquid carriers or excipients, or finely divided solid carriers or excipient, or both, and then, if necessary, shaping the product.

Formulations of the subject matter described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), and/or as mouthwashes and the like, each containing a predetermined amount of a compound of the subject matter described herein as an active ingredient. A compound of the subject matter described herein may also be administered as a bolus, electuary or paste.

In solid dosage forms of the subject matter described herein for oral administration (capsules, tablets, pills, dragees, powders, granules, and the like), the active ingredient is mixed with one or more pharmaceutically acceptable carriers or excipients, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose, and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, sodium lauryl sulfate, sodium dodecyl sulfate, cetyl alcohol, glycerol monostearate, and polyethylene oxide-polybutylene oxide copolymer; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutically acceptable formulation may also comprise buffering agents. Solid pharmaceutically acceptable formulation of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients or excipients. Compressed tablets may be prepared using binder (for example, gelatin or hydroxybutylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutically acceptable formulation of the subject matter described herein, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxybutylmethyl cellulose in varying proportions, to provide the desired release profile, other polymer matrices, liposomes, and/or microspheres. They may be sterilized by, for example, filtration through a bacteria-retaining filter, or by incorporating sterilizing agents in the form of sterile solid formulations, which can be dissolved in sterile water or some other sterile injectable medium immediately before use. These formulations may also optionally contain opacifying agents and may be of a formulation that they release the active ingredient(s) only, or preferentially, in a certain portion of the gastrointestinal tract, optionally, in a delayed manner. Examples of embedding formulations, which can be used include polymeric substances and waxes. The active ingredient can also be in micro-encapsulated form, if appropriate, with one or more of the above-described excipients.

Liquid dosage forms for oral administration of the compounds of the subject matter disclosed herein include pharmaceutically-acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isobutyl alcohol, ethyl carbonate, ethyl acetate, benzyl alcohol, benzyl benzoate, butylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxypropyl-β-cyclodextrin or sulfobutylether-β-cyclodextrin, may be used to solubilize compounds.

Besides inert diluents, the oral formulations can also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar, and tragacanth, and mixtures thereof.

When the compounds of the subject matter disclosed herein are administered as pharmaceuticals, to humans and animals, they can be given per se or as a pharmaceutically acceptable formulation containing, for example, 0.1% to 99.5% (more preferably, 0.5% to 90%) of active ingredient in combination with a pharmaceutically-acceptable carrier.

The compounds and pharmaceutically acceptable formulation of the subject matter disclosed herein can be employed in combination therapies, that is, the compounds and pharmaceutically acceptable formulation can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved.

It will also be appreciated that the therapies employed may achieve a desired effect for the same disorder (for example, the compound of the subject matter disclosed herein may be administered concurrently with another anti cancer agents).

In some embodiments, the compounds of the subject matter disclosed herein may be used to treat arthritic conditions in mammals (e.g., humans, livestock, and domestic animals), race horses, birds, lizards, and any other organism which can tolerate the compounds.

The subject matter disclosed herein also provides a pharmaceutical pack or kit comprising one or more containers filled with one or more of the ingredients of the pharmaceutically acceptable formulation of the subject matter disclosed herein. Optionally associated with such container(s) can be a notice in the form prescribed by a governmental agency regulating the manufacture, use, or sale of pharmaceuticals or biological products, which notice reflects approval by the agency of manufacture, use, or sale for human administration.

Wetting agents, emulsifiers, and lubricants, such as sodium lauryl sulfate, magnesium stearate, and polyethylene oxide-polybutylene oxide copolymer, as well as coloring agents, release agents, coating agents, sweetening, flavoring and perfuming agents, preservatives, and antioxidants can also be present in the pharmaceutically acceptable formulation described herein.

In one embodiment, the pharmaceutically acceptable formulation useful according to the methods of the subject matter described herein can be formulated in any manner suitable for pharmaceutical use.

In one embodiment, the formulations of the subject matter disclosed herein can be administered in pharmaceutically acceptable solutions, which may routinely contain pharmaceutically acceptable concentrations of salt, buffering agents, preservatives, compatible carriers, adjuvants, excipients and optionally other therapeutic ingredients.

Administration

Some aspects of the subject matter disclosed herein involve administering an effective amount of a pharmaceutically acceptable formulation to a subject to achieve a specific outcome.

For use in therapy, an effective amount of the compound can be administered to a subject by any mode allowing the compound to be taken up by the appropriate target cells. "Administering" the pharmaceutical acceptable formulation of the subject matter described herein can be accomplished by any means known to the skilled artisan.

The concentration of compounds included in formulations used in the methods of the subject matter disclosed herein can range from about 1 nM to about 100 µM. Effective doses are believed to range from about 10 picomole/kg to about 100 micromole/kg.

The pharmaceutically acceptable formulation disclosed herein can be prepared and administered in dose units. Solid dose units are tablets, capsules, powders, and suppositories. For treatment of a patient, different doses may be necessary depending on activity of the compound, manner of administration, purpose of the administration (i.e., prophylactic or therapeutic), nature and severity of the disorder, age and body weight of the patient. The administration of a given dose can be carried out both by single administration in the form of an individual dose unit or else several smaller dose units. Repeated and multiple administration of doses at specific intervals of days, weeks, or months apart are also contemplated by the subject matter described herein.

The pharmaceutically acceptable formulation described herein can be administered per se (neat) or in the form of a pharmaceutically-acceptable salt. When used in medicine the salts should be pharmaceutically acceptable, but non-pharmaceutically-acceptable salts can conveniently be used to prepare pharmaceutically-acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

The compounds useful in the subject matter disclosed herein can be delivered in mixtures of more than two such compounds. A mixture can further include one or more adjuvants in addition to the combination of compounds.

A variety of administration routes may be available. The particular mode selected will depend, of course, upon the particular compound selected, the age and general health status of the subject, the particular condition being treated, and the dosage required for therapeutic efficacy. The methods of the subject matter described herein, generally speaking, can be practiced using any mode of administration that is medically acceptable, meaning any mode that produces effective levels of response without causing clinically unacceptable adverse effects. Preferred modes of administration are discussed above.

The formulations can conveniently be presented in unit dosage form and can be prepared by any of the methods well known in the art of pharmacy. All methods include the step of bringing the compounds into association with a carrier which constitutes one or more accessory ingredients. In general, the formulations are prepared by uniformly and intimately bringing the compounds into association with a liquid carrier, a finely divided solid carrier, or both, and then, if necessary, shaping the product.

Other delivery systems can include time-release, delayed release, or sustained-release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids, or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the subject matter described herein is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686.

In one aspect, the pharmaceutically acceptable formulation of rofecoxib as provided herein can be administered in a variety of manners, including without limitation, orally. The form in which the drug will be administered (e.g., tablet, capsule, solution, suspension, emulsion) will depend on the route by which it is administered. In one aspect, the subject matter disclosed herein includes a pharmaceutically acceptable formulation comprising substantially pure or highly pure rofecoxib as provided herein and a pharmaceutically acceptable carrier, wherein the pharmaceutically acceptable formulation is in the form of a tablet, and wherein the amount of the rofecoxib as provided herein is 10 mg, 10.5 mg, 11 mg, 11.5 mg, 12 mg, 12.5 mg, 20 mg, 21 mg, 22 mg, 22.5 mg, or 25 mg. In another aspect, the subject matter disclosed herein includes a pharmaceutically acceptable formulation comprising substantially pure or highly pure rofecoxib as provided herein and a pharmaceutically acceptable carrier or excipient, wherein the pharmaceutically acceptable formulation is in the form of a tablet, and wherein the amount of the rofecoxib as provided herein is about 1 mg, 2 mg, 3 mg, 5 mg, 6.25 mg, 7.5 mg, 10 mg, 10.5 mg, 11 mg, 11.5 mg, 12 mg, 12.5 mg, 20 mg, 21 mg, 22 mg, 22.5 mg, 25 mg, 50 mg, 60 mg, or 70 mg.

In another aspect, the subject matter disclosed herein includes a pharmaceutically acceptable formulation comprising substantially pure or highly pure rofecoxib as provided herein and a pharmaceutically acceptable carrier or excipient, wherein the pharmaceutically acceptable formulation is in the form of a tablet, and wherein the amount of the rofecoxib as provided herein is about 0.10 mg/kg, 0.15 mg/kg, 0.20 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, or 0.70 mg/kg.

In one aspect, the pharmaceutically acceptable formulation comprising rofecoxib as provided herein may be packaged with a set of instructions warning the patient of cardiovascular and/or gastrointestinal risks associated with administration of the formulation.

The formulations, both for human medical use and veterinary use, of compounds according to the subject matter described herein typically include such compounds in association with a pharmaceutically acceptable carrier.

As used herein, the phrase "pharmaceutically-acceptable carrier" includes but is not limited to a pharmaceutically-acceptable material, formulation or vehicle, such as a solid filler, diluent, excipient, or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose, and sucrose; starches, such as corn starch and potato starch; cellulose and its derivatives, such as sodium carboxymethyl cellulose, ethyl cellulose, and cellulose acetate; powdered tragacanth; malt; gelatin; and talc; excipients, such as cocoa butter and suppository waxes. The term "carrier" denotes an organic or inorganic ingredient, natural or synthetic, with which the active ingredient is combined to facilitate the application. The components of the pharmaceutically acceptable formulation also are capable of being comingled with the compounds of the present subject matter, and with each other, in a manner such that there is no interaction which would substantially impair the desired pharmaceutical efficiency.

The carrier should be "acceptable" in the sense of being compatible with compounds of the subject matter described herein and not deleterious to the recipient. Pharmaceutically acceptable carriers, in this regard, are intended to include any and all solvents, dispersion media, coatings, absorption delaying agents, and the like, compatible with pharmaceutical administration. The use of such media and agents for pharmaceutically active substances is known in the art. Except insofar as any conventional media or agent is incompatible with the active compound, use thereof in the formulations is contemplated. Supplementary active compounds (identified or designed according to the subject matter disclosed herein and/or known in the art) also can be incorporated into the formulations. The formulations can conveniently be presented in dosage unit form and can be prepared by any of the methods well known in the art of pharmacy. In general, some formulations are prepared by bringing the compound into association with a liquid carrier or a finely divided solid carrier or both, and then, if necessary, shaping the product into the desired formulation. A pharmaceutically acceptable formulation of the subject matter disclosed herein should be formulated to be compatible with its intended route of administration. Solutions or suspensions can include the following components: a sterile diluent such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

Useful solutions for oral administration can be prepared by any of the methods well known in the pharmaceutical art, described, for example, in Remington's Pharmaceutical Sciences, 18th ed. (Mack Publishing Company, 1990). Formulations of the subject matter described herein suitable for oral administration can be in the form of: discrete units such as capsules, gelatin capsules, sachets, tablets, troches, or lozenges, each containing a predetermined amount of the drug; a powder or granular formulation; a solution or a suspension in an aqueous liquid or non-aqueous liquid; or an oil-in-water emulsion or a water-in-oil emulsion. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral formulations generally include an inert diluent or an edible carrier. For the purpose of oral therapeutic administration, the active compound can be incorporated with excipients. Oral formulation prepared using a fluid carrier for use as a mouthwash include the compound in the fluid carrier and are applied orally and swished and expectorated or swallowed. Pharmaceutically compatible binding agents, and/or adjuvant materials can be included as part of the formulation. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Oral formulations can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the subject matter disclosed herein are dictated by and directly dependent on the unique characteristics of the active compound and the therapeutic effect to be achieved, and the limitations inherent in the art of compounding such an active compound for the treatment of individuals.

Methods of Use

A pharmaceutically acceptable formulation comprising substantially pure or highly pure rofecoxib as presented herein may be used in the treatment or prevention of conditions or diseases in humans.

In one aspect, the subject matter disclosed herein includes administering a pharmaceutically acceptable formulation comprising rofecoxib having a favorable impurity profile to a subject to treat or prevent a disease or condition, including but not limited to one of the following: osteoarthritis, rheumatoid arthritis, analgesia, systemic juvenile idiopathic arthritis, migraine or headaches, juvenile rheumatoid arthritis, ankylosing spondylitis, acute pain, and primary dysmenorrhea. In another aspect, the disease or condition is fibromyalgia. In another aspect, the disease or condition is lower back pain (e.g. chronic lower back pain). In another aspect, the disease or condition is psoriatic arthritis.

In other aspects, the disease or condition is pain-associated with a condition caused by a bleeding disorder, including migraine associated with von Willebrand deficiency. In another aspect, a patient receiving treatment for migraine associated with von Willebrand deficiency expresses von Willebrand factor at a level about 50% below normal.

In one aspect, the treatment described herein may be administered to a subject of any age. In another aspect, the patient is age 2 or older, or age 12 years or older. In another aspect, the patient is of age 12 to 75 years old, inclusive.

In one aspect, the subject is a healthy human subject. In another aspect, the subject is screened for all or certain of the study protocol inclusion or exclusion criteria described below as part of the treatment.

In another aspect, the subject is within a patient population that has a reduced risk of arterial thrombosis, cardiovascular thrombotic events, or other serious cardiovascular disease or events, for example humans with inherited bleeding disorders or coagulopathies such as hemophilia or von Willebrand disease, or humans with medically-induced bleeding disorders or coagulopathies.

In one aspect, the subject is screened for a history or current symptoms of cardiovascular disease. In one aspect, if the patient is determined to have a history or current symptoms of cardiovascular disease, the patient is not administered the pharmaceutically acceptable formulation. In another aspect, if it is determined that the patient does not have a history or current symptoms of cardiovascular disease, the patient is administered the pharmaceutically acceptable formulation as further set forth herein. In yet another aspect, the patient is screened for one or more risk factors that would increase the likelihood of the patient having a serious cardiovascular thrombotic event following administration of the pharmaceutically acceptable formulation as further set forth herein. In one aspect, if it is determined that the patient may be safely administered the pharmaceutically acceptable formulation as further set forth herein without increasing the likelihood of the patient having a serious cardiovascular thrombotic event, then the patient is administered the pharmaceutically acceptable formulation as further set forth herein.

In another aspect, the subject is screened for a history or current symptoms of gastrointestinal bleeding, ulceration, and perforation. In one aspect, if the patient is determined to have a history or current symptoms of gastrointestinal bleeding, ulceration, and perforation, the patient is not administered the pharmaceutically acceptable formulation. In another aspect, if it is determined that the patient does not have a history or current symptoms of gastrointestinal bleeding, ulceration, and perforation, the patient is administered the pharmaceutically acceptable formulation as further set forth herein.

The subject may be screened for a history or current symptoms of both cardiovascular disease or gastrointestinal bleeding, ulceration, and perforation, in addition to any of the study protocol inclusion or exclusion criteria listed below.

A pharmaceutically acceptable formulation comprising rofecoxib that is administered for any of the diseases or conditions described herein may be substantially pure or highly pure, or may be essentially free of, or free of, one or more of impurities.

In another aspect, a pharmaceutically acceptable formulation comprising rofecoxib as provided herein is administered to a subject who has mild, moderate, or severe pain or inflammation associated with a condition caused by a bleeding disorder. Pain may be measured through any clinically-validated pain assessment measure. In one aspect, pain is measured through the Pain Intensity Numerical Rating Scale. In another aspect, pain associated with a specific condition caused by a bleeding disorder, hemophilic arthropathy, is measured through the Pain Intensity Numerical Rating Scale or the Patient Assessment of Arthropathy Pain (Visual Analog Scale; VAS).

In one aspect, a pharmaceutically acceptable formulation comprising rofecoxib as provided herein is administered to a subject who has pain associated SJIA. In another aspect, a pharmaceutically acceptable formulation comprising rofecoxib as provided herein is administered to a subject who has migraine associated with von Willebrand deficiency, wherein the subject receiving treatment expresses von Willebrand factor at a level about 50% below normal.

In one aspect, the treatment of the subject matter disclosed herein includes administration of a pharmaceutically acceptable formulation comprising about 10 mg of rofecoxib as provided herein per day. In one aspect, the treatment of the subject matter disclosed herein includes administration of a pharmaceutically acceptable formulation comprising about 10.5 mg of rofecoxib as provided herein per day. In one aspect, the treatment of the subject matter disclosed herein includes administration of a pharmaceutically acceptable formulation comprising about 11 mg of rofecoxib as provided herein per day. In one aspect, the treatment of the subject matter disclosed herein includes administration of a pharmaceutically acceptable formulation comprising about 11.5 mg of rofecoxib as provided herein per day. In one aspect, the treatment of the subject matter disclosed herein includes administration of a pharmaceutically acceptable formulation comprising about 12 mg of rofecoxib as provided herein per day. In one aspect, the treatment of the subject matter disclosed herein includes administration of a pharmaceutically acceptable formulation comprising about 12.5 mg of rofecoxib as provided herein per day. In one aspect, the treatment of the subject matter disclosed herein includes administration of a pharmaceutically acceptable formulation comprising about 20 mg of rofecoxib as provided herein per day. In one aspect, the treatment of the subject matter disclosed herein includes administration of a pharmaceutically acceptable formulation comprising about 21 mg of rofecoxib as provided herein per day. In one aspect, the treatment of the subject matter disclosed herein includes administration of a pharmaceutically acceptable formulation comprising about 22 mg of rofecoxib as provided herein per day. In one aspect, the treatment of the subject matter disclosed herein includes administration of a pharmaceutically acceptable formulation comprising about 22.5 mg of rofecoxib as provided herein per day. In another aspect, the treatment includes the administration of a pharmaceutically acceptable formulation comprising about 25 mg of rofecoxib as provided herein per day. In one aspect, the treatment of the subject matter disclosed herein includes administration of a pharmaceutically acceptable formulation comprising about 50 mg of rofecoxib as provided herein per day. In another aspect, the treatment includes the administration of a pharmaceutically acceptable formulation comprising about 1 mg, 2 mg, 3 mg, 5 mg, 6.25 mg, 7.5 mg, 10 mg, 10.5 mg, 11 mg, 11.5 mg, 12 mg, 12.5 mg, 17.5 mg, 20 mg, 21 mg, 21.5 mg, 22.5 mg, 25 mg, 50 mg, 60 mg, or 70 mg of rofecoxib as provided herein per day. Treatment may be administered once daily in the form of one or more tablets. In other aspects, the pharmaceutically acceptable formulation comprising rofecoxib as provided herein is administered two times or more daily.

In one aspect, a treatment regimen is provided for the safe treatment of pain, inflammation, migraine and/or arthritis. The pain, inflammation, migraine and/or arthritis may be associated with a disease or condition caused by a bleeding disorder. In one aspect, the treatment subject is a human patient of any age. In another aspect, the patient is age 12 years or older.

The treatment regimen may comprise the administration of an initial (or first) dose of a pharmaceutically acceptable formulation comprising 4 mg, 8 mg, 10 mg, 10.5 mg, 11 mg, 11.5 mg, 12 mg, 12.5 mg, 17.5 mg, 20 mg, or 25 mg of rofecoxib once daily as further described herein. The treatment regimen may further comprise evaluating the subject after administration of the initial dose to determine if the initial dose was fully, partially, or not effective at treating the pain, inflammation, migraine and/or arthritis. In another aspect, the treatment regimen may comprise determining if the subject could benefit from the administration of a higher dose of rofecoxib. The evaluation and determining steps may take place after a single administration of the initial dose (e.g. two days, three days, one week, two weeks, or longer after the first administration of the initial dose), or after multiple administrations of the initial dose, and may be performed by a physician, physician's assistant, nurse, or other health care provider. In one aspect, the evaluation and determination steps may be based on subject-reported outcomes, and may include an assessment of the benefit of a higher dose of rofecoxib compared to any potential safety risks associated with that higher dose. For example, if a subject experiences a clinically meaningful decrease in pain after administration of the initial dose, it may be determined that the subject should continue on the initial dose through the duration of the bleeding episode that caused the pain.

The treatment regimen may further comprise the administration of a subsequent (or second) dose of a pharmaceutically acceptable formulation comprising 10 mg, 12.5 mg, 17.5 mg, 20 mg, 21 mg, 22 mg, 22.5 mg, 25 mg, 30 mg, 35 mg, 40 mg, 45 mg, or 50 mg of rofecoxib once daily if it was determined that the initial dose was not effective or only partially effective at treating the pain, inflammation, migraine and/or arthritis, or if it is determined that the subject could benefit from a higher daily dose of rofecoxib to treat the pain, inflammation, migraine and/or arthritis (e.g. that a higher dose could achieve a greater reduction in pain in the human). In one aspect, the subsequent dose is administered if it is determined that the initial dose did not achieve a clinically meaningful reduction in pain, inflammation, migraine and/or arthritis in the human. In another aspect, the subsequent dose is administered if it is determined that the subsequent dose may increase the effectiveness of the treatment without increasing the risk of adverse events or other side effects. In another aspect, a higher dose is not administered if it is determined that the initial dose was effective at treating the pain, inflammation, migraine and/or arthritis. In another aspect, a higher dose is not administered if it is determined that the higher dose would increase the risk of adverse events or other side effects in the subject. In another aspect, a higher dose is not administered if it is determined that the risk of administering the higher dose (e.g. in terms of adverse events or side effects) outweigh the benefits (e.g. in terms of effectiveness of treating the pain, inflammation, migraine and/or arthritis). In another aspect, the step of not administering a higher dose comprises instructing the subject not to take a higher dose of the pharmaceutical composition (e.g. not to take 12.5 mg of the pharmaceutical composition more than once daily).

In one aspect, the treatment includes the administration of pharmaceutically acceptable formulation comprising about 0.10 mg/kg, 0.15 mg/kg, 0.20 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, or 0.70 mg/kg.

In one aspect, an effective amount of rofecoxib as provided herein for treating pain associated with a disease or condition caused by a bleeding disorder is about 12.5 mg once daily, and, in another aspects, results fewer side effects or in a reduction of pain equal to or better than the use of a pharmaceutically acceptable formulation comprising about 25 mg rofecoxib that is not substantially pure or highly pure, or essentially free of, or free of, one or more of the impurities described herein that was present in previously available rofecoxib bulk drug product. In one aspect, an effective amount of rofecoxib as provided herein for treating pain associated with a disease or condition caused by a bleeding disorder is about 1 mg, 2 mg, 3 mg, 5 mg, 6.25 mg, 7.5 mg, 10 mg, 10.5 mg, 11 mg, 11.5 mg, 12 mg, 12.5 mg, 17.5 mg, 20 mg, 21 mg, 22 mg, 22.5 mg, 25 mg, 50 mg, 60 mg, or 70 mg once daily. As a result, a subject may not need to be administered the higher quantity of active ingredient in order to experience a reduction in pain.

In one aspect, an effective amount rofecoxib as provided herein for treating pain associated with a disease or condition caused by a bleeding disorder, pain associated with systemic juvenile idiopathic arthritis, or migraine associated with von Willebrand deficiency is about 0.10 mg/kg, 0.15 mg/kg, 0.20 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, or 0.70 mg/kg.

In one aspect, the treatment described herein is effective at treating mild, moderate, or severe pain in a subject without the co-administration of another pain medication or analgesic.

In another aspect, the treatment described herein results in the subject decreasing or discontinuing the use of another pain medication or analgesic, including rescue medications, during the course of the treatment when compared to before the initiation of the treatment. In yet another aspect, the treatment results in the subject decreasing or discontinuing the use of acetaminophen and/or opioid medications during the treatment during the course of the treatment when compared to before the initiation of the treatment.

In one aspect, a pharmaceutically acceptable formulation comprising rofecoxib as provided herein is co-administered with factor replacement therapy to a subject having a bleeding disorder. In another aspect, the treatment described herein is administered to a subject having a bleeding disorder who is being administered or is taking factor replacement therapy prophylactically. In one aspect, the a pharmaceutically acceptable formulation comprising 10 mg, 10.5 mg, 11 mg, 11.5 mg, 12 mg, 12.5 mg, 17.5 mg, 20 mg, 21 mg, 22 mg, 22.5 mg, or 25 mg rofecoxib as provided herein is administered once daily to a subject who is also being administered or is taking factor replacement therapy prophylactically.

In one aspect, a pharmaceutically acceptable formulation comprising rofecoxib as provided herein is administered daily and does not increase risk of cardiovascular diseases and/or gastrointestinal bleeding, ulceration, or perforation during the course of the treatment, as determined at 2 weeks, 4 weeks, 8 weeks, 12 weeks, 24 weeks, 52 weeks, and/or two or more years. In another aspect, the rofecoxib as provided herein may be administered during the course of the treatment without the use or co-administration of a gastro-protective agent including but not limited to an antacid therapy, an H2 antagonist, a proton pump inhibitor, or misoprostol.

In another aspect, a pharmaceutically acceptable formulation comprising rofecoxib as provided herein is administered only on an as-needed basis, for example when a subject experiences a pain "flare" described as an increase in pain rating of >1 or a pain rating of >4 to <9 based on the Pain Intensity Numerical Rating Scale. In yet another aspect, the pharmaceutically acceptable formulation comprising rofecoxib as further set forth herein is not administered as a maintenance therapy, prophylactically, or for long term use (e.g., >1 year). In one aspect, a pharmaceutically acceptable formulation comprising rofecoxib as provided herein is administered only on an as-needed basis and for short term use, for example, less than one week, two weeks, three weeks, or four weeks, or until the pain, migraine, arthritis, inflammation, or other conditions or symptoms subside or resolve, for example, until there is a clinically significant improvement in pain rating based on the based on the Pain Intensity Numerical Rating Scale.

In another aspect, the subject uses or is co-administered a gastro-protective agent during the course of treatment with a pharmaceutically acceptable formulation comprising rofecoxib as provided herein, which prevents or treats gastrointestinal bleeding, ulceration, and perforation in the subject.

In one aspect, the treatment described herein achieves a reduction in at least 1 from baseline in the Pain Intensity Numerical Rating Scale. In another aspect, the treatment described herein achieves a reduction in at least 2, 3, 4, or 5 from baseline in the Pain Intensity Numerical Rating Scale.

In one aspect, the reduction in the Pain Intensity Numerical Rating Scale is achieved within 1, 2, 3, 4, 5, or 6 days, or 1 week, or 2 weeks of first administering the pharmaceutically acceptable formulation.

In one aspect, the treatment of a disease or condition by the administering of a pharmaceutically acceptable formulation comprising substantially pure or highly pure rofecoxib does not result in one or more of the following adverse events: upper respiratory infection, headache, nausea, vomiting, and cough, or one or more of the following serious adverse events: hemorrhage and hypotension. In one aspect, the treatment of a disease or condition caused by a bleeding disorder by the administering of a pharmaceutically acceptable formulation comprising substantially pure or highly pure rofecoxib does not result in an increased number of joint bleeding events. In another aspect, the treatment of a disease or condition caused by a bleeding disorder by the administering of a pharmaceutically acceptable formulation comprising substantially pure or highly pure rofecoxib does not increase the risk of joint bleeding events. In one aspect, the treatment of a disease or condition caused by a bleeding disorder by the administering of a pharmaceutically acceptable formulation comprising substantially pure or highly pure rofecoxib does not result in an increase in the amount of factor use in the subject. In another aspect, the treatment of a disease or condition by the administering of a pharmaceutically acceptable formulation comprising substantially pure or highly pure rofecoxib does not result in an increased risk of side effects (including but not limited to hemorrhaging, hypotension or serious cardiovascular thrombotic events) compared to the previously marketed "VIOXX" product when used in that disease or condition. In another aspect, a pharmaceutically acceptable formulation comprising substantially pure or highly pure rofecoxib as provided herein results in greater efficacy in a disease or condition compared to the previously marketed "VIOXX" product when used in that disease or condition (as measured by a clinically-validated measure, such as the Pain Intensity Numerical Rating Scale).

In another aspect, the treatment of a disease or condition by the administering of a pharmaceutically acceptable formulation comprising highly pure rofecoxib that is essentially free of, or free of, 4-[4-(methylsulfonyl)phenyl]-3-phenyl-5-hydroxyfuran-2-one and/or 4-[4-(methyl sulfonyl)phenyl]-3-phenyl-2,5-furandione does not result in one or more of the following adverse events: upper respiratory infection, headache, nausea, vomiting, and cough, or one or more of the following serious adverse events: hemorrhage and hypotension. In another aspect, a pharmaceutically acceptable formulation comprising highly pure rofecoxib that is essentially free of, or free of, 4-[4-(methylsulfonyl)phenyl]-3-phenyl-5-hydroxyfuran-2-one and/or 4-[4-(methylsulfonyl)phenyl]-3-phenyl-2,5-furandione as provided herein results in greater efficacy in a disease or condition, or reduced side effects (e.g. hemorrhaging, hypotension or serious cardiovascular thrombotic events) compared to the previously marketed "VIOXX" product when used in that disease or condition (as measured by a clinically-validated measure, such as the Pain Intensity Numerical Rating Scale). The purity of the resulting rofecoxib described as herein is determined as a percent area basis, typically as quantified by analytical chromatography, such as using HPLC, UHPLC, UPLC or other analytical means in the art.

EXAMPLES

Example 1

In some embodiments, the pharmaceutically acceptable formulation described herein relates to a tablet formulation as shown in Table 7 below:

TABLE 7

Formulation

| | Percent (w/w) |
|---|---|
| Intragranular | |
| Rofecoxib API | 12.50 |
| Lactose Monohydrate, NF, EP, JP, Fastflo 316 SDM | 39.85 |
| Microcrystalline Cellulose, NF, EP, JP Avicel PH 101 | 39.85 |
| Hydroxypropylcellulose, NF, EP, JP, Klucel EXF | 3.00 |
| Purified Water, USP, EP | NA |
| Extragranular | |
| Croscarmellose Sodium, NF, EP, JP, (Ac-Di-Sol SD711) | 4.00 |
| Pigment Blend Yellow (HTS:3206492000) | 0.30 |
| Magnesium Stearate, NF, EP, JP, Hyqual Vegetable Source 2257 | 0.50 |
| Total | 100.00 |

In some embodiments the water addition and spray rate in the granulation process of the pharmaceutically acceptable formulations as described here are as shown in Table 8 below:

TABLE 8

| Parameter | B18079 (Batch 1) | B18080 (Batch 2) | B18084 (Batch 3) | B18085 (Batch 4) |
|---|---|---|---|---|
| Water Addition (%) | 26% | 41% | 26% | 30% |
| Spray Rate (g/min) | 100.4 | 103.7 | 177.1 | 102.2 |

Figure 14:
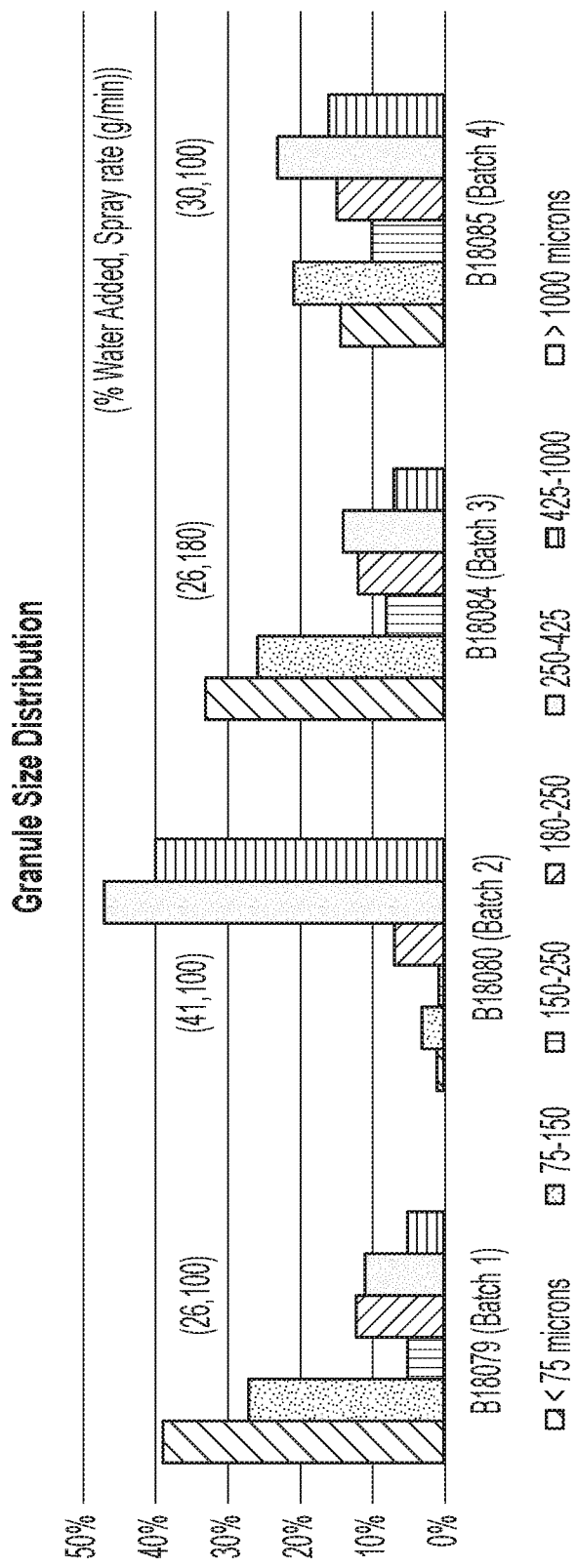
FIG. 14 shows granule size distribution across rofecoxib batches.

FIG. 14 shows the granule size distribution across batches. In some embodiments, the granule size distribution is W<75 (34-52% w/w) and W<150 (64-82% w/w).

Figures 15A, 15B:
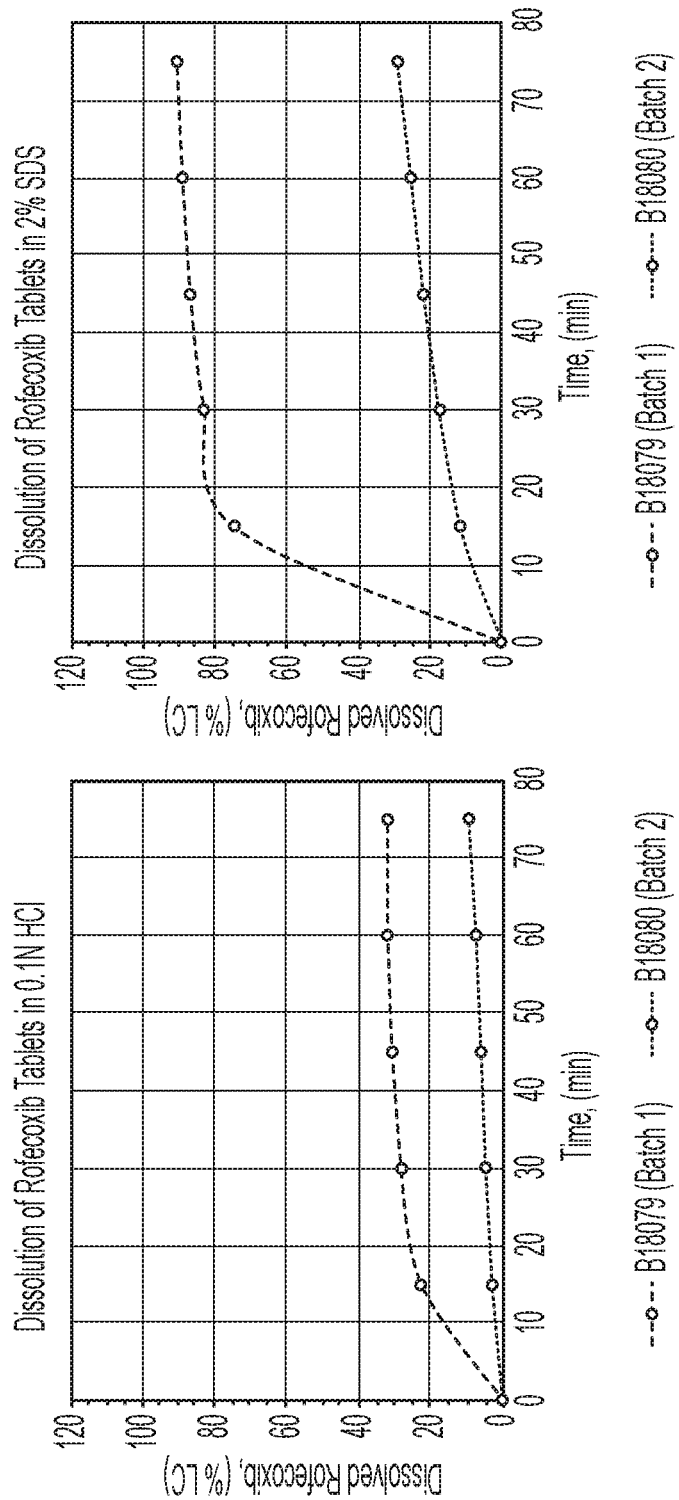
FIGS. 15A-B show dissolution of rofecoxib tablets.

FIGS. 15A-B show initial dissolution rates for 25 mg rofecoxib tablets. FIG. 15A shows dissolution of 25 mg rofecoxib tablets in 0.1N HCl for batches 1 and 2. FIG. 15B shows dissolution of 25 mg rofecoxib tablets in at least 2% SDS for batches 1 and 2. The paddle speed is 75 rpm and the number of tablets dissolved is 3 per batch.

Figures 16A, 16B:
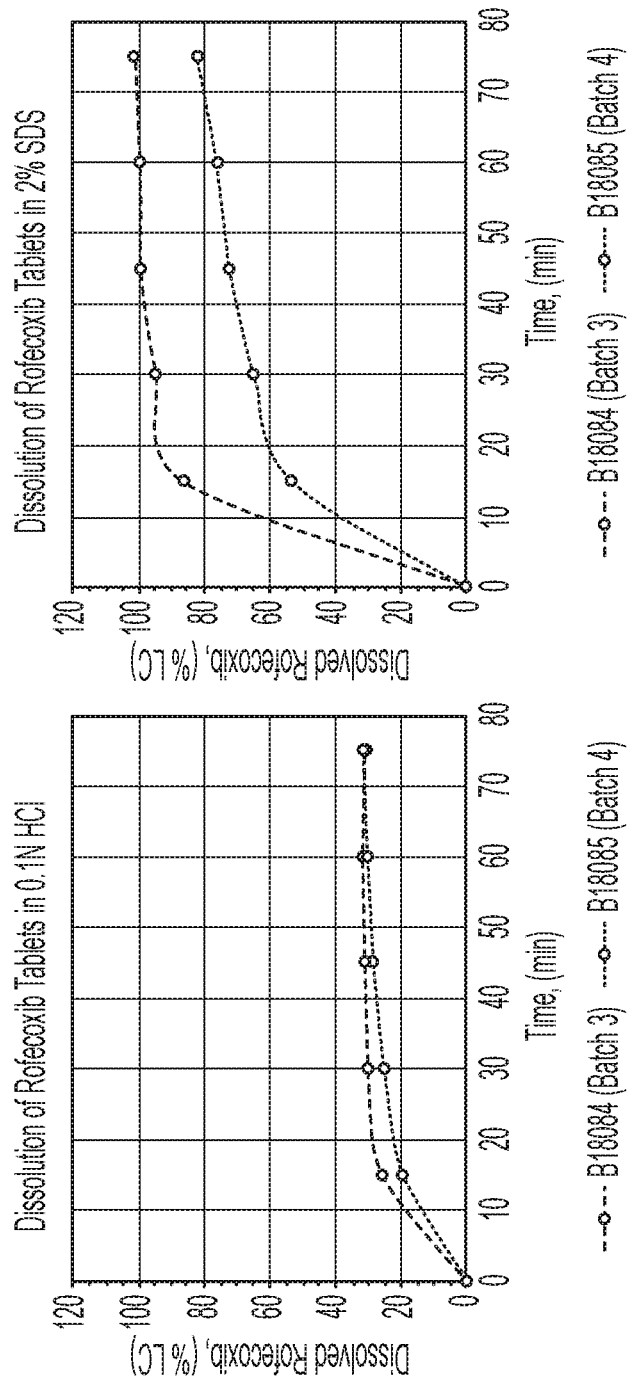
FIGS. 16A-B show dissolution of rofecoxib tablets.

FIGS. 16A-B show initial dissolution rates for 25 mg rofecoxib tablets. FIG. 16A shows dissolution of 25 mg rofecoxib tablets in 0.1N HCl for batches 3 and 4. FIG. 16B shows dissolution of 25 mg rofecoxib tablets in at least 2% SDS for batches 3 and 4. The paddle speed is 75 rpm and the number of tablets dissolved is 3 per batch.

Figure 17:
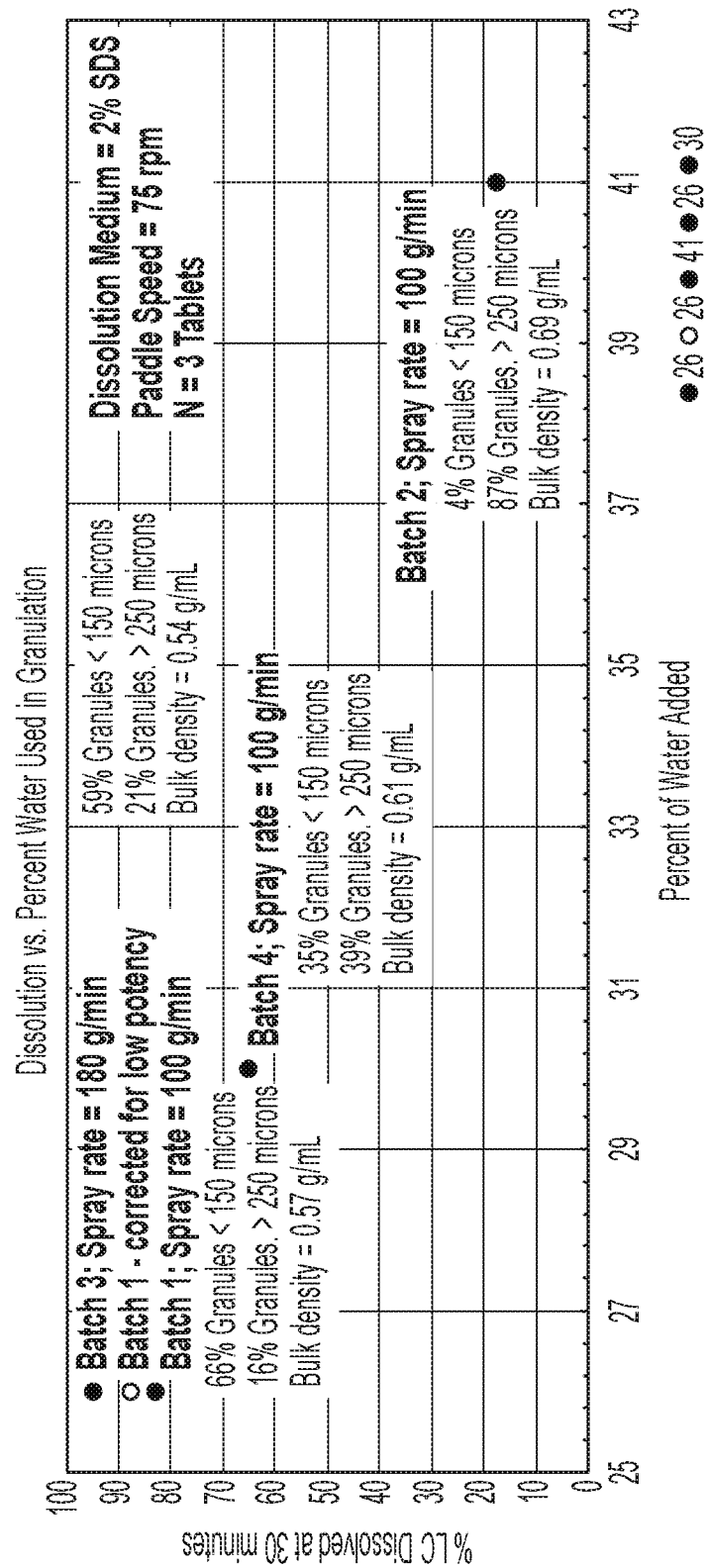
FIG. 17 shows dissolution versus percent water used in granulation.

FIG. 17 shows dissolution of 25 mg rofecoxib tablet as a function of percent water added.

Example 2

In some embodiments, the pharmaceutically acceptable formulation described herein relates to a tablet formulation as shown in Table 9 below:

TABLE 9

Tablet Formulations

| | Percent (w/w) | | |
|---|---|---|---|
| | Batches 1-4 (4 + 0) | Batches 5-6 (2 + 2) | Batches 6-7 (4 + 4) |
| Intragranular | | | |
| Rofecoxib API | 12.50 | 12.50 | 12.50 |
| Lactose Monohydrate, NF, EP, JP, Fastflo 316 SDM | 39.85 | 39.70 | 37.70 |
| Microcrystalline Cellulose, NF, EP, JP Avicel PH101 | 39.85 | 39.70 | 37.70 |
| Hydroxypropylcellulose, NF, EP, JP, Klucel EXF | 3.00 | 3.00 | 3.00 |
| Croscarmellose Sodium, NF, EP, JP, (Ac-Di-Sol SD711) | 0.00 | 2.00 | 4.00 |
| Purified Water, USP, EP | NA | NA | NA |
| Extragranular | | | |
| Croscarmellose Sodium, NF, EP, JP, (Ac-Di-Sol SD711) | 4.00 | 2.00 | 4.00 |
| Pigment Blend Yellow (HTS: 3206492000) | 0.30 | 0.60 | 0.60 |
| Magnesium Stearate, NF, EP, JP, Hyqual Vegetable Source 2257 | 0.50 | 0.50 | 0.50 |
| Total | 100.00 | 100.00 | 100.00 |

In some embodiments the water addition, spray rate, and disintegrant in the granulation process of the pharmaceutically acceptable formulations as described herein are as shown in Table 10 below:

TABLE 10

Water Addition, Spray Rate, and Disintegrant

| Parameter | B18090 (Batch 5) | B18091 (Batch 6) | B18092 (Batch 7) | B18093 (Batch 8) |
|---|---|---|---|---|
| Water Addition (%) | 26% | 32% | 26% | 32% |
| Spray Rate (g/min) | 100 | 100 | 100 | 100 |
| Disint | 2 + 2 | 2 + 2 | 4 + 4 | 4 + 4 |

Figure 18:
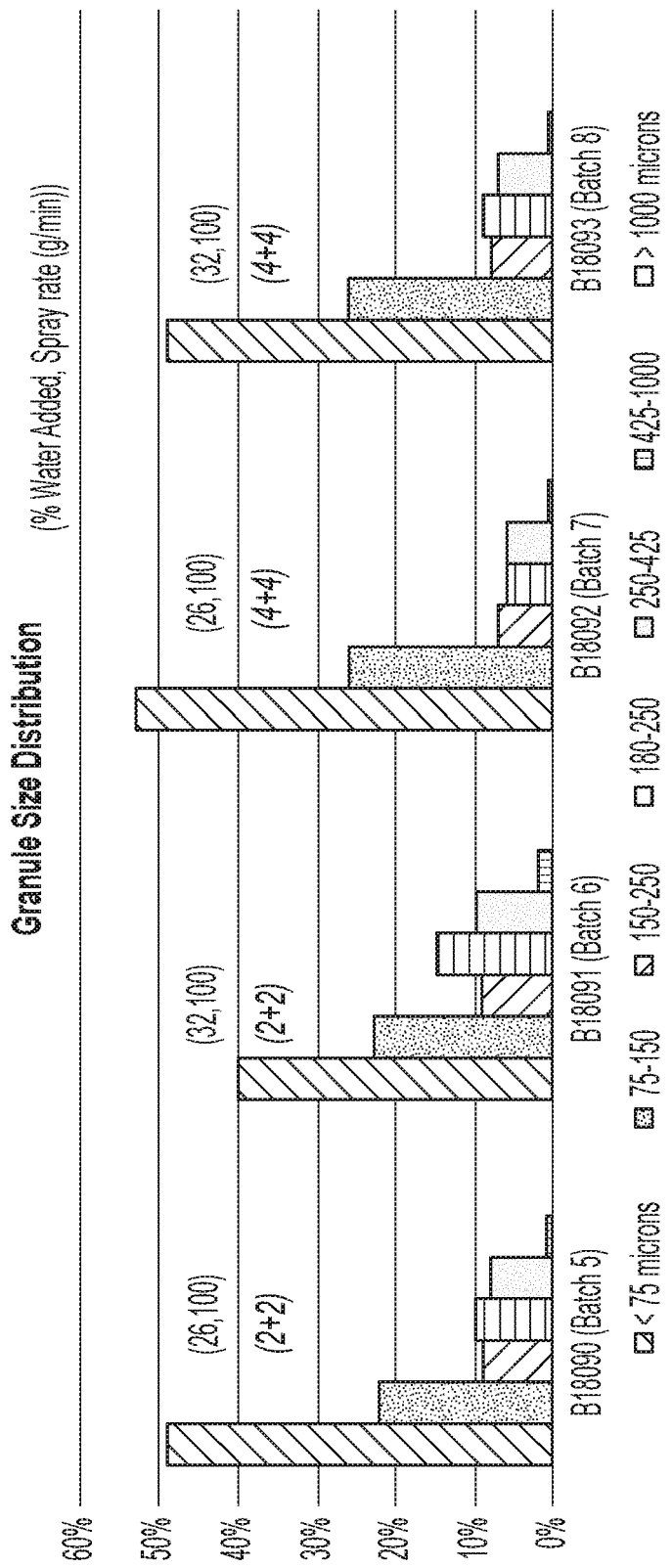
FIG. 18 shows granule size distribution across rofecoxib batches.

FIG. 18 shows the granule size distribution across batches.

Figures 19A, 19B:
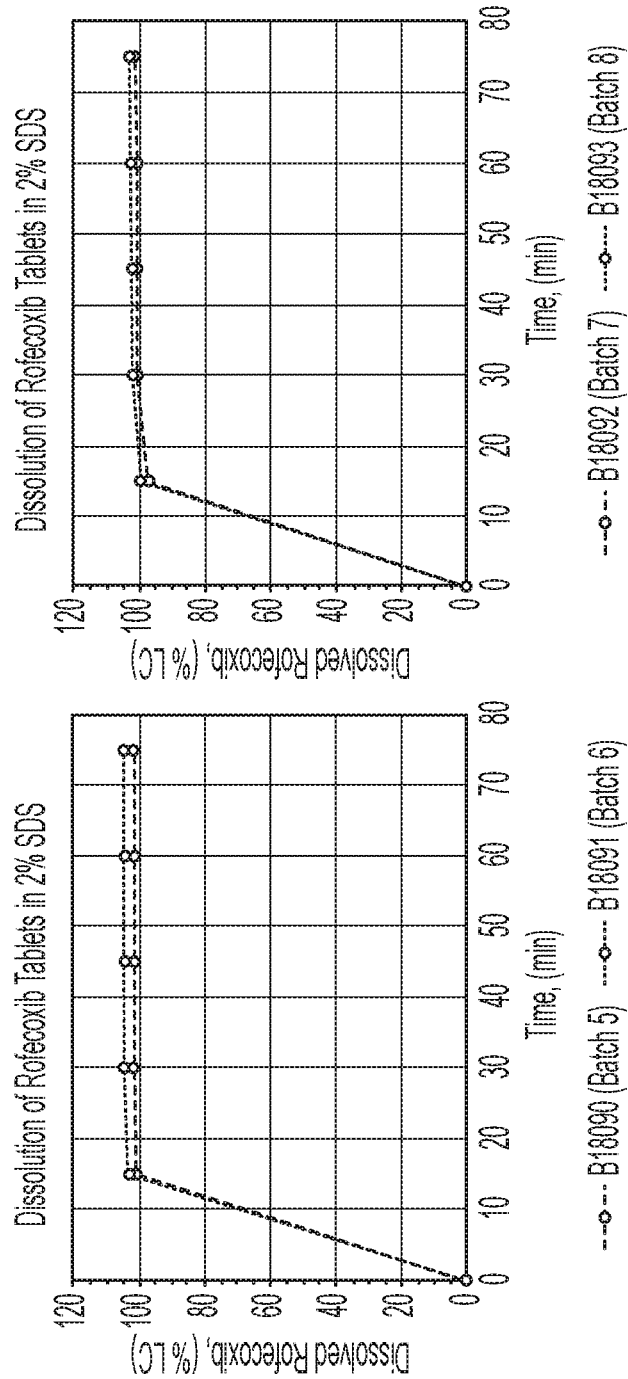
FIGS. 19A-B show dissolution of rofecoxib tablets.

FIGS. 19A-B show dissolution rates for 25 mg rofecoxib tablets. FIG. 19A shows dissolution of 25 mg rofecoxib tablets in at least 2% SDS for batches 5 and 6. FIG. 19B shows dissolution of 25 mg rofecoxib tablets in at least 2% SDS for batches 7 and 8. The paddle speed is 75 rpm and the number of tablets dissolved is 3 per batch.

Figures 20A, 20B:
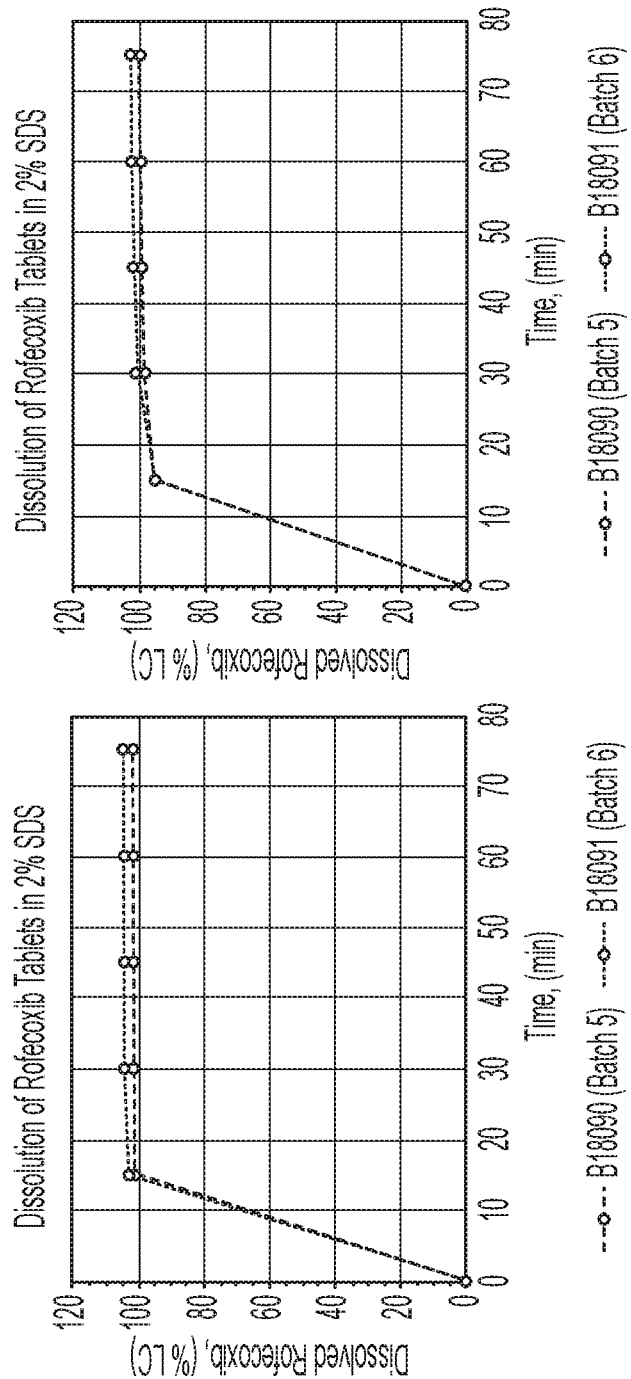
FIGS. 20A-B show dissolution of rofecoxib tablets.

FIGS. 20A-B show dissolution rates for 25 mg rofecoxib tablets. FIG. 20A shows dissolution of 25 mg rofecoxib tablets in at least 2% SDS for batches 5 and 6 at 75 rpm paddle speed. FIG. 20B shows dissolution of 25 mg rofecoxib tablets in at least 2% SDS for batches 5 and 6 at 50 rpm paddle speed. The number of tablets dissolved is 3 per batch.

All batches have 0.6% extragranular pigment. Two batches use 26% water during granulation. Batch 5 has 4% total disintegrant: 2% intragranular and 2% extragranular disintegrant. Batch 7 had 8% total disintegrant: 4% intragranular and 4% extragranular disintegrant.

Two batches will use 32% water during granulation. Batch 6 had 4% total disintegrant: 2% intragranular and 2% extragranular disintegrant. Batch 8 had 8% total disintegrant: 4% intragranular and 4% extragranular disintegrant.

100% Dissolution in 15 minutes is observed for Batches 5-8 at 75 rpm paddle speed. Previous maximum was 86% dissolved in 15 minutes. Based on the dissolution results and the manufacturing engineering data, there is no advantage to have 8% disintegrant in the formulation. Additionally, decreasing the paddle speed to 50 rpm leads to a slightly lower % dissolved (95% LC) at 15 minutes for Batches 5 and 6.

Example 3

There was no difference in dissolution profile of the two lead 25 mg rofecoxib tablet formulations in 1, 1.5, and 2% SDS at either 50 or 75 rpm paddle speed. All media and paddle speeds provided acceptable profiles. A conservative approach to the dissolution profile is advised at this stage of development:
Medium: 1.5 or 2% SDS
Paddle speed: 50 rpm Eight batches of 25-mg rofecoxib tablets were manufactured. Amount of water added during granulation is the most critical parameter:
Water amount affects granule size
Low water does not make granules
Excess water affects tablet properties (hardness, friability, disintegration, dissolution)
Water content in the 26-32% range yields acceptable tablet properties Disintegrant location affects dissolution properties in at least 2% SDS. Extragranular disintegrant (4%) only does not result in complete dissolution. Intragranular and extragranular disintegrant result in complete dissolution. No advantage to 8% total disintegrant over 4% total disintegrant when half is intragranular. Decreasing the paddle speed to 50 rpm from 75 rpm led to a slightly lower % rofecoxib dissolved at 15 minutes in at least 2% SDS.

In some embodiments, the pharmaceutically acceptable formulation described herein relates to a tablet formulation as shown in Table 11 below:

TABLE 11

A Tablet Formulation

| | Percent (w/w) | | |
|---|---|---|---|
| | Batches 1-4 (4 + 0) | Batches 5-6 (2 + 2) | Batches 6-7 (4 + 4) |
| Intragranular | | | |
| Rofecoxib API | 12.50 | 12.50 | 12.50 |
| Lactose Monohydrate, NF, EP, JP, Fastflo 316 SDM | 39.85 | 39.70 | 37.70 |
| Microcrystalline Cellulose, NF, EP, JP Avicel PH101 | 39.85 | 39.70 | 37.70 |
| Hydroxypropylcellulose, NF, EP, JP, Klucel EXF | 3.00 | 3.00 | 3.00 |
| Croscarmellose Sodium, NF, EP, JP, (Ac-Di-Sol SD711) | 0.00 | 2.00 | 4.00 |
| Purified Water, USP, EP | NA | NA | NA |
| Extragranular | | | |
| Croscarmellose Sodium, NF, EP, JP, (Ac-Di-Sol SD711) | 4.00 | 2.00 | 4.00 |
| Pigment Blend Yellow (HTS: 3206492000) | 0.30 | 0.60 | 0.60 |
| Magnesium Stearate, NF, EP, JP, Hyqual Vegetable Source 2257 | 0.50 | 0.50 | 0.50 |
| Total | 100.00 | 100.00 | 100.00 |

In some embodiments the water addition, spray rate, and disintegrant in the granulation process of the pharmaceutically acceptable formulations as described herein as shown in Table 12 below:

TABLE 12

Water, Spray Rate, and Disintegrant

| Parameter | B18090 (Batch 5) | B18091 (Batch 6) | B18092 (Batch 7) | B18093 (Batch 8) |
|---|---|---|---|---|
| Water Addition (%) | 26% | 32% | 26% | 32% |
| Spray Rate (g/min) | 100 | 100 | 100 | 100 |
| Disint | 2 + 2 | 2 + 2 | 4 + 4 | 4 + 4 |

Figure 21:
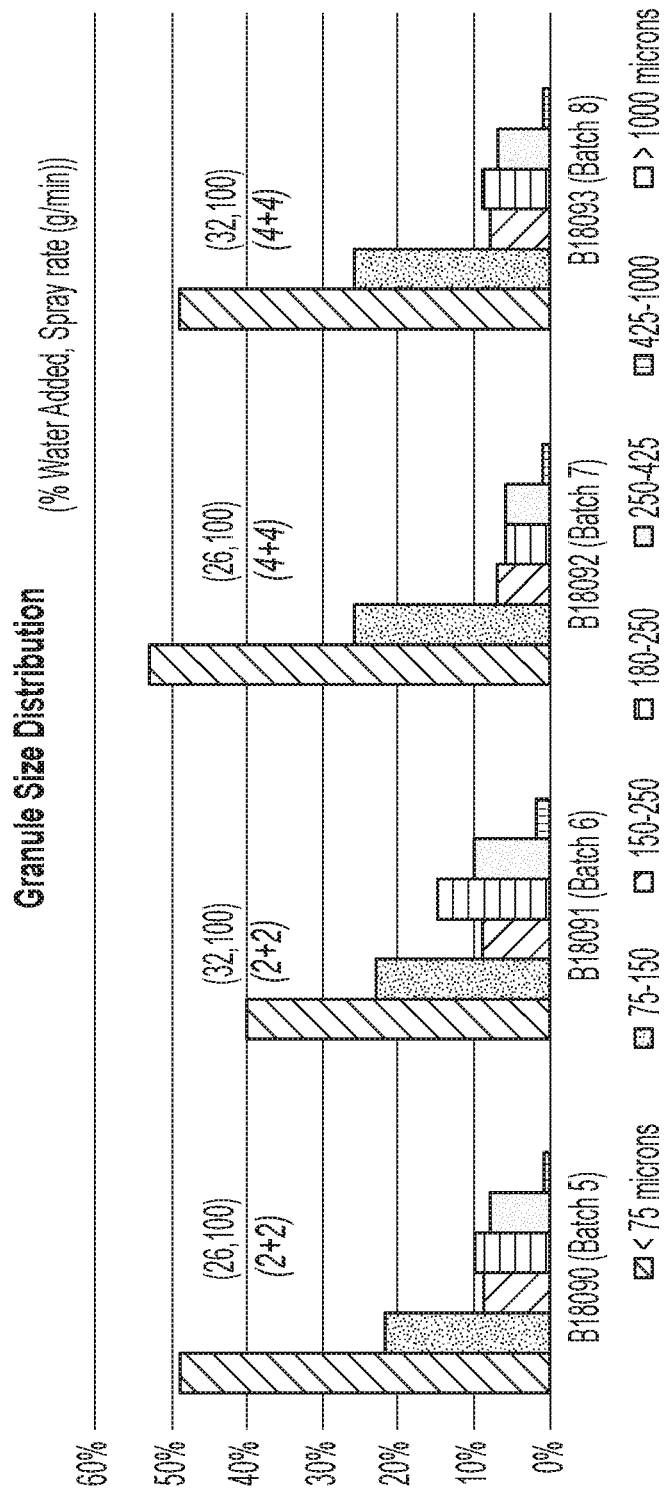
FIG. 21 shows granule size distribution across rofecoxib batches.

FIG. 21 shows the granule size distribution across batches.

Figures 22A, 22B:
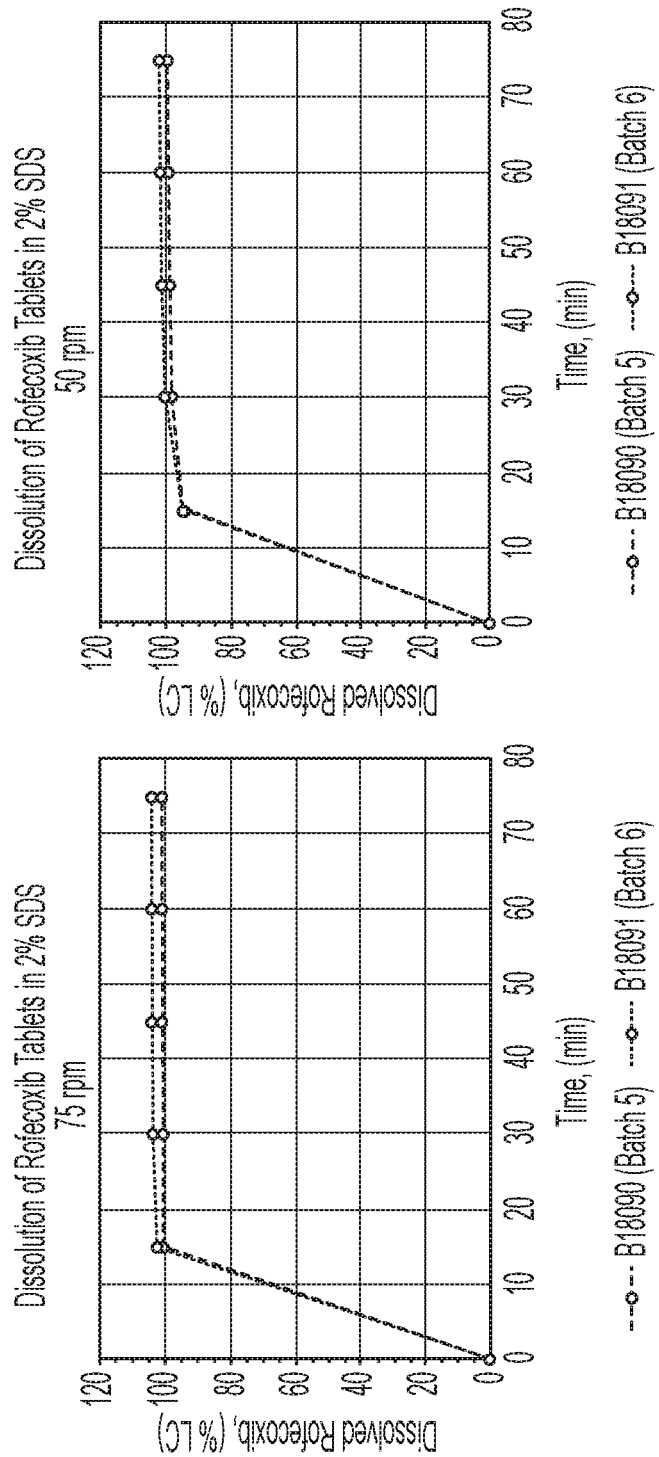
FIGS. 22A-B show dissolution of rofecoxib tablets.

FIGS. 22A-B show dissolution rates for 25 mg rofecoxib tablets. FIG. 22A shows dissolution of 25 mg rofecoxib tablets in at least 2% SDS for batches 5 and 6 at 75 rpm paddle speed. FIG. 22B shows dissolution of 25 mg rofecoxib tablets in at least 2% SDS for batches 5 and 6 at 50 rpm paddle speed. The number of tablets dissolved is 3 per batch.

Figures 23A, 23B:
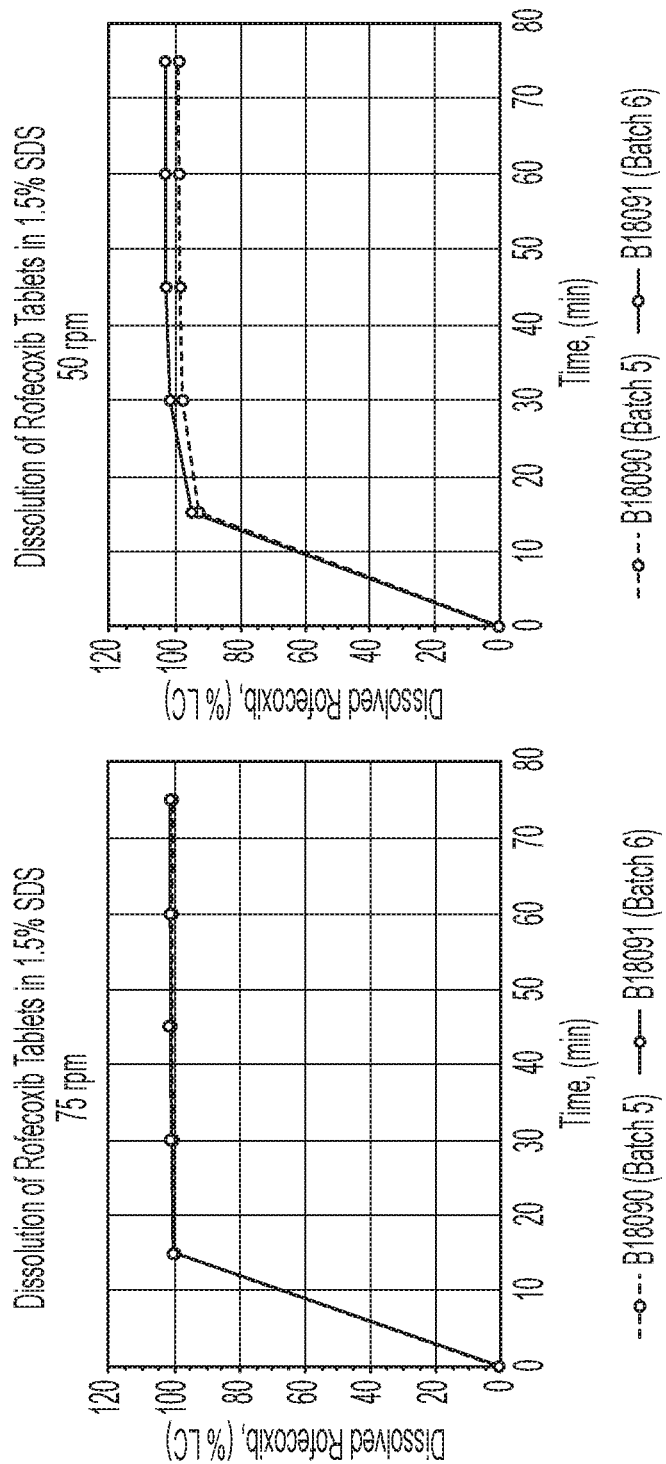
FIGS. 23A-B show dissolution of rofecoxib tablets.

FIGS. 23A-B show dissolution rates for 25 mg rofecoxib tablets. FIG. 23A shows dissolution of 25 mg rofecoxib tablets in 1.5% SDS for batches 5 and 6 at 75 rpm paddle speed. FIG. 23B shows dissolution of 25 mg rofecoxib tablets in 1.5% SDS for batches 5 and 6 at 50 rpm paddle speed. The number of tablets dissolved is 3 per batch.

Figures 24A, 24B:
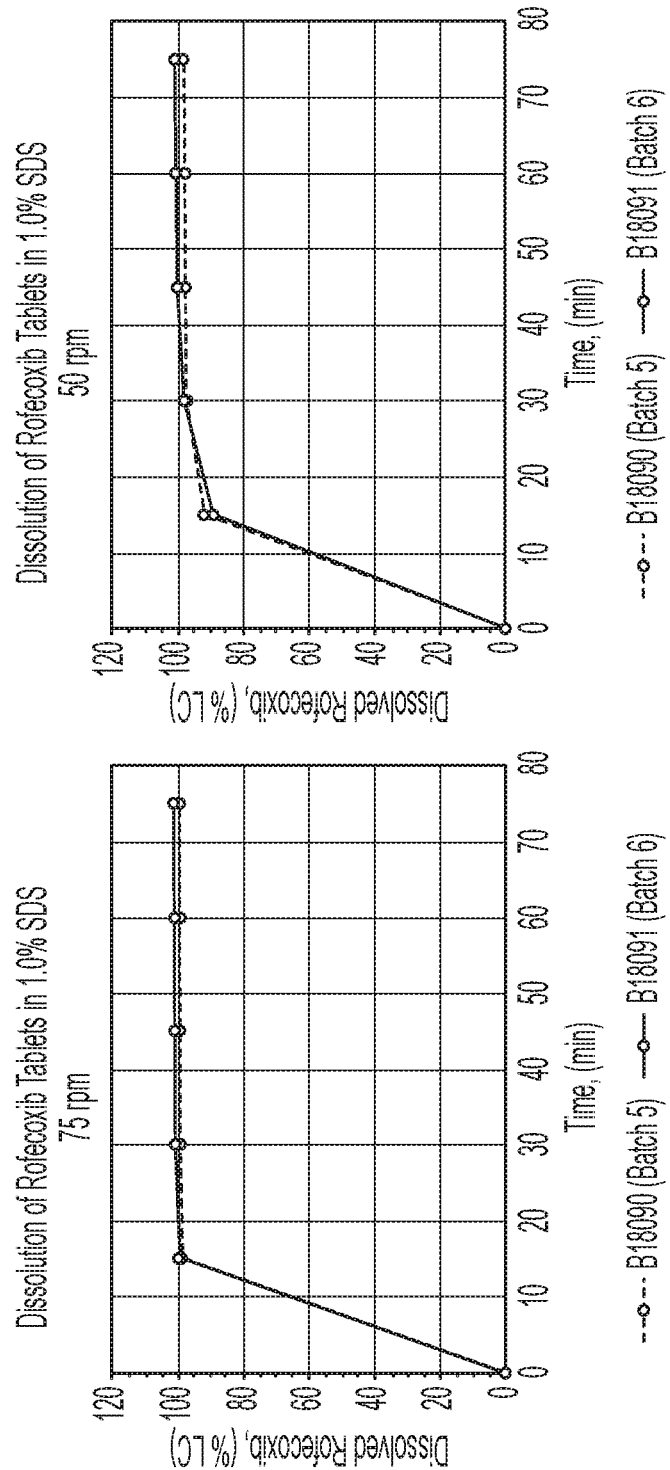
FIGS. 24A-B show dissolution of rofecoxib tablets.

FIGS. 24A-B show dissolution rates for 25 mg rofecoxib tablets. FIG. 24A shows dissolution of 25 mg rofecoxib tablets in 1% SDS for batches 5 and 6 at 75 rpm paddle speed. FIG. 24B shows dissolution of 25 mg rofecoxib tablets in 1% SDS for batches 5 and 6 at 50 rpm paddle speed. The number of tablets dissolved is 3 per batch.

Example 4

A Single-Dose, Open-Label, Phase 1, Adaptive Pharmacokinetic Study of TRM-201 (Rofecoxib) 25 mg Administered to Healthy Subjects in a Fasting State, with Comparison to Historical Pharmacokinetic Parameters of Previously Marketed Rofecoxib and a Food-Effect Substudy ("TRM-201-PK-101" or "101 PK Study")

Study Protocol
1. Study Objectives
1.1 Primary Objective:
MAIN Study: To evaluate key PK parameters ($AUC_{0-\infty}$, $C_{max}$) of a single dose of TRM-201 in healthy subjects in comparison to historical PK parameters ($AUC_{0-\infty}$, $C_{max}$) of previously marketed rofecoxib, both in a fasted state.
FOOD-EFFECT Substudy: To assess key pharmacokinetic parameters ($AUC_{0-\infty}$, $C_{max}$) of a single dose of TRM-201 in a fasted and fed state.
1.2 Secondary Objectives:
1. To assess the safety and tolerability of a single dose of TRM-201 in healthy subjects.
2. Investigational Plan
2.1 Study Design
This is a single-center, open-label, adaptive PK study of TRM-201 consisting of a MAIN study with a PILOT portion conducted under a fasted condition, and a two-period crossover, FOOD-EFFECT sub study under both fasted and fed conditions. The PILOT portion of the study (21 subjects) will include a single dose of TRM-201 in a single group to assess the PK of TRM-201 in healthy volunteers under fasted conditions. Following completion of the PILOT portion and the decision to move forward, an additional 16 subjects will be enrolled in the MAIN study and an additional 16 subjects will be enrolled in the FOOD-EFFECT sub study. The MAIN study will include a single dose of TRM-201 to assess the PK of TRM-201 in healthy volunteers under fasted conditions. The FOOD-EFFECT sub study is a single-dose, two-period crossover study. A single dose of TRM-201 will be given on Day 1 of each dosing period to assess the PK of TRM-201 in healthy volunteers under both fasted and fed conditions. Subjects will be randomized 1:1 into the two sequences fasted followed by fed, and fed followed by fasted.

The PK data from MAIN study (including the PILOT portion) will be combined with the PK data from the fasted portion of the FOOD-EFFECT sub study to form the basis of the comparison to historical pharmacokinetic parameters of previously marketed rofecoxib. The PK data from the fed portion of the FOOD-EFFECT sub study will only be compared with the PK data from the fasted portion of the FOOD-EFFECT sub study.

PILOT Portion and MAIN Study

The subjects will be screened in the 28 days before receiving the single dose of TRM-201. Subjects will check in to the clinic on the day before dosing, and their eligibility will be confirmed. Subjects will remain at the clinic from Check-In through the completion of the end-of-study (EOS) visit on Day 6.

After Check-In, subjects will fast overnight for at least 10 hours before study drug administration. While fasting, subjects will have nothing to eat and only water to drink. Water will be permitted as desired, except for the period between 1 hour before and 1 hour after study drug dosing (excepting as permitted for dosing). After the 2-hour PK blood sample, subjects will be allowed one 250-mL cup of clear apple juice. After the 4-hour PK blood sample, subjects will be served a light lunch. Following the light lunch, subjects should receive standardized meals according to the clinic's standard procedures that are scheduled at consistent times and at least 15 minutes before or 15 minutes after PK sampling time points. Blood will be withdrawn for PK analysis at predefined time points as defined in Table 8. The last time point will be 120 hours after dosing with study drug. After the 120-hour PK sample, the EOS procedures will be completed, and subjects will be discharged from the clinic.

FOOD-EFFECT Substudy

The subjects will be screened in the 28 days before receiving the single dose of TRM-201. Subjects will check in to the clinic on the day before dosing, and their eligibility will be confirmed. Subjects will remain at the clinic from Check-In through the completion of the EOS visit on Day 13 of Dosing Period 2.

After Check-In, subjects will fast overnight for at least 10 hours before study drug administration. In the morning of the dosing day of Period 1, subjects will be randomized in a 1:1 ratio within each gender to one of two dosing sequences:

Dosing sequence fasted/fed (8 subjects)
Dosing sequence fed/fasted (8 subjects)

Regardless of the dosing sequence assigned, all subjects will undergo the same assessments, pre- and post-dose.

Fasted Group

While participating in the fasted portion of the sub study, subjects will fast overnight for at least 10 hours before study drug dosing. While fasting, subjects will have nothing to eat and only water to drink. Water will be permitted as desired, except for the period between 1 hour before and 1 hour after study drug dosing (excepting as permitted for dosing). After the 2-hour PK blood sample, subjects will be allowed one 250-mL cup of clear apple juice. After the 4-hour PK blood sample, subjects will be served a light lunch. Following the light lunch, subjects should receive standardized meals according to the clinic's standard procedures that are scheduled at consistent times and at least 15 minutes before or 15 minutes after PK sampling time points.

Blood will be withdrawn for PK analysis at predefined time points. The last time point will be 120 hours after dosing with study drug (Day 6). After the 120-hour PK sample, the EOP procedures will be completed. Subjects will fast overnight on Day 7 of Dosing Period 1 for at least 10 hours and will commence with Dosing Period 2 in a fed condition on Day 8.

Fed Group

While participating in the fed portion of the sub study, subjects will fast overnight for at least 10 hours before study drug dosing. While fasting, subjects will have nothing to eat and only water to drink prior to being fed a high fat breakfast. Subjects in the fed group will start the high fat breakfast (defined per the FDA guidance as consisting of two eggs fried in butter, two strips of bacon, two slices of toast with butter, four ounces of hash brown potatoes and eight ounces of whole milk) 30 minutes prior to dosing with study drug. After the 4-hour PK blood sample, subjects will be served a light lunch. Following the light lunch, subjects should receive standardized meals according to the clinic's standard procedures that are scheduled at consistent times and at least 15 minutes before or 15 minutes after PK sampling time points.

Blood will be withdrawn for PK analysis at predefined time points as defined in Table 8. The last time point will be 120 hours after dosing with study drug (Day 6). After the 120-hour PK sample, the EOP procedures will be completed. Subjects will fast overnight on Day 7 of Period 1 for at least 10 hours and will commence with Dosing Period 2 in a fasted condition on Day 8.

The time between dosing in Period 1 and 2 is 7 days. Subjects will complete Period 1 of the FOOD-EFFECT sub study on Day 6, but will remain in the clinic and subsequently be dosed on Day 8 to ensure a full 7-day washout of study drug between Periods 1 and 2.

The assessments and requirements of Dosing Period 2 are the same as Dosing Period 1. All assessments done on Dosing Period 2/Day 1 should be done at approximately the same time of day as the assessments of Dosing Period 1/Day 1.

A subject's participation in the study is complete after the EOS visit of Period 2.

Pharmacokinetic and safety endpoints will be evaluated in the study.

2.1.1 Rationale of Study Design

A scientific bridge will be established between TRM-201 and the previously marketed rofecoxib. Because there are presently no FDA-approved rofecoxib products commercially available globally with which to conduct a directly comparative bioavailability/bioequivalence study, the present study is designed to provide PK data for a cross-study comparison to a published study (Schwartz, J. I., et al. Clin. Drug Invent. 2003, 23 (8): 503-509; hereafter "the Schwartz study").

The 25-mg dose of rofecoxib was selected for this study because it is the anticipated maximum daily dose for the treatment of HA. The data from the Schwartz study were chosen for comparison because they represent PK data generated with the labeled version of rofecoxib at 25 mg. The eligibility criteria for this current PK study have been selected to mirror the subject demographics and subgroups (gender, age, body mass index [BMI], race, and ethnicity) in the Schwartz study.

The FOOD-EFFECT sub study is a standard 2-period crossover study evaluating TRM-201 in the fasted and fed states.

A validated bioanalytical method for rofecoxib will be developed and used for the PK analyses.

3. Subject Selection and Withdrawal Criteria 3.1 Selection of Study Population

A sufficient number of subjects will be screened to ensure that at least 50 evaluable subjects complete the study.

In order to mirror the population of subjects in the Schwartz PK study every effort will be made to enroll subjects in the following proportion: White or European American (80%), Black (20%). Of the White subjects enrolled, every effort will be made to enroll approximately 60% of the subjects who identify themselves as being of Hispanic or Latino ethnicity.

Subjects will be enrolled only if they meet all the inclusion criteria and none of the exclusion criteria and all of the continuing eligibility criteria. Deviations from the inclusion and exclusion criteria are not allowed because they can potentially jeopardize the scientific integrity of the study, regulatory acceptability, or subject safety. Therefore, adherence to the criteria as specified in the protocol is essential.

3.1.1 Inclusion Criteria

Inclusion Criteria:

1. The subject is male or female and is 18 to 60 years of age, inclusive, at Screening. Similar numbers of male and female subjects should be enrolled.
2. The subject has a BMI at Screening of 18 to 32 kg/m$^2$, inclusive, with a minimum weight of 47 kg for women and 66 kg for men and a maximum weight of 80 kg for women and 90 kg for men.
3. The subject is not a smoker (or user of e-cigarettes).
4. The investigator considers the subject to be in good general health as determined by medical history, clinical laboratory test results, vital sign measurements, 12-lead ECG results, and physical examination findings at Screening and Check-in.
5. All female subjects must have a negative pregnancy test at Screening. Female subjects of childbearing potential must also have a negative pregnancy test at Check-in and must be using an acceptable method of birth control during the study (i.e., diaphragm with spermicide, intrauterine device, condom with foam or vaginal spermicide, oral contraceptives, or abstinence). Women who are surgically sterile (i.e., hysterectomy, bilateral tubal ligation or bilateral oophorectomy), or postmenopausal (defined as amenorrhea for 12 consecutive months and documented serum follicle-stimulating hormone level>40 IU/mL) are exempt from the adequate contraception requirement.
6. The subject agrees to comply with all protocol requirements as well as the particular requirements and specific Phase 1 unit policies.
7. The subject provides written informed consent.

Exclusion Criteria:

1. The subject has a history of relevant drug allergy or food allergy/sensitivity (e.g., allergy to rofecoxib or excipients of TRM-201, allergy to other NSAIDs, or gluten intolerance that could preclude consumption of a standard clinic diet).
2. A female subject is pregnant or lactating.
3. The subject has a history of intolerance or hypersensitivity to aspirin or any other NSAID.
4. The subject has a positive test result for hepatitis B surface antigen, hepatitis C virus antibody, or human immunodeficiency virus types 1 or 2 antibodies at Screening.
5. The subject has used any prescription (excluding hormonal birth control) or OTC medications including NSAIDs (i.e., ibuprofen, naproxen, and aspirin) as well as herbal or nutritional supplements, within 14 days before the study drug dosing. Subjects may have taken acetaminophen (up to 2 g per day) in the 14 days prior to study drug dosing.
6. The subject has any clinically significant abnormalities before dosing on Day 1 or has a history of disease, including: uncontrolled or poorly controlled hypertension; asthma or pulmonary disease; major cardiac ischemic symptoms, events, or interventions such as angina pectoris, myocardial infarction, acute coronary syndrome, decompensated congestive heart failure, coronary stent or bypass; history of cerebrovascular ischemic events (transient ischemic attack or stroke); major vascular ischemic symptoms such as intermittent claudication or vascular bypass or replacement surgery; significant cardiovascular, GI, neurological, endocrine, or renal disease; hepatic impairment; cholecystectomy; other condition known to interfere with the absorption, distribution, metabolism, or excretion of drugs; or clinically significant GI events.
7. The subject has a history or presence of any clinically significant abnormality in vital signs, ECG, or laboratory tests, or has any medical or psychiatric condition that, in the opinion of the investigator, may interfere with the study procedures or compromise subject safety (assessed at Screening and Check-in).
8. The subject is a cigarette smoker or has used nicotine or nicotine-containing products (e.g., snuff, nicotine patch, nicotine chewing gum, e-cigarettes) within 6 months before study drug dosing.
9. The subject has a history of alcohol abuse or drug addiction within the last year or consumes more than 1 unit (1 unit is equal to approximately ¼ pint [200 mL] of beer, 1 small glass [100 mL] of wine, or 1 measure [25 mL] of spirits) of alcohol a day. Alcohol is not allowed within 7 days before study drug dosing.
10. The subject has a positive test result for drugs of abuse, alcohol, or cotinine (indicating active current smoking) at Screening.
11. The subject is a habitual and heavy coffee drinker (more than 4 cups a day, 28 cups a week).
12. The subject is involved in strenuous activity or contact sports within at least 24 hours before study drug dosing.
13. The subject has donated blood or blood products within at least 30 days before the dose of study drug in this study.
14. The subject has received study drug in another investigational study within at least 30 days (or less than 5 half-lives of the investigational agent) prior to dosing in this study.
15. The subject is not suitable for entry into the study, in the opinion of the investigator.
16. The subject is an employee or family member of the investigator or clinic staff.

Continuing Eligibility at Check-in

Applies to Day −1 of the PILOT portion, Day −1 of the MAIN study and Day −1 of the first period of the FOOD-EFFECT sub study:

1. Females must have a negative serum pregnancy test.
2. All subjects must have a negative test results for drugs of abuse and alcohol
3. Subjects must have had no significant changes in overall health status since screening including the use of medications.
4. The subject is involved in strenuous activity or contact sports within at least 24 hours before study drug dosing.

Subjects with test results which do not meet the above inclusion/exclusion criteria may have the relevant test repeated once if it is thought to represent a laboratory error, a reversible, clinically insignificant intermittent condition, or is not consistent with the subject's historical values. If inclusion/exclusion criteria are not met after the repeat test, the subject should be considered a screen failure and should not be enrolled in the study. Subjects may be retested once.

3.2 Withdrawal/Discontinuation of Subjects from the Study

The duration of the study is defined for each subject as the date signed written informed consent is provided through the EOS procedures. Participation in the study is scheduled for a maximum duration of 34 days for each subject participating in the PILOT portion or MAIN study (27 days for Screening, 1 day for Check-In (Day −1), dosing on Day 1, PK blood sampling (Days 1-6), and the EOS procedures on Day 6) and 41 days for subjects who participate in the FOOD-EFFECT sub study. Period 1: 27 days for Screening, 1 day for Check-In (Day −1), dosing on Day 1, PK blood sampling (Days 1-6), EOP on Day 6; Period 2: 1 additional day for study drug washout (Day 7), dosing on Day 8, PK blood sampling (Days 9-13), and the EOS procedures on Day 13).

3.2.1 Reasons for Withdrawal/Discontinuation

Subjects may withdraw from the study at any time and for any reason. Every effort should be made to keep subjects in the study. The reasons for subjects not completing the study will be recorded. A subject must be withdrawn/discontinued from the study for any of the following reasons:
1. The subject tests positive for pregnancy.
2. The subject withdraws consent to participate in the study.
3. The subject does not continue to meet the protocol inclusion or exclusion criteria.
4. The subject experiences AEs or an AE that, in the investigator's opinion, require(s) withdrawal from the study.
5. The subject is noncompliant with the protocol.
6. The investigator decides to withdraw the subject for any medical reason.

A subject will also be discontinued if the study is terminated. Upon occurrence of a serious or intolerable AE, the investigator will confer with the sponsor. If a subject is discontinued because of an AE, the event will be followed until it is resolved or considered clinically stable.

3.2.2 Handling of Withdrawals/Discontinuations

Subjects are free to withdraw from the study at any time upon request. Subject participation in the study may also be stopped at any time.

Each subject in the PILOT portion and MAIN study is scheduled to receive a single dose of study drug. Subjects who participate in the FOOD-EFFECT sub study will receive a single dose of study drug twice, once in a fasted condition and once in a fed condition. When a subject withdraws from the PILOT portion, MAIN study, or FOOD-EFFECT sub study, the reason(s) for withdrawal shall be recorded by the investigator on the relevant page of the electronic case report form (eCRF). Whenever possible, any subject who receives a dose of study drug and then withdraws from the study prematurely will undergo all EOS assessments scheduled for Day 6 (Table 13).

It is vital to obtain follow-up data on any subject discontinued because of an AE or serious AE (SAE). In every case, efforts must be made to undertake protocol-specified, safety, follow-up procedures.

3.2.3 Subject Replacement

The intent is that subjects will not be replaced unless it is deemed that a critical number of subjects are not evaluable.

4. Study Drug

This is an open-label PK study. Each subject is scheduled to receive a single 25-mg dose of TRM-201 in the PILOT portion and the MAIN study, and a single 25-mg dose of TRM-201 twice in the FOOD-EFFECT sub study. TRM-201 manufactured and formulated as Batch 5 (B18090) and Batch 6 (B18091), above, will be used in the study.

4.1 Administration of Study Drug

Study drug will be co-administered orally with approximately 250 mL of room temperature water, and up to an additional 250 mL of water will be allowed, if necessary, to aid in swallowing the study drug. Study staff will ensure that at least 250 ml of water is consumed with the dose of study drug and will perform a hand and mouth check after dosing to ensure the tablet has been swallowed.

PILOT Portion and MAIN Study

After fasting for at least 10 hours overnight (Table 13), subjects will take, a single dose (1 tablet) of TRM-201 on the morning of Day 1 administered as described above, supervised by clinic staff. A hand and mouth check will be performed after dosing to ensure the tablet has been swallowed. During the period between 1 hour before and 1 hour after study drug dosing, subjects may drink only the water permitted for study drug administration.

FOOD-EFFECT Substudy

Subjects will be randomized 1:1 into the two sequences: fasted followed by fed, and fed followed by fasted. During the fasted period, subjects will fast and be administered a single dose of TRM-201 as described above. A hand and mouth check will be performed after dosing to ensure the tablet has been swallowed. During the period between 1 hour before and 1 hour after study drug dosing, subjects may drink only the water permitted for study drug administration.

During the fed period, subjects will fast overnight for at least 10 hours and will take a single dose (1 tablet) of TRM-201 as described above within at least 30 minutes of starting a high fat breakfast. A hand and mouth check will be performed after dosing to ensure the tablet has been swallowed. During the period between 1 hour before and 1 hour after study drug dosing, subjects may drink only the water permitted for study drug administration.

4.2 Identity of Study Drug

The study drug, TRM-201, is an immediate-release tablet that contains 25-mg rofecoxib. The 7.25-mm diameter tablets are off-white, round, and uncoated with no markings. TRM-201 tablets are for oral administration.

TRM-201 tablets contain the active ingredient rofecoxib (25 mg) and inactive excipients. Each tablet contains the following inactive excipients: croscarmellose sodium, hydroxypropyl cellulose, lactose, magnesium stearate, microcrystalline cellulose, and yellow ferric oxide. All excipients comply with standards described in United States Pharmacopeia-National Formulary, European Pharmacopeia, and Japanese Pharmacopeia.

4.3 Management of Clinical Supplies 4.3.1 Study Drug Packaging and Storage

TRM-201 oral tablets will be provided as bulk supply in high-density polyethylene bottles. All packaging and labeling will be performed according to Good Manufacturing Practice and Good Clinical Practice (GCP) rules. The lot number and date of manufacture for the clinical lot used in the study will be provided to the clinical site and will be reported in the Clinical Study Report. All study drug will be labeled with:

Protocol number

Sponsor's name and address

Investigational New Drug statement

Instructions for use and storage

All study drug must be stored at 20 to 25° C. (excursions permitted in the range of 15 to 30° C.), in accordance with the labeled instructions, in a secure cabinet or room with access restricted to necessary clinic personnel. The site will keep a temperature log to establish a record of compliance with storage conditions.

The clinical unit pharmacy will prepare the dosing for each subject according to the schedule of events (Table 13).

4.3.2 Study Drug Accountability

The investigator will maintain accurate records of receipt of all study drug, including dates of receipt. In addition, accurate records will be kept regarding when and how much study drug is dispensed and used by each subject in the study. Reasons for departure from the expected dispensing regimen must also be recorded on standard clinic drug accountability and packaging forms. At the completion of the study, to satisfy regulatory requirements regarding drug accountability, all study drug will be reconciled and retained or destroyed according to applicable regulations.

4.4 Method of Assigning Subjects to Treatment

In the PILOT portion, subjects who meet all inclusion criteria and none of the exclusion criteria and all of the continuing eligibility criteria will receive TRM-201 according to the schedule of events (Table 13). Similar numbers of male and female subjects should be enrolled. Additional subjects may be screened to attain the overall demographic parameters of the subjects enrolled in the Schwartz PK study.

Once a decision to continue is made after the PILOT portion is completed, subjects will be screened to enter the MAIN study or the FOOD-EFFECT sub study. In the MAIN study and FOOD-EFFECT sub study, subjects who meet all of the inclusion criteria and none of the exclusion criteria and all of the continuing eligibility criteria will receive TRM-201 according to the schedule of events (Table 13).

Similar numbers of male and female subjects should be enrolled. Additional subjects may be screened to attain the overall demographic parameters of the subjects enrolled in the Schwartz PK study.

Subjects will be randomized in a 2:1:1 ratio to one of three groups:

Main study—fasted (16 subjects)

FOOD-EFFECT sub study—fasted/fed sequence (8 subjects)

FOOD-EFFECT sub study—fed/fasted sequence (8 subjects)

4.5 Blinding

This is an open-label study: there is no blinding of study drug.

4.6 Treatment Compliance

All doses of study drug will be administered in the clinic under direct observation of clinic staff and will be recorded in the eCRF. Clinic staff will confirm that the subject has swallowed the dose of study drug.

The date and time of study drug dosing will be recorded on the appropriate page of the eCRF.

4.7 Prior and Concomitant Therapy

The investigator or designee must record the use of prior medications (all medication taken within at least 28 days before Screening) and concomitant therapy (including both drug and nondrug therapies and all prescribed, OTC, and alternative medicines) in the eCRF. This includes drugs that are used as-needed. Any changes in concomitant medications will also be recorded in the subject's eCRF. The minimum requirement is that the drug name and dates of dosing are to be recorded.

Use of prescription medications (excluding hormonal birth control) and OTC medications (except acetaminophen), including NSAIDs (i.e., ibuprofen, naproxen, and aspirin) as well as herbal or nutritional supplements (exclusion criterion 5), is prohibited from 14 days before study drug dosing through the EOS. Use of acetaminophen is prohibited from Check-In through the EOS. Violation of these prohibitions will result in the subject's discontinuation from the study.

5. Study Procedures, Assessments, and Endpoints

Before performing any study procedures, all potential subjects will sign an informed consent form (ICE). Subjects will have the opportunity to have any questions answered before signing the ICE. The investigator must address all questions raised by the subject. The investigator or designee will also sign the ICE.

The schedule of events for the study is presented in Table 13. The ECG recordings must precede blood sampling for PK assessments at the specified time points on Day 1 and at the EOS visit, and PK blood sampling must occur within the sampling windows. Timings of PK blood sampling and ECG assessments will be calculated from time 'O', the time of study drug dosing on Day 1 and complete on Day 6 at the 120 hour PK sample draw and from time 'O', the time of study drug dosing on Day 8 and complete on Day 13 for subjects who participate in the FOOD-EFFECT sub study.

TABLE 13

Schedule of Events

| Phase | Screening | Check-in | Pharmacokinetic Sampling | | | | | EOP/EOSg | Period-2 Subjects Only |
|---|---|---|---|---|---|---|---|---|---|
| Day | −28 to −2 | −1 | 1 | 2 | 3 | 4 | 5 | 6 | 7 |
| Period-2 Days | | | 8 | 9 | 10 | 11 | 12 | 13 | |
| Informed consent | X | | | | | | | | |
| Demographics | X | | | | | | | | |
| Medical history | X | X | | | | | | | |
| Viral serology | X | | | | | | | | |

TABLE 13-continued

Schedule of Events

| Phase | Screening | Check-in | Pharmacokinetic Sampling | | | | | EOP/EOSg | Period-2 Subjects Only |
|---|---|---|---|---|---|---|---|---|---|
| Serum follicle-stimulating hormone (females only) | X | | | | | | | | |
| Admission to clinic | | X | | | | | | | |
| Serum pregnancy test (females only) | X | X | | | | | | X | |
| Urine drug screen (including alcohol and cotinine) | X | X | | | | | | | |
| Clinical laboratory testing (blood/urine) | X | X | | | | | | X | |
| Height, weight, and body mass index | X | weight ONLY | | | | | | weight ONLY | |
| Physical examination[a] | X | X | | | | | | X (EOS ONLY) | |
| Vital sign measurements[b] | X | X | X | X | X | X | X | X | |
| 12-Lead ECG assessment[c] | X | X | X | | | | | X (EOS ONLY) | |
| Eligibility assessment (initial and continuing) | X | X | | | | | | | |
| PILOT, MAIN STUDY and fasted-period meal scheduled[i] | | X | X | X | X | X | X | X | X |
| Study drug administration[e] | | X | | | | | | | |
| FOOD-EFFECT fed-period meal schedule[f] | | X | X | X | X | X | X | X | X |
| Pharmacokinetic sample collection (see Table 8) | | | X | X | X | X | X | | |
| Adverse event assessment | | | X | X | X | X | X | X | |
| Prior or concomitant medication assessment | X | X | X | X | X | X | X | | |
| Discharge from clinic | | | | | | | | X (EOS ONLY) | |

Abbreviations: ECG, electrocardiogram; EOS, end of study; EOP, end of period.

Note: The order of procedures on each day should follow the order of presentation in Table 13 (top to bottom). When procedures overlap or occur at the same time point, all blood sampling should follow vital signs or ECGs, and PK sampling should be timed to occur last and as close to the scheduled time window as possible. Timings of PK blood sampling and electrocardiogram assessments will be calculated from time "0", the time of study drug dosing. Period-2 subjects will remain in the clinic and be dosed on Day 8, 2 days after EOP.

[a]A full physical examination will be performed at Screening (at minimum, assessment of skin, head, ears, eyes, nose, throat, neck, thyroid, lungs, heart, cardiovascular, abdomen, lymph nodes, and musculoskeletal system/extremities). A brief physical examination will be performed at Check-In and EOS (at minimum, assessment of skin, lungs, cardiovascular system, and abdomen). Interim physical examinations may be performed at the discretion of the investigator, if necessary, to evaluate adverse events or clinical laboratory abnormalities.

[b]Vital signs will include systolic and diastolic blood pressure, pulse rate, respiratory rate, and oral body temperature, after the subject has been seated for at least 5 minutes. On Day 1 (and Day 8 of FOOD-EFFECT study), vital signs will be measured within 120 minutes before study drug dosing and at the 2-hour, 3-hour and 7.5-hour time points. At these time points (2 h, 3 h and 7.5 h) only systolic and diastolic blood pressure, pulse rate and respiratory rate will be assessed. On Days 2 through 6, vital signs will be assessed within 15 minutes before the first PK blood sample of the day. See Note.

[c]After the subject has been in the supine position for at least 5 minutes, single 12-lead ECG recordings will be taken at Screening, Check-in, the 2-hour and 3-hour time point, and EOS.

[d]For all portions of the study the fasting period will begin at the day of Check-In, for at least 10 hours overnight before study drug administration and again on Day 7 for the FOOD-EFFECT study.

[e]Study drug will be administered after vital sign measurements have been completed. Study drug will be administered with ~250 mL of room temperature water. Up to an additional ~250 mL of water will be allowed, if necessary, to aid in swallowing the study drug. Subjects will maintain an upright position (seated or standing) for at least 4 hours after dosing. Dosing for Period-2 subjects must occur at least 7 days after Period-1 dosing.

[f]FOOD-EFFECT substudy - fed portion: Subjects will fast at least 10 hours overnight. In the morning prior to study drug administration they will be given a high-fat breakfast to begin at least 30 minutes prior to dosing. After the 4-hour PK blood sampling, Subjects should then receive standardized meals according to the clinic's standard procedures and scheduled at consistent times. Meal may begin immediately after a PK timepoint and should end at least 15 minutes before a PK sampling time point.

[g]For subjects in the FOOD-EFFECT substudy - this visit is considered the end of the period (EOP) for Dosing Period 1 and EOS after Dosing Period 2.

5.1 Pharmacokinetic Procedures, Assessments, and Endpoints

The time points and windows for PK blood sampling for the PILOT portion, Main study and FOOD-EFFECT substudy are presented in Table 14 below. For each sample, approximately 3 mL of blood will be drawn. The samples may be obtained by a straight stick or via an in-dwelling intravenous (IV) catheter in a forearm vein. Additional details for the collection, processing, storage, and shipping of PK samples will be provided in the study manual.

TABLE 14

Times and Windows for Pharmacokinetic Blood Sampling for PILOT portion, Main Study and FOOD-EFFECT substudy

| Unit of Time | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| Minutes | | | | Hours | | | | | | | | | | | | | | | | | | | | | | | | | | |
| Timepoint | | | | | | | | | | | | | | | | | | | | | | | | | | | | | | |
| 0[a] | 15 | 30 | 45 | 1 | 1.5 | 2 | 3 | 4 | 5 | 6 | 7.5 | 9 | 12 | 15 | 18 | 21 | 24 | 27 | 30 | 33 | 36 | 39 | 42 | 48 | 52 | 60 | 72 | 96 | 120 |
| Window (min) | ±5 min | | | | ±10 min | | | | ±15 min | | | | ±30 min | | | | | | | ±60 min | | | | | | | | | | |

Abbreviation: mm; minutes.
[a]The blood sample for time 0 should be taken within 1 hour before dosing with study drug, and prior to breakfast in the fed-state period.
Note - Samples will be collected after each rofecoxib dose in the food-effect substudy Pharmacokinetic samples will be analyzed using a validated assay for rofecoxib in human plasma. Assay results and validation details will be provided in a separate bioanalytical report.

The following PK parameters for rofecoxib will be calculated as primary endpoints using standard noncompartmental methods for both the PILOT portion and MAIN study, and the FOOD-EFFECT sub study: $AUC_{0-\infty}$ and $C_{max}$. Secondary endpoints include $T_{max}$, and $t_{1/2}$. Additional PK parameters (e.g., CL/F, and $V_d/F$) will also be calculated using standard noncompartmental methods.

5.2 Safety Assessments

The timing and frequency of all safety assessments is listed in the schedule of events (Table 13).

Safety and tolerability will include monitoring and recording of AEs, clinical laboratory assessments (hematology, serum chemistry, and urinalysis), vital sign measurements, 12-lead ECG assessments, and physical examination findings.

For all safety assessments, the investigator will determine whether results are clinically significant, which is defined as any variation in a result that has medical relevance and may result in an alteration in medical care (e.g., active observation, diagnostic measures, or therapeutic measures). If clinical significance is noted, the result and reason for significance will be documented on the AE page of the subject's eCRF and the investigator will monitor the subject until the result has reached the reference range or the result at Screening, or until the investigator determines that follow-up is no longer medically necessary.

Any abnormal laboratory test results (hematology, clinical chemistry, or urinalysis) or other safety assessments (e.g., ECGs, vital sign measurements), including those that worsen from baseline, felt to be clinically significant in the medical and scientific judgment of the investigator are to be recorded as AEs or SAEs.

5.2.1 Adverse Events 5.2.1.1 Definitions of Adverse Events

The investigator is responsible for reporting all AEs that are observed or reported during the study, regardless of their relationship to study drug or their clinical significance. If there is any doubt as to whether a clinical observation is an AE, the event should be reported.

An AE is defined as any untoward medical occurrence in a subject enrolled into this study regardless of its causal relationship to study drug. Subjects will be instructed to contact the investigator at any time after enrollment if any symptoms develop.

A treatment-emergent AE (TEAE) is defined as any event not present before exposure to study drug or any event already present that worsens in either intensity or frequency after exposure to study drug.

5.2.1 Serious Adverse Events

An SAE is defined as any event that
results in death
is immediately life threatening
requires inpatient hospitalization or prolongation of existing hospitalization
results in persistent or significant disability/incapacity
is a congenital anomaly/birth defect Important medical events that may not result in death, be life threatening, or require hospitalization may be considered SAEs when, based upon appropriate medical judgment, they may jeopardize the subject or may require medical or surgical intervention to prevent one of the outcomes listed in this definition. Examples of such medical events include allergic bronchospasm requiring intensive treatment in an emergency room or at home, blood dyscrasias or convulsions that do not result in inpatient hospitalization, or the development of drug dependency or drug abuse.

5.2.1.3 Eliciting and Documenting Adverse Events

Adverse events will be assessed from the time of study drug dosing until all EOS procedures are complete.

Subjects will be asked a standard nonleading question to elicit any medically related changes in their well-being.

In addition to subject observations, AEs identified from any study data (e.g., laboratory values, physical examination findings, ECG changes) or identified from review of other documents that are relevant to subject safety will be documented on the AE page in the eCRF.

5.2.1.4 Reporting Adverse Events

All AEs reported or observed during the study will be recorded on the AE page in the eCRF. Information to be collected includes the following:
event term
time of onset
investigator-specified assessment of severity and relationship to study drug
time of resolution of the event
seriousness
any required treatment or evaluations
outcome All AEs will be followed to adequate resolution. The Medical Dictionary for Regulatory Activities (MedDRA; Version 21.1) will be used to code all AEs.

5.2.1.5 Reporting Serious Adverse Events

Any AE that is considered serious by the investigator or which meets SAE criteria must be reported to the medical monitor (i.e., within at least 24 hours) after the clinic staff first learn about the event. The investigator will assess whether there is a reasonable possibility that the study drug caused the SAE.

5.2.1.6 Suspected Unexpected Serious Adverse Reactions

The sponsor will promptly evaluate all suspected unexpected serious adverse reactions (SUSARs) against cumulative product experience to identify and expeditiously communicate possible new safety findings to the investigator, IRB, and applicable health authorities based on applicable legislation.

To determine reporting requirements for single AE cases, the sponsor will assess the expectedness of these events using the TRM-201 investigator's brochure. The sponsor will compare the severity of each SUSAR, and the cumulative event frequency reported for the study with the severity and frequency reported in the TRM-201 investigator's brochure.

Reporting requirements will also be based on the investigator's assessment of causality and seriousness, with allowance for upgrading by the sponsor as needed.

5.2.1.7 Assessment of Severity

The severity, or intensity, of an AE refers to the extent to which an AE affects the subject's daily activities. The intensity of the AE will be rated as mild, moderate, or severe using the following criteria:

Mild: These events require minimal or no treatment and do not interfere with the subject's daily activities.

Moderate: These events result in a low level of inconvenience or require minor therapeutic measures. Moderate events may cause some interference with normal functioning.

Severe: These events interrupt a subject's usual daily activity and may require systemic drug therapy or other treatment. Severe events are usually incapacitating.

Changes in the severity of an AE should be documented to allow an assessment of the duration of the event at each level of intensity to be performed. Adverse events characterized as intermittent do not require documentation of onset and duration of each episode.

5.2.1.8 Assessment of Causality

The investigator's assessment of an AE's relationship to study drug is part of the documentation process, but it is not a factor in determining what is or is not reported in the study.

The investigator will assess causality (i.e., whether there is a reasonable possibility that the study drug caused the event) for all AEs and SAEs. The relationship will be classified as follows:

Not related: There is not a reasonable possibility of relationship to study drug. The AE does not follow a reasonable temporal sequence from study drug administration, or can be reasonably explained by the subject's clinical state or other factors (e.g., disease under study, concurrent diseases, and concomitant medications).

Related: There is a reasonable possibility of relationship to study drug. The AE follows a reasonable temporal sequence from study drug administration and cannot be reasonably explained by the subject's clinical state or other factors (e.g., disease under study, concurrent diseases, or concomitant medications), represents a known reaction to the study drug or other drugs in its class, is consistent with the known pharmacological properties of the study drug (and/or recurs with re-challenge, if applicable).

5.2.1.9 Follow-Up of Subjects Reporting Adverse Events

All AEs must be reported in detail on the appropriate page in the eCRF and followed to satisfactory resolution, until the investigator deems the event to be chronic or not clinically significant, or until the subject is considered stable.

5.2.2 Clinical Laboratory Assessments

The following clinical laboratory assessments will be performed:

Hematology: hematocrit, hemoglobin, mean corpuscular hemoglobin, mean corpuscular hemoglobin concentration, mean corpuscular volume, platelet count, red blood cell count, and total and differential leukocyte count Serum Chemistry: Alanine aminotransferase, albumin, alkaline phosphatase, aspartate aminotransferase, bilirubin (total), blood urea nitrogen, calcium, carbon dioxide, chloride, total cholesterol, creatine phosphokinase, creatinine, gamma-glutamyltransferase, globulin, glucose, lactate dehydrogenase, phosphorus, potassium, sodium, total protein, triglycerides, and uric acid Urinalysis: Appearance, bilirubin, color, glucose, ketones, leukocyte esterase, reflex microscopy (performed if dipstick is positive for protein or the blood value is 1+ or greater; and includes bacteria, casts, crystals, epithelial cells, red blood cells, and white blood cells), nitrites, occult blood, pH, protein, specific gravity, turbidity, and urobilinogen Serology: Hepatitis B surface antigen, hepatitis C virus antibody, and human immunodeficiency virus antibody types 1 and 2 (Screening only)

Other analyses: All subjects: Urine drug screen (alcohol, amphetamines, barbiturates, benzodiazepines, cannabinoids, cocaine, cotinine, methylenedioxymethamphetamine, opiates, phencyclidine, propoxyphene, and tetrahydrocannabinol) Female subjects: serum Follicle-stimulating hormone, serum and urine β-human chorionic gonadotropin.

The clinical laboratory that performs the tests will provide the reference ranges for all clinical laboratory parameters. Clinical laboratory tests may be repeated at the discretion of the investigator, if necessary, for assessment of inclusion and exclusion criteria or evaluation of clinical laboratory abnormalities.

5.2.3 Vital Sign Measurements

Vital signs will include systolic and diastolic blood pressure, pulse rate, respiratory rate, and oral body temperature, after the subject has been seated for at least 5 minutes. Vital sign measurements will be conducted within the 120 minutes before dosing of study drug (applicable on Day 1 only) and 15 minutes before any blood sampling. A single repeat measurement is permitted at Screening to determine eligibility and Check-In to confirm continued eligibility. On Day 1 and Day 8 (Dosing Period 2 of FOOD-EFFECT study) systolic and diastolic blood pressure, pulse rate and respiratory rate will be assessed at the 2-hour, 3-hour and 7.5 hour time points.

5.2.4 Electrocardiogram Assessments

After the subject has been in the supine position for at least 5 minutes, single 12-lead ECG recordings will be made at Screening, Check-in, the 2-hour and 3-hour time points, and EOS. A single repeat measurement is permitted at Screening to determine eligibility and at Check-In to confirm continued eligibility. Measurements of the following intervals will be reported: RR interval, PR interval, QRS width, QT interval, and QTcF and may be interpreted for abnormality by the ECG machine. Any abnormalities including rhythm; presence of arrhythmia or conduction defects; morphology; any evidence of myocardial infarction; or ST-segment, T-Wave, and U-Wave abnormalities should be assessed for clinical significance and noted.

5.3 Pregnancy

Pregnancy is not regarded as an AE unless there is a suspicion that an investigational product may have interfered with the effectiveness of a contraceptive medication. Any pregnancy that is detected after study drug administration and during study participation must be reported using the same procedures as an SAE, but using a clinical study pregnancy form. The pregnancy must be followed up (with the subject's consent) to determine outcome (including spontaneous miscarriage, elective termination, normal birth, or congenital abnormality) and status of mother and child, even if the subject was discontinued from the study. Pregnancy complications and elective terminations for medical reasons should not be reported as an AE or SAE. Spontaneous miscarriages must be reported as an SAE.

Any SAE occurring in association with a pregnancy, brought to the investigator's attention after the subject has completed the study, and considered by the investigator as possibly related to the study treatment, must be promptly reported to the Sponsor.

5.3.1 Physical Examination Findings

A full physical examination will be performed at Screening (at minimum, assessment of skin, head, ears, eyes, nose, throat, neck, thyroid, lungs, heart, cardiovascular, abdomen, lymph nodes, and musculoskeletal system/extremities). A brief physical examination will be performed at Check-In and at the EOS. At a minimum, assessment of skin, lungs, cardiovascular system, and abdomen will be performed. Interim physical examinations may be performed at the discretion of the investigator, if necessary, to evaluate AEs or clinical laboratory abnormalities.

samples: 180 mL, clinical laboratory samples: 40 mL) for subjects participating in the FOOD-EFFECT study. Additional assessments may be required, but the maximum amount of blood drawn for any subject will not exceed 250 mL.

6. Statistical and Analytical Plan

The interim analysis of the PILOT portion is only for futility; hence, there is no impact of that interim analysis on the type-1 error potential for the final analyses (all fasted data from PILOT portion, MAIN study, and the FOOD-EFFECT sub study combined).

6.1 Sample Size Calculations 6.2 Comparability of TRM-201 with Previously Marketed Rofecoxib Consistent with the Schwartz study, the total sample size of 50 evaluable subjects is considered sufficient for the objectives of the study. Back-calculation of summary statistics from the Schwartz data yielded natural-log-scale SDs of 0.33 and 0.31 for $AUC_{0-\infty}$ and $C_{max}$, respectively. Power is computed as the probability that the upper limit of a 90% CI for the geometric mean ratio (GMR=observed geometric mean from this trial divided by the historical control value) for these parameters falls below 1.25. Assuming a natural-log-scale SD equal to 0.33, N=50 has approx. 80% power if the TRUE underlying geometric mean ratio (GMR)=1.11, and approximately 90% power if the TRUE underlying GMR=1.08. The maximum OBSERVED GMR that would reject the null hypothesis is 1.15. The power for $C_{max}$ is slightly greater since associated SD is smaller than that for $AUC_{0-\infty}$; however, for perspective on actual values for the new formulation, Table 15 shows $AUC_{0-\infty}$ and $C_{max}$ geometric mean values associated with the ratios computed from SD=0.33.

TABLE 15

Power Estimates for Comparability between TRM-201 and Previously Marketed Rofecoxib

| | Geometric Mean Ratios | | | |
|---|---|---|---|---|
| Maximum OBS. Fold-Incr for Comparability | | 1.15[a] | | |
| TRUE Fold-Incr. for ~80% power | | 1.11[a] | | |
| TRUE Fold-Incr. for ~90% power | | 1.08[a] | | |
| PK Parameter | Parameter | Geometric Means | Historical mean value from the Schwartz study | 1.25 Times the historical mean value |
| $C_{max}$ | Max. OBS. Geo.Mean for Comparability | 250 | 217 | $C_{max}$ 25 mg | 271 |
| | TRUE Geo.Mean for ~80% power | 241 | 217 | | 271 |
| | TRUE Geo.Mean for ~90% power | 234 | 217 | | 271 |
| $AUC_{0-\infty}$ | Max. OBS.Geo. Mean for Comparability | 4369 | 3799 | $AUC_{0-\infty}$ 25 mg | 4749 |
| | TRUE Geo.Mean for ~80% power | 4217 | 3799 | | 4749 |
| | TRUE Geo.Mean for ~90% power | 4103 | 3799 | | 4749 |
| $C_{max}$ | Max. OBS.Geo. Mean for Comparability | 281 | 244 | $C_{max}$ 12.5 mg dose- | 305 |
| | TRUE Geo.Mean for ~80% power | 271 | 244 | adjusted to | 305 |
| | TRUE Geo.Mean for ~90% power | 264 | 244 | 25 mg | 305 |

Abbreviations;
Geo.Mean, geometric mean;
Incr, increase;
Max., maximum;
OBS., observed.
[a]Fold-increase expressed relative to the historical mean value 5.4 Sample Collections The total amount of blood collected from each subject over the duration of the study is expected to be approximately 130 mL (PK samples: 90 mL, clinical laboratory samples: 40 mL) for subjects participating in the PILOT portion and MAIN study and approximately 220 mL (PK 6.1.2 Comparison of TRM-201 Under Fed and Fasted Conditions There are not pre-specified bounds for the fed/fasted GMR's for AUC and Cmax derived from the FOOD-EFFECT sub study. However, those GMR's and associated 90% CI's will be derived from the 2-period crossover model to estimate the food effect. Koytchev, et al. reported data from which intra-subject SB's for AUC and Cmax were back-calculated as 0.11 and 0.14 on the natural-log-scale, respectively (Koytchev, R. et al., *Arzneimittelforschung*, 2004, 54(9), 624-628). Conservatively, using the value 0.15 for natural log-scale within-subject SD, Table 16 below indicates 90% CI's for GMR, back-transformed from the natural-log calculation scale via a standard crossover design ANOVA.

TABLE 16

Power estimates for FOOD-EFFECT Substudy

| OBSERVED | N = 12 | | N = 15 | |
|---|---|---|---|---|
| GMR | 90% LCL | 90% UCL | 90% LCL | 90% UCL |
| 0.5 | 0.45 | 0.56 | 0.45 | 0.55 |
| 0.67 | 0.60 | 0.75 | 0.61 | 0.74 |
| 0.8 | 0.72 | 0.89 | 0.73 | 0.88 |
| 1 | 0.89 | 1.12 | 0.91 | 1.10 |
| 1.25 | 1.12 | 1.40 | 1.13 | 1.38 |
| 1.5 | 1.34 | 1.68 | 1.36 | 1.65 |
| 2 | 1.79 | 2.23 | 1.82 | 2.20 |

NOTE:
calculations via standard 2-period crossover design ANOVA assuming natural-log-scale SD = 0.15

6.2 Analysis Sets

The following analysis sets will be used in the statistical analyses:

The PK analysis set will include subjects who receive a single dose of TRM-201 and have sufficient concentration data to support accurate estimation of at least one PK parameter. Subjects who experience vomiting within at least 2 times the median $T_{max}$ (approximately 6 hours) after study drug dosing will be excluded from the PK analysis.

The PK data from Main study (including the PILOT portion) will be combined with the PK data from the fasted portion of the FOOD-EFFECT sub study to form the basis of the comparison to historical pharmacokinetic parameters of previously marketed rofecoxib. The PK data from the fed portion of the FOOD-EFFECT sub study will only be compared with the PK data from the fasted portion of the FOOD-EFFECT sub study.

The safety analysis set will include all subjects who receive at least 1 dose of study drug.

6.3 Description of Subgroups to be Analyzed

The relationship of $AUC_{0-\infty}$ and $C_{max}$ to age and to BMI will each be assessed via scatter plots and correlation coefficients. If appropriate, additional modeling of those relationships may be carried out. Summary statistics for $AUC_{0-\infty}$ and $C_{max}$ will be provide by gender, age categories (divided into tertiles), race categories, and ethnicity categories.

6.4 Statistical Analysis Methodology

Details of all statistical analyses will be described in a separate statistical analysis plan. All data collected will be presented in data listings. Data from subjects excluded from an analysis population will be presented in the data listings but will not be included in the calculation of summary statistics or statistical analysis.

For categorical variables, frequencies and percentages will be presented. Continuous variables will be summarized using descriptive statistics (number of subjects, mean, median, SD, minimum, maximum, geometric mean, natural-log-scale SD).

Baseline demographic and background variables will be summarized overall for all subjects. The number of subjects who enroll in the study and the number and percentage of subjects who complete the study will be presented. Frequency and percentage of subjects who withdraw or discontinue from the study, and the reason for withdrawal or discontinuation, will also be summarized. Statistical analysis will be performed using SAS software Version 9.4 or later. Continuous variables will be summarized using the mean, the standard deviation, median, minimum value, and maximum value. Categorical variables will be summarized using frequency counts and percentages. Data will be listed in data listings.

6.4.1 Analysis of Pharmacokinetic Endpoints

Individual plasma concentrations for rofecoxib and PK sampling time deviation data will be presented in a data listing. Plasma concentration data will be summarized by time point using the following descriptive statistics: number of subjects, arithmetic mean, SD, coefficient of variation (CV), geometric mean, natural-log-scale SD, geometric CV, median, minimum, and maximum. Individual plasma concentration versus actual time profiles will be presented on both linear and semilogarithmic scales. Additionally, arithmetic mean concentration versus scheduled time profiles will be presented on linear scales and geometric means on semilogarithmic scales.

The PK parameters of rofecoxib will be analyzed based on the actual sampling times. All parameters will be calculated using the Phoenix® WinNonlin® version 6.4 or higher (Certara USA Inc., Princeton, N.J.) or SAS® version 9.3 or higher (SAS Institute Inc., Cary, N.C.). The individual PK parameters will be presented in data listings.

6.4.1.1 PILOT Portion, MAIN Study and FOOD-EFFECT Substudy

Summary statistics for the primary PK endpoints, $AUC_{0-\infty}$ and $C_{max}$, will include n, arithmetic mean, CV, SD, geometric mean, natural-log-scale SD, median, minimum, and maximum, along with the associated 90% CI computed on the natural-log-scale and back-transformed to the original measurement scale. The GMR to historical control values and associated 90% CIs will be computed on log scale and back-transformed to the ratio scale; the reference values are from the Schwartz study: 3799 ng·hr/mL and 217 ng/mL for $AUC_{0-\infty}$ and $C_{max}$, respectively.

Without being bound by theory, the primary hypotheses for both $AUC_{0-\infty}$ and $C_{max}$ are:

Null Hypothesis: the TRUE underlying GMR (new formulation versus historical control) is at least 1.25

Alternative Hypothesis: the TRUE underlying GMR (new formulation versus historical control) is less than 1.25

These null hypotheses will each be tested via comparing to 1.25 the upper limit of a 90% CI for the geometric mean computed on the natural-log-scale and back-transformed to the original scale. If the upper 90% CI lies below 1.25 times the historical control geometric mean value, the null hypothesis will be rejected, and the alternative hypothesis will be concluded. The $AUC_{0-\infty}$ and $C_{max}$ null hypotheses need to be rejected to support a conclusion that the new formulation is sufficiently similar to the formulation that yielded the historical control data.

Sensitivity analyses will be carried out separately for $AUC_{0-\infty}$ and $C_{max}$ using age- and race-adjusted geometric means that match the mean age and race distribution of the historical control data. Secondary analyses similar to the primary will be carried out in comparison to a lower limit of 0.8 times the respective historical control values.

The $T_{max}$ will be summarized by n, arithmetic mean, CV, SD, median, minimum, maximum, and 90% CI for the median via normal approximation. Apparent $t_{1/2}$ will be summarized by n, arithmetic mean, CV, SD, harmonic mean, jack-knife SD, median, minimum, and maximum. The 90% CI for harmonic mean will be computed on the inverse scale and back-transformed to the actual scale. The 90% CIs for median $T_{max}$ and harmonic mean $t_{1/2}$ will be compared to their respective historical control values.

In addition to the proposed statistical approach to calculate the maximum observed geometric mean ratio for the primary PK parameters using the traditional bioequivalence reference range of 1.25, an alternative approach considered incorporating the variability in the PK parameters observed in the Schwartz study. The results for the maximum observed geometric mean ratio for $AUC_{0-\infty}$ and $C_{max}$ that would yield 90% CI<1.33 were similar to those of the proposed approach.

Summary statistics for the secondary PK endpoints, including apparent plasma clearance (CL/F) and apparent volume of distribution ($V_d$/F) will include n, arithmetic mean, SD, CV, geometric mean, natural-log-scale SD, median, minimum, maximum, along with the associated 90% CI computed on the natural-log-scale and back-transformed to the original measurement scale, as appropriate.

6.4.1.2 FOOD-EFFECT Sub-Study (all PK Parameters from Subjects Who Received 2 Single Doses, One Fasted, and One Fed)

The PK parameters computed from the FOOD-EFFECT sub study will be analyzed via the standard 2-period crossover design ANOVA including factors for treatment, period, and subject via the same transformations as for the MAIN study. The same summary statistics for the FOOD-EFFECT study will be derived from that analysis model via similar methods as for the MAIN study, however, there are no pre-specified criteria for the AUC and Cmax GMR 90% CI's.

6.4.2 Analysis of Safety Endpoints

All safety data will be summarized for the PILOT portion, MAIN study, and FOOD-EFFECT sub study combined. Subjects who received 2 single doses will be counted once with all of their safety data combined. The incidence of adverse events will be presented by the MedDRA system organ class and preferred term, relationship to the test article, and severity. Descriptive statistics of clinical laboratory results and vital signs will be presented, as well as summaries of changes from baseline (from the Check-in visit(s)) and of clinically notable values.

All AE data will be presented in a data listing by study part and within the FOOD-EFFECT sub study by treatment sequence. TEAEs will be summarized overall, as well as by severity and relationship to study drug. Serious AEs and AEs leading to discontinuation of study drug will also be presented in the data listings and summarized.

Actual values and changes from Baseline for clinical laboratory test results, vital sign measurements, and 12-lead ECG results will be summarized at each time point using descriptive statistics (number of subjects, mean, SD, median, minimum, and maximum). Shift tables will be generated for clinical laboratory test results. Physical examination findings will be presented in a data listing.

6.4.3 Other Analyses

Summary statistics will be provided for demographics, medical history, physical examination and social history.

6.4.4 Handling of Missing Data

Plasma concentrations that are below the limit of quantification (BLQ) will be treated as zero for descriptive statistics. Mean BLQ concentrations will be presented as BLQ, and the SD and CV will be reported as not applicable. Missing concentrations will be excluded from the calculations.

For the PK analysis, BLQ values will be treated as zero with the exception that a BLQ value between 2 quantifiable concentrations will be set as missing. Missing concentrations will be treated as missing from the PK parameter calculations. If consecutive BLQ concentrations are followed by quantifiable concentrations in the terminal phase, those concentrations after BLQ concentrations will be treated as missing.

6.4.5 Interim Analyses

Samples will be assayed, and PK calculations will be performed on the samples obtained from the subjects enrolled in the PILOT study. If substantial differences in the exposure of TRM-201 are observed in the PILOT study compared to the expected historical data for rofecoxib the study may not continue with the current formulation of study drug.

Note that the interim analysis of the PILOT portion is only for futility; hence, there is no impact of that interim analysis on the type 1 error potential for the final analyses (all fasted data from the PILOT portion, MAIN study, and the FOOD-EFFECT sub study combined).

B. Results from PK 101 Pharmacokinetic Study

The Cmax and $AUC_{0-\infty}$ values in individual subjects for a 25 mg dosage of rofecoxib (TRM-201) are presented in Table 17 below.

TABLE 17

AUC and Cmax values by subject (fasted)

| Subject | AUC Infinity Obs (h*ng/mL) | Total CL Obs by F (L/h) | Max Conc (ng/mL) | Half-Life Lambda z (h) | Time of CMAX (h) | Vz Obs by F (L) |
|---|---|---|---|---|---|---|
| 100-001 | 4789.36 | 5.22 | 365 | 13.56 | 2 | 102.08 |
| 100-002 | 4637.44 | 5.39 | 243 | 12.58 | 1.5 | 97.84 |
| 100-003 | 2939.58 | 8.50 | 194 | 8.31 | 5 | 101.94 |
| 100-004 | 3603.33 | 6.94 | 188 | 11.56 | 7.5 | 115.72 |
| 100-005 | 4122.74 | 6.06 | 355 | 7.46 | 3 | 65.28 |
| 100-006 | 2441.04 | 10.24 | 283 | 9.77 | 1.5 | 144.29 |
| 100-007 | 2956.81 | 8.46 | 237 | 9.01 | 4 | 109.95 |
| 100-008 | 3107.86 | 8.04 | 259 | 9.46 | 4 | 109.80 |
| 100-009 | 3507.21 | 7.13 | 309 | 12.68 | 1.5 | 130.43 |
| 100-010 | 5499.09 | 4.55 | 270 | 9.92 | 15 | 65.09 |
| 100-011 | 5010.35 | 4.99 | 495 | 10.71 | 1.5 | 77.11 |
| 100-012 | 6291.34 | 3.97 | 362 | 15.07 | 5 | 86.39 |
| 100-013 | 3680.45 | 6.79 | 249 | 12.42 | 3 | 121.75 |
| 100-014 | 4918.55 | 5.08 | 289 | 14.54 | 2 | 106.65 |
| 100-015 | 7556.68 | 3.31 | 521 | 15.76 | 1.5 | 75.21 |

TABLE 17-continued

AUC and Cmax values by subject (fasted)

| Subject | AUC Infinity Obs (h*ng/mL) | Total CL Obs by F (L/h) | Max Conc (ng/mL) | Half-Life Lambda z (h) | Time of CMAX (h) | Vz Obs by F (L) |
|---|---|---|---|---|---|---|
| 100-016 | 3031.10 | 8.25 | 191 | 10.13 | 5 | 120.51 |
| 100-017 | 4598.78 | 5.44 | 332 | 14.25 | 3 | 111.79 |
| 100-018 | 5636.28 | 4.44 | 271 | 14.65 | 4 | 93.72 |
| 100-019 | 6316.53 | 3.96 | 435 | 14.60 | 1.5 | 83.35 |
| 100-020 | 5933.57 | 4.21 | 573 | 12.70 | 2 | 77.19 |
| 100-021 | 4716.13 | 5.30 | 287 | 12.75 | 3 | 97.54 |
| 100-022 | 6474.80 | 3.86 | 371 | 12.34 | 2 | 68.75 |
| 100-023 | 4255.72 | 5.87 | 310 | 9.94 | 0.75 | 84.21 |
| 100-024 | 6666.45 | 3.75 | 495 | 11.73 | 3 | 63.45 |
| 100-025 | 5586.21 | 4.48 | 423 | 9.59 | 2 | 61.89 |
| 100-026 | 4278.71 | 5.84 | 287 | 10.57 | 3 | 89.13 |
| 100-027 | 7541.99 | 3.31 | 347 | 13.79 | 3 | 65.97 |
| 100-028 | 3252.18 | 7.69 | 233 | 9.50 | 3 | 105.32 |
| 100-029 | 6730.23 | 3.71 | 443 | 11.66 | 2 | 62.51 |
| 100-030 | 5578.20 | 4.48 | 546 | 9.19 | 1.5 | 59.42 |
| 100-031 | 9821.40 | 2.55 | 589 | 24.75 | 5 | 90.88 |
| 100-032 | 4936.93 | 5.06 | 381 | 8.67 | 3 | 63.36 |
| 100-033 | 3913.08 | 6.39 | 296 | 10.76 | 2 | 99.14 |
| 100-034 | 5323.39 | 4.70 | 303 | 13.14 | 3 | 89.03 |
| 100-035 | 3740.84 | 6.68 | 331 | 9.14 | 2 | 88.12 |
| 100-036 | 4568.89 | 5.47 | 275 | 12.60 | 4 | 99.47 |
| 100-037 | 5274.36 | 4.74 | 299 | 13.49 | 1.5 | 92.24 |
| 100-038 | 4317.48 | 5.79 | 254 | 9.69 | 5 | 80.93 |
| 100-039 | 10044.52 | 2.49 | 401 | 12.72 | 1.5 | 45.67 |
| 100-040 | 5447.91 | 4.59 | 392 | 10.54 | 1.5 | 69.79 |
| 100-041 | 4199.46 | 5.95 | 358 | 8.37 | 3 | 71.88 |
| 100-042 | 2404.47 | 10.40 | 284 | 5.11 | 2 | 76.71 |
| 100-043 | 6742.96 | 3.71 | 397 | 12.50 | 5 | 66.85 |
| 100-044 | 5025.11 | 4.98 | 302 | 14.44 | 4 | 103.65 |
| 100-045 | 3205.43 | 7.80 | 282 | 11.59 | 1.5 | 130.40 |
| 100-046 | 4055.32 | 6.16 | 248 | 9.71 | 4 | 86.41 |
| 100-047 | 2522.47 | 9.91 | 207 | 11.42 | 5 | 163.24 |
| 100-048 | 5008.86 | 4.99 | 370 | 14.01 | 2 | 100.92 |
| 100-049 | 3141.52 | 7.96 | 226 | 8.92 | 3 | 102.38 |
| 100-050 | 5703.73 | 4.38 | 274 | 14.60 | 5 | 92.34 |
| 100-051 | 4610.93 | 5.42 | 294 | 10.48 | 1.5 | 81.95 |
| 100-052 | 6876.95 | 3.64 | 366 | 13.82 | 5 | 72.49 |
| 100-053 | 4283.72 | 5.84 | 345 | 9.60 | 2 | 80.81 |

FIG. 25 shows a summary of fasted $AUC_{0-\infty}$ and Cmax observed in the pharmacokinetic study. The geometric mean (natural –log SD) for the $AUC_{0-\infty}$ is 4640 ng*hr/mL.

The geometric mean (natural –log SD) for the Cmax is 318 ng/mL.

Figure 26:
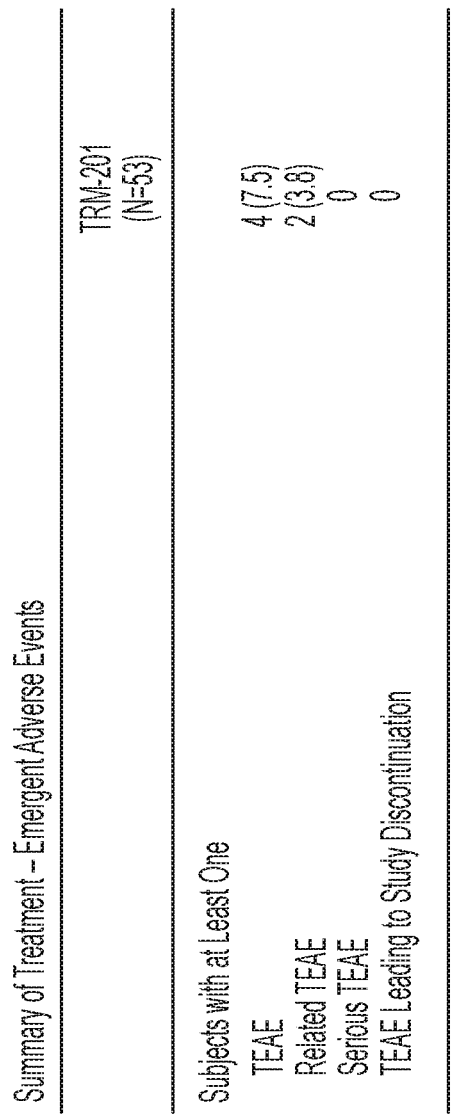
FIG. 26 shows a summary of treatment-emergent adverse events (101 study only).

FIG. 26 shows a summary of treatment-emergent adverse events (TEAE). There were four subjects observed with TEAEs, which constitutes 7.5% of the cohort. TEAE related to the rofecoxib treatment were observed in 2 subjects, which constitutes 3.8% of the cohort. No subjects presented with serious TEAE or TEAE, which would lead to discontinuation of the study.

Figure 27:
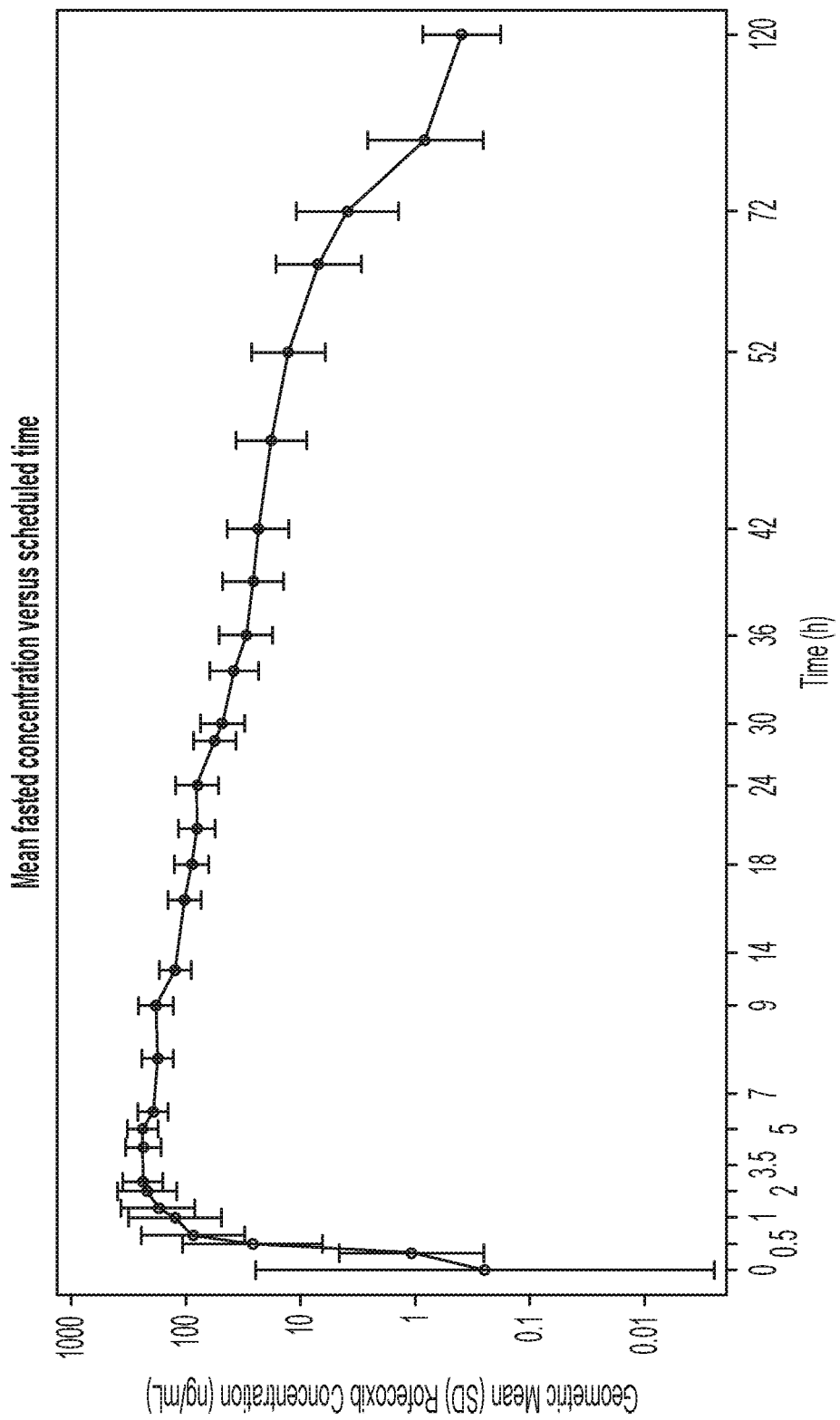
FIG. 27 shows mean fasted concentration versus scheduled time (101 study only).

FIG. 27 shows mean fasted concentration of rofecoxib versus scheduled time. A peak is observed between 2 hours and 5 hours after a single administration of the rofecoxib (TRM-201) formulation.

FIG. 28 shows analysis of $AUC_{0-\infty}$ and Cmax compared to historical data derived from Schwartz, J. I., et al. Clin. Drug Invent. 2003, 23 (8): 503-509. The rofecoxib (TRM-201) disclosed herein achieves larger $AUC_{0-\infty}$ and higher Cmax than historical data.

Figure 29:
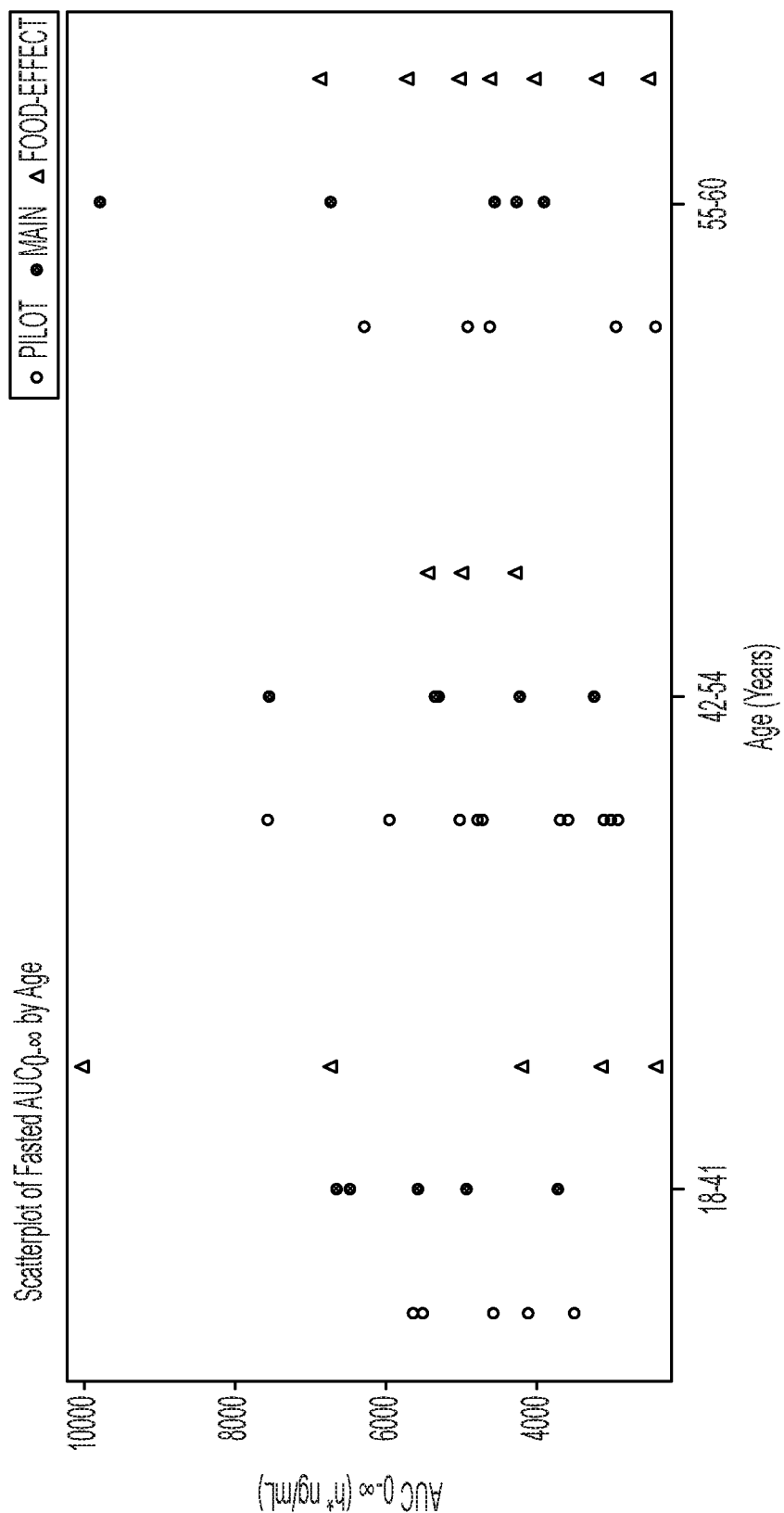
FIG. 29 shows a scatterplot of $AUC_{0-\infty}$ by age (101 study only).
Figure 30:
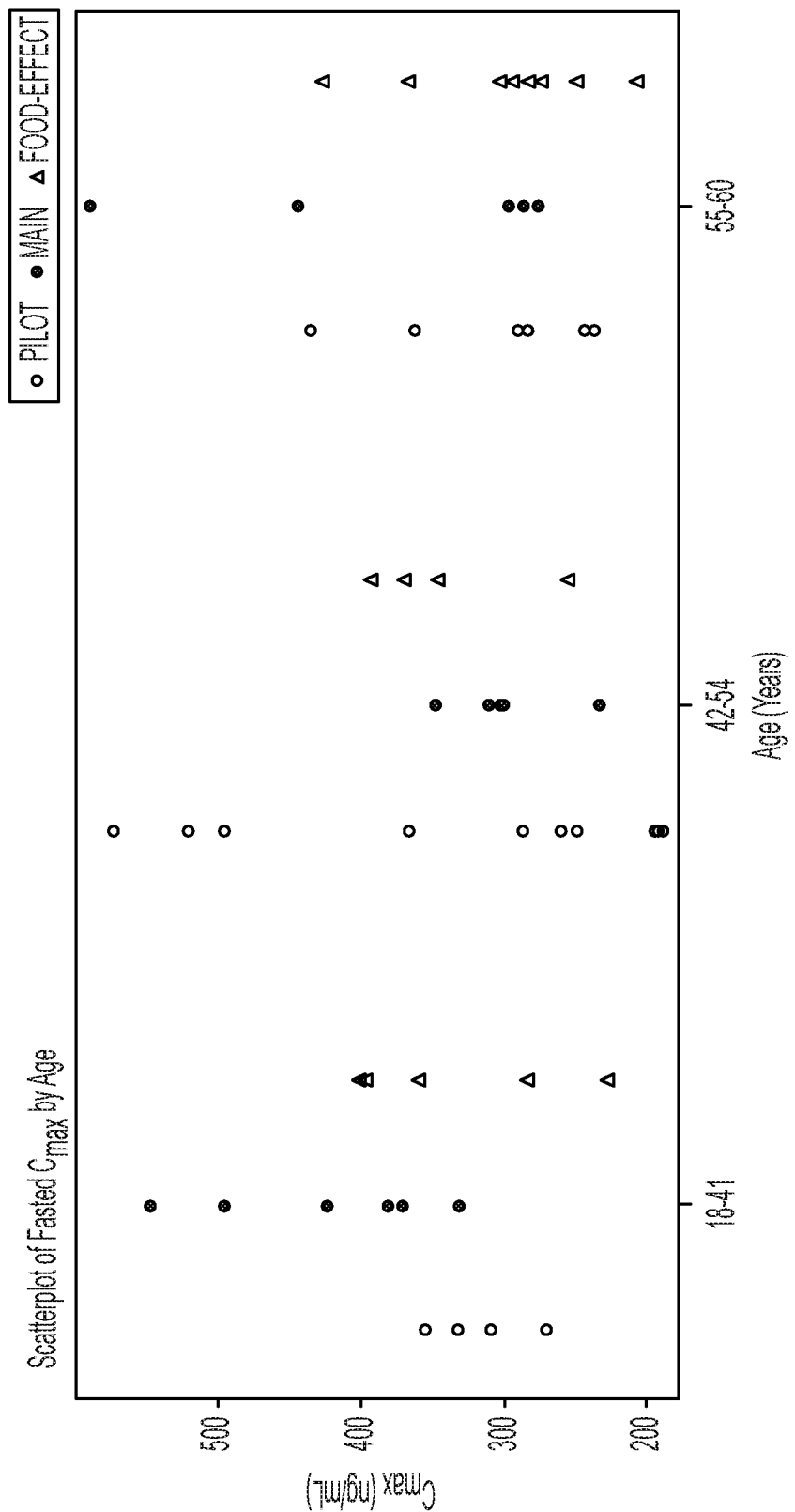
FIG. 30 shows a scatterplot of Cmax by age (101 study only).

FIG. 29 shows a scatterplot of $AUC_{0-\infty}$ by age in fasted subjects. FIG. 30 shows a scatterplot of Cmax by age in fasted subjects.

REFERENCES FOR EXAMPLE 4

Bresalier R S, Sandler R S, Quan H, et al. Cardiovascular events associated with rofecoxib in a colorectal adenoma chemoprevention trial. New Engl J Med 2005; 352:1092-102.

Matthews C Z, Woolf E J, Matuszewski B K. Improved procedure for the determination of rofecoxib in human plasma involving 96-well solid-phase extraction and fluorescence detection. J Chromatogr A. 2002; 949(1-2):83-9.

Schwartz J I, Larson P J, Porras A G, et al. Pharmacokinetic evaluation of rofecoxib: comparison of tablet and suspension formulations. Clin Drug Invest. 2003; 23(8):503-9.

Tsoukas C, Eyster M E, Sbingo S, et al. Evaluation of the efficacy and safety of etoricoxib in the treatment of hemophilic arthropathy. Blood. 2006; 107(5): 1785-90.

U S. Food and Drug Administration. Analysis and recommendations for agency action regarding nonsteroidal anti-inflammatory drugs and cardiovascular risk. J Pain Palliat Care Pharmacother. 2005; 19(4):83-97.

VIOXX (rofecoxib) [package insert], Merck & Co., Inc. Whitehouse Station, N.J.; 2016. 26 p.

Example 5

Extrapolated PK Values for Dosages Less than 25 mg of Rofecoxib.

FIG. 31 shows extrapolated pharmacokinetic values for 17.5 mg and 20 mg of rofecoxib. For 17.5 mg of rofecoxib, the $AUC_{0-\infty}$ is 3248 h*ng/mL and Cmax is 222.6 ng/mL. For 20 mg of rofecoxib, the $AUC_{0-\infty}$ is 3712 h*ng/mL and Cmax is 254.4 ng/mL. These values are extrapolated from the pharmacokinetic study of Example 4 based on results obtained from a single administration of 25 mg of rofecoxib in healthy subjects, and assumes dose linearity across the dosage strengths.

Example 6

A Single-Dose, Open-Label, Phase 1, Four-Period Crossover Pharmacokinetic Study of TRM-201 (Rofecoxib) 12.5 mg, 17.5 mg, 20 mg and 25 mg Administered to Healthy Subjects in a Fasting State, with Comparison to Historical Pharmacokinetic Parameters of Previously Marketed Rofecoxib ("TRM-201-PK-102" or "102 PK Study")
Introduction TRM-201 (rofecoxib) was developed for the treatment of hemophilic arthropathy (HA). Rofecoxib is a cyclooxygenase-2 (COX-2) selective, non-steroidal anti-inflammatory drug (NSAID) with analgesic, anti-inflammatory, and anti-pyretic properties. At therapeutic concentrations, rofecoxib inhibits COX-2 but not cyclooxygenase 1 (COX-1). The U S. Food and Drug Administration (FDA) first approved rofecoxib for marketing in 1999, and rofecoxib was eventually approved for the following indications in adults: relief of the signs and symptoms of osteoarthritis, relief of the signs and symptoms of rheumatoid arthritis, management of acute pain in adults, treatment of primary dysmenorrhea, and acute treatment of migraine attacks with or without aura. The approved doses for osteoarthritis were 12.5 mg/day or 25 mg/day, and the approved dose for rheumatoid arthritis was 25 mg/day.

The safety profile was established in over 17,000 patients in placebo- and active-controlled studies at therapeutic and supra-therapeutic doses, with some patients having had exposure for up to 2 years. On 30 Sep. 2004 Merck and Co., Inc. voluntarily withdrew rofecoxib from all markets worldwide following the observation of an increased risk of serious adverse cardiovascular events compared to placebo in a long-term controlled clinical trial (Bresalier et al 2005).

In April 2005, FDA issued a memorandum concluding its Analysis and Recommendations for Agency Action regarding NSAIDs and cardiovascular risk. Related to rofecoxib, FDA concluded in part (FDA 2005):

Along with the other approved COX-2 selective NSAIDs available at the time (i.e., celecoxib, and valdecoxib), rofecoxib was associated with an increased risk of serious adverse cardiovascular events compared to placebo.

Data from large long-term controlled clinical trials that have included a comparison of COX 2 selective and non-selective NSAIDs did not clearly demonstrate that the COX-2 selective agents confer a greater risk of serious adverse cardiovascular events than non-selective NSAIDs.

Along with the other approved COX-2 selective NSAIDs available at the time (i.e., celecoxib, and valdecoxib), rofecoxib had demonstrated a reduction in the incidence of gastrointestinal (GI) ulcers visualized at endoscopy compared to certain non-selective NSAIDs. Only rofecoxib had been shown to reduce the risk of serious GI bleeding compared to a non-selective NSAID (naproxen) following chronic use.

Should a sponsor seek to resume marketing for rofecoxib, a supplemental new drug application with revised labeling will be required. The supplemental application should specifically outline the sponsor's proposal for revised labeling designed to provide for safe and effective use of the drug in populations where the potential benefits of the drug may outweigh potential risks, and all data and arguments that support resumption of marketing.

In a two-part study focused on the efficacy of etoricoxib, another COX-2 inhibitor, in patients with HA, (Tsoukas et al 2006), rofecoxib (19 subjects) exhibited similar efficacy to etoricoxib (74 patients) in the 6-month extension of the study (Part 2) for the primary endpoint (Patient Global Assessment of Arthropathy Pain) and the two secondary endpoints (Patient Global Assessment of Arthropathy Disease Status and Investigator Global Assessment of Arthropathy Disease Status). In the six weeks of Part 1, etoricoxib provided clinically and statistically significant improvement on all endpoints versus placebo (P<0.001), including the following additional endpoints: Patient's Global Assessment of Response to Therapy, Investigator's Assessment of Response to Therapy, Patient Discontinuation Due to Lack of Efficacy, and Average Rescue Acetaminophen Usage per Day.

In view of preliminary evidence of efficacy of rofecoxib in treating pain associated with HA, the associated reduction of risk in GI adverse events (AEs) compared to nonselective NSAIDs, the comparability of risk of serious cardiovascular events with rofecoxib to comparably effective doses of nonselective NSAIDs, and the risks associated with the use of opioids to treat pain in this patient population, the use of rofecoxib will be evaluated for the treatment of HA.

Given that there have been no approved rofecoxib products available globally since September 2004, the first Phase I study under an investigational new drug (IND) application was a PK study (TRM-201-PK-101, as described in Example 4) in healthy volunteers designed to assess the PK profile of a 25-mg dose of TRM-201, for comparison to published data for the previously marketed rofecoxib (see Example 4). Top-line results from the combined dataset of Fasted subjects from the PILOT, MAIN and FOOD-EFFECT portions of TRM-201-PK-101 yielded significantly greater exposure to key PK parameters as compared to historical data reported in literature. Based on this result and the need to establish a scientific bridge in order "to rely on the systemic safety findings of Vioxx" and "demonstrate the exposure of your rofecoxib product is comparable to, or lower than, that of Vioxx", this second PK study was conducted. The current study was designed to evaluate a single dose of TRM-201 at 12.5 mg, 17.5 mg, 20 mg and 25 mg in a four-period crossover design in 24 subjects in a fasted condition to match the exposure to that of Vioxx. This study was designed to be evaluated along with the PK data from the fasted portion of the TRM-201-PK-101 study to select a dose comparable to the 25-mg dose of previously marketed rofecoxib based on historical PK parameters.

Primary Objectives:

1. To evaluate key PK parameters of TRM 201 at doses of 12.5 mg 17.5 mg, 20 mg and 25 mg in healthy subjects and use these data along with the data from the TRM-201-PK-101 study to compare TRM-201 to historical PK parameters of previously marketed rofecoxib, all in a fasted state. The key PK parameters for rofecoxib were the following:

Area under the plasma concentration-time curve from time zero to infinity ($AUC_{0-\infty}$)

Observed maximum plasma concentration ($C_{max}$)

Secondary Objectives:
1. To assess the safety and tolerability of TRM-201 at doses of 12.5 mg, 17.5 mg, 20 mg and 25 mg in healthy subjects.
2. To evaluate additional PK parameters of TRM-201 at doses of 12.5 mg, 17.5 mg, 20 mg and 25 mg in healthy subjects and use these data along with the data from the TRM-201-PK-101 study to compare to historical PK parameters of previously marketed rofecoxib, all in a fasted state including:

Time to observed maximum concentration ($T_{max}$)

Apparent terminal elimination half-life ($t_{1/2}$)

Study Population

A sufficient number of subjects were screened, and 24 subjects were enrolled to ensure that at least 20 evaluable subjects complete the study. In order to mirror the population of subjects in the PK study (Schwartz et al. 2003) every effort was made to enroll subjects in the following proportion: White or European American (80%), Black (20%). Of the White subjects enrolled, every effort was made to enroll approximately 60% of the subjects who identify themselves as being of Hispanic or Latino ethnicity resulting in an overall percentage approximately 48% Hispanic or Latino participants in the study. Subjects were enrolled only if they met all the inclusion criteria and none of the exclusion criteria and all of the continuing eligibility criteria.

Deviations from the inclusion and exclusion criteria were not allowed.

Inclusion Criteria:
1. The subject was male or female and was 18 to 60 years of age, inclusive, at Screening. Similar numbers of male and female subjects were enrolled.
2. The subject had a BMI at Screening of 18 to 32 kg/m², inclusive, with a minimum weight of 47 kg for women and 66 kg for men and a maximum weight of 80 kg for women and 90 kg for men.
3. The subject was not a smoker (or user of e-cigarettes).
4. The investigator considered the subject was in good general health as determined by medical history, clinical laboratory test results, vital sign measurements, 12-lead electrocardiogram (ECG) results, and physical examination findings at Screening and Check-in.
5. All female subjects had a negative pregnancy test at Screening. Female subjects of childbearing potential also had a negative pregnancy test at Check-in and were using an acceptable method of birth control during the study (i.e., diaphragm with spermicide, intrauterine device, condom with foam or vaginal spermicide, oral contraceptives, or abstinence). Women who were surgically sterile (i.e., hysterectomy, bilateral tubal ligation or bilateral oophorectomy), or postmenopausal (defined as amenorrhea for 12 consecutive months and documented serum follicle-stimulating hormone level>40 IU/mL) were exempt from the adequate contraception requirement.
6. The subject agreed to comply with all protocol requirements as well as the particular requirements and specific Phase I unit policies.
7. The subject provided written informed consent.

Exclusion Criteria:
1. The subject had a history of relevant drug allergy or food allergy/sensitivity (e.g., allergy to rofecoxib or excipients of TRM-201, allergy to other non-steroidal anti-inflammatory drugs (NSAIDs), or gluten intolerance that could preclude consumption of a standard clinic diet).
2. A female subject was pregnant or lactating.
3. The subject had a history of intolerance or hypersensitivity to aspirin or any other NSAID.
4. The subject had a positive test result for hepatitis B surface antigen, hepatitis C virus antibody, or human immunodeficiency virus types 1 or 2 antibodies at Screening.
5. The subject had used any prescription (excluding hormonal birth control) or over the counter medications (OTC) including NSAIDs (e.g., ibuprofen, naproxen, and aspirin) as well as herbal or nutritional supplements, within 14 days before the study drug dosing. Subjects could have taken acetaminophen (up to 2 g per day) in the 14 days prior to study drug dosing.
6. The subject had any clinically significant abnormalities before dosing on Day 1 or had a history of disease, including: uncontrolled or poorly controlled hypertension; asthma or pulmonary disease; major cardiac ischemic symptoms, events, or interventions such as angina pectoris, myocardial infarction, acute coronary syndrome, decompensated congestive heart failure, coronary stent or bypass; history of cerebrovascular ischemic events (transient ischemic attack or stroke); major vascular ischemic symptoms such as intermittent claudication or vascular bypass or replacement surgery; significant cardiovascular, gastrointestinal (GI), neurological, endocrine, or renal disease; hepatic impairment; cholecystectomy; other condition known to interfere with the absorption, distribution, metabolism, or excretion of drugs; or clinically significant GI events.
7. The subject had a history or presence of any clinically significant abnormality in vital signs, ECG, or laboratory tests, or had any medical or psychiatric condition that, in the opinion of the investigator, could interfere with the study procedures or compromise subject safety (assessed at Screening and Check-in).
8. The subject was a cigarette smoker or had used nicotine or nicotine-containing products (e.g., snuff, nicotine patch, nicotine chewing gum, e-cigarettes) within 6 months before study drug dosing.
9. The subject had a history of alcohol abuse or drug addiction within the last year or consumes more than 1 unit (1 unit is equal to approximately 14 pint [200 mL] of beer, 1 small glass [100 mL] of wine, or 1 measure [25 mL] of spirits) of alcohol a day. Alcohol was not allowed within 7 days before study drug dosing.
10. The subject had a positive test result for drugs of abuse, alcohol, or cotinine (indicating active current smoking) at Screening.
11. The subject was a habitual and heavy coffee drinker (more than 4 cups a day, 28 cups a week).
12. The subject was involved in strenuous activity or contact sports within 24 hours before study drug dosing.
13. The subject had donated blood or blood products within 30 days before the dose of study drug in this study.
14. The subject had received study drug in another investigational study within 30 days (or less than 5 half-lives of the investigational agent) prior to dosing in this study.
15. The subject was not suitable for entry into the study, in the opinion of the investigator.

16. The subject was an employee or family member of the investigator or clinic staff.

Continuing Eligibility at Check-in
1. Females had a negative serum pregnancy test.
2. All subjects had a negative test results for drugs of abuse and alcohol
3. Subjects had no significant changes in overall health status since screening including the use of medications.
4. The subject was involved in strenuous activity or contact sports within 24 hours before study drug dosing.

Subjects with test results which did not meet the above inclusion/exclusion criteria could have the relevant test repeated once if it was thought to represent a laboratory error, a reversible, clinically insignificant intermittent condition, or was not consistent with the subject's historical values. If inclusion/exclusion criteria were not met after the repeat test, the subject was considered a screen failure and was not enrolled in the study. Subjects were retested once.

Study Design

This was a single-center, open-label four-period crossover PK study of TRM-201. The study included 24 subjects who received TRM-201 as a single dose of 12.5 mg, 17.5 mg, 20 mg and 25 mg to assess the PK of TRM-201 in healthy volunteers under fasted conditions. Subjects were randomized to one of four treatment sequences. The PK data from the current study along with the data from the TRM-201-PK-101 study (Example 4) was used to compare to historical pharmacokinetic parameters of previously marketed rofecoxib, all in a fasted state.

The subjects were screened in the 28 days before receiving the single dose of TRM-201 in the first period. Subjects checked in to the clinic on the day before dosing for Dosing Period 1, and their eligibility was confirmed. Subjects remained at the clinic from Check-In through the completion of the end of study (EOS) visit on Day 27 of Dosing Period 4. The total duration of the study was approximately 55 days.

After Check-In, subjects fasted overnight for at least 10 hours before study drug administration. In the morning of the dosing day of Period 1, subjects were randomized to one of four treatment sequences:

Dosing Period 1: ADBC
Dosing Period 2: BACD
Dosing Period 3: CBDA
Dosing Period 4: DCAB
Where A=12.5 mg, B=17.5 mg, C=20 mg and D=25 mg Regardless of the dosing sequence assigned, all subjects underwent the same assessments, pre and post-dose.

In each of the four dosing periods, subjects fasted overnight for at least 10 hours before study drug dosing. While fasting, subjects had nothing to eat and only water to drink. Water was permitted as desired, except for the period between 1 hour before and 1 hour after study drug dosing (excepting as permitted for dosing). After the 2-hour PK blood sample, subjects were allowed one 250-mL cup of clear apple juice. After the 4-hour PK blood sample, subjects were served a light lunch. Following the light lunch, subjects received standardized meals according to the clinic's standard procedures that were scheduled at consistent times and at least 15 minutes before or 15 minutes after PK sampling time points. Blood was withdrawn for PK analysis at pre-defined time points. For each dosing period the last time point was 120 hours after dosing with study drug (Day 6).

After the 120 hour PK sample, the EOP procedures was completed, subjects remained in-clinic for the in-between dose period day (Days 7, 14, and 21) and began the next dosing period starting with an overnight fast for at least 10 hours on Day −1 of the subsequent dosing period. Pharmacokinetic and safety endpoints were evaluated.

Rationale of Study Design

The subject matter disclosed herein relates to a scientific bridge between TRM-201 and the previously marketed rofecoxib in support of a 505(b)(2) new drug application. Because there are presently no FDA-approved rofecoxib products commercially available globally with which to conduct a directly comparative bioavailability/bioequivalence study, the present study, along with the data from the TRM-201-PK-101 study, was designed to provide PK data for a cross-study comparison to a published study (Schwartz et al. 2003) that was submitted to FDA, accepted by FDA, and used in the approved package insert for rofecoxib.

The four doses of rofecoxib (12.5 mg, 17.5 mg, 20 mg and 25 mg) were selected for this study to combine with the 25-mg dose data from TRM-201-PK-101 to select a dose that is comparable to the 25-mg dose of previously marketed rofecoxib because it is the anticipated maximum daily dose for the treatment of HA. The data from the study by Schwartz et al. (2003) were chosen for comparison because they represent PK data generated with the labeled version of rofecoxib at 25 mg. The eligibility criteria for this current PK study were selected to mirror the subject demographics and subgroups (gender, age, body mass index [BMI], race, and ethnicity) in both the TRM-201-PK-101 and Schwartz studies. A validated bioanalytical method for rofecoxib was developed and used for the PK analyses.

Administration of Study Drug

Study drug was co-administered orally with approximately 250 mL of room temperature water, and up to an additional 250 mL of water was allowed, if necessary, to aid in swallowing the study drug. Study staff ensured that at least 250 ml of water was consumed with the dose of study drug and performed a hand and mouth check after dosing to ensure the tablet was swallowed.

After fasting for at least 10 hours overnight (Table 19), subjects took, a single dose (1 tablet) of TRM 201 on the morning of Day 1 in each of the four Dosing Periods administered as described above and supervised by clinic staff. During the period between 1 hour before and 1 hour after study drug dosing, subjects drank only the water permitted for study drug administration.

Identity of Study Drug

The study drug, TRM-201, was an immediate-release tablet that contained 12.5 mg rofecoxib, 17.5 mg rofecoxib, 20 mg rofecoxib or 25 mg rofecoxib. The 7.25-mm diameter tablets were off-white, round, and uncoated with no markings. TRM-201 tablets were for oral administration.

TRM-201 tablets contained the active ingredient rofecoxib (12.5 mg, 17.5 mg, 20 mg or 25 mg) and inactive excipients. Each tablet contained the following inactive excipients: croscarmellose sodium, hydroxypropyl cellulose, lactose, magnesium stearate, microcrystalline cellulose, and yellow pigment. Table 18 shows the specific formulation of the tablets used in the this study:

TABLE 18

Composition of Rofecoxib Tablets

| Components | 25-mg Tablet % (w/w) per tablet | 25-mg Tablet mg per tablet | 20-mg Tablet % (w/w) per tablet | 20-mg Tablet mg per tablet | 17.5-mg Tablet % (w/w) per tablet | 17.5-mg Tablet mg per tablet | 12.5-mg Tablet % (w/w) per tablet | 12.5-mg Tablet mg per tablet |
|---|---|---|---|---|---|---|---|---|
| Intragranular | | | | | | | | |
| Rofecoxib[a] | 12.50 | 25.0 | 10.00 | 20.0 | 8.75 | 17.5 | 6.25 | 12.5 |
| Lactose monohydrate | 39.85 | 79.7 | 41.10 | 82.2 | 41.725 | 83.45 | 42.975 | 85.95 |
| Microcrystalline cellulose | 39.85 | 79.7 | 41.10 | 82.2 | 41.725 | 83.45 | 42.975 | 85.95 |
| Hydroxypropylcellulose | 3.00 | 6.0 | 3.00 | 6.00 | 3.00 | 6.0 | 3.00 | 6.0 |
| Croscarmellose sodium | 2.00 | 4.0 | 2.00 | 4.0 | 2.00 | 4.0 | 2.00 | 4.0 |
| Pigment blend yellow | 0.30 | 0.6 | 0.30 | 0.6 | 0.30 | 0.6 | 0.30 | 0.6 |
| Water | NA[b] | NA[b] | NA[b] | NA[b] | NA[b] | NA[b] | NA[b] | NA[b] |
| Extragranular | | | | | | | | |
| Croscarmellose sodium | 2.00 | 4.0 | 2.00 | 4.0 | 2.00 | 4.0 | 2.00 | 4.0 |
| Magnesium stearate | 0.50 | 1.0 | 0.50 | 1.0 | 0.50 | 1.0 | 0.50 | 1.0 |
| Totals | 100.00 | 200.0 | 100.00 | 200.0 | 100.00 | 200.0 | 100.00 | 200.0 |

[a]Note that the amount of rofecoxib may be adjusted for purity and moisture content. An adjustment will be made to the amounts of lactose monohydrate and microcrystalline cellulose used to maintain tablet weight.
[b]Water for granulation is removed upon drying of the wet mass.

TABLE 19

Schedule of events

| Phase | Screening | Check-in | In-clinic between-period day | Dosing Periods 1,2, 3 and 4 Pharmacokinetic Sampling | | | | | EOP/EOS |
|---|---|---|---|---|---|---|---|---|---|
| Period 1 Days | −28 to −2 | −1 | NA | 1 | 2 | 3 | 4 | 5 | 6 |
| Period 2 Days | | | 7 | 8 | 9 | 10 | 11 | 12 | 13 |
| Period 3 Days | | | 14 | 15 | 16 | 17 | 18 | 19 | 20 |
| Period 4 Days | | | 21 | 22 | 23 | 24 | 25 | 26 | 27 |
| Informed consent | X | | | | | | | | |
| Demographics | X | | | | | | | | |
| Medical history | X | X | | | | | | | |
| Viral serology | X | | | | | | | | |
| Serum follicle-stimulating hormone (females only) | X | | | | | | | | |
| Admission to clinic | | X | | | | | | | |
| Serum pregnancy test (females only) | X | X | | | | | | | X |
| Urine drug screen (including alcohol and cotinine) | X | X | | | | | | | |
| Clinical laboratory testing (blood/urine) | X | X | | | | | | | X |
| Height, weight, and body mass index | X | weight ONLY | | | | | | | weight ONLY |
| Physical examination[a] | X | X | | | | | | | X (EOS ONLY) |
| Vital sign measurements[b] | X | X | X | X | X | X | X | X | X |
| 12-Lead ECG assessment | X | X | | X | | | | | X (EOS ONLY) |
| Eligibility assessment (initial and continuing) | X | X | | | | | | | |
| Study meal schedule[d] | | X | X | X | X | X | X | X | X |
| Study drug administration' | | | | X | | | | | |
| Pharmacokinetic sample collection | | | | X | X | X | X | X | |
| Adverse event assessment | | | X | X | X | X | X | X | X |
| Prior or concomitant medication assessment | X | X | X | X | X | X | X | X | X |

TABLE 19-continued

| | | | Schedule of events | | |
|---|---|---|---|---|---|
| Phase | Screening | Check-in | In-clinic between-period day | Dosing Periods 1,2, 3 and 4 Pharmacokinetic Sampling | EOP/EOS |
| Discharge from clinic | | | | | X (EOS ONLY) |

Abbreviations: ECG, electrocardiogram; EOP, end of period; EOS, end of study.
Note: The order of procedures on each day followed the order of presentation in Table 19 (top to bottom). When procedures overlapped or occurred at the same time point, all blood sampling followed vital signs or ECGs, and PK sampling was timed to occur last and as close to the scheduled time window as possible. Timings of PK blood sampling and electrocardiogram assessments were calculated from time "0", the time of study drug dosing.
[a]A complete physical examination was performed at Screening (at minimum, assessment of skin, head, ears, eyes, nose, throat, neck, thyroid, lungs, heart, cardiovascular, abdomen, lymph nodes, and musculoskeletal system/extremities). A brief physical examination was performed at Check-In and EOS (at minimum, assessment of skin, lungs, cardiovascular system, and abdomen). Interim physical examinations was performed at the discretion of the investigator, if necessary, to evaluate adverse events or clinical laboratory abnormalities.
[b]Vital signs included systolic and diastolic blood pressure, pulse rate, respiratory rate, and oral body temperature, after the subject had been seated for at least 5 minutes. On Day 1 of each Dosing Period, vital signs were measured within 120 minutes before study drug dosing and at the 2-hour, 3-hour and 7.5-hour post dose time points. At these time points (2 h, 3 h and 7.5 h) only systolic and diastolic blood pressure, pulse rate and respiratory rate were assessed. On Days 2 through 6 of each dosing period, vital signs were assessed within 15 minutes before the first PK blood sample of the day.
[c]After the subject had been in the supine position for at least 5 minutes, single 12-lead ECG recordings were taken at Screening and Check-in, and on Dosing Day 1 pre-dose and at the 2-hour and 3-hour post-dose time point for each of the four dosing periods and at EOS.
[d]The fasting period began at the day of Check-In and on each in-clinic between Dosing Period Day (Days 7, 14, 21) for at least 10 hours overnight before study drug administration for each period.
[e]Study drug was administered after vital sign measurements has been completed. Study drug was administered with ~250 mL of room temperature water. Up to an additional ~250 mL of water were allowed, if necessary, to aid in swallowing the study drug. Subjects maintained an upright position (seated or standing) for at least 4 hours after dosing. The dosing for each Dosing Period for each subject occurred at least 7 days after Period-1 dosing.

Pharmacokinetic Procedures, Assessments, and Endpoints

The time points and windows for PK blood sampling were presented in Table 20 below. For each sample, approximately 3 mL of blood were drawn. The samples were obtained by a straight stick or via an in-dwelling intravenous (IV) catheter in a forearm vein. Additional details for the collection, processing, storage, and shipping of PK samples were provided in the study manual.

assessments, and physical examination findings. For all safety assessments, the investigator determined whether results were clinically significant, which was defined as any variation in a result that had medical relevance and could have resulted in an alteration in medical care (e.g., active observation, diagnostic measures, or therapeutic measures). If clinical significance was noted, the result and reason for significance were documented. Any abnormal laboratory test results (hematology, clinical chemistry, or urinalysis) or

TABLE 20

Times and Windows for Dosing Period 1,2, 3 and 4 Pharmacokinetic Blood Sampling

| | Unit of Time | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | Minutes | | | | Hours | | | | | | | | | | | | | | | | | | | | | | | | | |
| | Timepoint | | | | | | | | | | | | | | | | | | | | | | | | | | | | | |
| | $0^a$ | 15 | 30 | 45 | 1 | 1.5 | 2 | 3 | 4 | 5 | 6 | 7.5 | 9 | 12 | 15 | 18 | 21 | 24 | 27 | 30 | 33 | 36 | 39 | 42 | 48 | 52 | 60 | 72 | 96 | 120 |
| Window (mm) | ±5 min | | | | ±10 min | | | | ±15 min | | | | ±30 min | | | | | | | | ±60 min | | | | | | | | | |

Abbreviation: mm; minutes.
[a]The blood sample for time 0 were taken within 1 hour before dosing with study drug.

Pharmacokinetic samples will be analyzed using a validated assay for rofecoxib in human plasma. Assay results and validation details will be provided in a separate bioanalytical report. The following PK parameters for rofecoxib will be calculated as primary endpoints using standard noncompartmental methods: $AUC_{0-\infty}$ and $C_{max}$. Secondary endpoints include $T_{max}$, and $t_{1/2}$. Additional PK parameters (e.g., CL/F, and $V_d$/F) will also be calculated using standard noncompartmental methods.

Safety Assessments

The timing and frequency of all safety assessments was listed in the schedule of events (Table 19). Safety and tolerability included monitoring and recording of AEs, clinical laboratory assessments (hematology, serum chemistry, and urinalysis), vital sign measurements, 12-lead ECG other safety assessments (e.g., ECGs, vital sign measurements), including those that worsen from baseline, felt to be clinically significant in the medical and scientific judgment of the investigator were to be recorded as AEs or SAEs.

Adverse Events

Definitions of Adverse Events

The investigator was responsible for reporting all AEs that were observed or reported during the study, regardless of their relationship to study drug or their clinical significance. If there was any doubt as to whether a clinical observation was an AE, the event was reported. An AE was defined as any untoward medical occurrence in a subject enrolled into this study regardless of its causal relationship to study drug. Subjects were instructed to contact the investigator at any time after enrollment if any symptoms developed. A treatment-emergent AE (TEAE) was defined as any event not present before exposure to study drug or any event already present that worsens in either intensity or frequency after exposure to study drug.

Serious Adverse Events (SAE)
An SAE was defined as any event that:
resulted in death
was immediately life threatening
required inpatient hospitalization or prolongation of existing hospitalization
resulted in persistent or significant disability/incapacity
was a congenital anomaly/birth defect Important medical events that did not result in death, were not life threatening, or did not require hospitalization were considered SAEs when, based upon appropriate medical judgment, they jeopardized the subject or required medical or surgical intervention to prevent one of the outcomes listed in this definition. Examples of such medical events included allergic bronchospasm requiring intensive treatment in an emergency room or at home, blood dyscrasias or convulsions that did not result in inpatient hospitalization, or the development of drug dependency or drug abuse.

Comparability of TRM-201 with Previously Marketed Rofecoxib

Consistent with the data of Schwartz et al. (2003) and Trial TRM-201-PK-101, the total sample size of 20 evaluable subjects was considered sufficient for the objectives of the study. Power was computed as the probability that the upper limit of a 90% CI for the geometric mean ratio (GMR=observed geometric mean from this trial divided by the historical control value) for these parameters fell below 1.25. Observed natural-log-scale between-subject SDs from Trial TRM-201-PK-101 were approximately 0.31 and 0.30 for $AUC_{0-\infty}$ and $C_{max}$, respectively; within-subject SB's from the food effect sub-study were 0.10 and 0.12, respectively. Geometric mean AUC and Cmax from the 25 mg formulation in TRM-201-PK-101 were 4685 ng·hr/ml and 320 ng/ml, respectively. These were higher than the corresponding values from Schwartz et al. (2003), which were 3799 and 217, respectively. Since rofecoxib PK was found to be linear across the 12.5 to 50-mg dose range (Vioxx Package Insert), the 20 mg formulation in this trial was estimated to have AUC~3741 and Cmax~266; for the 17.5 mg formulation, AUC~3276 and Cmax~238.

The primary analysis model for data from this trial included data from this trial and that from the 25-mg dose from TRM-201-PK-101 (fasted results only), which were combined via mixed model repeated measures analysis (MMRM) in order to maximize the precision of the estimates. An MMRM analysis on natural log scale was simulated for the 25-mg dose (N=50) data using the between-subject SD of 0.31 from TRM-201-PK-101 and for the estimated 25-mg and 20-mg data that N=20 subjects were expected to yield in this study. The purpose of this simulation was to estimate the SD for the least squares natural log scale mean for the 20-mg dose. This SD estimate was identical for the 17.5-mg dose since that expected least squares mean was a constant shift lower than that for 20 mg; hence, it sufficed to run the simulation only once. The subject effect data expected for this study was simulated from the back-calculated variance of the between-subject mean effect (Var (between-subject-mean)=SDbetween^2−SDwithin^2). For the maximum between- and within-SB's 0.31 and 0.12, 1000 simulations yielded an effective SD of 0.21 for the least squares mean of 20 mg, which was used for the following power calculations.

Note that if this combined analysis of both PK trials were not carried out, then the comparison of AUC and Cmax from each dose in this trial would be based on only N=20 subjects using the between-subject SD (~0.3 or 0.31). The MMRM analysis of both trials combined leverages the 25 mg vs 20 mg (and 25 mg vs 17 mg, and 25 mg vs 12.5 mg) difference from this trial which was based on the within-subject SD ~0.10 subtracted from the pooled estimate of the 25 mg AUC or Cmax from N=70 subjects using the between-subject SD. This yields an effective SD for each of the 20 mg, 17.5 mg, and 12.5 mg comparisons to the historic control value.

Power was computed as the probability that the upper limit of a 90% CI for the geometric mean ratio (GMR=observed geometric mean from this trial divided by the historical control value) for these parameters fell below 1.25. Assuming a natural-log-scale SD equal to 0.21, N=20 had approximately 81% power if the TRUE underlying geometric mean ratio (GMR)=1.10, and approximately 90% power if the TRUE underlying GMR=1.08. The maximum OBSERVED GMR that would reject the null hypothesis is 1.14. Table 21 shows $AUC_{0-\infty}$ and $C_{max}$ geometric mean values associated with the ratios computed from the effective SD=0.21,

TABLE 21

Power Estimates for Comparability between TRM-201 and Previously Marketed Rofecoxib

| | Geometric Mean Ratios | | | |
|---|---|---|---|---|
| Maximum OBS. Fold-Increase for Comparability | 1.15[a] | | | |
| TRUE Fold-Incr. for ~80% power | 1.11[a] | | | |
| TRUE Fold-Incr. for ~90% power | 1.08[a] | | | |
| PK Parameter | Parameter | Geometric Means | Historical mean value from Schwartz (2003) | | 1.25 Times the historical mean value |
| $C_{max}$ | Max. OBS. Geo.Mean for Comparability | 250 | 217 | $C_{max}$ 25 mg | 271 |
| | TRUE Geo.Mean for ~80% power | 241 | 217 | | 271 |
| | TRUE Geo.Mean for ~90% power | 234 | 217 | | 271 |
| $AUC_{0-\infty}$ | Max. OBS.Geo. Mean for Comparability | 4369 | 3799 | $AUC_{0-\infty}$ 25 mg | 4749 |
| | TRUE Geo.Mean for ~80% power | 4217 | 3799 | | 4749 |
| | TRUE Geo.Mean for ~90% power | 4103 | 3799 | | 4749 |

TABLE 21-continued

Power Estimates for Comparability between TRM-201 and Previously Marketed Rofecoxib

| | Geometric Mean Ratios | | | |
|---|---|---|---|---|
| Maximum OBS. Fold-Increase for Comparability | 1.15[a] | | | |
| TRUE Fold-Incr. for ~80% power | 1.11[a] | | | |
| TRUE Fold-Incr. for ~90% power | 1.08[a] | | | |
| PK Parameter | Parameter | Geometric Means | Historical mean value from Schwartz (2003) | 1.25 Times the historical mean value |
| $C_{max}$ | Max. OBS.Geo. Mean for Comparability | 281 | $C_{max}$ 12.5 mg dose- adjusted to 25 mg | 305 |
| | TRUE Geo.Mean for ~80% power | 271 | 244 | 305 |
| | TRUE Geo.Mean for ~90% power | 264 | 244 | 305 |

Abbreviations;
Geo.Mean, geometric mean;
Incr, increase;
Max., maximum;
OBS., observed.
[a]Fold-increase expressed relative to the historical mean value Analysis Sets The PK analysis set included subjects who receive a single dose of TRM-201 and had sufficient concentration data to support accurate estimation of at least one PK parameter. Subjects who experience vomiting within 2 times the median $T_{max}$ (approximately 6 hours) after study drug dosing will be excluded from the PK analysis. The safety analysis set will include all subjects who received at least 1 dose of study drug.

Description of Subgroups to be Analyzed

The relationship of $AUC_{0-\infty}$ and $C_{max}$ to age and to BMI were each assessed via scatter plots and correlation coefficients. If appropriate, additional modeling of those relationships may be carried out. Summary statistics for $AUC_{0-\infty}$ and $C_{max}$ were provide by gender, age categories (divided into tertiles), race categories, and ethnicity categories.

Statistical Analysis Methodology

For categorical variables, frequencies and percentages were presented. Continuous variables were summarized using descriptive statistics (number of subjects, mean, median, SD, minimum, maximum, geometric mean, natural-log-scale SD). Baseline demographic and background variables were summarized overall for all subjects. The number of subjects who enrolled in the study and the number and percentage of subjects who completed the study were presented. Frequency and percentage of subjects who withdrew or discontinued from the study, and the reason for withdrawal or discontinuation, was also summarized. Statistical analysis was performed using SAS software Version 9.4 or later. Continuous variables were summarized using the mean, the standard deviation, median, minimum value, and maximum value. Categorical variables were summarized using frequency counts and percentages. Data were listed in data listings.

Analysis of Pharmacokinetic Endpoints

Individual plasma concentrations for rofecoxib and PK sampling time deviation data will be presented in a data listing. Plasma concentration data will be summarized by time point using the following descriptive statistics: number of subjects, arithmetic mean, SD, coefficient of variation (CV), geometric mean, natural-log-scale SD, geometric CV, median, minimum, and maximum. Individual plasma concentration versus actual time profiles were presented on both linear and semilogarithmic scales. Additionally, arithmetic mean concentration versus scheduled time profiles were presented on linear scales and geometric means on semilogarithmic scales.

The PK parameters of rofecoxib were analyzed based on the actual sampling times. All parameters were calculated using the Phoenix® WinNonlin® version 6.4 or higher (Certara USA Inc., Princeton, N.J.) or SAS® version 9.3 or higher (SAS Institute Inc., Cary, N.C.). The individual PK parameters were presented in data listings. Summary statistics for the primary PK endpoints, $AUC_{0-\infty}$ and $C_{max}$, included n, arithmetic mean, CV, SD, geometric mean, natural-log-scale SD, median, minimum, and maximum, along with the associated 90% CI computed on the natural-log-scale and back-transformed to the original measurement scale. The GMR to historical control values and associated 90% CIs were computed on log scale and back-transformed to the ratio scale; the reference values are from Schwartz et al. (2003): 3799 ng·hr/mL and 217 ng/mL for $AUC_{0-\infty}$ and $C_{max}$, respectively.

The primary hypotheses for both $AUC_{0-\infty}$ and $C_{max}$ for each of the 17.5 mg and 20 mg doses (tested via step-down approach: AUC followed by Cmax for the 17.5 mg dose, followed by AUC and Cmax for the 20 mg dose) were:

Null Hypothesis: the TRUE underlying GMR (new formulation versus historical control) was at least 1.25

Alternative Hypothesis: the TRUE underlying GMR (new formulation versus historical control) was less than 1.25

These null hypotheses were each tested via comparing to 1.25 the upper limit of a 90% CI for the geometric mean computed on the natural-log-scale and back-transformed to the original scale. If the upper 90% CI lied below 1.25 times the historical control geometric mean value, the null hypothesis would have been rejected, and the alternative hypothesis would have been concluded. The $AUC_{0-\infty}$ and $C_{max}$ null hypotheses needed to be rejected to support a conclusion that the new formulation was sufficiently similar to the formulation that yielded the historical control data. Sensitivity analyses will be carried out separately for $AUC_{0-\infty}$ and $C_{max}$ using age- and race-adjusted geometric means that match the mean age and race distribution of the historical control data. Secondary analyses similar to the primary were carried out in comparison to a lower limit of 0.8 times the respective historical control values.

The $T_{max}$ was summarized by n, arithmetic mean, CV, SD, median, minimum, maximum, and 90% CI for the median via normal approximation. Apparent $t_{1/2}$ was summarized by n, arithmetic mean, CV, SD, harmonic mean, jack-knife SD, median, minimum, and maximum. The 90% CI for harmonic mean was computed on the inverse scale and back-transformed to the actual scale. The 90% CIs for median $T_{max}$ and harmonic mean $t_{1/2}$ was compared to their respective historical control values. In addition to the proposed statistical approach to calculate the maximum observed geometric mean ratio for the primary PK parameters using the traditional bioequivalence reference range of 1.25, an alternative approach considered incorporating the variability in the PK parameters observed in the reference Schwartz et al. (2003) study. The results for the maximum observed geometric mean ratio for $AUC_{0-\infty}$ and $C_{max}$ that would yield 90% CI<1.33 were similar to those of the proposed approach. Summary statistics for the secondary PK endpoints, including apparent plasma clearance (CL/F) and apparent volume of distribution ($V_d/F$) included n, arithmetic mean, SD, CV, geometric mean, natural-log-scale SD, median, minimum, maximum, along with the associated 90% CI computed on the natural-log-scale and back-transformed to the original measurement scale, as appropriate. An exploratory analysis was carried out to estimate the dose that yielded values of AUC and Cmax equal to those observed in the Schwartz (2003) paper. This analysis was carried out via a linear regression fit in the MMRM analysis of the log-transformed observations across the 12.5 to 25 mg range of doses in this study.

Analysis of Safety Endpoints

All safety data were summarized. The incidence of adverse events was presented by the MedDRA system organ class and preferred term, relationship to the test article, and severity. Descriptive statistics of clinical laboratory results and vital signs were presented, as well as summaries of changes from baseline (from the Check-in visit(s)) and of clinically notable values. All AE data were presented in a data listing TEAEs were summarized overall, as well as by severity and relationship to study drug. Serious AEs and AEs leading to discontinuation of study drug were also presented in the data listings and summarized. Actual values and changes from Baseline for clinical laboratory test results, vital sign measurements, and 12-lead ECG results were summarized at each time point using descriptive statistics (number of subjects, mean, SD, median, minimum, and maximum).

Results for Example 6

Figure 32:
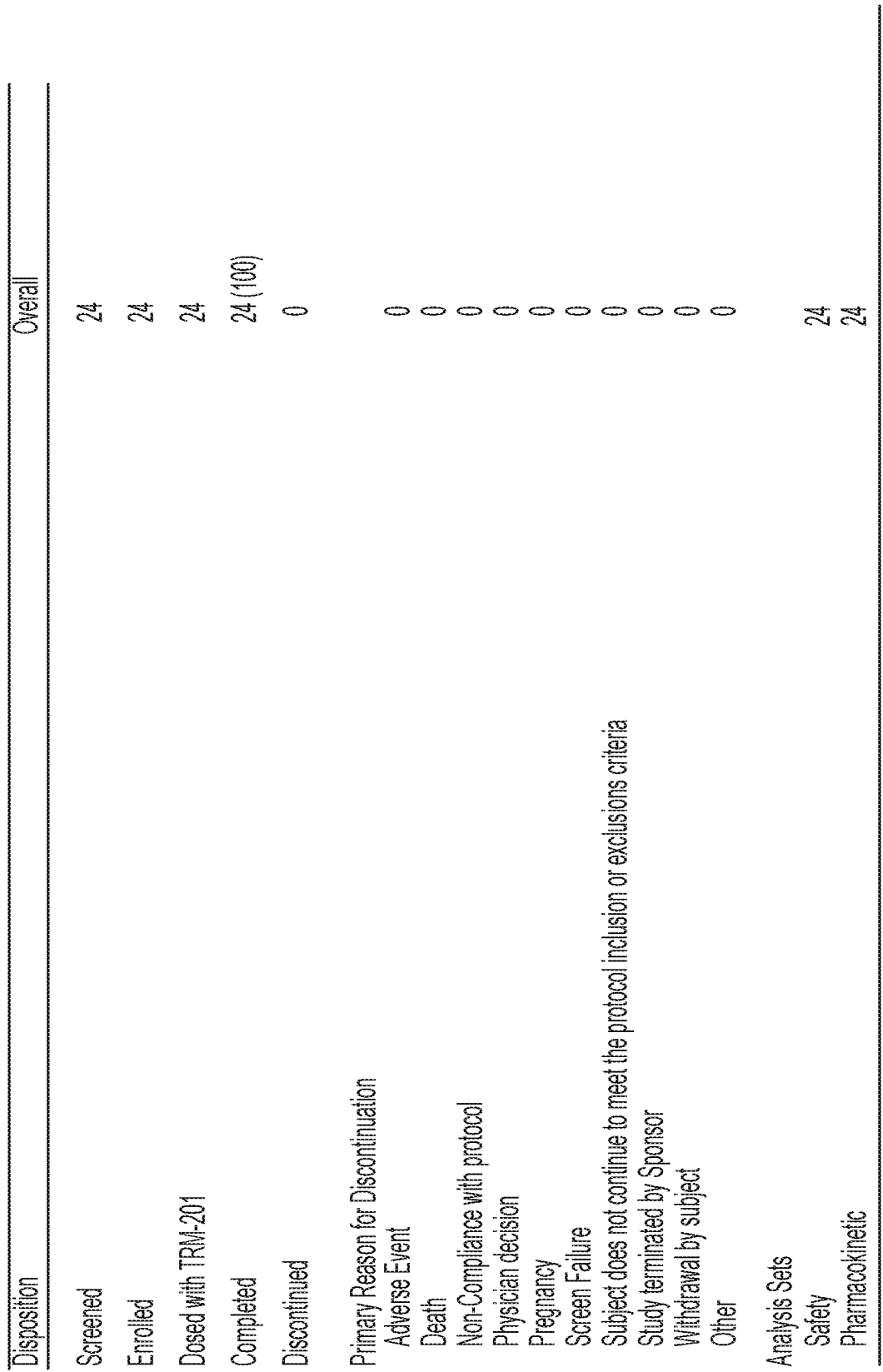
FIG. 32 shows a summary of subject disposition for all screened subjects (102 study only).

As shown in the summary of subjects in FIG. 32, 24 subjects were administered TRM-201 and all subjects completed the study. The median age of the tested demographic is 49 years old with approximately 50% males and females as shown in FIG. 33. The subjects also included 5 black or African-American subjects and 12 Hispanic or Latino subjects. FIG. 34 shows that the median body mass index (BMI) of the tested cohort was 26.95 kg/m².

FIG. 35 shows demographic and baseline characteristics of the cohort tested in the pharmacokinetics (PK) study. FIG. 36 shows demographic and baseline characteristics of BMI indicator in PK study. FIGS. 37-46 show the summary of fasted plasma rofecoxib concentration (ng/mL) across various time points 0 hours and 120 hours following 12.5 mg, 17.5 mg, 20 mg, or 25 mg of TRM-201 administration for the 102 PK study. As shown in FIGS. 37 and 38, the arithmetic mean plasma concentration for 12.5 mg of TRM-201 at 15 minutes is 1.03 ng/ml and the geometric mean is 0.529 ng/ml. The arithmetic mean plasma concentration for 17.5 mg of TRM-201 at 15 minutes is 2.42 mg/ml and the geometric mean is 0.669 ng/ml. The arithmetic mean plasma concentration for 20 mg of TRM-201 at 15 minutes is 5.75 ng/ml and the geometric mean is 1.16 ng/ml. The arithmetic mean plasma concentration for 25 mg of TRM-201 at 15 minutes is 5.63 ng/ml and the geometric mean is 1.37 ng/ml. The arithmetic mean plasma concentration for 12.5 mg of TRM-201 at 45 minutes is 56.8 ng/ml and the geometric mean is 33.9 ng/ml. The arithmetic mean plasma concentration for 17.5 mg of TRM-201 at 45 minutes is 93.0 mg/ml and the geometric mean is 51.6 ng/ml. The arithmetic mean plasma concentration for 20 mg of TRM-201 at 45 minutes is 121 ng/ml and the geometric mean is 72.6 ng/ml. The arithmetic mean plasma concentration for 25 mg of TRM-201 at 45 minutes is 159 ng/ml and the geometric mean is 97.6 ng/ml.

FIG. 47 shows a summary of fasted $AUC_{0-\infty}$ and $C_{max}$ values for the 101-PK (Example 4) and 102-PK (Example 6) studies, combining those results for the 25 mg of TRM-201 dosage across the 101-PK and 102-PK studies. The arithmetic mean $AUC_{0-\infty}$ for 12.5 mg of TRM-201 is 2010 ng·hr/mL. The geometric mean $AUC_{0-\infty}$ for 12.5 mg of TRM-201 is 1880 ng·hr/mL. The arithmetic mean $AUC_{0-\infty}$ for 17.5 mg of TRM-201 is 3290 ng·hr/mL. The geometric mean $AUC_{0-\infty}$ for 17.5 mg of TRM-201 is 3110 ng·hr/mL. The arithmetic mean $AUC_{0-\infty}$ for 20 mg of TRM-201 is 3750 ng·hr/mL. The geometric mean $AUC_{0-\infty}$ for 20 mg of TRM-201 is 3550 ng·hr/mL. The arithmetic mean $AUC_{0-\infty}$ for 25 mg of TRM-201 is 4810 ng·hr/mL. The geometric mean $AUC_{0-\infty}$ for 25 mg of TRM-201 is 4590 ng·hr/mL. The arithmetic mean $C_{max}$ for 12.5 mg of TRM-201 is 151 ng/mL. The geometric mean $C_{max}$ for 12.5 mg of TRM-201 is 144 ng/mL. The arithmetic mean $C_{max}$ for 17.5 mg of TRM-201 is 236 ng/mL. The geometric mean $C_{max}$ for 17.5 mg of TRM-201 is 224 ng/mL. The arithmetic mean $C_{max}$ for 20 mg of TRM-201 is 277 ng/mL. The geometric mean $C_{max}$ for 20 mg of TRM-201 is 259 ng/mL. The arithmetic mean $C_{max}$ for 25 mg of TRM-201 is 336 ng/mL. The geometric mean $C_{max}$ for 25 mg of TRM-201 is 325 ng/mL.

FIG. 48 shows a summary of fasted $AUC_{0-\infty}$ for the 102 PK study only. The arithmetic mean $AUC_{0-\infty}$ for 12.5 mg of TRM-201 is 2010 ng·hr/mL. The geometric mean $AUC_{0-\infty}$ for 12.5 mg of TRM-201 is 1880 ng·hr/mL. The arithmetic mean $AUC_{0-\infty}$ for 17.5 mg of TRM-201 is 3290 ng·hr/mL. The geometric mean $AUC_{0-\infty}$ for 17.5 mg of TRM-201 is 3110 ng·hr/mL. The arithmetic mean $AUC_{0-\infty}$ for 20 mg of TRM-201 is 3750 ng·hr/mL. The geometric mean $AUC_{0-\infty}$ for 20 mg of TRM-201 is 3550 ng·hr/mL. The arithmetic mean $AUC_{0-\infty}$ for 25 mg of TRM-201 is 4630 ng·hr/mL. The geometric mean $AUC_{0-\infty}$ for 25 mg of TRM-201 is 4490 ng·hr/mL. FIG. 48 also shows values for two model projections (calculated via an MMRM model) of $AUC_{0-\infty}$ geometric means across dosages.

FIG. 49 shows a summary of fasted $C_{max}$ for the 102 PK study only. The arithmetic mean $C_{max}$ for 12.5 mg of TRM-201 is 151 ng/mL. The geometric mean $C_{max}$ for 12.5 mg of TRM-201 is 144 ng/mL. The arithmetic mean $C_{max}$ for 17.5 mg of TRM-201 is 236 ng/mL. The geometric mean $C_{max}$ for 17.5 mg of TRM-201 is 224 ng/mL. The arithmetic mean $C_{max}$ for 20 mg of TRM-201 is 277 ng/mL. The geometric mean $C_{max}$ for 20 mg of TRM-201 is 259 ng/mL. The arithmetic mean $C_{max}$ for 25 mg of TRM-201 is 349 ng/mL. The geometric mean $C_{max}$ for 25 mg of TRM-201 is 341 ng/mL.

FIG. 50 shows a summary of fasted $AUC_{0-\infty}$ and $C_{max}$ by gender for the 102 PK study only for 12.5 mg of TRM-201. For males, the arithmetic mean $AUC_{0-\infty}$ is 1750 ng·hr/mL and the arithmetic mean $C_{max}$ is 132 ng/mL. For males, the geometric mean $AUC_{0-\infty}$ is 1580 ng·hr/mL and the geometric mean $C_{max}$ is 127 ng/mL. For females, the arithmetic mean $AUC_{0-\infty}$ is 2240 ng·hr/mL and the arithmetic mean $C_{max}$ is 168 ng/mL. For females, the geometric mean $AUC_{0-\infty}$ is 2170 ng·hr/mL and the geometric mean $C_{max}$ is 160 ng/mL.

FIG. 51 shows a summary of fasted $AUC_{0-\infty}$ and $C_{max}$ by gender for the 102 PK study only for 17.5 mg of TRM-201. For males, the arithmetic mean $AUC_{0-\infty}$ is 2860 ng·hr/mL and the arithmetic mean $C_{max}$ is 201 ng/mL. For males, the geometric mean $AUC_{0-\infty}$ is 2710 ng·hr/mL and the geometric mean $C_{max}$ is 196 ng/mL. For females, the arithmetic mean $AUC_{0-\infty}$ is 3650 ng·hr/mL and the arithmetic mean $C_{max}$ is 266 ng/mL. For females, the geometric mean $AUC_{0-\infty}$ is 3490 ng·hr/mL and the geometric mean $C_{max}$ is 251 ng/mL.

FIG. 52 shows a summary of fasted $AUC_{0-\infty}$ and $C_{max}$ by gender for the 102 PK study only for 20 mg of TRM-201. For males, the arithmetic mean $AUC_{0-\infty}$ is 3130 ng·hr/mL and the arithmetic mean $C_{max}$ is 234 ng/mL. For males, the geometric mean $AUC_{0-\infty}$ is 2940 ng·hr/mL and the geometric mean $C_{max}$ is 224 ng/mL. For females, the arithmetic mean $AUC_{0-\infty}$ is 4270 ng·hr/mL and the arithmetic mean $C_{max}$ is 314 ng/mL. For females, the geometric mean $AUC_{0-\infty}$ is 4160 ng·hr/mL and the geometric mean $C_{max}$ is 293 ng/mL.

FIG. 53 shows a summary of fasted $AUC_{0-\infty}$ and $C_{max}$ by gender for the 102 PK study only for 25 mg of TRM-201. For males, the arithmetic mean $AUC_{0-\infty}$ is 4080 ng·hr/mL and the arithmetic mean $C_{max}$ is 302 ng/mL. For males, the geometric mean $AUC_{0-\infty}$ is 3940 ng·hr/mL and the geometric mean $C_{max}$ is 298 ng/mL. For females, the arithmetic mean $AUC_{0-\infty}$ is 5090 ng·hr/mL and the arithmetic mean $C_{max}$ is 388 ng/mL. For males, the geometric mean $AUC_{0-\infty}$ is 5020 ng·hr/mL and the geometric mean $C_{max}$ is 382 ng/mL.

FIG. 54 shows a summary of fasted $AUC_{0-\infty}$ and $C_{max}$ by age for the 102 PK study only for 12.5 mg of TRM-201. For 18-40 years, the arithmetic mean $AUC_{0-\infty}$ is 1680 ng·hr/mL and the arithmetic mean $C_{max}$ is 164 ng/mL. For 18-40 years, the geometric mean $AUC_{0-\infty}$ is 1570 ng·hr/mL and the geometric mean $C_{max}$ is 156 ng/mL. For 41-52 years, the arithmetic mean $AUC_{0-\infty}$ is 2090 ng·hr/mL and the arithmetic mean $C_{max}$ is 140 ng/mL. For 41-52 years, the geometric mean $AUC_{0-\infty}$ is 1880 ng·hr/mL and the geometric mean $C_{max}$ is 133 ng/mL. For 53-60 years, the arithmetic mean $AUC_{0-\infty}$ is 2270 ng·hr/mL and the arithmetic mean $C_{max}$ is 150 ng/mL. For 53-60 years, the geometric mean $AUC_{0-\infty}$ is 2240 ng·hr/mL and the geometric mean $C_{max}$ is 143 ng/mL.

FIG. 55 shows a summary of fasted $AUC_{0-\infty}$ and $C_{max}$ by age for the 102 PK study only for 17.5 mg of TRM-201. For 18-40 years, the arithmetic mean $AUC_{0-\infty}$ is 2820 ng·hr/mL and the arithmetic mean $C_{max}$ is 237 ng/mL. For 18-40 years, the geometric mean $AUC_{0-\infty}$ is 2750 ng·hr/mL and the geometric mean $C_{max}$ is 229 ng/mL. For 41-52 years, the arithmetic mean $AUC_{0-\infty}$ is 3520 ng·hr/mL and the arithmetic mean $C_{max}$ is 232 ng/mL. For 41-52 years, the geometric mean $AUC_{0-\infty}$ is 3160 ng·hr/mL and the geometric mean $C_{max}$ is 213 ng/mL. For 53-60 years, the arithmetic mean $AUC_{0-\infty}$ is 3510 ng·hr/mL and the arithmetic mean $C_{max}$ is 239 ng/mL. For 53-60 years, the geometric mean $AUC_{0-\infty}$ is 3470 ng·hr/mL and the geometric mean $C_{max}$ is 230 ng/mL.

FIG. 56 shows a summary of fasted $AUC_{0-\infty}$ and $C_{max}$ by age for the 102 PK study only for 20 mg of TRM-201. For 18-40 years, the arithmetic mean $AUC_{0-\infty}$ is 3580 ng·hr/mL and the arithmetic mean $C_{max}$ is 308 ng/mL. For 18-40 years, the geometric mean $AUC_{0-\infty}$ is 3420 ng·hr/mL and the geometric mean $C_{max}$ is 289 ng/mL. For 41-52 years, the arithmetic mean $AUC_{0-\infty}$ is 3730 ng·hr/mL and the arithmetic mean $C_{max}$ is 262 ng/mL. For 41-52 years, the geometric mean $AUC_{0-\infty}$ is 3360 ng·hr/mL and the geometric mean $C_{max}$ is 242 ng/mL. For 53-60 years, the arithmetic mean $AUC_{0-\infty}$ is 3940 ng·hr/mL and the arithmetic mean $C_{max}$ is 260 ng/mL. For 53-60 years, the geometric mean $AUC_{0-\infty}$ is 3880 ng·hr/mL and the geometric mean $C_{max}$ is 249 ng/mL.

FIG. 57 shows a summary of fasted $AUC_{0-\infty}$ and $C_{max}$ by age for the 102 PK study only for 25 mg of TRM-201. For 18-40 years, the arithmetic mean $AUC_{0-\infty}$ is 4140 ng·hr/mL and the arithmetic mean $C_{max}$ is 366 ng/mL. For 18-40 years, the geometric mean $AUC_{0-\infty}$ is 4050 ng·hr/mL and the geometric mean $C_{max}$ is 356 ng/mL. For 41-52 years, the arithmetic mean $AUC_{0-\infty}$ is 4810 ng·hr/mL and the arithmetic mean $C_{max}$ is 326 ng/mL. For 41-52 years, the geometric mean $AUC_{0-\infty}$ is 4580 ng·hr/mL and the geometric mean $C_{max}$ is 321 ng/mL. For 53-60 years, the arithmetic mean $AUC_{0-\infty}$ is 4940 ng·hr/mL and the arithmetic mean $C_{max}$ is 354 ng/mL. For 53-60 years, the geometric mean $AUC_{0-\infty}$ is 4880 ng·hr/mL and the geometric mean $C_{max}$ is 347 ng/mL.

FIG. 58 shows a summary of fasted $AUC_{0-\infty}$ and $C_{max}$ by race for the 102 PK study only for 12.5 mg of TRM-201. For Black or African-American subjects, the arithmetic mean $AUC_{0-\infty}$ is 1660 ng·hr/mL and the arithmetic mean $C_{max}$ is 143 ng/mL. For Black or African-American subjects, the geometric mean $AUC_{0-\infty}$ is 1590 ng·hr/mL and the geometric mean $C_{max}$ is 142 ng/mL. For White subjects, the arithmetic mean $AUC_{0-\infty}$ is 2110 ng·hr/mL and the arithmetic mean $C_{max}$ is 153 ng/mL. For White subjects, the geometric mean $AUC_{0-\infty}$ is 1960 ng·hr/mL and the geometric mean $C_{max}$ is 144 ng/mL.

FIG. 59 shows a summary of fasted $AUC_{0-\infty}$ and $C_{max}$ by race for the 102 PK study only for 17.5 mg of TRM-201. For Black or African-American subjects, the arithmetic mean $AUC_{0-\infty}$ is 2840 ng·hr/mL and the arithmetic mean $C_{max}$ is 217 ng/mL. For Black or African-American subjects, the geometric mean $AUC_{0-\infty}$ is 2800 ng·hr/mL and the geometric mean $C_{max}$ is 211 ng/mL. For White subjects, the arithmetic mean $AUC_{0-\infty}$ is 3400 ng·hr/mL and the arithmetic mean $C_{max}$ is 241 ng/mL. For White subjects, the geometric mean $AUC_{0-\infty}$ is 3200 ng·hr/mL and the geometric mean $C_{max}$ is 228 ng/mL.

FIG. 60 shows a summary of fasted $AUC_{0-\infty}$ and $C_{max}$ by race for the 102 PK study only for 20 mg of TRM-201. For Black or African-American subjects, the arithmetic mean $AUC_{0-\infty}$ is 3380 ng·hr/mL and the arithmetic mean $C_{max}$ is 298 ng/mL. For Black or African-American subjects, the geometric mean $AUC_{0-\infty}$ is 3300 ng·hr/mL and the geometric mean $C_{max}$ is 295 ng/mL. For White subjects, the arithmetic mean $AUC_{0-\infty}$ is 3850 ng·hr/mL and the arithmetic mean $C_{max}$ is 271 ng/mL. For White subjects, the geometric mean $AUC_{0-\infty}$ is 3610 ng·hr/mL and the geometric mean $C_{max}$ is 250 ng/mL.

FIG. 61 shows a summary of fasted $AUC_{0-\infty}$ and $C_{max}$ by race for the 102 PK study only for 25 mg of TRM-201. For Black or African-American subjects, the arithmetic mean $AUC_{0-\infty}$ is 3990 ng·hr/mL and the arithmetic mean $C_{max}$ is 340 ng/mL. For Black or African-American subjects, the geometric mean $AUC_{0-\infty}$ is 3940 ng·hr/mL and the geometric mean $C_{max}$ is 339 ng/mL. For White subjects, the arithmetic mean $AUC_{0-\infty}$ is 4800 ng·hr/mL and the arithmetic mean $C_{max}$ is 351 ng/mL. For White subjects, the geometric mean $AUC_{0-\infty}$ is 4650 ng·hr/mL and the geometric mean $C_{max}$ is 341 ng/mL.

FIG. 62 shows a summary of fasted $AUC_{0-\infty}$ and $C_{max}$ by body weight for the 102 PK study only for 12.5 mg of TRM-201. For 47-70 kg, the arithmetic mean $AUC_{0-\infty}$ is 1850 ng·hr/mL and the arithmetic mean $C_{max}$ is 175 ng/mL. For 47-70 kg, the geometric mean $AUC_{0-\infty}$ is 1690 ng·hr/mL and the geometric mean $C_{max}$ is 165 ng/mL. For 70.1-77 kg, the arithmetic mean $AUC_{0-\infty}$ is 2500 ng·hr/mL and the arithmetic mean $C_{max}$ is 155 ng/mL. For 70.1-77 kg, the geometric mean $AUC_{0-\infty}$ is 2420 ng·hr/mL and the geometric mean $C_{max}$ is 147 ng/mL. For 77.1-90 kg, the arithmetic mean $AUC_{0-\infty}$ is 1790 ng·hr/mL and the arithmetic mean $C_{max}$ is 127 ng/mL. For 77.1-90 kg, the geometric mean $AUC_{0-\infty}$ is 1690 ng·hr/mL and the geometric mean $C_{max}$ is 125 ng/mL.

FIG. 63 shows a summary of fasted $AUC_{0-\infty}$ and $C_{max}$ by body weight for the 102 only for 17.5 mg of TRM-201. For 47-70 kg, the arithmetic mean $AUC_{0-\infty}$ is 3180 ng·hr/mL and the arithmetic mean $C_{max}$ is 261 ng/mL. For 47-70 kg, the geometric mean $AUC_{0-\infty}$ is 2930 ng·hr/mL and the geometric mean $C_{max}$ is 242 ng/mL. For 70.1-77 kg, the arithmetic mean $AUC_{0-\infty}$ is 3890 ng·hr/mL and the arithmetic mean $C_{max}$ is 254 ng/mL. For 70.1-77 kg, the geometric mean $AUC_{0-\infty}$ is 3730 ng·hr/mL and the geometric mean $C_{max}$ is 246 ng/mL. For 77.1-90 kg, the arithmetic mean $AUC_{0-\infty}$ is 2910 ng·hr/mL and the arithmetic mean $C_{max}$ is 200 ng/mL. For 77.1-90 kg, the geometric mean $AUC_{0-\infty}$ is 2850 ng·hr/mL and the geometric mean $C_{max}$ is 194 ng/mL.

FIG. 64 shows a summary of fasted $AUC_{0-\infty}$ and $C_{max}$ by body weight for the 102 PK study only for 20 mg of TRM-201. For 47-70 kg, the arithmetic mean $AUC_{0-\infty}$ is 3650 ng·hr/mL and the arithmetic mean $C_{max}$ is 336 ng/mL. For 47-70 kg, the geometric mean $AUC_{0-\infty}$ is 3340 ng·hr/mL and the geometric mean $C_{max}$ is 307 ng/mL. For 70.1-77 kg, the arithmetic mean $AUC_{0-\infty}$ is 4500 ng·hr/mL and the arithmetic mean $C_{max}$ is 259 ng/mL. For 70.1-77 kg, the geometric mean $AUC_{0-\infty}$ is 4400 ng·hr/mL and the geometric mean $C_{max}$ is 248 ng/mL. For 77.1-90 kg, the arithmetic mean $AUC_{0-\infty}$ is 3250 ng·hr/mL and the arithmetic mean $C_{max}$ is 238 ng/mL. For 77.1-90 kg, the geometric mean $AUC_{0-\infty}$ is 3170 ng·hr/mL and the geometric mean $C_{max}$ is 231 ng/mL.

FIG. 65 shows a summary of fasted $AUC_{0-\infty}$ and $C_{max}$ by body weight for the 102 PK study only for 25 mg of TRM-201. For 47-70 kg, the arithmetic mean $AUC_{0-\infty}$ is 4450 ng·hr/mL and the arithmetic mean $C_{max}$ is 385 ng/mL. For 47-70 kg, the geometric mean $AUC_{0-\infty}$ is 4310 ng·hr/mL and the geometric mean $C_{max}$ is 376 ng/mL. For 70.1-77 kg, the arithmetic mean $AUC_{0-\infty}$ is 5470 ng·hr/mL and the arithmetic mean $C_{max}$ is 371 ng/mL. For 70.1-77 kg, the geometric mean $AUC_{0-\infty}$ is 5410 ng·hr/mL and the geometric mean $C_{max}$ is 368 ng/mL. For 77.1-90 kg, the arithmetic mean $AUC_{0-\infty}$ is 4130 ng·hr/mL and the arithmetic mean $C_{max}$ is 299 ng/mL. For 77.1-90 kg, the geometric mean $AUC_{0-\infty}$ is 4040 ng·hr/mL and the geometric mean $C_{max}$ is 294 ng/mL.

FIG. 66 shows a summary of fasted $AUC_{0-\infty}$ and $C_{max}$ by ethnicity for the 102 PK study only for 12.5 mg of TRM-201. For Hispanic or Latino subjects, the arithmetic mean $AUC_{0-\infty}$ is 2210 ng·hr/mL and the arithmetic mean $C_{max}$ is 157 ng/mL. For Hispanic or Latino subjects, the geometric mean $AUC_{0-\infty}$ is 2090 ng·hr/mL and the geometric mean $C_{max}$ is 146 ng/mL. For non-Hispanic or non-Latino subjects, the arithmetic mean $AUC_{0-\infty}$ is 1820 ng·hr/mL and the arithmetic mean $C_{max}$ is 146 ng/mL. For non-Hispanic or non-Latino subjects, the geometric mean $AUC_{0-\infty}$ is 1680 ng·hr/mL and the geometric mean $C_{max}$ is 141 ng/mL.

FIG. 67 shows a summary of fasted $AUC_{0-\infty}$ and $C_{max}$ by ethnicity for the 102 PK study only for 17.5 mg of TRM-201. For Hispanic or Latino subjects, the arithmetic mean $AUC_{0-\infty}$ is 3520 ng·hr/mL and the arithmetic mean $C_{max}$ is 258 ng/mL. For Hispanic or Latino subjects, the geometric mean $AUC_{0-\infty}$ is 3330 ng·hr/mL and the geometric mean $C_{max}$ is 243 ng/mL. For non-Hispanic or non-Latino subjects, the arithmetic mean $AUC_{0-\infty}$ is 3050 ng·hr/mL and the arithmetic mean $C_{max}$ is 214 ng/mL. For non-Hispanic or non-Latino subjects, the geometric mean $AUC_{0-\infty}$ is 2910 ng·hr/mL and the geometric mean $C_{max}$ is 207 ng/mL.

FIG. 68 shows a summary of fasted $AUC_{0-\infty}$ and $C_{max}$ by ethnicity for the 102 PK study only for 20 mg of TRM-201. For Hispanic or Latino subjects, the arithmetic mean $AUC_{0-\infty}$ is 3840 ng·hr/mL and the arithmetic mean $C_{max}$ is 281 ng/mL. For Hispanic or Latino subjects, the geometric mean $AUC_{0-\infty}$ is 3630 ng·hr/mL and the geometric mean $C_{max}$ is 258 ng/mL. For non-Hispanic or non-Latino subjects, the arithmetic mean $AUC_{0-\infty}$ is 3660 ng·hr/mL and the arithmetic mean $C_{max}$ is 272 ng/mL. For non-Hispanic or non-Latino subjects, the geometric mean $AUC_{0-\infty}$ is 3470 ng·hr/mL and the geometric mean $C_{max}$ is 260 ng/mL.

FIG. 69 shows a summary of fasted $AUC_{0-\infty}$ and $C_{max}$ by ethnicity for the 102 PK study only for 25 mg of TRM-201. For Hispanic or Latino subjects, the arithmetic mean $AUC_{0-\infty}$ is 4980 ng·hr/mL and the arithmetic mean $C_{max}$ is 358 ng/mL. For Hispanic or Latino subjects, the geometric mean $AUC_{0-\infty}$ is 4870 ng·hr/mL and the geometric mean $C_{max}$ is 351 ng/mL. For non-Hispanic or non-Latino subjects, the arithmetic mean $AUC_{0-\infty}$ is 4280 ng·hr/mL and the arithmetic mean $C_{max}$ is 340 ng/mL. For non-Hispanic or non-Latino subjects, the geometric mean $AUC_{0-\infty}$ is 4150 ng·hr/mL and the geometric mean $C_{max}$ is 331 ng/mL.

FIG. 70 shows a sensitivity analysis of fasted $AUC_{0-\infty}$ and $C_{max}$ compared to historical data. The geometric mean ratio $AUC_{0-\infty}$ of TRM-201 17.5 mg to historical data for the 25 mg VIOXX product is 0.819. The geometric mean ratio $C_{max}$ of TRM-201 17.5 mg to historical data for the 25 mg VIOXX product is 1.03. The geometric mean ratio $AUC_{0-\infty}$ of TRM-201 20 mg to historical data for the 25 mg VIOXX product is 0.934. The geometric mean ratio $C_{max}$ of TRM-201 20 mg to historical data for the 25 mg VIOXX product is 1.19. The $AUC_{0-\infty}$ and $C_{max}$ data for the 25 mg VIOXX product were obtained from Schwartz, J. I., et al. Clin. Drug Invent. 2003, 23 (8): 503-509.

FIG. 71 shows a summary of fasted $T_{max}$ and $t_{1/2}$ for the 101 and 102 PK studies combined. The median time at which the $C_{max}$ is observed ($T_{max}$) for 12.5 mg of TRM-201 is 2.00 hours. The median $T_{max}$ for 17.5 mg of TRM-201 is 2.00 hours. The $T_{max}$ for 20 mg of TRM-201 is 2.00 hours. The $T_{max}$ for 25 mg of TRM-201 is 2.50 hours. The median $t_{1/2}$ for 12.5 mg of TRM-201 is 12 hours. The $t_{1/2}$ is generally comparable across dosages. The median $t_{1/2}$ for 17.5 mg of TRM-201 is 11.7 hours. The median $t_{1/2}$ for 20 mg of TRM-201 is 12.2 hours. The median $t_{1/2}$ for 25 mg of TRM-201 is 11.6 hours.

FIG. 72 shows a summary of fasted CL/F and $V_d$/F for the 102 PK study only. FIG. 73 shows exploratory analysis of fasted $AUC_{0-\infty}$ and $C_{max}$ to estimate the dose that yields values equal to those observed in the historical data (for the 102 PK study only). FIG. 74 shows summary of treatment-emergent adverse events (TEAE). A total of three subjects exhibited a TEAE in the 102 PK study. One of these subjects was administered 12.5 mg of TRM-201 and the other two subjects were administered 25 mg of TRM-201. No subjects exhibited related TEAE, serious TEAE, TEAE leading to study discontinuation, or severe TEAE.

FIG. 75 shows incidence of treatment-emergent adverse events (TEAE) by system organ class and preferred term. At 12.5 mg of TRM-201, the TEAE in preferred term was constipation. At 25 mg of TRM-201, the TEAE in preferred term was ear discomfort and headache.

FIG. 76 shows no incidence of related TEAE at any dosage. FIG. 77 shows no incidence of serious TEAE at any dosage. FIG. 78 shows no incidence of TEAE leading to study discontinuation at any dosage. FIG. 79 shows incidence of TEAE by system organ class, preferred term, and severity. All reported TEAE were mild.

Figure 80:
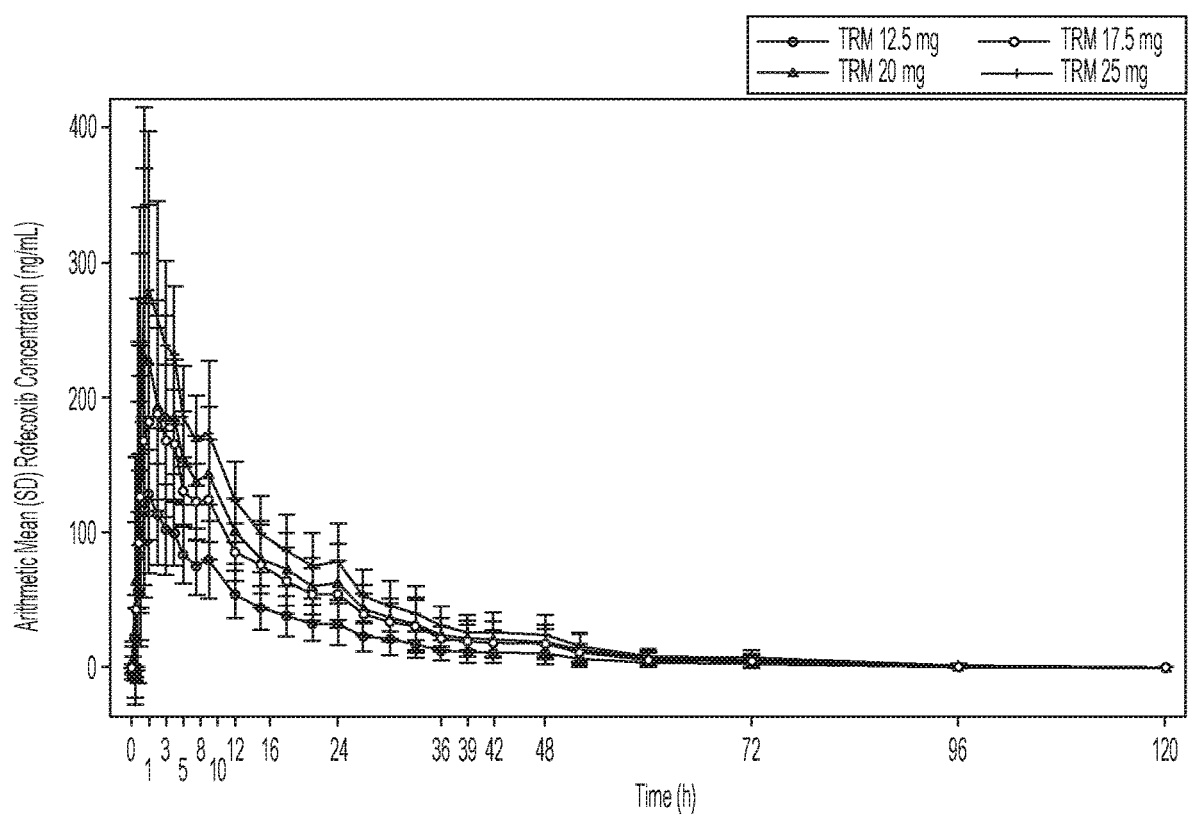
FIG. 80 shows arithmetic mean (SD) fasted concentration versus scheduled time profiles on the linear scale (102 study only).
Figure 81:
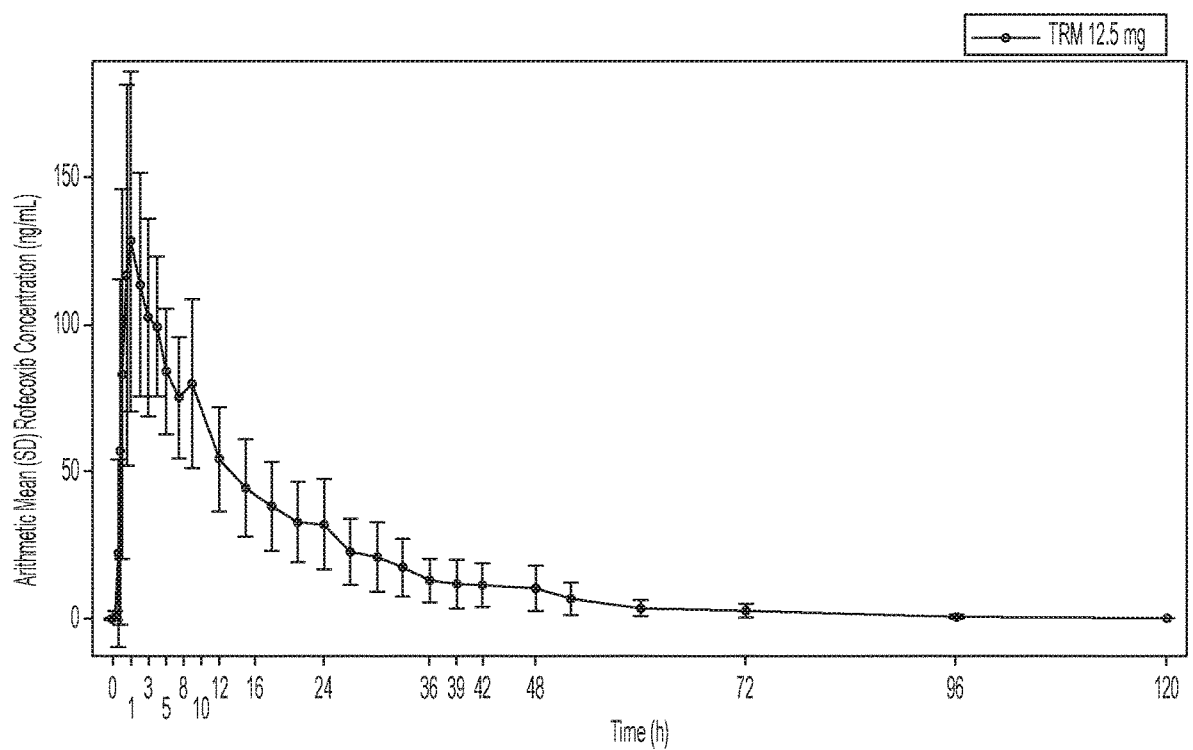
FIG. 81 shows TRM-201 12.5 mg arithmetic mean (SD) fasted concentration versus scheduled time profiles on the linear scale (102 study only).
Figure 82:
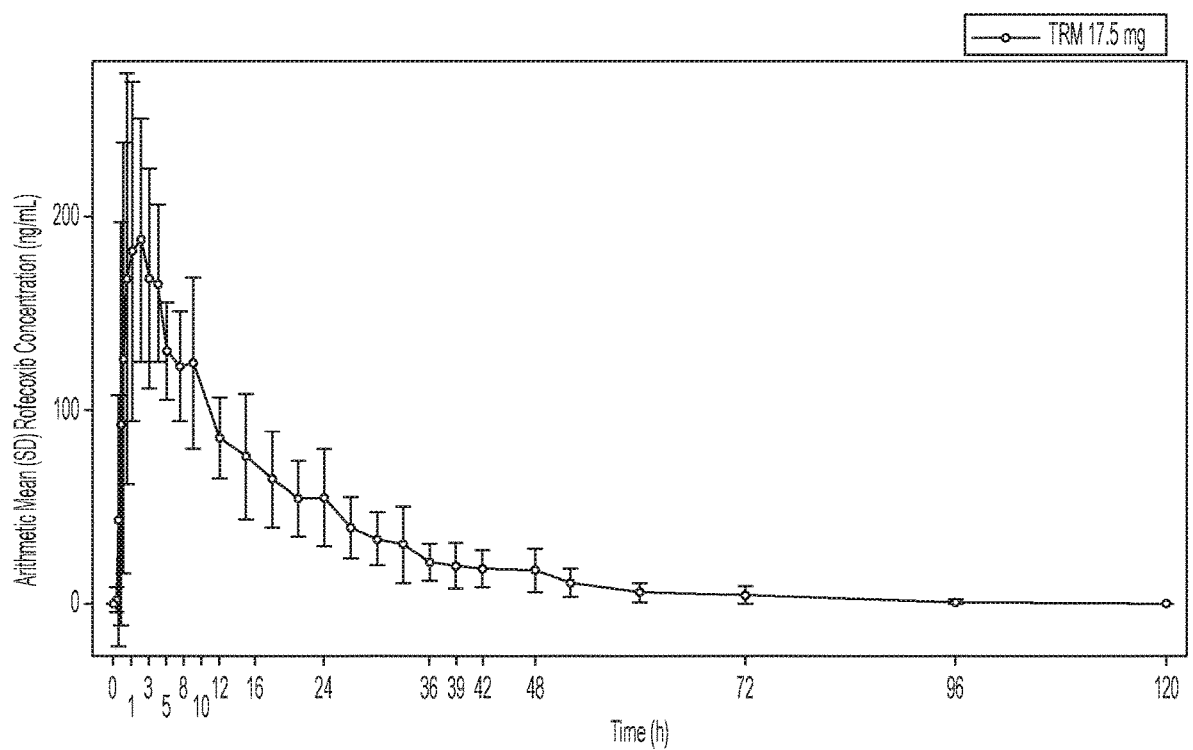
FIG. 82 shows TRM-201 17.5 mg arithmetic mean (SD) fasted concentration versus scheduled time profiles on the linear scale (102 study only).
Figure 83:
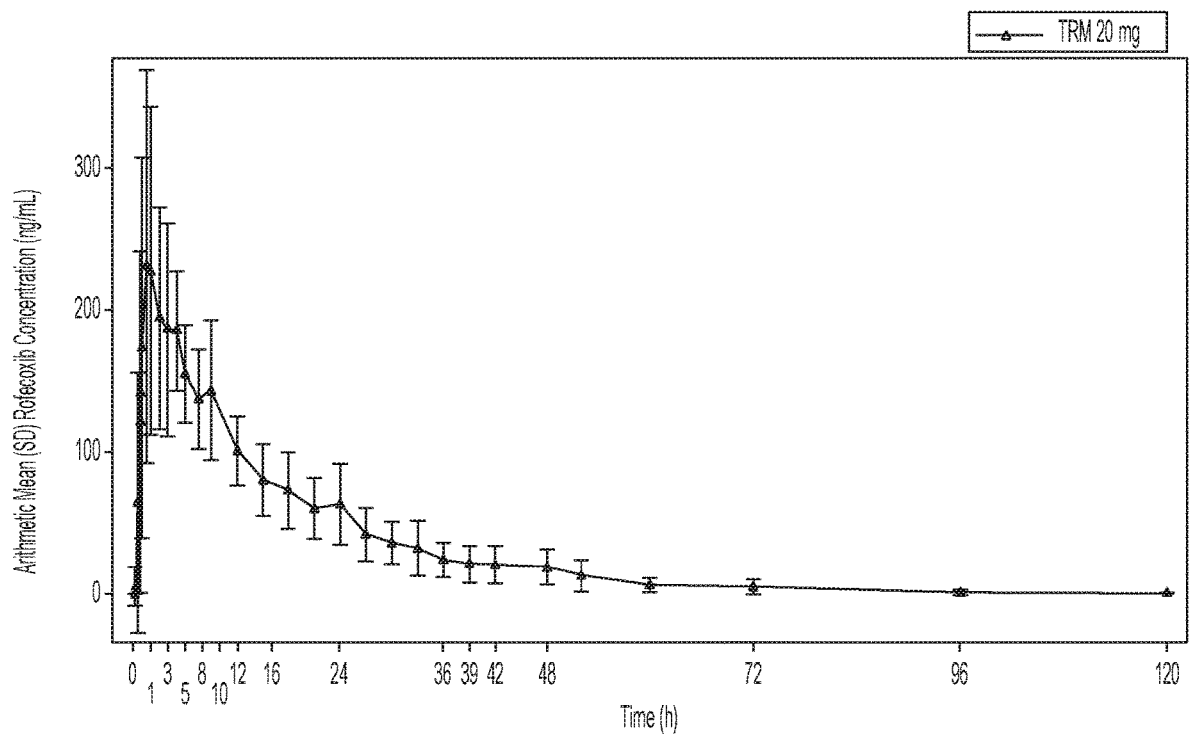
FIG. 83 shows TRM-201 20 mg arithmetic mean (SD) fasted concentration versus scheduled time profiles on the linear scale (102 study only).
Figure 84:
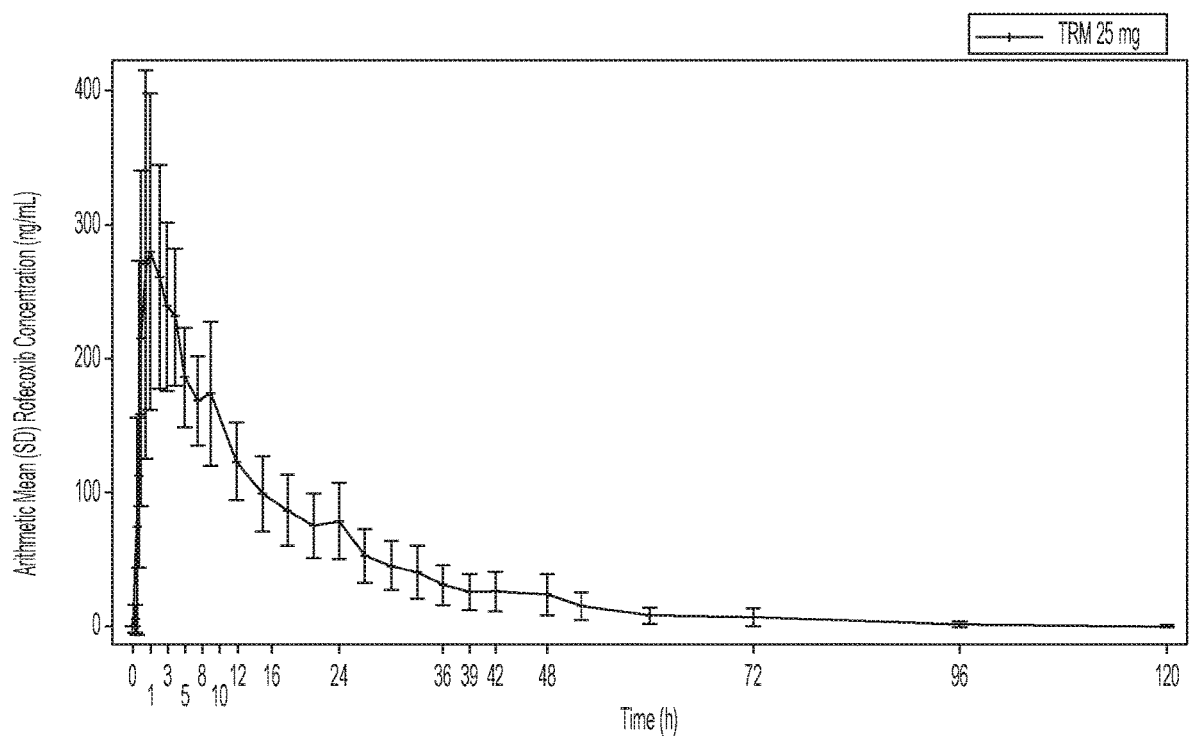
FIG. 84 shows TRM-201 25 mg arithmetic mean (SD) fasted concentration versus scheduled time profiles on the linear scale (102 study only).

FIG. 80 shows arithmetic mean (SD) fasted rofecoxib concentration across scheduled time profiles on the linear scale. The peak rofecoxib concentration was observed between 0 and 5 hours following administration for all dosages. FIGS. 81-84 show arithmetic mean (SD) fasted rofecoxib concentration across scheduled time profiles on the linear scale presented by dosage.

Figure 85:
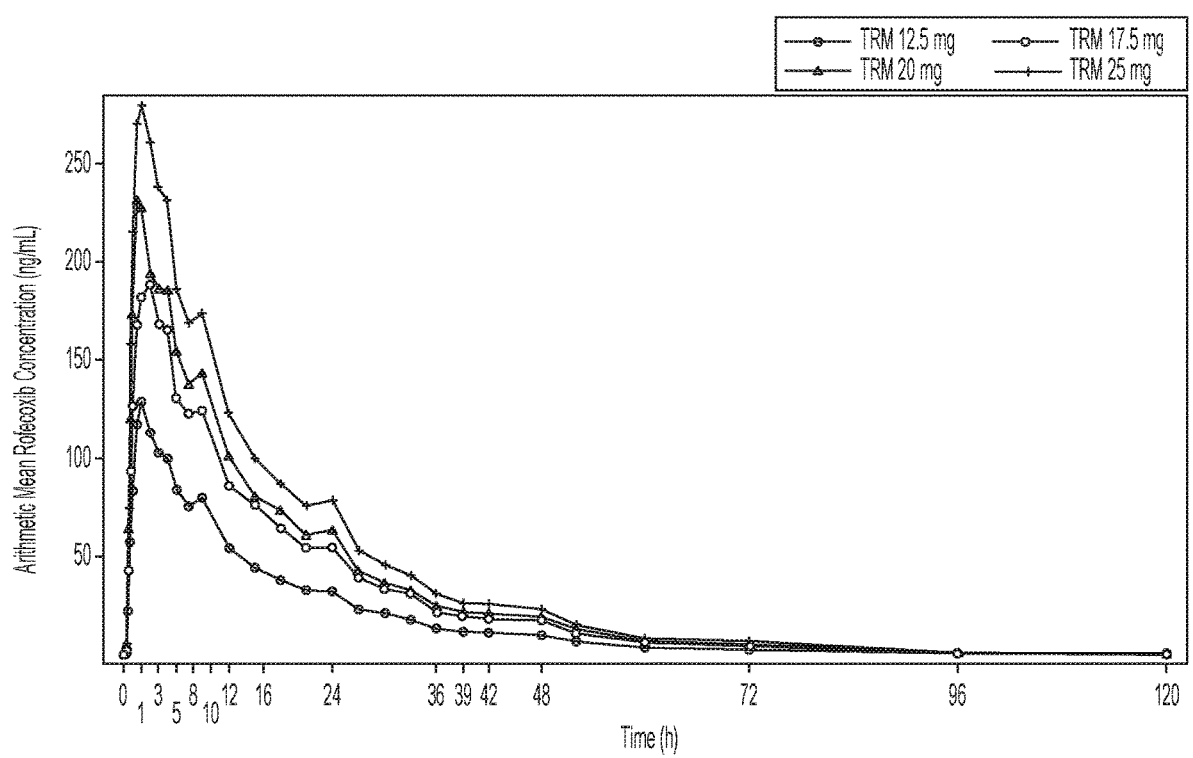
FIG. 85 shows arithmetic mean fasted concentration versus scheduled time profiles on the linear scale (102 study only).

FIG. 85 shows arithmetic mean fasted concentration across scheduled time profiles on the linear scale across dosages without standard deviations.

Figure 86:
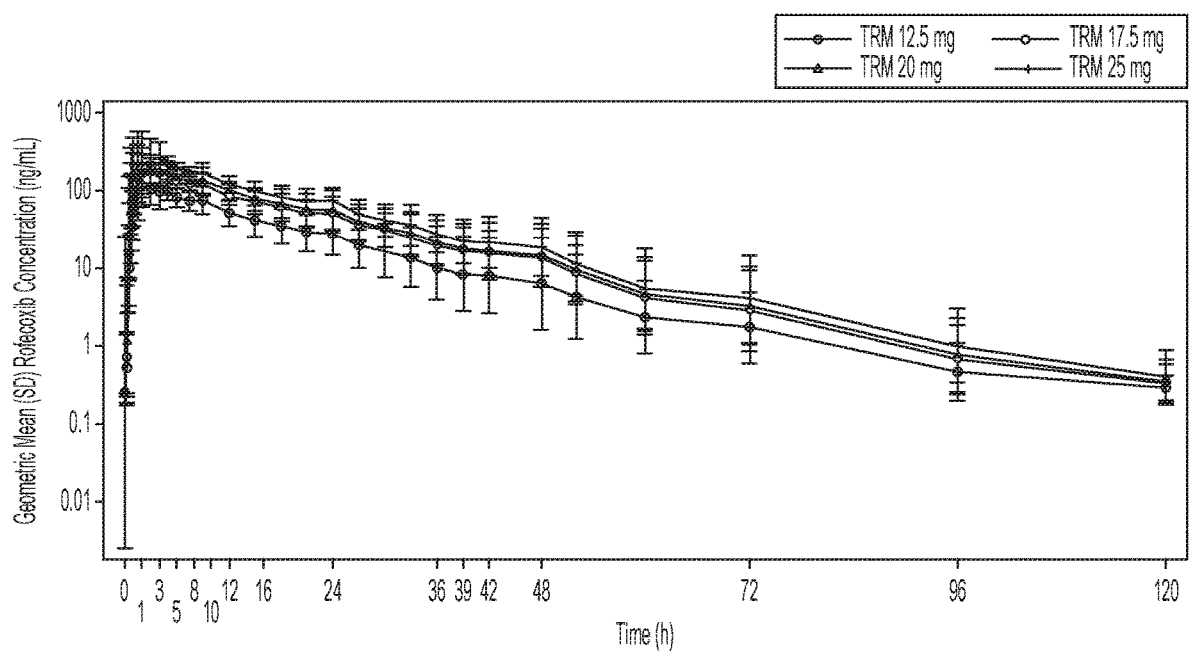
FIG. 86 shows geometric mean (SD) fasted concentration versus scheduled time profile on the semi-logarithmic scale (102 study only).
Figure 87:
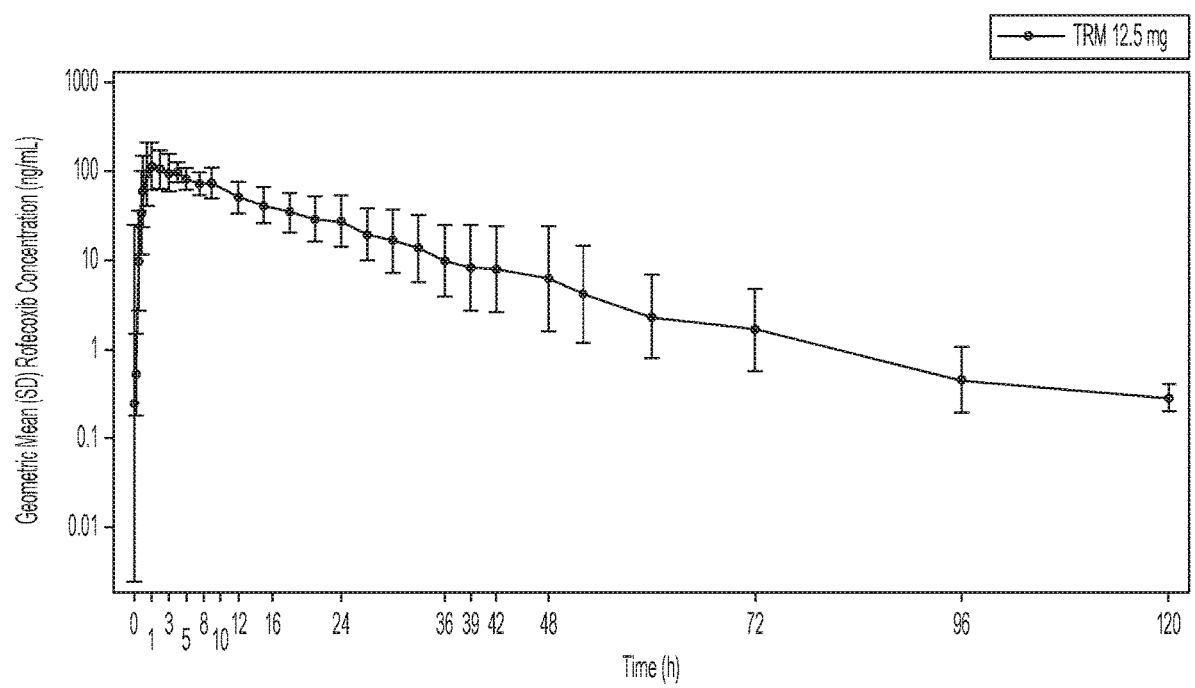
FIG. 87 shows TRM-201 12.5 mg geometric mean (SD) fasted concentration versus scheduled time profiles on the semi-logarithmic scale (102 study only).
Figure 88:
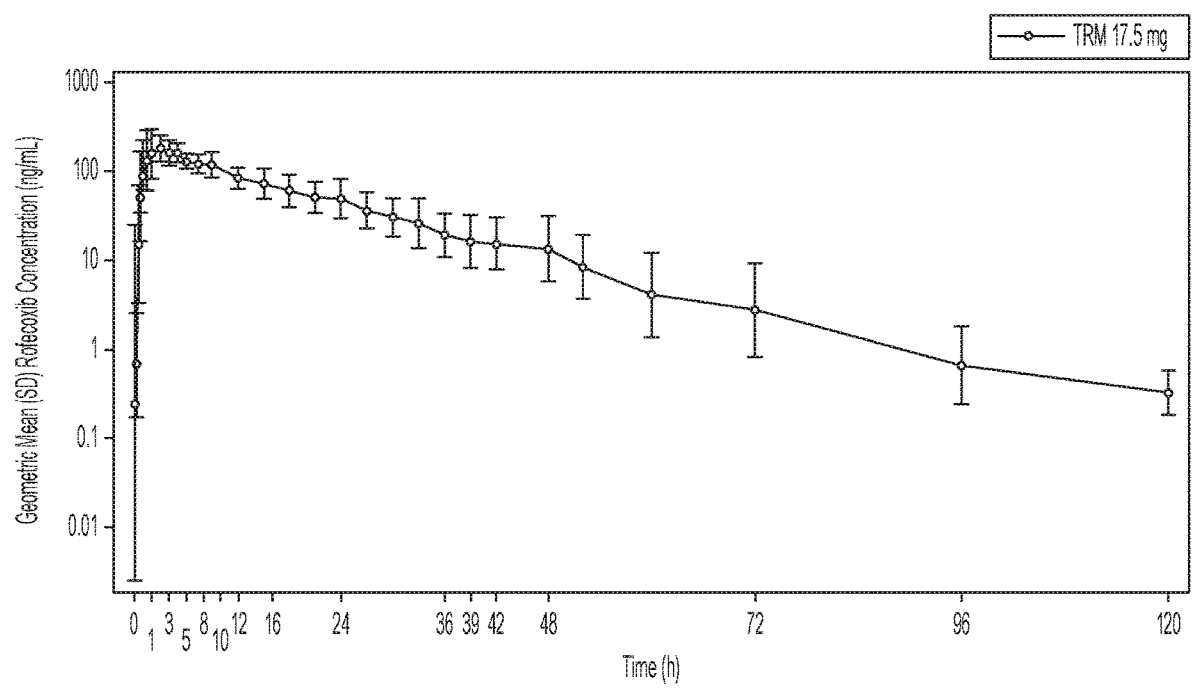
FIG. 88 shows TRM-201 17.5 mg geometric mean (SD) fasted concentration versus scheduled time profiles on the semi-logarithmic scale (102 study only).
Figure 89:
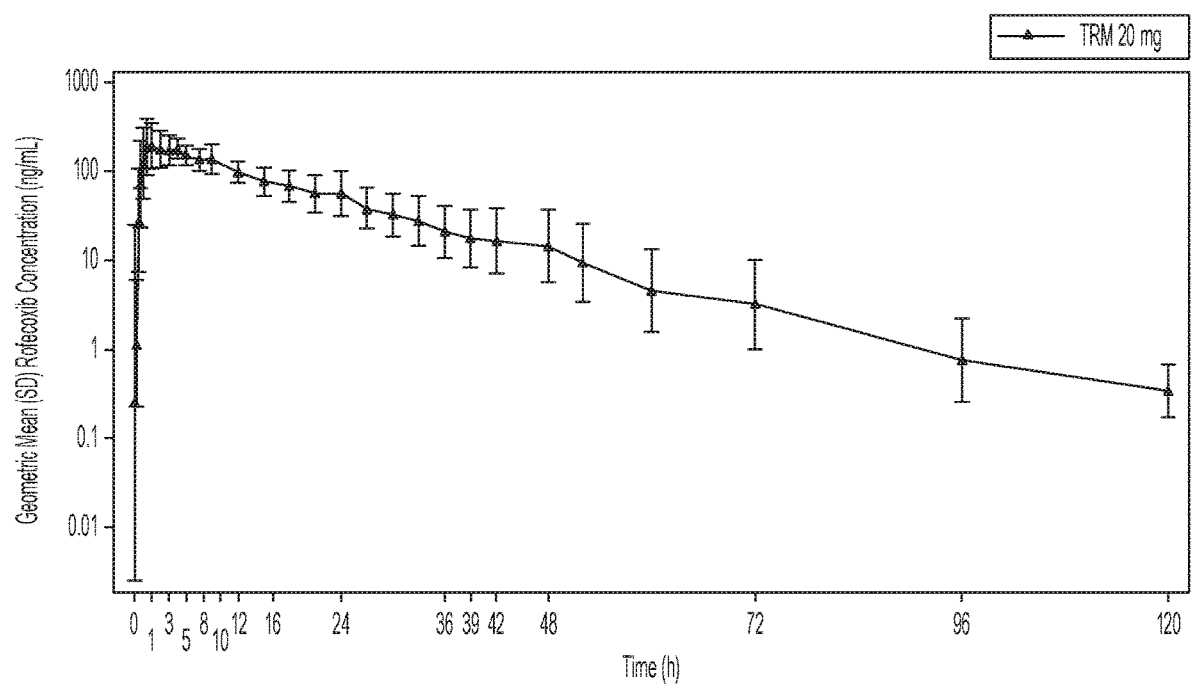
FIG. 89 shows TRM-201 20 mg geometric mean (SD) fasted concentration versus scheduled time profiles on the semi-logarithmic scale (102 study only).
Figure 90:
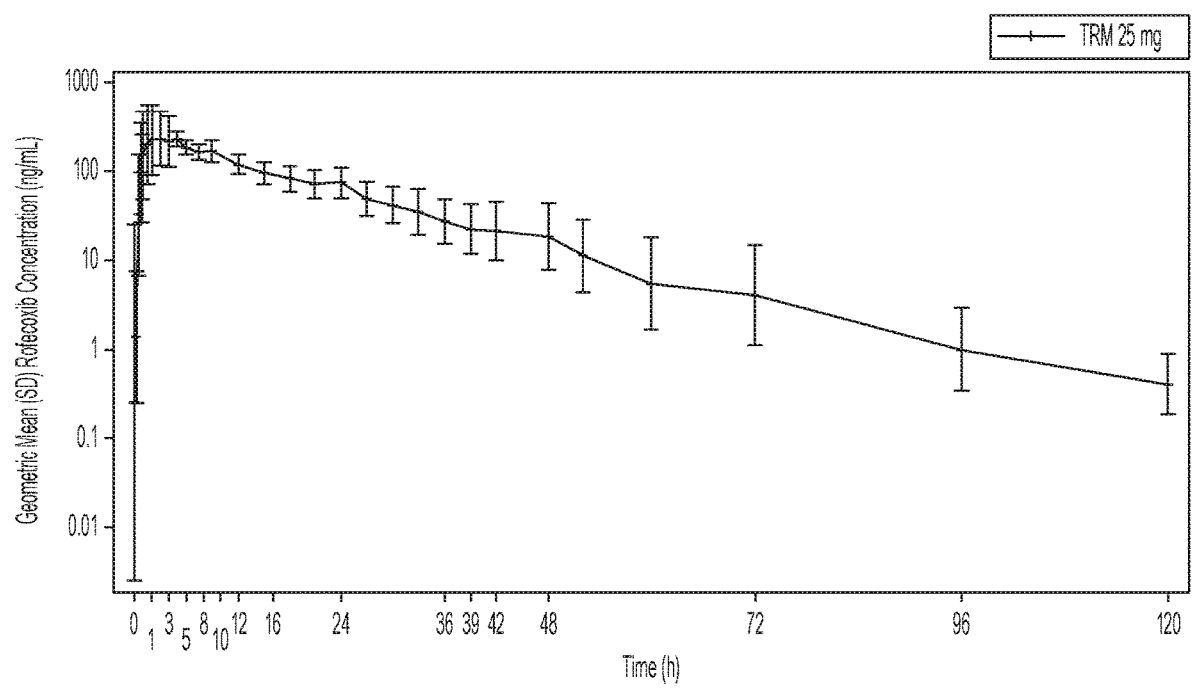
FIG. 90 shows TRM-201 25 mg geometric mean (SD) fasted concentration versus scheduled time profiles on the semi-logarithmic scale (102 study only).

FIG. 86 shows geometric mean (SD) fasted concentration across scheduled time profile on the semi-logarithmic scale. The peak rofecoxib concentration was observed between 0 and 5 hours following administration for all dosages. FIGS. 87-90 show geometric mean (SD) fasted concentration of rofecoxib across scheduled time profiles on the semi-logarithmic scale broken down by concentration.

Figure 91:
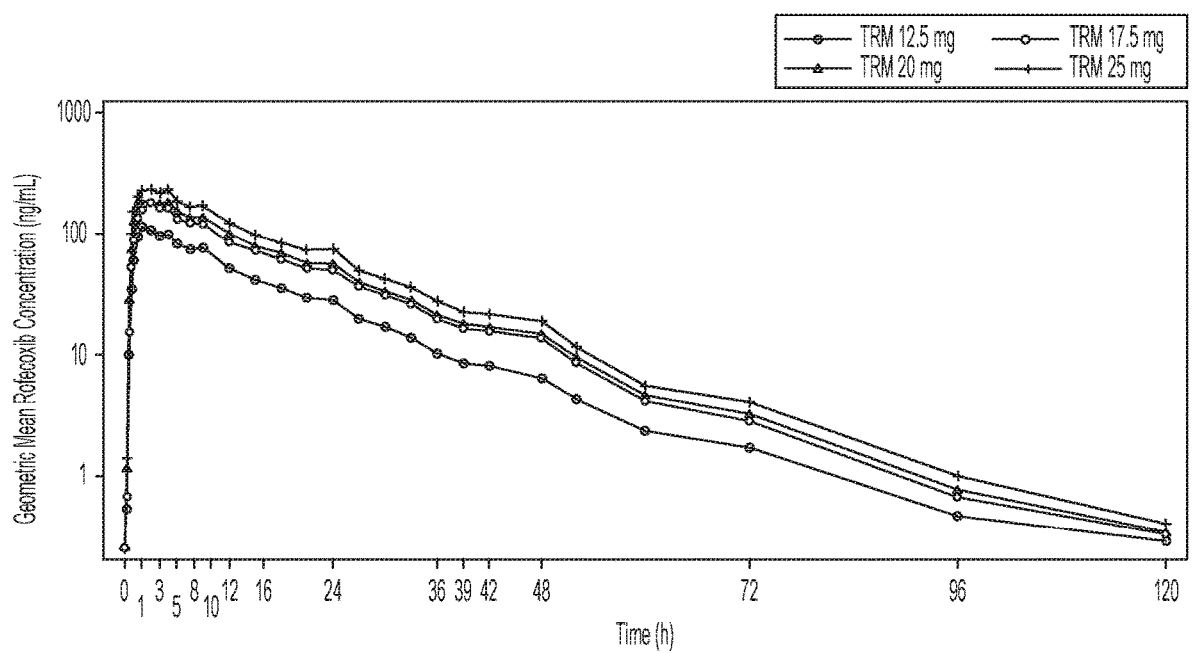
FIG. 91 shows geometric mean fasted concentration versus scheduled time profiles on the semi-logarithmic scale (102 study only).

FIG. 91 shows geometric mean fasted concentration versus scheduled time profiles on the semi-logarithmic scale for all dosages without standard deviations.

Figure 92:
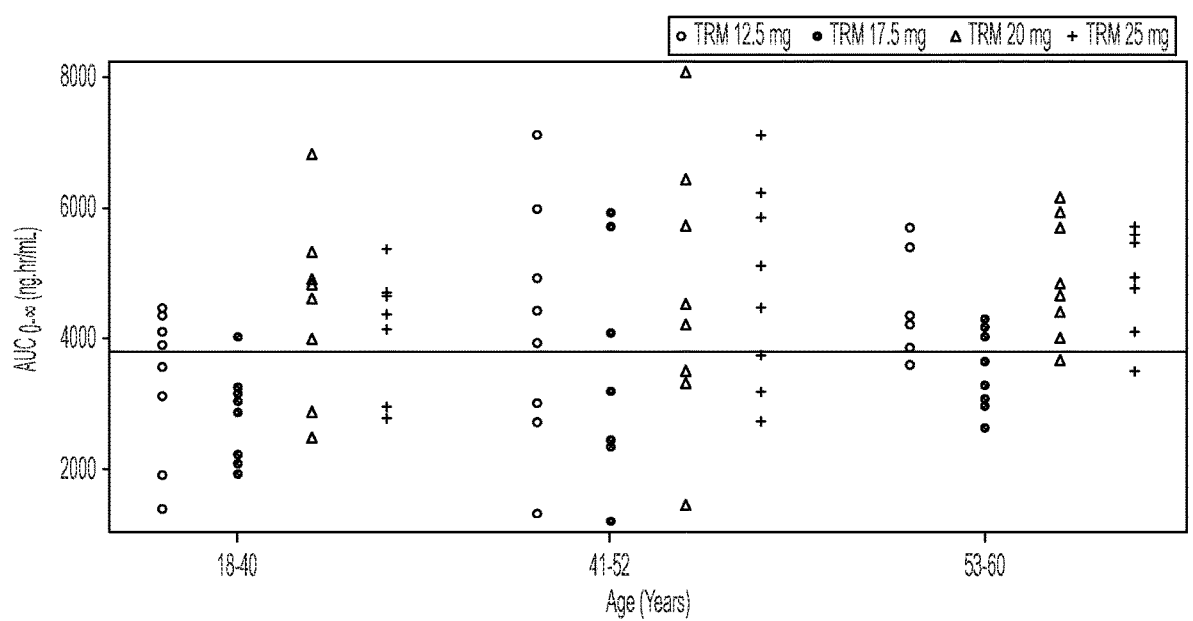
FIG. 92 shows a scatterplot of fasted $AUC_{0-\infty}$ by age (102 study only).
Figure 93:
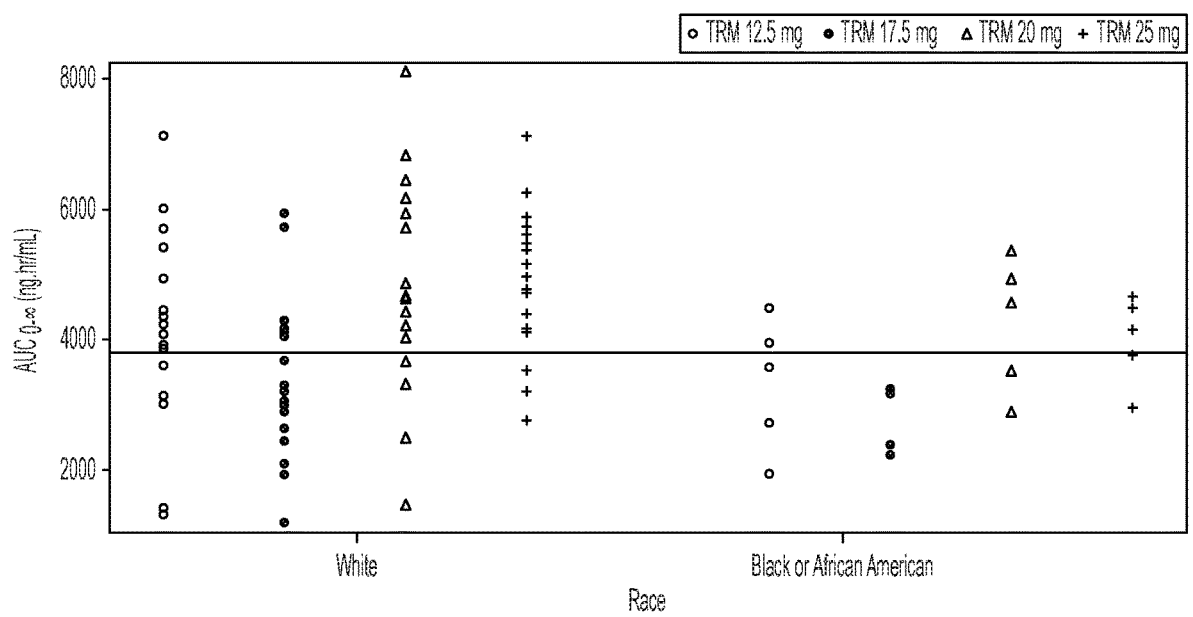
FIG. 93 shows a scatterplot of fasted $AUC_{0-\infty}$ by race (102 study only).
Figure 94:
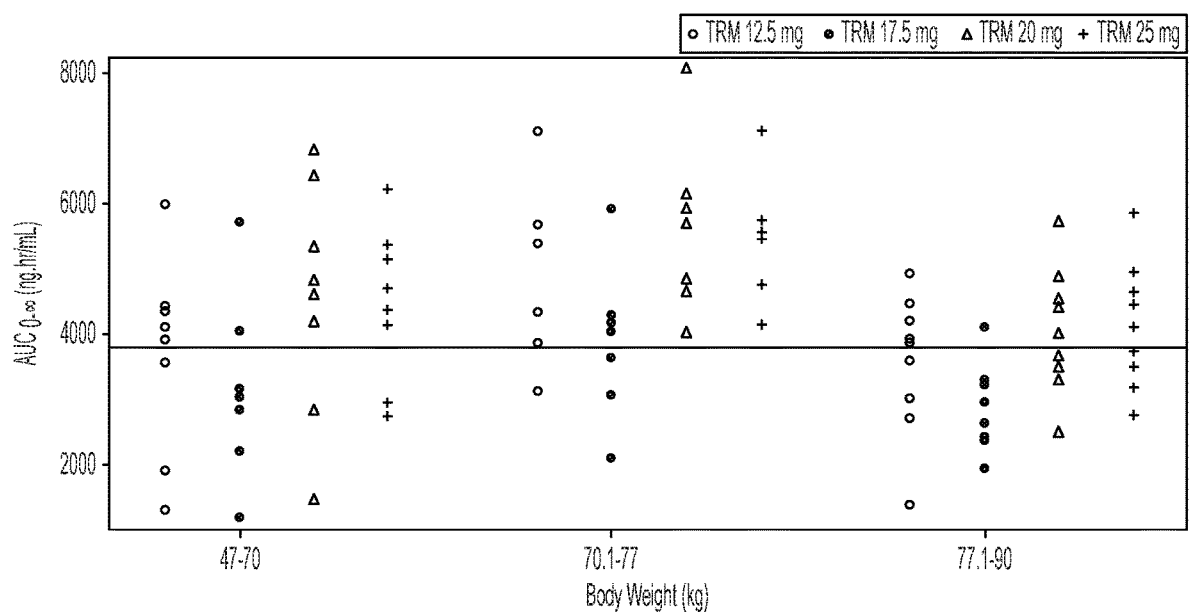
FIG. 94 shows a scatterplot of fasted $AUC_{0-\infty}$ by body weight (102 study only).
Figure 95:
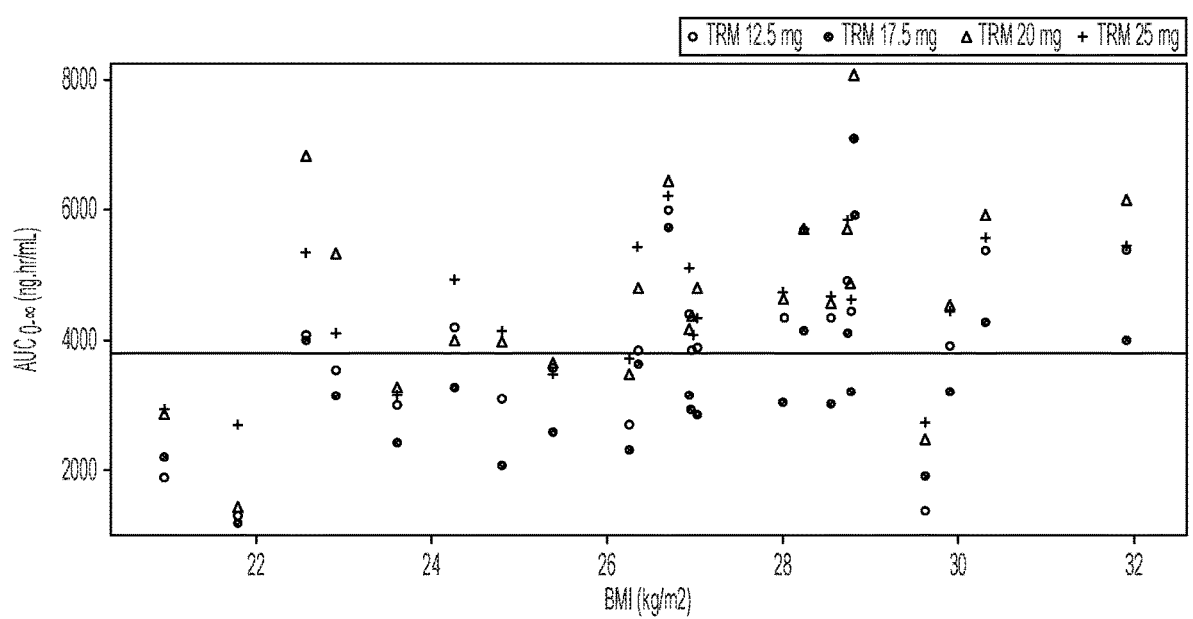
FIG. 95 shows a scatterplot of fasted $AUC_{0-\infty}$ by BMI (102 study only).

FIG. 92 shows a scatterplot of fasted $AUC_{0-\infty}$ values by age and by TRM-201 dosage. FIG. 93 shows a scatterplot of fasted $AUC_{0-\infty}$ values by race and by TRM-201 dosage. FIG. 94 shows a scatterplot of fasted $AUC_{0-\infty}$ values by body weight and by TRM-201 dosage. FIG. 95 shows a scatterplot of fasted $AUC_{0-\infty}$ values by BMI and by TRM-201 dosage.

Figure 96:
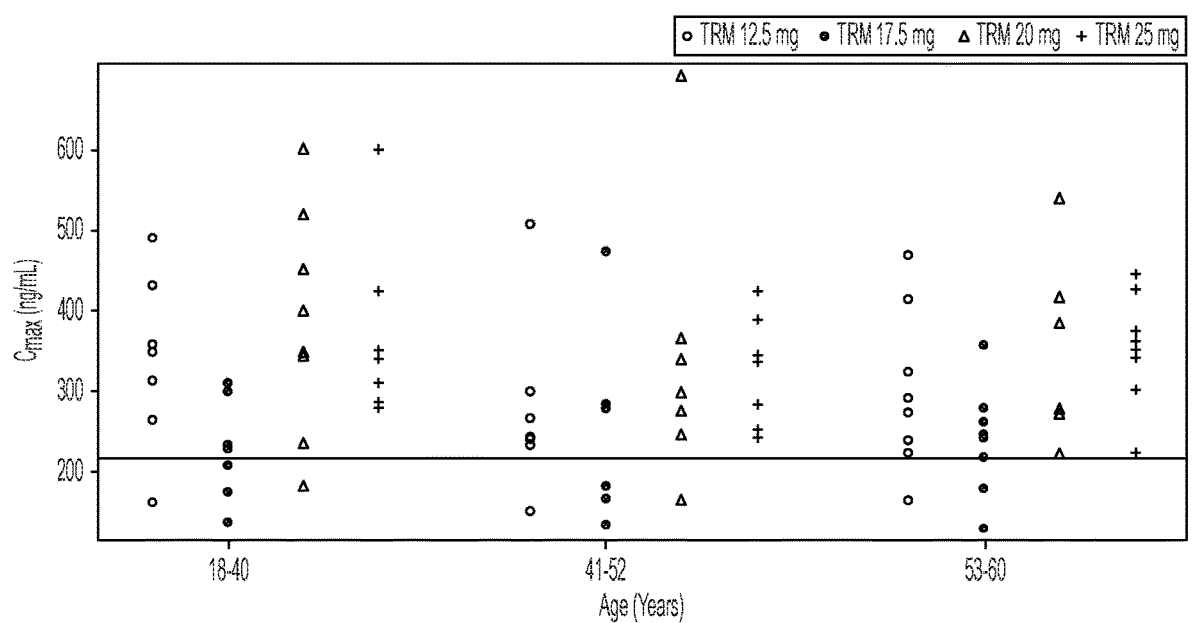
FIG. 96 shows a scatterplot of fasted $C_{max}$ by age (102 study only).
Figure 97:
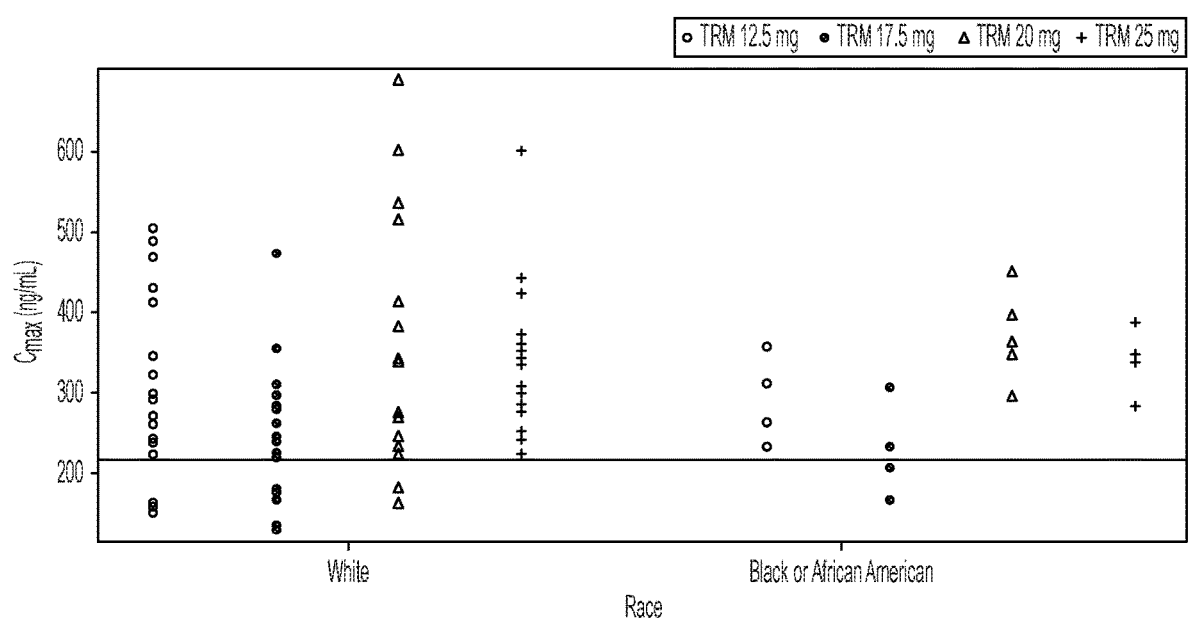
FIG. 97 shows a scatterplot of fasted $C_{max}$ by race (102 study only).
Figure 98:
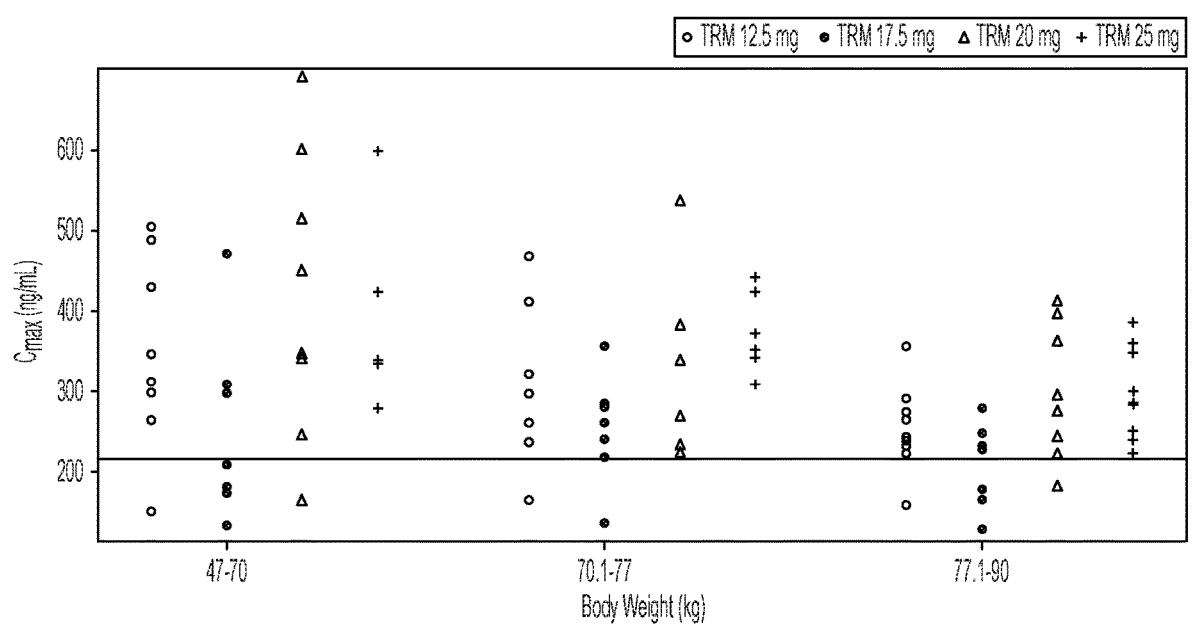
FIG. 98 shows a scatterplot of fasted $C_{max}$ by body weight (102 study only).
Figure 99:
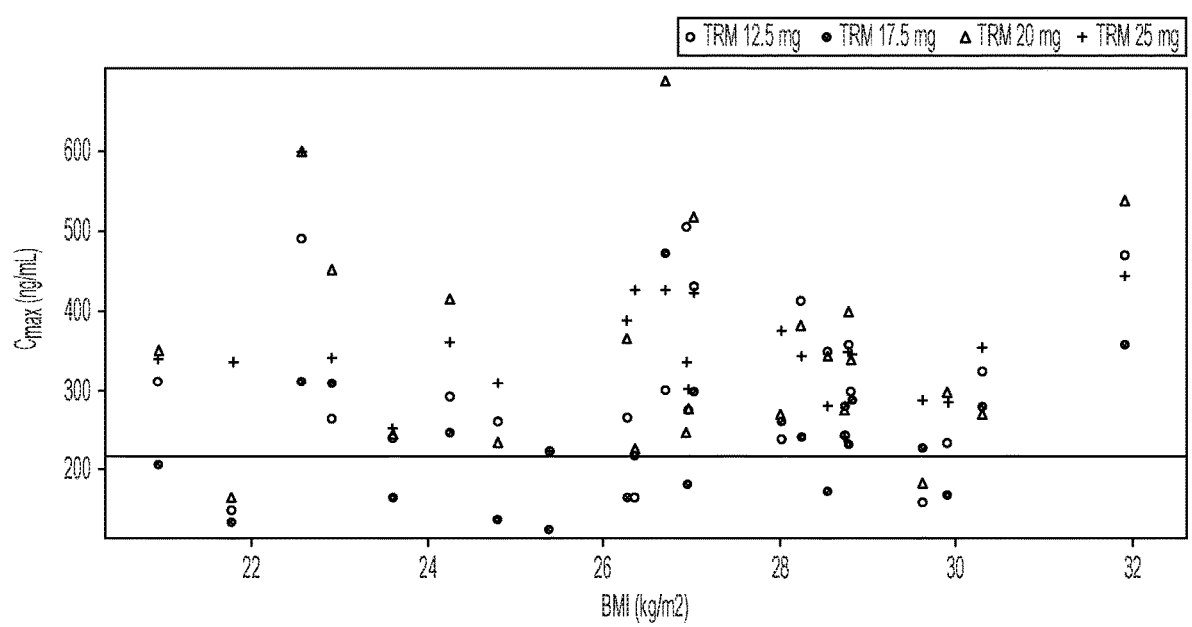
FIG. 99 shows a scatterplot of fasted $C_{max}$ by BMI (102 study only).

FIG. 96 shows a scatterplot of fasted $C_{max}$ values by age and by TRM-201 dosage. FIG. 97 shows a scatterplot of fasted $C_{max}$ values by race and by TRM-201 dosage. FIG. 98 shows a scatterplot of fasted $C_{max}$ values by body weight and by TRM-201 dosage. FIG. 99 shows a scatterplot of fasted $C_{max}$ values by BMI and by TRM-201 dosage.

Figure 100:
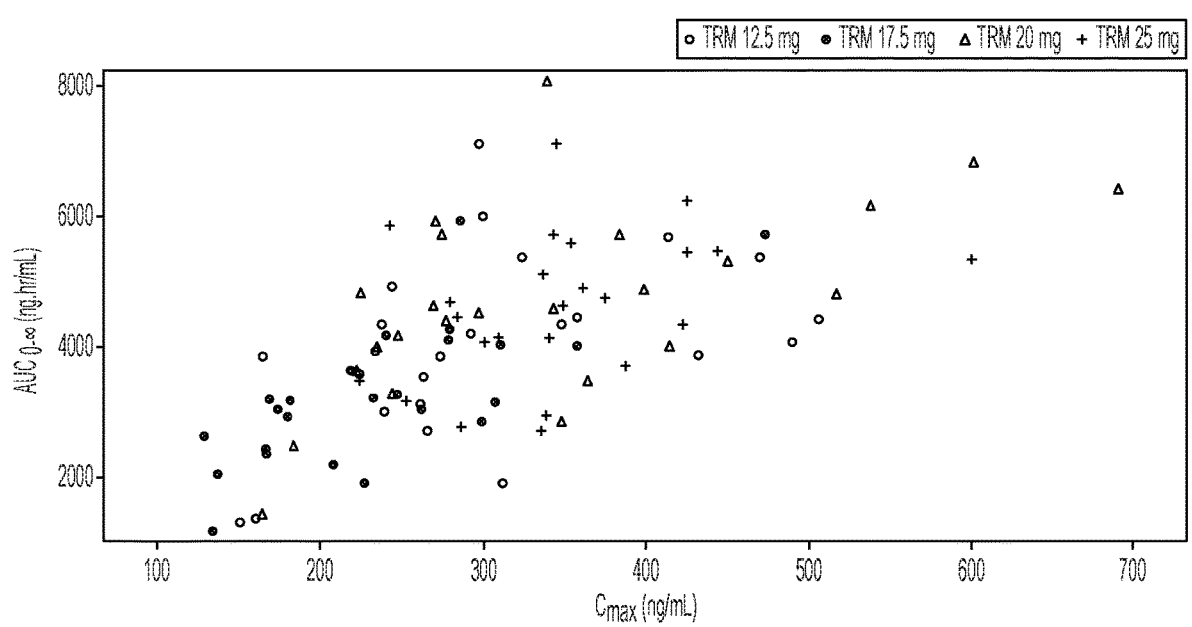
FIG. 100 shows a scatterplot of fasted $AUC_{0-\infty}$ and $C_{max}$ (dose-adjusted on raw scale) (102 study only).
Figure 101:
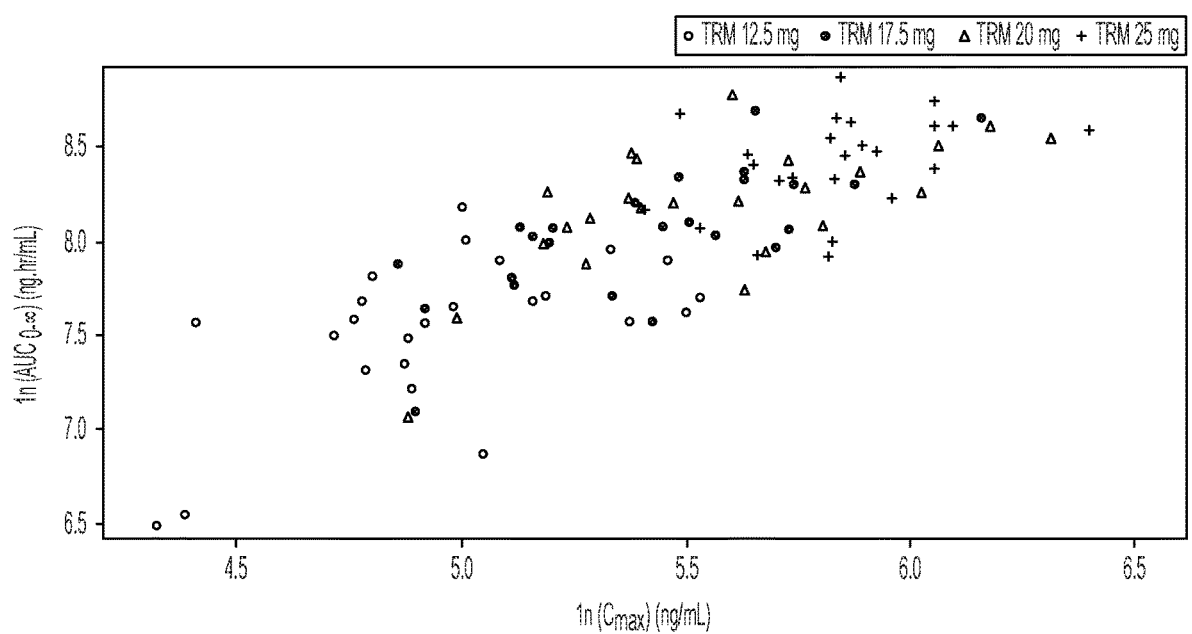
FIG. 101 shows a scatterplot of fasted $AUC_{0-\infty}$ and $C_{max}$ (not dose-adjusted on natural-log scale) (102 study only).
Figure 102A:
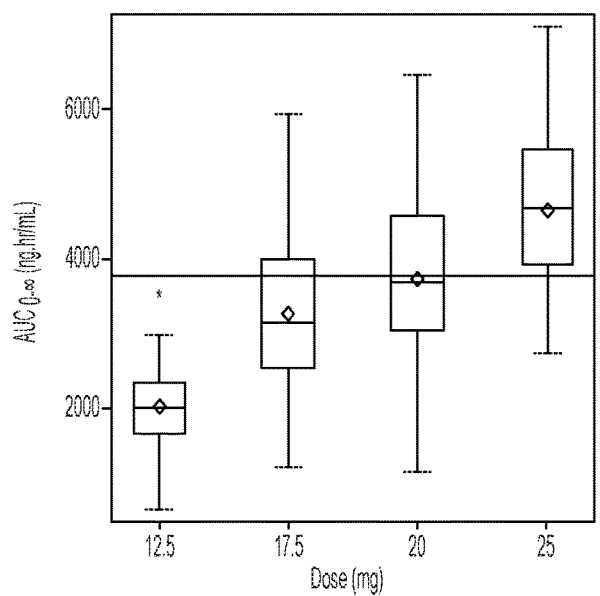
FIGS. 102A-B show a boxplot of fasted $AUC_{0-\infty}$ and $C_{max}$, respectively.
Figure 102B:
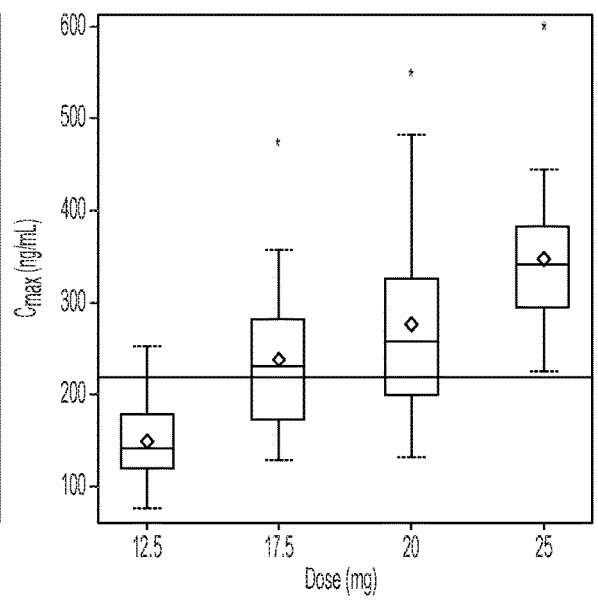

FIG. 100 shows a scatterplot of fasted $AUC_{0-\infty}$ and $C_{max}$ values, dose-adjusted on raw scale, for each TRM-201 dosage. FIG. 101 shows a scatterplot of fasted $AUC_{0-\infty}$ and $C_{max}$ values, not dose-adjusted on natural-log scale, for each TRM-201 dosage. FIGS. 102A-B show a boxplot of fasted $AUC_{0-\infty}$ and $C_{max}$ indices, respectively, for each dosage.

Figure 103:
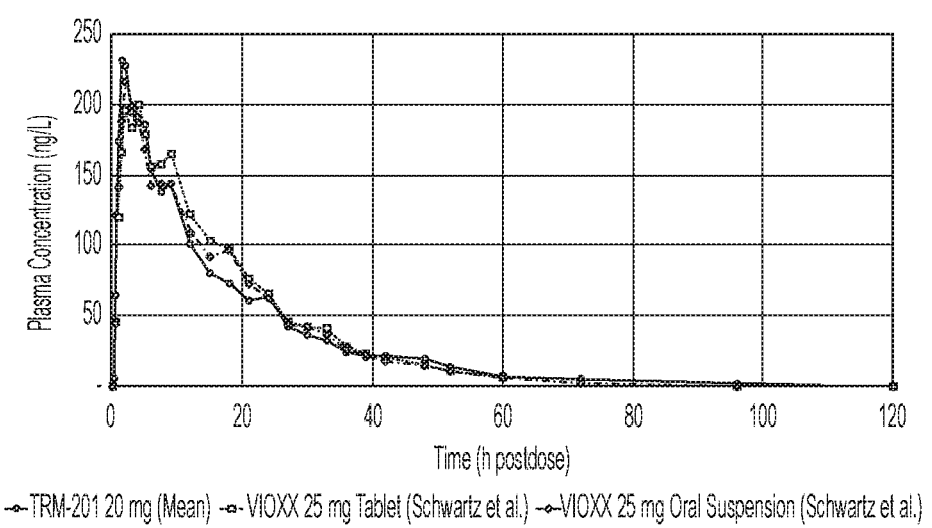
FIG. 103 shows a comparison of the mean plasma concentration (ng/L) versus time for TRM-201 20 mg and the 25 mg "VIOXX" tablet and oral suspension reported in Schwartz, J. I., et al. Clin. Drug Invent. 2003, 23 (8): 503-509.

FIGS. 103-104 show a comparison of the mean plasma concentration (ng/L) versus time for TRM-201 20 mg and the 25 mg "VIOXX" tablet and oral suspension products reported in Schwartz, J. I., et al. Clin. Drug Invent. 2003, 23 (8): 503-509.

Unexpected Results

The FDA-approved label for the "VIOXX" product provided that "[t]he pharmacokinetics of rofecoxib are comparable in men and women," and that "[m]eta-analysis of pharmacokinetic studies has suggested a slightly (10-15%) higher AUC of rofecoxib in Blacks and Hispanics as compared to Caucasians." See the "VIOXX" label at p. 2.

In some embodiments, the subject matter disclosed herein relates to the surprising and unexpected discovery that certain of the formulations and methods described herein can achieve different pharmacokinetic profiles in men and women following single administration of the same amount of rofecoxib, contrary to what was described in the FDA-approved label for the "VIOXX" product. It was also surprisingly and unexpectedly discovered that certain of the formulations and methods described herein can achieve a higher AUC in Caucasian subjects than African American subjects following single administration of the formulations comprising rofecoxib as described herein.

REFERENCES FOR EXAMPLE 6

Bresalier R S, Sandler R S, Quan H, et al. Cardiovascular events associated with rofecoxib in a colorectal adenoma chemoprevention trial. New Engl J Med 2005; 352:1092-102.

Matthews C Z, Woolf E J, Matuszewski B K. Improved procedure for the determination of rofecoxib in human plasma involving 96-well solid-phase extraction and fluorescence detection. J Chromatogr A. 2002; 949(1-2):83-9.

Schwartz J I, Larson P J, Porras A G, et al. Pharmacokinetic evaluation of rofecoxib: comparison of tablet and suspension formulations. Clin Drug Invest. 2003; 23(8):503-9.

Tsoukas C, Eyster M E, Sbingo S, et al. Evaluation of the efficacy and safety of etoricoxib in the treatment of hemophilic arthropathy. Blood. 2006; 107(5): 1785-90.

U S. Food and Drug Administration. Analysis and recommendations for agency action regarding nonsteroidal anti-inflammatory drugs and cardiovascular risk. J Pain Palliat Care Pharmacother. 2005; 19(4):83-97.

Vioxx (rofecoxib) [package insert], Merck & Co., Inc. Whitehouse Station, N.J.; 2016.

Example 7—Bioanalytical Method to Measure Rofecoxib Plasma Concentrations

Introduction

In order to support clinical studies with TRM-201 (rofecoxib), a method was developed for the determination of rofecoxib in human plasma by LC-MS/MS. This method was validated in accordance with the FDA Good Laboratory Practice Regulations (GLP) as set forth in Title 21 of the U S. Code of Federal Regulations Part 58 as well as FDA Guidance for Industry: Bioanalytical Method Validation, May 2018. A summary of the validated method is provided in Table 22.

TABLE 22

Validation Summary for Rofecoxib

| Report Title | Validation of a Method for the Determination of Rofecoxib in Human Plasma by LC-MS/MS |
| --- | --- |
| Analyte Name | Rofecoxib |
| Internal Standard (IS) | Rofecoxib-$d_5$ |
| Analytical Method Type | LC-MS/MS |
| Extraction Method | Liquid-liquid |
| Sample Volume | 100 μL |
| QC Concentrations | 0.5, 1.5, 20, 200, and 400 ng/mL |
| Standard Curve Concentrations | 0.5, 1, 5, 10, 50, 100, 450, and 500 ng/mL |
| Lower Limit Of Quantitation | 0.5 ng/mL |
| Upper Limit Of Quantitation | 500 ng/mL |
| Mean Recovery of Analyte (%) | 92.6 |
| Mean Recovery of Internal Standard (%) | 92.7 |
| Variation of Matrix Effect from Six Lots of Matrix (% CV) | ≤2.6 |
| Sensitivity | Analyte response [LLOQ/zero calibrator (i.e. Blank + IS)] > five |
| LLOQ QC Intra-run Precision Range (% CV) | 2.0 to 7.8 |
| LLOQ QC Intra-run Accuracy Range (% RE) | −11.8 to −1.8 |

TABLE 22-continued

Validation Summary for Rofecoxib

| Report Title | Validation of a Method for the Determination of Rofecoxib in Human Plasma by LC-MS/MS |
|---|---|
| Analytical QC Intra-run Precision Range (% CV) | 0.8 to 6.6 |
| Analytical QC Intra-run Accuracy Range (% RE) | −4.0 to 3.0 |
| LLOQ QC Inter-run Precision (% CV) | 7.3 |
| LLOQ QC Inter-run Accuracy (% RE) | −5.2 |
| Analytical QC Inter-run Precision Range (% CV) | 3.0 to 4.9 |
| Analytical QC Inter-run Accuracy Range (% RE) | −2.5 to 0.7 |
| Stock Solution Stability in Dimethyl Sulfoxide | 202 Days at −20° C. |
| Processed Sample Stability | 17 Hours at Ambient Temperature |
| Benchtop Stability in Plasma | 174 Hours at 4° C. |
| Freeze/Thaw Stability in Plasma | 26 Hours at Ambient Temperature |
| Benchtop Stability in Whole Blood | 5 Cycles at −20° C. and −70° C. |
| | 2 Hours in an Ice Bath when Centrifuged at 4° C. or Ambient Temperature |
| Long-term Storage Stability in Plasma | 184 Days at −20° C. and −70° C. |
| Dilution Integrity | 100 ng/mL diluted 20-fold |
| Selectivity | ≤20.0% LLOQ for analyte; ≤5.0% for IS |
| Spike-in Selectivity | Meets Acceptance Criteria |
| 2% Hemolyzed Plasma Test | No impact on assay performance |
| Lipemic Plasma Test | No impact on assay performance |
| Batch Size Test | 192 Injections |
| Carryover | <20% LLOQ (Rofecoxib) <5% Carryover IS (Rofecoxib-$d_5$) |

EQUIVALENTS

The invention can be embodied in other specific forms without departing from the spirit or essential characteristics thereof. The foregoing embodiments are therefore to be considered in all respects illustrative rather than limiting on the invention described herein.

What is claimed is:

1. A method for treating pain, fever, or inflammation in a human subject, the method comprising orally administering to the subject once daily a solid dosage formulation comprising 17.5 mg of rofecoxib, wherein the formulation achieves a mean Cmax plasma concentration of more than 180 ng/ml following oral administration of a single dose of the formulation to a population of healthy adults less than 65 years of age.

2. The method of claim 1, wherein the method comprises treating pain, fever, or inflammation associated with one or more of the following diseases or conditions: migraine associated with von Willebrand deficiency; rheumatoid arthritis (RA); pauciarticular or polyarticular course Juvenile Rheumatoid Arthritis; acute pain; primary dysmenorrhea; migraine attacks with or without aura; chronic lower back pain; psoriatic arthritis; fibromyalgia; and hemophilic arthropathy.

3. The method of claim 1, wherein the formulation achieves a mean Cmax plasma concentration of more than 190 ng/ml following oral administration of a single dose of the formulation to a population of healthy adults less than 65 years of age.

4. The method of claim 1, wherein the formulation achieves a mean Cmax plasma concentration of more than 200 ng/ml following oral administration of a single dose of the formulation to a population of healthy adults less than 65 years of age.

5. The method of claim 4, wherein the formulation achieves a mean Cmax plasma concentration of about 224 ng/ml following oral administration of a single dose of the formulation to a population of healthy adults less than 65 years of age.

6. The method of claim 1, wherein the formulation achieves a mean Cmax plasma concentration within 80-125% of 224 ng/ml following oral administration of a single dose of the formulation to a population of healthy adults less than 65 years of age.

7. The method of claim 1, wherein the formulation achieves a mean plasma $AUC_{0-\infty}$ of more than 3000 h*ng/ml following oral administration of a single dose of the formulation to a population of healthy adults less than 65 years of age.

8. The method of claim 1, wherein the formulation achieves a higher mean plasma Cmax and a higher mean plasma $AUC_{0-\infty}$ in a population of healthy female adults less than 65 years of age compared to a population of healthy male adults less than 65 years of age following oral administration of a single dose of the formulation.

9. The method of claim 1, wherein the formulation achieves a higher mean plasma $AUC_{0-\infty}$ in Caucasian adults less than 65 years of age compared to healthy African American adults less than 65 years of age following oral administration of a single dose of the formulation.

10. The method of claim 1, wherein the formulation achieves an arithmetic mean plasma concentration of at least 2.0 ng/ml at 15 minutes following oral administration of a single dose of the formulation to a population of healthy adults less than 65 years of age.

11. The method of claim 1, wherein the formulation achieves an arithmetic mean plasma concentration of at least 79 ng/ml at 45 minutes following oral administration of a single dose of the formulation to a population of healthy adults less than 65 years of age.

12. The method of claim 2, wherein the method comprises treating pain, fever, or inflammation associated with one or more of the following diseases or conditions: chronic lower back pain, psoriatic arthritis, fibromyalgia, hemophilic arthropathy, and migraine associated with von Willebrand deficiency.

13. The method of claim 2, wherein the method comprises treating pain, fever, or inflammation that is associated with hemophilic arthropathy.

14. The method of claim 1, wherein the solid dosage formulation further comprises a disintegrant.

15. A method for treating pain, fever, or inflammation in a human subject, the method comprising orally administering to the subject once daily a solid dosage formulation comprising 17.5 mg of rofecoxib, wherein the formulation achieves a mean plasma $AUC_{0-\infty}$ of more than 3000 h*ng/ml following oral administration of a single dose of the formulation to a population of healthy adults less than 65 years of age.

16. The method of claim 15, wherein the method comprises treating pain, fever, or inflammation associated with one or more of the following diseases or conditions: migraine associated with von Willebrand deficiency; rheumatoid arthritis (RA); pauciarticular or polyarticular course Juvenile Rheumatoid Arthritis; acute pain; primary dysmenorrhea; migraine attacks with or without aura; chronic lower back pain; psoriatic arthritis; fibromyalgia; and hemophilic arthropathy.

17. The method of claim 15, wherein the formulation achieves a mean Cmax plasma concentration of more than 167 ng/ml following oral administration of a single dose of the formulation to a population of healthy adults less than 65 years of age.

18. The method of claim 17, wherein the formulation achieves a mean Cmax plasma concentration of about 224 ng/ml following oral administration of a single dose of the formulation to a population of healthy adults less than 65 years of age.

19. The method of claim 15, wherein the formulation achieves a mean Cmax plasma concentration within 80-125% of 224 ng/ml following oral administration of a single dose of the formulation to a population of healthy adults less than 65 years of age.

20. The method of claim 15, wherein the formulation achieves a higher mean plasma Cmax and a higher mean plasma $AUC_{0-\infty}$ in a population of healthy female adults less than 65 years of age compared to a population of healthy male adults less than 65 years of age following oral administration of a single dose of the formulation.

21. The method of claim 15, wherein the formulation achieves a higher mean plasma $AUC_{0-\infty}$ in Caucasian adults less than 65 years of age compared to healthy African American adults less than 65 years of age following oral administration of a single dose of the formulation.

22. The method of claim 15, wherein the formulation achieves an arithmetic mean plasma concentration of at least 79 ng/ml at 45 minutes following oral administration of a single dose of the formulation to a population of healthy adults less than 65 years of age.

23. The method of claim 16, wherein the method comprises treating pain, fever, or inflammation that is associated with one or more of the following diseases or conditions: chronic lower back pain, psoriatic arthritis, fibromyalgia, hemophilic arthropathy, and migraine associated with von Willebrand deficiency.

24. The method of claim 16, wherein the method comprises treating pain, fever, or inflammation that is associated with hemophilic arthropathy.

25. The method of claim 15, wherein the solid dosage formulation further comprises a disintegrant.

26. A method for treating pain, fever, or inflammation in a human subject, the method comprising orally administering to the subject once daily a solid dosage formulation comprising 17.5 mg of rofecoxib, wherein the formulation achieves an arithmetic mean plasma concentration of at least 2.0 ng/ml at 15 minutes following oral administration of a single dose of the formulation to a population of healthy adults less than 65 years of age.

27. The method of claim 26, wherein the formulation achieves an arithmetic mean plasma concentration of at least 79 ng/ml at 45 minutes following oral administration of a single dose of the formulation to a population of healthy adults less than 65 years of age.

28. The method of claim 26, wherein the solid dosage formulation further comprises a disintegrant.

* * * * *

UNITED STATES PATENT AND TRADEMARK OFFICE
CERTIFICATE OF CORRECTION

| | | |
|---|---|---|
| PATENT NO. | : 10,945,992 B1 | Page 1 of 1 |
| APPLICATION NO. | : 16/867514 | |
| DATED | : March 16, 2021 | |
| INVENTOR(S) | : Bradford C. Sippy et al. | |

It is certified that error appears in the above-identified patent and that said Letters Patent is hereby corrected as shown below:

On the Title Page

In the title of the invention at Item (54), the text:
"DOSAGE FORMS OF ROFECOXIB AND RELATED METHODS"
Should be replaced with:
-- NOVEL DOSAGE FORMS OF ROFECOXIB AND RELATED METHODS --.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*